(12) United States Patent
Hanenberg et al.

(10) Patent No.: US 11,634,472 B2
(45) Date of Patent: Apr. 25, 2023

(54) TREATMENT OF MONOGENETIC DISORDERS

(71) Applicant: Zentrum für Forschungsförderung in der Pädiatrie GmbH, Hannover (DE)

(72) Inventors: Helmut Hanenberg, Düsseldorf (DE); Maj-Kristin Holz, Essen (DE); Katharina Röllecke, Dortmund (DE); Katharina Waack-Buchholz, Essen (DE)

(73) Assignee: ZENTRUM FÜR FORSCHUNGSFÖRDERUNG IN DER PÄDIATRIE GMBH

( * ) Notice: Subject to any disclaimer, the term of this patent is extended or adjusted under 35 U.S.C. 154(b) by 521 days.

(21) Appl. No.: 16/611,904

(22) PCT Filed: Feb. 21, 2018

(86) PCT No.: PCT/EP2018/054274
§ 371 (c)(1),
(2) Date: Nov. 8, 2019

(87) PCT Pub. No.: WO2018/206168
PCT Pub. Date: Nov. 15, 2018

(65) Prior Publication Data
US 2020/0291092 A1 Sep. 17, 2020

(30) Foreign Application Priority Data

May 11, 2017 (EP) .................... 17170681
Jun. 22, 2017 (EP) .................... 17177443
Sep. 28, 2017 (WO) ......... PCT/EP2017/074630

(51) Int. Cl.
C12N 15/67 (2006.01)
C07K 14/745 (2006.01)
A61K 9/51 (2006.01)
A61K 48/00 (2006.01)
C07K 14/755 (2006.01)
C12N 15/85 (2006.01)

(52) U.S. Cl.
CPC .......... *C07K 14/745* (2013.01); *A61K 9/5115* (2013.01); *A61K 48/0025* (2013.01); *A61K 48/0066* (2013.01); *C07K 14/755* (2013.01); *C12N 15/85* (2013.01); *C12N 2800/22* (2013.01); *C12N 2830/46* (2013.01)

(58) Field of Classification Search
CPC ........ C12N 15/85; C12N 15/63; C12N 15/79; C12N 2800/22; C12N 15/67; A61K 48/00; A61K 38/37; A61K 48/0066; A61K 48/005
See application file for complete search history.

(56) References Cited

U.S. PATENT DOCUMENTS

2013/0095187 A1    4/2013  Hahn et al.
2016/0304902 A1*  10/2016  Kim ..................... C12P 21/00
2018/0319854 A1*  11/2018  Gummadova ........... C12Q 1/66

FOREIGN PATENT DOCUMENTS

| EP | 3088527 | 11/2016 | |
|---|---|---|---|
| WO | 2006123097 | 11/2006 | |
| WO | 2007144173 | 12/2007 | |
| WO | 2013153361 | 10/2013 | |
| WO | 2014016580 | 1/2014 | |
| WO | 2015095340 | 6/2015 | |
| WO | WO-2015195547 A1 * | 12/2015 | ........... A61K 35/545 |

OTHER PUBLICATIONS

Dooriss et al.; Comparison of Factor VIII Transgenes Bioengineered for Improved Expression in Gene Therapy of Hemophilia A; Human Gene Therapy, vol. 20, No. 5, pp. 465-478; May 2009.
Petrus et al.; Gene Therapy Strategies for Hemophilia: Benefits versus Risks; Journal of Gene Medicine, vol. 12, No. 10, pp. 797-809; Oct. 2010.
Cebrin et al. ; Size-Dependent Transfection Efficiency of PEI-Coated Gold Nanoparticles; ACTA Biomaterialia, Elsevier, Amsterdam, NL, vol. 7, No. 10, pp. 3645-3655; Jun. 2011.
Jha et al.; Binding and Uptake into Human Hepatocellular Carcinoma Cells of Peptide-Functionalized Gold Nanoparticles; Bioconjugate Chemistry, vol. 28, No. 1, pp. 222-229; Nov. 2016.
Hardee et al.; Advances in Non-Viral DNA Vectors for Gene Therapy; Genes, vol. 8, No. 2, p. 65; Feb. 2017.

* cited by examiner

*Primary Examiner* — Dana H Shin
(74) *Attorney, Agent, or Firm* — Edward E. Sowers; Brannon Sowers & Cracraft PC

(57) ABSTRACT

The present invention relates to a nucleic acid expression cassette, in particular for the expression of a human liver-specific and/or liver-expressed protein and/or preferably physiologically active domains and/or fragments thereof in a patient suffering from a monogenetic disorder caused by a mutation in the gene coding for the liver-specific and/or liver-expressed protein.

8 Claims, 37 Drawing Sheets

Specification includes a Sequence Listing.

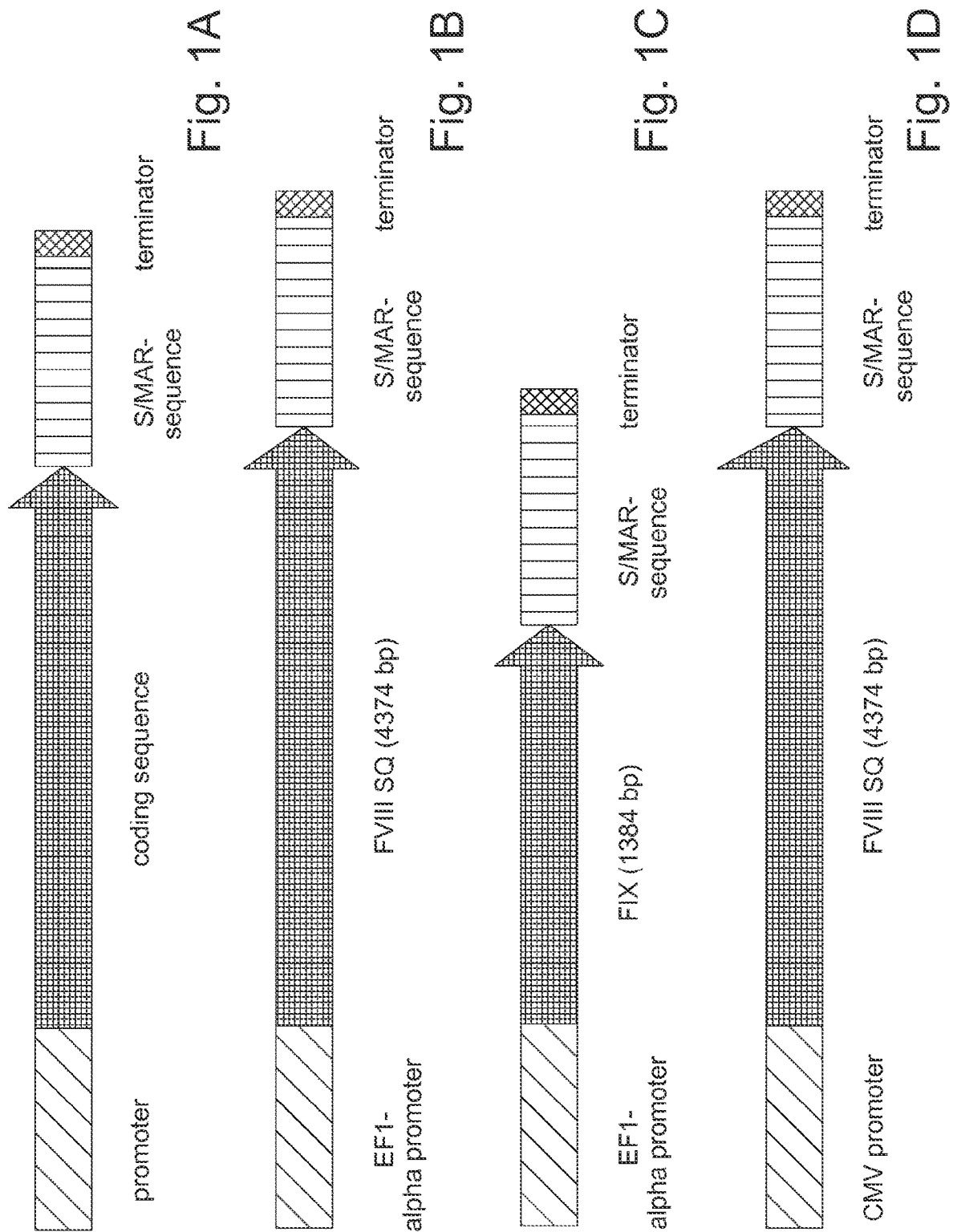

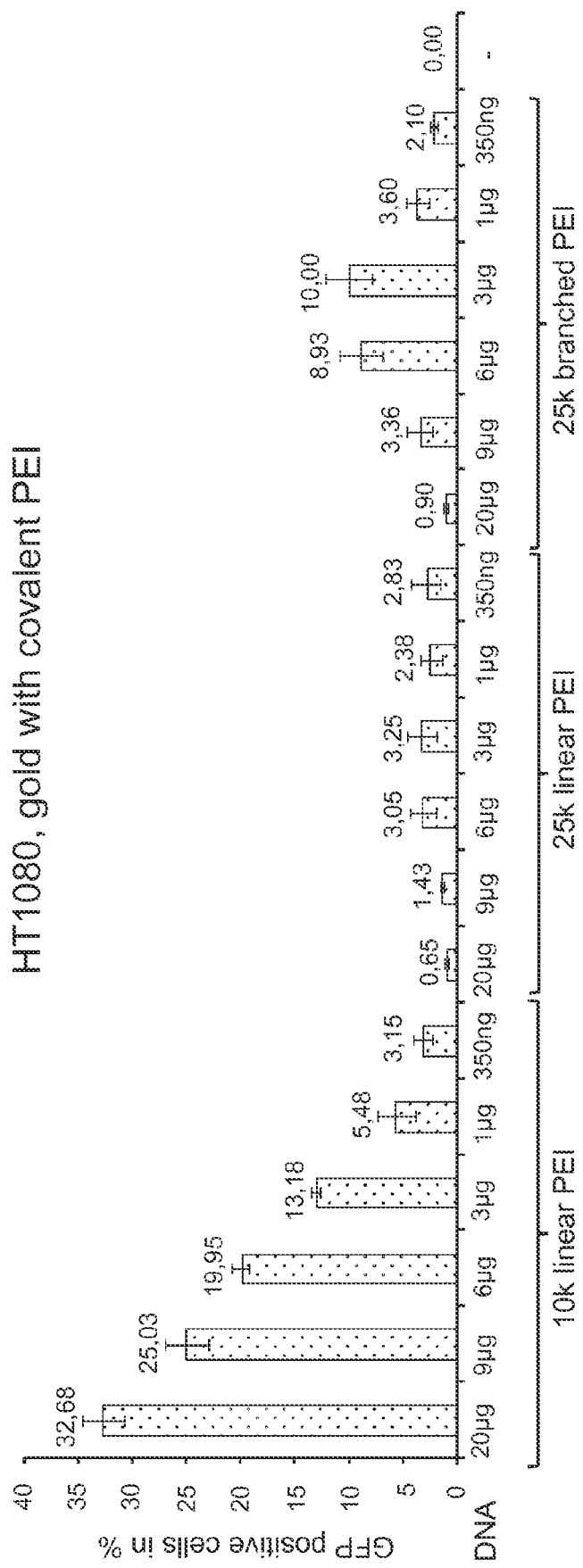

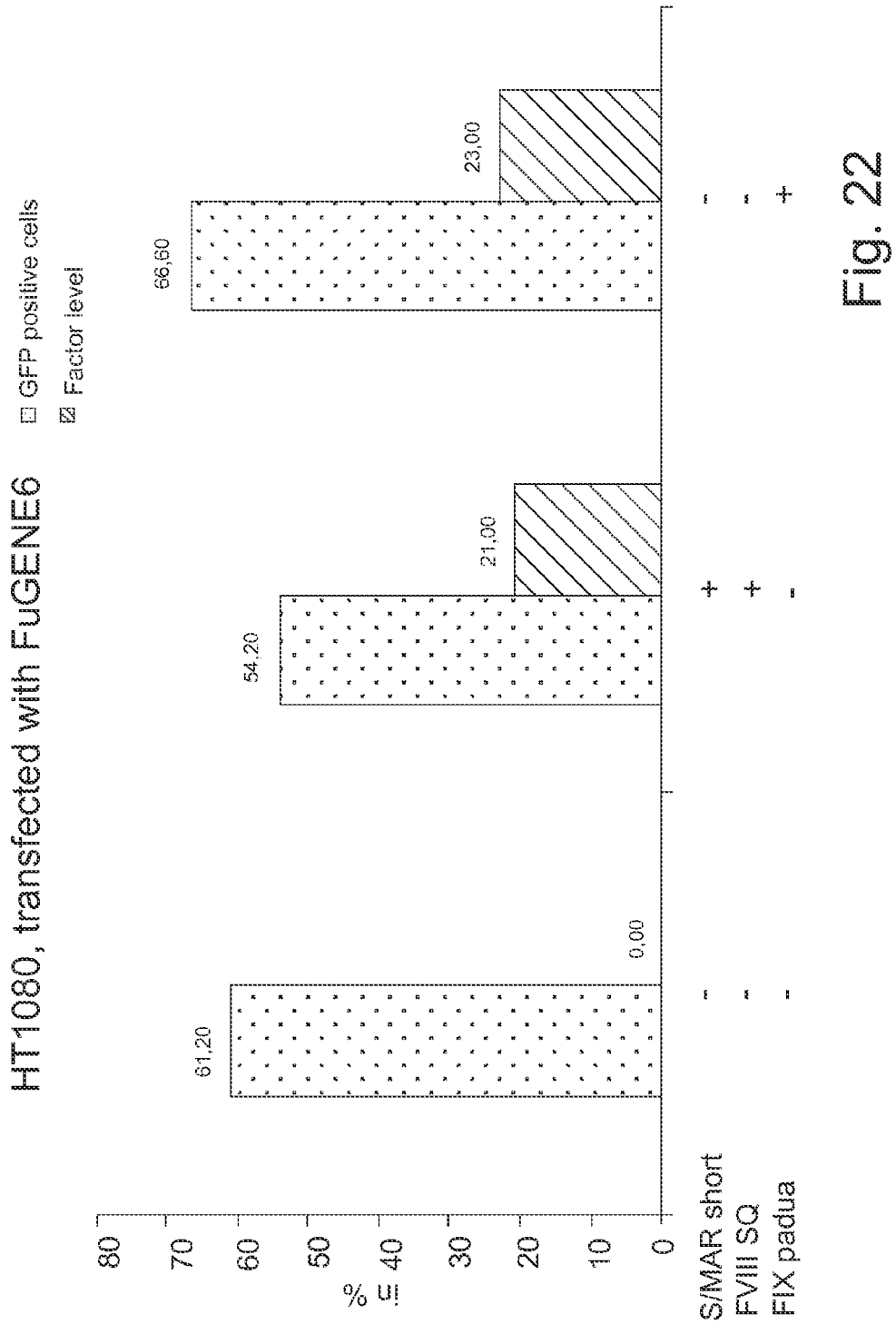

SEQUENCE LISTING

```
<160> NUMBER OF SEQ ID NOS: 28

<210> SEQ ID NO 1
<211> LENGTH: 211
<212> TYPE: DNA
<213> ORGANISM: Homo sapiens
<220> FEATURE:
<223> OTHER INFORMATION: EF1-alpha Promoter

<400> SEQUENCE: 1
ggctccggtg cccgtcagtg ggcagagcgc acatcgccca cagtccccga gaagttgggg      60
ggaggggtcg gcaattgaac cggtgcctag agaaggtggc gcggggtaaa ctgggaaagt     120
gatgtcgtgt actggctccg ccttttcc gagggtgggg gagaaccgta tataagtgca      180
gtagtcgccg tgaacgttct ttttcgcaac g                                     211

<210> SEQ ID NO 2
<211> LENGTH: 4374
<212> TYPE: DNA
<213> ORGANISM: Homo sapiens
<220> FEATURE:
<221> NAME/KEY: misc_feature
<222> LOCATION: (1)..(4374)
<223> OTHER INFORMATION: factor FVIII SQ with deleted B-domain
<220> FEATURE:
<221> NAME/KEY: misc_feature
<222> LOCATION: (1)..(4374)
```

<223> OTHER INFORMATION: factor FVIII SQ with deleted B-domain, wt sequence

<400> SEQUENCE: 2

| | |
|---|---:|
| atgcaaatag agctctccac ctgcttcttt ctgtgccttt tgcgattctg ctttagtgcc | 60 |
| accagaagat actacctggg tgcagtggaa ctgtcatggg actatatgca aagtgatctc | 120 |
| ggtgagctgc ctgtggacgc aagatttcct cctagagtgc aaaatctttt ccattcaac | 180 |
| acctcagtcg tgtacaaaaa gactctgttt gtagaattca cggatcacct tttcaacatc | 240 |
| gctaagccaa ggccaccctg gatgggtctg ctaggtccta ccatccaggc tgaggtttat | 300 |
| gatacagtgg tcattacact taagaacatg gcttcccatc ctgtcagtct tcatgctgtt | 360 |
| ggtgtatcct actggaaagc ttctgaggga gctgaatatg atgatcagac cagtcaaagg | 420 |
| gagaaagaag atgataaagt cttccctggt ggaagccata catatgtctg gcaggtcctg | 480 |
| aaagagaatg gtccaatggc ctctgaccca ctgtgcctta cctactcata tctttctcat | 540 |
| gtggacctgg taaaagactt gaattcaggc ctcattggag ccctactagt atgtagagaa | 600 |
| gggagtctgg ccaaggaaaa gacacagacc ttgcacaaat ttatactact ttttgctgta | 660 |
| tttgatgaag ggaaaagttg gcactcagaa acaaagaact ccttgatgca ggataggggat | 720 |
| gctgcatctg ctcgggcctg gcctaaaatg cacacagtca atggttatgt aaacaggtct | 780 |
| ctgccaggtc tgattggatg ccacaggaaa tcagtctatt ggcatgtgat tggaatgggc | 840 |
| accactcctg aagtgcactc aatattcctc gaaggtcaca catttcttgt gaggaaccat | 900 |
| cgccaggcgt ccttggaaat ctcgccaata actttcctta ctgctcaaac actcttgatg | 960 |
| gaccttggac agtttctact gttttgtcat atctcttccc ccaacatga tggcatggaa | 1020 |
| gcttatgtca agtagacag ctgtccagag aaccccaac tacgaatgaa aaataatgaa | 1080 |
| gaagcggaag actatgatga tgatcttact gattctgaaa tggatgtggt caggtttgat | 1140 |
| gatgacaact ctccttcctt tatccaaatt cgctcagttg ccaagaagca tcctaaaact | 1200 |
| tgggtacatt acattgctgc tgaagaggag gactgggact atgctccctt agtcctcgcc | 1260 |
| cccgatgaca aagttataa agtcaatat ttgaacaatg ccctcagcg gattggtagg | 1320 |
| aagtacaaaa aagtccgatt tatggcatac acagatgaaa cctttaagac tcgtgaagct | 1380 |
| attcagcatg aatcaggaat cttgggaccct ttactttatg gggaagttgg agacacactg | 1440 |
| ttgattatat ttaagaatca agcaagcaga ccatataaca tctaccctca cggaatcact | 1500 |
| gatgtccgtc ctttgtattc aaggagatta ccaaaaggtg taaaacattt gaaggatttt | 1560 |
| ccaattctgc cagagaaat attcaaatat aaatggacag tgactgtaga agatgggcca | 1620 |
| actaaatcag atcctcggtg cctgacccgc tattactcta gtttcgttaa tatggagaga | 1680 |
| gatctagctt caggactcat tggccctctc ctcatctgct acaaagaatc tgtagatcaa | 1740 |
| agaggaaacc agataatgtc agacaagagg aatgtcatcc tgttttctgt atttgatgag | 1800 |
| aaccgaagct ggtacctcac agaaatata caacgctttc tccccaatcc agctggagtg | 1860 |
| cagcttgagg atccagagtt ccaagcctcc aacatcatgc acagcatcaa tggctatgtt | 1920 |
| tttgatagtt tgcagttgtc agtttgtttg catgaggtgg catactggta cattctaagc | 1980 |
| attggagcac agactgactt cctttctgtc ttcttctctg gatataccti caaacacaaa | 2040 |
| atggtctatg aagacacact caccctattc ccattctcag agaaactgt cttcatgtcg | 2100 |
| atggaaaacc caggtctatg gattctgggg tgccacaact cagactttcg gaacagaggc | 2160 |
| atgaccgcct tactgaaggt ttctagttgt gacaagaaca ctggtgatta ttacgaggac | 2220 |

```
agttatgaag atatttcagc atacttgctg agtaaaaaca atgccattga accaagaagc    2280
ttctcccaga atccaccagt cttaaaaaga caccagagag aaataactcg tactactctt    2340
cagtcagatc aagaggaaat tgactatgat gataccatat cagttgaaat gaagaaggaa    2400
gattttgaca tttatgatga ggatgaaaat cagagccccc gcagctttca aaagaaaaca    2460
cgacactatt ttattgctgc agtggagagg ctctgggatt atgggatgag tagctcccca    2520
catgttctaa gaaacagggc tcagagtggc agtgtccctc agttcaagaa agttgttttc    2580
caggaattta ctgatggctc ctttactcag cccttatacc gtggagaact aaatgaacat    2640
ttgggactcc tggggccata taagagcaa gaagttgaag ataatatcat ggtaactttc    2700
agaaatcagg cctctcgtcc ctattccttc tattctagcc ttatttctta tgaggaagat    2760
cagaggcaag gagcagaacc tagaaaaaac tttgtcaagc ctaatgaaac caaaacttac    2820
ttttggaaag tgcaacatca tatggcaccc actaaagatg agtttgactg caaagcctgg    2880
gcttatttct ctgatgttga cctgaaaaaa gatgtgcact caggcctgat tggacccctt    2940
ctggtctgcc acactaacac actgaaccct gctcatggga gacaagtgac agtacaggaa    3000
tttgctctgt ttttcaccat ctttgatgag accaaaagct ggtacttcac tgaaaatatg    3060
gaaagaaact gcagggctcc ctgcaatatc cagatgaaga tcccactttt aaagagaat    3120
tatcgcttcc atgcaatcaa tggctacata atggatacac tacctggctt agtaatggct    3180
caggatcaaa ggattcgatg gtatctgctc agcatgggca gcaatgaaaa catccattct    3240
attcatttca gtggacatgt gttcactgta cgaaaaaaag aggagtataa aatggcactg    3300
tacaatctct atccaggtgt ttttgagaca gtggaaatgt taccatccaa agctggaatt    3360
tggcgggtgg aatgccttat tggcgagcat ctacatgctg ggatgagcac actttttctg    3420
gtgtacagca ataagtgtca gactcccctg ggaatggctt ctggacacat tagagatttt    3480
cagattacag cttcaggaca atatggacag tgggccccaa agctggccag acttcattat    3540
tccggatcaa tcaatgcctg gagcaccaag gagcccttt cttggatcaa ggtggatctg    3600
ttggcaccaa tgattattca cggcatcaag acccagggtg cccgtcagaa gttctccagc    3660
ctctacatct ctcagtttat catcatgtat agtcttgatg gaagaagtg gcagacttat    3720
cgaggaaatt ccactggaac cttaatggtc ttctttggca atgtggattc atctgggata    3780
aaacacaata ttttttaaccc tccaattatt gctcgataca tccgtttgca cccaactcat    3840
tatagcattc gcagcactct tcgcatggag ttgatgggct gtgatttaaa tagttgcagc    3900
atgccattgg gaatggagag taaagcaata tcagatgcac agattactgc ttcatcctac    3960
tttaccaata tgtttgccac ctggtctcct tcaaaagctc gacttcacct ccaagggagg    4020
agtaatgcct ggagaccta ggtgaataat ccaaaagagt ggctgcaagt ggacttccag    4080
aagacaatga aagtcacagg agtaactact cagggagtaa aatctctgct taccagcatg    4140
tatgtgaagg agttcctcat ctccagcagt caagatggcc atcagtggac tctcttttt    4200
cagaatggca aagtaaaggt ttttcaggga aatcaagact ccttcacacc tgtggtgaac    4260
tctctagacc caccgttact gactcgctac cttcgaattc accccagag ttgggtgcac    4320
cagattgccc tgaggatgga ggttctgggc tgcgaggcac aggacctcta ctga         4374
```

<210> SEQ ID NO 3
<211> LENGTH: 1457
<212> TYPE: PRT
<213> ORGANISM: Homo sapiens
<220> FEATURE:
<221> NAME/KEY: MISC_FEATURE
<222> LOCATION: (1)..(1457)
<223> OTHER INFORMATION: Factor FVIII SQ with deleted B-domain

<400> SEQUENCE: 3

```
Met Gln Ile Glu Leu Ser Thr Cys Phe Phe Leu Cys Leu Leu Arg Phe
1               5                   10                  15

Cys Phe Ser Ala Thr Arg Arg Tyr Tyr Leu Gly Ala Val Glu Leu Ser
            20                  25                  30

Trp Asp Tyr Met Gln Ser Asp Leu Gly Glu Leu Pro Val Asp Ala Arg
        35                  40                  45

Phe Pro Pro Arg Val Pro Lys Ser Phe Pro Phe Asn Thr Ser Val Val
50                  55                  60

Tyr Lys Lys Thr Leu Phe Val Glu Phe Thr Asp His Leu Phe Asn Ile
65                  70                  75                  80

Ala Lys Pro Arg Pro Pro Trp Met Gly Leu Leu Gly Pro Thr Ile Gln
                85                  90                  95

Ala Glu Val Tyr Asp Thr Val Val Ile Thr Leu Lys Asn Met Ala Ser
            100                 105                 110

His Pro Val Ser Leu His Ala Val Gly Val Ser Tyr Trp Lys Ala Ser
        115                 120                 125

Glu Gly Ala Glu Tyr Asp Asp Gln Thr Ser Gln Arg Glu Lys Glu Asp
130                 135                 140

Asp Lys Val Phe Pro Gly Gly Ser His Thr Tyr Val Trp Gln Val Leu
145                 150                 155                 160

Lys Glu Asn Gly Pro Met Ala Ser Asp Pro Leu Cys Leu Thr Tyr Ser
                165                 170                 175

Tyr Leu Ser His Val Asp Leu Val Lys Asp Leu Asn Ser Gly Leu Ile
            180                 185                 190

Gly Ala Leu Leu Val Cys Arg Glu Gly Ser Leu Ala Lys Glu Lys Thr
        195                 200                 205

Gln Thr Leu His Lys Phe Ile Leu Leu Phe Ala Val Phe Asp Glu Gly
210                 215                 220

Lys Ser Trp His Ser Glu Thr Lys Asn Ser Leu Met Gln Asp Arg Asp
225                 230                 235                 240

Ala Ala Ser Ala Arg Ala Trp Pro Lys Met His Thr Val Asn Gly Tyr
                245                 250                 255

Val Asn Arg Ser Leu Pro Gly Leu Ile Gly Cys His Arg Lys Ser Val
            260                 265                 270

Tyr Trp His Val Ile Gly Met Gly Thr Thr Pro Glu Val His Ser Ile
        275                 280                 285

Phe Leu Glu Gly His Thr Phe Leu Val Arg Asn His Arg Gln Ala Ser
290                 295                 300

Leu Glu Ile Ser Pro Ile Thr Phe Leu Thr Ala Gln Thr Leu Leu Met
305                 310                 315                 320

Asp Leu Gly Gln Phe Leu Leu Phe Cys His Ile Ser Ser His Gln His
                325                 330                 335

Asp Gly Met Glu Ala Tyr Val Lys Val Asp Ser Cys Pro Glu Glu Pro
            340                 345                 350

Gln Leu Arg Met Lys Asn Asn Glu Glu Ala Glu Asp Tyr Asp Asp Asp
        355                 360                 365

Leu Thr Asp Ser Glu Met Asp Val Val Arg Phe Asp Asp Asp Asn Ser
370                 375                 380

Pro Ser Phe Ile Gln Ile Arg Ser Val Ala Lys Lys His Pro Lys Thr
385                 390                 395                 400
```

-continued

```
Trp Val His Tyr Ile Ala Ala Glu Glu Asp Trp Asp Tyr Ala Pro
                405                 410                 415
Leu Val Leu Ala Pro Asp Arg Ser Tyr Lys Ser Gln Tyr Leu Asn
                420                 425                 430
Asn Gly Pro Gln Arg Ile Gly Arg Lys Tyr Lys Val Arg Phe Met
                435                 440                 445
Ala Tyr Thr Asp Glu Thr Phe Lys Thr Arg Glu Ala Ile Gln His Glu
        450                 455                 460
Ser Gly Ile Leu Gly Pro Leu Leu Tyr Gly Glu Val Gly Asp Thr Leu
465                 470                 475                 480
Leu Ile Ile Phe Lys Asn Gln Ala Ser Arg Pro Tyr Asn Ile Tyr Pro
                485                 490                 495
His Gly Ile Thr Asp Val Arg Pro Leu Tyr Ser Arg Arg Leu Pro Lys
                500                 505                 510
Gly Val Lys His Leu Lys Asp Phe Pro Ile Leu Pro Gly Glu Ile Phe
                515                 520                 525
Lys Tyr Lys Trp Thr Val Thr Val Glu Asp Gly Pro Thr Lys Ser Asp
                530                 535                 540
Pro Arg Cys Leu Thr Arg Tyr Tyr Ser Ser Phe Val Asn Met Glu Arg
545                 550                 555                 560
Asp Leu Ala Ser Gly Leu Ile Gly Pro Leu Leu Ile Cys Tyr Lys Glu
                565                 570                 575
Ser Val Asp Gln Arg Gly Asn Gln Ile Met Ser Asp Lys Arg Asn Val
                580                 585                 590
Ile Leu Phe Ser Val Phe Asp Glu Asn Arg Ser Trp Tyr Leu Thr Glu
                595                 600                 605
Asn Ile Gln Arg Phe Leu Pro Asn Pro Ala Gly Val Gln Leu Glu Asp
                610                 615                 620
Pro Glu Phe Gln Ala Ser Asn Ile Met His Ser Ile Asn Gly Tyr Val
625                 630                 635                 640
Phe Asp Ser Leu Gln Leu Ser Val Cys Leu His Glu Val Ala Tyr Trp
                645                 650                 655
Tyr Ile Leu Ser Ile Gly Ala Gln Thr Asp Phe Leu Ser Val Phe Phe
                660                 665                 670
Ser Gly Tyr Thr Phe Lys His Lys Met Val Tyr Glu Asp Thr Leu Thr
                675                 680                 685
Leu Phe Pro Phe Ser Gly Glu Thr Val Phe Met Ser Met Glu Asn Pro
                690                 695                 700
Gly Leu Trp Ile Leu Gly Cys His Asn Ser Asp Phe Arg Asn Arg Gly
705                 710                 715                 720
Met Thr Ala Leu Leu Lys Val Ser Ser Cys Asp Lys Asn Thr Gly Asp
                725                 730                 735
Tyr Tyr Glu Asp Ser Tyr Glu Asp Ile Ser Ala Tyr Leu Leu Ser Lys
                740                 745                 750
Asn Asn Ala Ile Glu Pro Arg Ser Phe Ser Gln Asn Pro Pro Val Leu
                755                 760                 765
Lys Arg His Gln Arg Glu Ile Thr Arg Thr Thr Leu Gln Ser Asp Gln
                770                 775                 780
Glu Glu Ile Asp Tyr Asp Asp Thr Ile Ser Val Glu Met Lys Lys Glu
785                 790                 795                 800
Asp Phe Asp Ile Tyr Asp Glu Asp Glu Asn Gln Ser Pro Arg Ser Phe
                805                 810                 815
```

-continued

Gln Lys Lys Thr Arg His Tyr Phe Ile Ala Ala Val Glu Arg Leu Trp
820                 825                 830

Asp Tyr Gly Met Ser Ser Pro His Val Leu Arg Asn Arg Ala Gln
    835                 840                 845

Ser Gly Ser Val Pro Gln Phe Lys Lys Val Val Phe Gln Glu Phe Thr
850                 855                 860

Asp Gly Ser Phe Thr Gln Pro Leu Tyr Arg Gly Glu Leu Asn Glu His
865                 870                 875                 880

Leu Gly Leu Leu Gly Pro Tyr Ile Arg Ala Glu Val Glu Asp Asn Ile
            885                 890                 895

Met Val Thr Phe Arg Asn Gln Ala Ser Arg Pro Tyr Ser Phe Tyr Ser
            900                 905                 910

Ser Leu Ile Ser Tyr Glu Glu Asp Gln Arg Gln Gly Ala Glu Pro Arg
            915                 920                 925

Lys Asn Phe Val Lys Pro Asn Glu Thr Lys Thr Tyr Phe Trp Lys Val
            930                 935                 940

Gln His His Met Ala Pro Thr Lys Asp Glu Phe Asp Cys Lys Ala Trp
945                 950                 955                 960

Ala Tyr Phe Ser Asp Val Asp Leu Glu Lys Asp Val His Ser Gly Leu
            965                 970                 975

Ile Gly Pro Leu Leu Val Cys His Thr Asn Thr Leu Asn Pro Ala His
            980                 985                 990

Gly Arg Gln Val Thr Val Gln Glu Phe Ala Leu Phe Phe Thr Ile Phe
            995                 1000                1005

Asp Glu Thr Lys Ser Trp Tyr Phe Thr Glu Asn Met Glu Arg Asn
    1010                1015                1020

Cys Arg Ala Pro Cys Asn Ile Gln Met Glu Asp Pro Thr Phe Lys
    1025                1030                1035

Glu Asn Tyr Arg Phe His Ala Ile Asn Gly Tyr Ile Met Asp Thr
    1040                1045                1050

Leu Pro Gly Leu Val Met Ala Gln Asp Gln Arg Ile Arg Trp Tyr
    1055                1060                1065

Leu Leu Ser Met Gly Ser Asn Glu Asn Ile His Ser Ile His Phe
    1070                1075                1080

Ser Gly His Val Phe Thr Val Arg Lys Lys Glu Glu Tyr Lys Met
    1085                1090                1095

Ala Leu Tyr Asn Leu Tyr Pro Gly Val Phe Glu Thr Val Glu Met
    1100                1105                1110

Leu Pro Ser Lys Ala Gly Ile Trp Arg Val Glu Cys Leu Ile Gly
    1115                1120                1125

Glu His Leu His Ala Gly Met Ser Thr Leu Phe Leu Val Tyr Ser
    1130                1135                1140

Asn Lys Cys Gln Thr Pro Leu Gly Met Ala Ser Gly His Ile Arg
    1145                1150                1155

Asp Phe Gln Ile Thr Ala Ser Gly Gln Tyr Gly Gln Trp Ala Pro
    1160                1165                1170

Lys Leu Ala Arg Leu His Tyr Ser Gly Ser Ile Asn Ala Trp Ser
    1175                1180                1185

Thr Lys Glu Pro Phe Ser Trp Ile Lys Val Asp Leu Leu Ala Pro
    1190                1195                1200

Met Ile Ile His Gly Ile Lys Thr Gln Gly Ala Arg Gln Lys Phe
    1205                1210                1215

Ser Ser Leu Tyr Ile Ser Gln Phe Ile Ile Met Tyr Ser Leu Asp

Gly Lys Lys Trp Gln Thr Tyr Arg Gly Asn Ser Thr Gly Thr Leu
1235                1240                1245

Met Val Phe Phe Gly Asn Val Asp Ser Ser Gly Ile Lys His Asn
1250                1255                1260

Ile Phe Asn Pro Pro Ile Ile Ala Arg Tyr Ile Arg Leu His Pro
1265                1270                1275

Thr His Tyr Ser Ile Arg Ser Thr Leu Arg Met Glu Leu Met Gly
1280                1285                1290

Cys Asp Leu Asn Ser Cys Ser Met Pro Leu Gly Met Glu Ser Lys
1295                1300                1305

Ala Ile Ser Asp Ala Gln Ile Thr Ala Ser Ser Tyr Phe Thr Asn
1310                1315                1320

Met Phe Ala Thr Trp Ser Pro Ser Lys Ala Arg Leu His Leu Gln
1325                1330                1335

Gly Arg Ser Asn Ala Trp Arg Pro Gln Val Asn Asn Pro Lys Glu
1340                1345                1350

Trp Leu Gln Val Asp Phe Gln Lys Thr Met Lys Val Thr Gly Val
1355                1360                1365

Thr Thr Gln Gly Val Lys Ser Leu Leu Thr Ser Met Tyr Val Lys
1370                1375                1380

Glu Phe Leu Ile Ser Ser Ser Gln Asp Gly His Gln Trp Thr Leu
1385                1390                1395

Phe Phe Gln Asn Gly Lys Val Lys Val Phe Gln Gly Asn Gln Asp
1400                1405                1410

Ser Phe Thr Pro Val Val Asn Ser Leu Asp Pro Pro Leu Leu Thr
1415                1420                1425

Arg Tyr Leu Arg Ile His Pro Gln Ser Trp Val His Gln Ile Ala
1430                1435                1440

Leu Arg Met Glu Val Leu Gly Cys Glu Ala Gln Asp Leu Tyr
1445                1450                1455

<210> SEQ ID NO 4
<211> LENGTH: 1386
<212> TYPE: DNA
<213> ORGANISM: Homo sapiens
<220> FEATURE:
<221> NAME/KEY: misc_feature
<222> LOCATION: (1)..(1386)
<223> OTHER INFORMATION: Factor FIX, codon optimized

<400> SEQUENCE: 4
atgcaacgcg tgaacatgat tatggccgag agccctggcc tgatcaccat ctgcctgctg    60
ggctacctgc tgagcgccga gtgcaccgtg tttctggacc acgagaacgc caacaagatc    120
ctgaaccggc ccaagcggta caacagcggc aagctggaag agttcgtgca gggcaacctg    180
gaacgcgagt gcatggaaga agtgcagctt cgaaagg ccagagaggt gttcgagaac    240
accgagcgga ccaccgagtt ctggaagcag tacgtggacg gcgaccagtg cgagagcaac    300
ccctgtctga atggcggcag ctgcaaggac gacatcaaca gctacgagtg ctggtgcccc    360
ttcggcttcg agggcaagaa ctgcgagctg gacgtgacct gcaacatcaa gaacggcaga    420
tgcgagcagt tctgcaagaa cagcgccgac aacaaggtcg tgtgctcctg caccgagggc    480
tacagactgg ccgagaacca gaagtcctgc gagcccgccg tgcctttccc atgtggaaga    540
gtgtccgtgt cccagaccag caagctgacc agagccgaga cagtgttccc cgacgtggac    600

| | |
|---|---|
| tacgtgaaca gcaccgaggc cgagacaatc ctggacaaca tcacccagag cacccagtcc | 660 |
| ttcaacgact tcaccagagt cgtgggcggc gaggatgcca agcctggaca gttcccgtgg | 720 |
| caggtggtgc tgaacggaaa ggtggacgcc ttttgcggcg gcagcatcgt gaacgagaag | 780 |
| tggatcgtga cagccgccca ctgcgtggaa accggcgtga agattacagt ggtggccggc | 840 |
| gagcacaaca tcgaggaaac cgagcacaca gagcagaaac ggaacgtgat cagaatcatc | 900 |
| ccccaccaca actacaacgc cgccatcaac aagtacaacc acgatatcgc cctgctggaa | 960 |
| ctggacgagc ccctggtgct gaatagctac gtgaccccca tctgtatcgc cgacaaagag | 1020 |
| tacaccaaca tctttctgaa gttcggcagc ggctacgtgt ccggctgggg cagagtgttt | 1080 |
| cacaagggca gatccgctct ggtgctgcag tacctgagag tgcctctggt ggaccgggcc | 1140 |
| acctgtctga aagcaccaa gttcaccatc tacaacaaca tgttctgcgc cggcttccac | 1200 |
| gagggcggca gagatagctg tcagggcgat tctggcggcc ctcacgtgac agaggtggaa | 1260 |
| ggcaccagct ttctgaccgg catcatcagc tggggcgagg aatgcgccat gaaggggaag | 1320 |
| tacggcatct acaccaaggt gtccagatac gtgaactgga tcaaagaaaa gaccaagctg | 1380 |
| acatga | 1386 |

<210> SEQ ID NO 5
<211> LENGTH: 1386
<212> TYPE: DNA
<213> ORGANISM: Homo sapiens
<220> FEATURE:
<221> NAME/KEY: misc_feature
<222> LOCATION: (1)..(1386)
<223> OTHER INFORMATION: Factor FIX padua, codon optimized

<400> SEQUENCE: 5

| | |
|---|---|
| atgcaacgcg tgaacatgat tatggccgag agccctggcc tgatcaccat ctgcctgctg | 60 |
| ggctacctgc tgagcgccga gtgcaccgtg tttctggacc acgagaacgc caacaagatc | 120 |
| ctgaaccggc ccaagcggta caacagcggc aagctggaag agttcgtgca gggcaacctg | 180 |
| gaacgcgagt gcatggaaga gaagtgcagc ttcgaagagg ccagagaggt gttcgagaac | 240 |
| accgagcgga ccaccgagtt ctggaagcag tacgtggacg gcgaccagtg cgagagcaac | 300 |
| ccctgtctga atggcggcag ctgcaaggac gacatcaaca gctacgagtg ctggtgcccc | 360 |
| ttcggcttcg agggcaagaa ctgcgagctg gacgtgacct gcaacatcaa gaacggcaga | 420 |
| tgcgagcagt tctgcaagaa cagcgccgac aacaaggtcg tgtgctcctg cacccagggc | 480 |
| tacagactgg ccgagaacca gaagtcctgc gagcccgccg tgcctttccc atgtggaaga | 540 |
| gtgtccgtgt cccagaccag caagctgacc agagccgaga cagtgttccc cgacgtggac | 600 |
| tacgtgaaca gcaccgaggc cgagacaatc ctggacaaca tcacccagag cacccagtcc | 660 |
| ttcaacgact tcaccagagt cgtgggcggc gaggatgcca agcctggaca gttcccgtgg | 720 |
| caggtggtgc tgaacggaaa ggtggacgcc ttttgcggcg gcagcatcgt gaacgagaag | 780 |
| tggatcgtga cagccgccca ctgcgtggaa accggcgtga agattacagt ggtggccggc | 840 |
| gagcacaaca tcgaggaaac cgagcacaca gagcagaaac ggaacgtgat cagaatcatc | 900 |
| ccccaccaca actacaacgc cgccatcaac aagtacaacc acgatatcgc cctgctggaa | 960 |
| ctggacgagc ccctggtgct gaatagctac gtgaccccca tctgtatcgc cgacaaagag | 1020 |
| tacaccaaca tctttctgaa gttcggcagc ggctacgtgt ccggctgggg cagagtgttt | 1080 |
| cacaagggca gatccgctct ggtgctgcag tacctgagag tgcctctggt ggaccgggcc | 1140 |
| acctgtctgc tgagcaccaa gttcaccatc tacaacaaca tgttctgcgc cggcttccac | 1200 |

```
gagggcggca gagatagctg tcagggcgat tctggcggcc ctcacgtgac agaggtggaa    1260
ggcaccagct ttctgaccgg catcatcagc tggggcgagg aatgcgccat gaaggggaag    1320
tacggcatct acaccaaggt gtccagatac gtgaactgga tcaaagaaaa gaccaagctt    1380
acatga                                                               1386

<210> SEQ ID NO 6
<211> LENGTH: 3195
<212> TYPE: DNA
<213> ORGANISM: Homo sapiens
<220> FEATURE:
<221> NAME/KEY: misc_feature
<222> LOCATION: (1)..(3195)
<223> OTHER INFORMATION: fusion of FIX and albumin, codon optimized

<400> SEQUENCE: 6
atgcaacgcg tgaacatgat tatggccgag agccctggcc tgatcaccat ctgcctgctg      60
ggctacctgc tgagcgccga gtgcaccgtg tttctggacc acgagaacgc caacaagatc     120
ctgaaccggc ccaagcggta caacagcggc aagctggaag agttcgtgca gggcaacctg     180
gaacgcgagt gcatggaaga agtgcagc ttcgaagagg ccagagaggt gttcgagaac       240
accgagcgga ccaccgagtt ctggaagcag tacgtggacg gcgaccagtg cgagagcaac     300
ccctgtctga atggcggcag ctgcaaggac gacatcaaca gctacgagtg ctggtgcccc     360
ttcggcttcg agggcaagaa ctgcgagctg gacgtgacct gcaacatcaa gaacggcaga     420
tgcgagcagt tctgcaagaa cagcgccgac aacaaggtcg tgtgctcctg caccgagggc     480
tacagactgg ccgagaacca gaagtcctgc gagcccgccg tgcctttccc atgtggaaga     540
gtgtccgtgt cccagaccag caagctgacc agagccgaga cagtgttccc cgacgtggac     600
tacgtgaaca gcaccgaggc cgagacaatc ctggacaaca tcacccagag cacccagtcc     660
ttcaacgact tcaccagagt cgtgggcggc gaggatgcca agcctggaca gttcccgtgg     720
caggtggtgc tgaacggaaa ggtggacgcc ttttgcggcg gcagcatcgt gaacgagaag     780
tggatcgtga cagccgccca ctgcgtggaa accggcgtga agattacagt ggtggccggc     840
gagcacaaca tcgaggaaac cgagcacaca gagcagaaac ggaacgtgat cagaatcatc     900
ccccaccaca actacaacgc cgccatcaac aagtacaacc acgatatcgc cctgctggaa     960
ctggacgagc ccctggtgct gaatagctac gtgacccca tctgtatcgc cgacaaagag    1020
tacaccaaca tctttctgaa gttcggcagc ggctacgtgt ccggctgggg cagagtgttt    1080
cacaagggca atccgctct ggtgctgcag tacctgagag tgcctctggt ggaccggcc    1140 acctgtctga aagcaccaa gttcaccatc tacaacaaca tgttctgcgc cggcttccac    1200
gagggcggca gagatagctg tcagggcgat tctggcggcc ctcacgtgac agaggtggaa    1260
ggcaccagct ttctgaccgg catcatcagc tggggcgagg aatgcgccat gaaggggaag    1320
tacggcatct acaccaaggt gtccagatac gtgaactgga tcaaagaaaa gaccaagctt    1380
acacccgtgt ctcagacctc taagctgacc cgggctgaaa ctgtgtttcc agatgtggac    1440
gcccacaaga gcgaggtggc ccacagattc aaggacctgg agaagagaa cttcaaggct    1500 ctggtgctga tcgccttcgc tcagtacctc cagcagtgcc cattcgagga ccatgtgaag    1560
ctggtcaacg aagtgaccga gttcgccaag acctgcgtgg ccgatgagtc cgccgagaac    1620
tgtgataaga gcctgcacac cctgttcggc gacaagctgt gtacagtggc cacactgaga    1680
gaaacctacg gcgagatggc cgactgctgc gccaaacaag agcccgagag aaacgagtgc    1740
```

```
ttcctccagc acaaggacga taaccccaac ctgcctagac tcgtgcggcc cgaagtggat   1800
gtcatgtgca ccgccttcca cgacaacgag gaaaccttcc tgaagaagta cctgtacgag   1860
atcgccagac ggcacccta cttttacgcc cctgagctgc tgttctttgc caagagatac   1920
aaggccgcct tcaccgagtg ttgccaggcc gctgataagg ccgcttgtct gctgcctaag   1980
ctggatgagc tgcgcgacga gggcaaagcc tcttctgcca agcagagact gaagtgcgcc   2040
agcctccaga gtttggcga gagagccttt aaggcctggg ccgtcgctag actgagccag   2100
agatttccca aggccgagtt tgccgaggtg tccaagctgg ttaccgacct gaccaaggtg   2160
cacacagagt gctgtcacgg cgatctgctg gaatgcgccg acgatagagc cgatctggcc   2220
aagtacatct gcgagaatca ggacagcatc agctccaagc tgaaagaatg ctgcgagaag   2280
cccctgctcg aaaagagcca ctgtatcgct gaggtggaaa acgacgagat gcccgccgat   2340
ctgccttctc tggccgccga ttttgtggaa agcaaggacg tgtgcaagaa ttacgccgag   2400
gccaaggatg tgttcctggg catgtttctg tatgagtacg cccgcagaca ccccgactac   2460
tctgttgtgc tgctgctgag actggccaaa acctacgaga ctaccctgga aaagtgctgt   2520
gccgccgctg atcctcacga gtgttacgcc aaagtgttcg acgagttcaa gccactggtg   2580
gaagaacccc agaacctgat caaacagaac tgcgaactgt tcgagcagct gggcgagtac   2640
aagttccaga acgccctgct cgtgcggtac accaagaagg tgccccaggt ttcaacccct   2700
acactggttg aggtgtcccg gaacctgggc aaagtgggca gcaagtgttg caagcaccct   2760
gaggccaaga aatgcccctg cgccgaggat tacctgagcg tcgtgctgaa tcagctgtgc   2820
gtgctgcacg agaaaacccc tgtgtccgac agagtgacca gtgctgtac cgagagcctg   2880
gtcaacagac ggccttgctt tagcgccctt gaggtggacg agacatacgt gcccaaagag   2940
ttcaacgccg agacattcac cttccacgcc gacatctgta ccctgagcga aaagagcggg   3000
cagatcaaga acagaccgc tctggtggaa ctggtcaagc acaagcccaa ggccaccaaa   3060
gaacaactga aggccgtgat ggacgacttc gccgcctttg tcgagaagtg ctgcaaggcc   3120
gatgacaaag agacatgctt cgccgaagag ggaaagaaac tggtggccgc ctctcaagcc   3180
gctctgggac tttaa                                                    3195
```

<210> SEQ ID NO 7
<211> LENGTH: 3195
<212> TYPE: DNA
<213> ORGANISM: Homo sapiens
<220> FEATURE:
<221> NAME/KEY: misc_feature
<222> LOCATION: (1)..(3195)
<223> OTHER INFORMATION: fusion of FIX padua and albumin, codon
       optimized <400> SEQUENCE: 7

```
atgcaacgcg tgaacatgat tatggccgag agccctggcc tgatcaccat ctgcctgctg    60
ggctacctgc tgagcgccga gtgcaccgtg tttctggacc acgagaacgc caacaagatc   120
ctgaaccggc ccaagcggta caacagcggc aagctggaag agttcgtgca gggcaacctg   180
gaacgcgagt gcatggaaga agagtgcagc ttcgaagagg ccagagaggt gttcgagaac   240
accgagcgga ccaccgagtt ctggaagcag tacgtggacg gcgaccagtg cgagagcaac   300
ccctgtctga atggcggcag ctgcaaggac gacatcaaca gctacgagtg ctggtgcccc   360
ttcggcttcg agggcaagaa ctgcgagctg gacgtgacct gcaacatcaa gaacggcaga   420
tgcgagcagt tctgcaagaa cagcgccgac aacaaggtcg tgtgctcctg caccgagggc   480
```

```
tacagactgg ccgagaacca gaagtcctgc gagcccgccg tgccttccc atgtggaaga      540
gtgtccgtgt cccagaccag caagctgacc agagccgaga cagtgttccc cgacgtggac    600
tacgtgaaca gcaccgaggc cgagacaatc ctggacaaca tcacccagag cacccagtcc    660
ttcaacgact tcaccagagt cgtgggcggc gaggatgcca agcctggaca gttcccgtgg    720
caggtggtgc tgaacggaaa ggtggacgcc ttttgcggcg gcagcatcgt gaacgagaag    780
tggatcgtga cagccgccca ctgcgtggaa accggcgtga agattacagt ggtgccggc     840
gagcacaaca tcgaggaaac cgagcacaca gagcagaaac ggaacgtgat cagaatcatc    900
ccccaccaca actacaacgc cgccatcaac aagtacaacc acgatatcgc cctgctggaa    960
ctggacgagc ccctggtgct gaatagctac gtgacccca tctgtatcgc cgacaaagag    1020
tacaccaaca tctttctgaa gttcggcagc ggctacgtgt ccggctgggg cagagtgttt    1080
cacaagggca gatccgctct ggtgctgcag tacctgagag tgcctctggt ggaccgggcc    1140
acctgtctgc tgagcaccaa gttcaccatc tacaacaaca tgttctgcgc cggcttttac    1200
gagggcggca gagatagctg tcagggcgat tctggcggcc ctcacgtgac agaggtggaa    1260
ggcaccagct ttctgaccgg catcatcagc tggggcgagg aatgcgccat gaaggggaag    1320
tacggcatct acaccaaggt gtccagatac gtgaactgga tcaaagaaaa gaccaagctt    1380
acacccgtgt ctcagacctc taagctgacc cgggctgaaa ctgtgtttcc agatgtggac    1440
gcccacaaga gcgaggtggc ccacagattc aaggacctgg agaagagaa cttcaaggct     1500
ctggtgctga tcgccttcgc tcagtacctc cagcagtgcc cattcgagga ccatgtgaag    1560
ctggtcaaca agtgaccga gttcgccaag acctgcgtgg ccgatgagtc cgccgagaac    1620
tgtgataaga gcctgcacac cctgttcggc gacaagctgt gtacagtggc cacactgaga    1680
gaaacctacg cgagatggc cgactgctgc gccaaacaag agcccgagag aaacgagtgc    1740
ttcctccagc acaaggacga taaccccaac ctgcctagac tcgtgcggcc cgaagtggat    1800
gtcatgtgca ccgccttcca cgacaacgag gaaaccttcc tgaagaagta cctgtacgag    1860
atcgccagac ggcacccta cttttacgcc cctgagctgc tgttctttgc caagagatac    1920
aaggccgcct tcaccgagtg ttgccaggcc gctgataagg ccgcttgtct gctgcctaag    1980
ctggatgagc tgcgcgacga gggcaaagcc tcttctgcca agcagagact gaagtgcgcc    2040
agcctccaga gtttggcga gagagccttt aaggctggg ccgtcgctag actgagccag     2100
agatttccca aggccgagtt tgccgaggtg tccaagctgg ttaccgacct gaccaaggtg    2160
cacacagagt gctgtcacgg cgatctgctg gaatgcgccg acgatagagc cgatctggcc    2220
aagtacatct gcgagaatca ggacagcatc agctccaagc tgaaagaatg ctgcgagaag    2280
cccctgctcg aaaagagcca ctgtatcgct gaggtggaaa acgacgagat gcccgccgat    2340
ctgccttctc tggccgccga ttttgtggaa agcaaggacg tgtgcaagaa ttacgccgag    2400
gccaaggatg tgttcctggg catgtttctg tatgagtacg cccgcagaca ccccgactac    2460
tctgttgtgc tgctgctgag actggccaaa acctacgaga ctaccctgga aaagtgctgt    2520
gccgccgctg atcctcacga gtgttacgcc aaagtgttcg acgagttcaa gccactggtg    2580
gaagaacccc agaacctgat caaacagaac tgcgaactgt tcgagcagct gggcgagtac    2640
aagttccaga acgccctgct cgtgcggtac accaagaagg tgccccaggt ttcaccccct    2700
acactggttg aggtgtcccg gaacctgggc aaagtgggca gcaagtgttg caagcaccct    2760
gaggccaaga aatgccctg cgccgaggat tacctgagcg tcgtgctgaa tcagctgtgc    2820
gtgctgcacg agaaaacccc tgtgtccgac agagtgacca agtgctgtac cgagagcctg    2880
```

| | |
|---|---:|
| gtcaacagac ggccttgctt tagcgcccatt gaggtggacg agacatacgt gcccaaagag | 2940 |
| ttcaacgccg agacattcac cttccacgcc gacatctgta ccctgagcga gaaagagcgg | 3000 |
| cagatcaaga aacagaccgc tctggtggaa ctggtcaagc acaagcccaa ggccaccaaa | 3060 |
| gaacaactga aggccgtgat ggacgacttc gccgcctttg tcgagaagtg ctgcaaggcc | 3120 |
| gatgacaaag agacatgctt cgccgaagag ggaaagaaac tggtggccgc ctctcaagcc | 3180 |
| gctctgggac tttaa | 3195 |

<210> SEQ ID NO 8
<211> LENGTH: 1757
<212> TYPE: DNA
<213> ORGANISM: Homo sapiens
<220> FEATURE:
<221> NAME/KEY: misc_feature
<222> LOCATION: (1)..(1757)
<223> OTHER INFORMATION: albumin, codon optimized

<400> SEQUENCE: 8

| | |
|---|---:|
| gacgcccaca agagcgaggt ggcccacaga ttcaaggacc tgggagaaga gaacttcaag | 60 |
| gctctggtgc tgatcgcctt cgctcagtac ctccagcagt gcccattcga ggaccatgtg | 120 |
| aagctggtca acgaagtgac cgagttcgcc aagacctgcg tggccgatga gtccgccgag | 180 |
| aactgtgata gagcctgcaa cccctgttc ggcgacaagc tgtgtacagt ggccacactg | 240 |
| agagaaacct acggcgagat ggccgactgc tgcgccaaac aagagcccga gagaaacgag | 300 |
| tgcttcctcc agcacaagga cgataacccc aacctgccta gactcgtgcg gcccgaagtg | 360 |
| gatgtcatgt gcaccgcctt ccacgacaac gaggaaacct tcctgaagaa gtacctgtac | 420 |
| gagatcgcca acggcaccc ctacttttac gcccctgagc tgctgttctt tgccaagaga | 480 |
| tacaaggccg ccttcaccga gtgttgccag gccgctgata aggccgcttg tctgctgcct | 540 |
| aagctggatg agctgcgcga cgagggcaaa gcctcttctg ccaagcagag actgaagtgc | 600 |
| gccagcctcc agaagtttgg cgagagagcc tttaaggcct gggccgtcgc tagactgagc | 660 |
| cagagatttc ccaaggccga gtttgccgag gtgtccaagc tggttaccga cctgaccaag | 720 |
| gtgcacacag agtgctgtca cggcgatctg ctggaatgcg ccgacgatag agccgatctg | 780 |
| gccaagtaca tctgcgagaa tcaggacagc atcagctcca agctgaaaga atgctgcgag | 840 |
| aagcccctgc tcgaaaagag ccactgtatc gctgaggtgg aaaacgacga gatgcccgcc | 900 |
| gatctgcctt ctctggccgc cgattttgtg gaaagcaagg acgtgtgcaa gaattacgcc | 960 |
| gaggccaagg atgtgttcct gggcatgttt ctgtatgagt acgcccgcag acaccccgac | 1020 |
| tactctgttg tgctgctgct gagactggcc aaaacctacg agactaccct ggaaaagtgc | 1080 |
| tgtgccgccg ctgatcctca cgagtgttac gccaaagtgt tcgacgagtt caagccactg | 1140 |
| gtggaagaac ccagaaacct gatcaaacag aactgcgaac tgttcgagca gctgggcgag | 1200 |
| tacaagttcc agaacgccct gctcgtgcgc tacaccaaga aggtgccca ggtttcaacc | 1260 |
| cctacactgg ttgaggtgtc ccggaacctg ggcaaagtgg gcagcaagtg ttgcaagcac | 1320 |
| cctgaggcca agagaatgcc ctgcgccgag gattacctga gcgtcgtgct gaatcagctg | 1380 |
| tgcgtgctgc acgagaaaac ccctgtgtcc gacagagtga ccaagtgctg taccgagagc | 1440 |
| ctggtcaaca cgacggcctt ctttagcgcc cttgaggtgg acgagacata cgtgcccaaa | 1500 |
| gagttcaacg ccgagacatt caccttccac gccgacatct gtaccctgag cgagaaagag | 1560 |
| cggcagatca agaaacagac cgctctggtg gaactggtca agcacaagcc caaggccacc | 1620 |

```
aaagaacaac tgaaggccgt gatggacgac ttcgccgcct tgtcgagaa gtgctgcaag      1680 gccgatgaca agagacatg cttcgccgaa gagggaaaga aactggtggc cgcctctcaa      1740
gccgctctgg gacttta                                                    1757
```

<210> SEQ ID NO 9
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(42)
<223> OTHER INFORMATION: synthetic linker for replacement of B-domain in
      FVIII

<400> SEQUENCE: 9

```
agcttctccc agaatccacc agtcttaaaa agacaccaga ga                          42
```

<210> SEQ ID NO 10
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MISC_FEATURE
<222> LOCATION: (1)..(14)
<223> OTHER INFORMATION: synthetic linker to replace B-domain in FVIII

<400> SEQUENCE: 10

```
Ser Phe Ser Gln Asn Pro Pro Val Leu Lys Arg His Gln Arg
1               5                   10
```

<210> SEQ ID NO 11
<211> LENGTH: 742
<212> TYPE: DNA
<213> ORGANISM: Homo sapiens
<220> FEATURE:
<221> NAME/KEY: misc_feature
<222> LOCATION: (1)..(742)
<223> OTHER INFORMATION: S/MAR_short derived from IFN_beta

<400> SEQUENCE: 11

```
aattgagatc taaataaact tataaattgt gagagaaatt aatgaatgtc taagttaatg       60
cagaaacgga gagacatact atattcatga actaaaagac ttaatattgt gaaggtatac     120
tttctttcca cataaatttg tagtcaatat gttcacccca aaaagctgt tgttaacttt      180 gccaaccctca ttctaaaatg tatatagaag cccaaaagac aataacaaaa atattcttgt    240
agaacaaaat gggaaagaat gttccactaa atatcaagat ttagagcaaa gcatgagatg    300
tgtggggata gacagtgagg ctgataaaat agagtagagc tcagaaacag acccattgat    360
atatgtaagt gacctatgaa aaaaatatgg cattttacaa tgggaaatg atgatctttt     420 tctttttag aaaacaggg aaatatattt atatgtaaaa ataaaaggg aacccatatg       480 tcataccata cacacaaaaa aattccagtg aattataagt ctaaatggag aaggcaaaac    540
tttaaatctt ttagaaaata atatagaagc atgccatcat gacttcagtg tagagaaaaa   600 ttcttatga ctcaaagtcc taaccacaaa gaaaagattg ttaatttgaa tgatttagga     660
agtattccct ctgcttctgt cttctgaaag agattgtaga aagttgatac aattttttt     720 tctttaaata tttgatagaa tt                                             742
```

<210> SEQ ID NO 12
<211> LENGTH: 1983
<212> TYPE: DNA
<213> ORGANISM: Homo sapiens
<220> FEATURE:
<221> NAME/KEY: misc_feature
<222> LOCATION: (1)..(1983)
<223> OTHER INFORMATION: S/MAR_long derived from IFN-beta

<400> SEQUENCE: 12

| | | |
|---|---|---|
| gatctaaata aacttataaa ttgtgagaga aattaatgaa tgtctaagtt aatgcagaaa | 60 |
| cggagagaca tactatattc atgaactaaa agacttaata ttgtgaaggt atactttctt | 120 |
| tccacataaa tttgtagtca atatgttcac cccaaaaaag ctgtttgtta acttgccaac | 180 |
| ctcattctaa aatgtatata gaagcccaaa agacaataac aaaaatattc ttgtagaaca | 240 |
| aaatgggaaa gaatgttcca ctaaatatca agatttagag caaagcatga gatgtgtggg | 300 |
| gatagacagt gaggctgata aaatagagta gagctcagaa acagacccat tgatatatgt | 360 |
| aagtgaccta tgaaaaaaat atggcatttt acaatgggaa aatgatgatc ttttctttt | 420 |
| ttagaaaaac agggaaatat atttatatgt aaaaaataaa agggaaccca tatgtcatac | 480 |
| catacacaca aaaaaattcc agtgaattat aagtctaaat ggagaaggca aaactttaaa | 540 |
| tcttttagaa aataatatag aagcatgcca tcatgacttc agtgtagaga aaaatttctt | 600 |
| atgactcaaa gtcctaacca caagaaaag attgttaatt agattgcatg aatattaaga | 660 |
| cttattttta aaattaaaaa accattaaga aaagtcaggc catagaatga cagaaaatat | 720 |
| ttgcaacacc ccagtaaaga gaattgtaat atgcagatta taaaagaag tcttacaaat | 780 |
| cagtaaaaaa taaaactaga caaaaatttg aacagatgaa agagaaactc taaataatca | 840 |
| ttacacatga gaaactcaat ctcagaaatc agagaactat cattgcatat acactaaatt | 900 |
| agagaaatat taaaaggcta agtaacatct gtggcaatat tgatggtata taaccttgat | 960 |
| atgatgtgat gagaacagta ctttaccccca tgggcttcct ccccaaaccc ttaccccagt | 1020 |
| ataaatcatg acaaatatac tttaaaaacc attaccctat atctaaccag tactcctcaa | 1080 |
| aactgtcaag gtcatcaaaa ataagaaaag tctgaggaac tgtcaaaact aagaggaacc | 1140 |
| caaggagaca tgagaattat atgtaatgtg gcattctgaa tgagatccca gaacagaaaa | 1200 |
| agaacagtag ctaaaaaact aatgaaatat aaataaagtt tgaactttag ttttttttaa | 1260 |
| aaaagagtag cattaacacg gcaaagccat tttcatattt ttcttgaaca ttaagtacaa | 1320 |
| gtctataatt aaaaattttt taatgtagt ctggaacatt gccagaaaca gaagtacaac | 1380 |
| agctatctgt gctgtcgcct aactatccat agctgattgg tctaaaatga gatacatcaa | 1440 |
| cgctcctcca tgttttttgt ttctttttta aatgaaaaac tttatttttt aagaggagtt | 1500 |
| tcaggttcat agcaaaattg agaggaaggt acattcaagc tgaggaagtt ttcctctatt | 1560 |
| cctagtttac tgagagattg catcatgaat gggtgttaaa ttttgtcaaa tgcttttct | 1620 |
| gtgtctatca atatgaccat gtgattttct tctttaacct gttgatggga caaattacgt | 1680 |
| taattgattt tcaaacgttg aaccaccctt acatatctgg aataaattct acttggttgt | 1740 |
| ggtgtatatt ttttgataca ttcttggatt cttttgctta atattttgtt gaaatgttt | 1800 |
| gtatctttgt tcatgagaga tattggtctg ttgttttctt ttcttgtaat gtcattttct | 1860 |
| agttccggta ttaaggtaat gctggcctag ttgaatgatt taggaagtat tccctctgct | 1920 |
| tctgtcttct gaaagagatt gtagaaagtt gatacaattt ttttttcttt aaatatttga | 1980 | tag                                                                      1983

<210> SEQ ID NO 13
<211> LENGTH: 56
<212> TYPE: DNA
<213> ORGANISM: Homo sapiens
<220> FEATURE:
<221> NAME/KEY: misc_feature
<222> LOCATION: (1)..(56)
<223> OTHER INFORMATION: promoter CBX3, part of UCOE

<400> SEQUENCE: 13
cccgggaggt ggtccctgca gttacgccaa tgataacccc cgccagaaaa atctta        56

<210> SEQ ID NO 14
<211> LENGTH: 621
<212> TYPE: DNA
<213> ORGANISM: Homo sapiens
<220> FEATURE:
<221> NAME/KEY: misc_feature
<222> LOCATION: (1)..(621)
<223> OTHER INFORMATION: transcript to CBX3, part of UCOE

<400> SEQUENCE: 14
tagccttccc ttttttgtttt ccgtgcccca actcggcgga ttgactcggc cccttccgga        60
aacacccgaa tcaacttcta gtcaaattat tgttcacgcc gcaatgaccc accctggcc        120 cgcgtctgtg gaactgaccc ctggtgaaca ggagagttcg ctgctgaaag tggtcccaaa        180
ggggtactag tttttaagct cccaactccc cctcccccag cgtctggagg attccacacc        240
ctcgcaccgc aggggcgagg aagtgggcgg agtccggttt tggcgccagc cgctgaggct        300
gccaagcaga aaagccaccg ctgaggagac tccggtcact gtcctcgccc cgcctccccc        360
ttccctcccc ttggggacca ccgggcgcca cgccgcgaac gctaagtgcc gcggtcgtcg        420
gcgcctccgc cctccccctt gggccccaat tccagcggg cgcggcgcgc ggcccctccc        480
cccgccgggc gcgcgcccgc tgccccgccc ttcgtggccg cccggcgtgg gcggtgccac        540 ccctccccccc ggcggcccccg cgcgcagctc ccggctccct ccccccttcgg atgtggcttg        600 agctgtaggc gcggagggcc g                                                 621

<210> SEQ ID NO 15
<211> LENGTH: 86
<212> TYPE: DNA
<213> ORGANISM: Homo sapiens
<220> FEATURE:
<221> NAME/KEY: misc_feature
<222> LOCATION: (1)..(86)
<223> OTHER INFORMATION: HNRNPA2 promoter, part of UCOE

<400> SEQUENCE: 15
gccgctagag ccgctgccgc cgcttttcta gaaccttccc ccccactaac gcgtcttccg        60
ctacgtcagg ccgtcgcgta aacgcc                                            86

<210> SEQ ID NO 16
<211> LENGTH: 165
<212> TYPE: DNA
<213> ORGANISM: Homo sapiens
<220> FEATURE:
<221> NAME/KEY: misc_feature
<222> LOCATION: (1)..(165)
<223> OTHER INFORMATION: transcript to HNRNPA2, part of UCOE

<400> SEQUENCE: 16
gactcagtcg cttcagcccg atttcccgca gccgagcgag atgagagaca tctccgcgga        60
cgaacacgaa ccggactcgt cctggcgctg tagtgagaac tgccgctgat cgagaaacaa    120
ctctgcgagg agcacctccg cacgggaccc ggcgctgctg ctact                    165

<210> SEQ ID NO 17
<211> LENGTH: 588
<212> TYPE: DNA
<213> ORGANISM: Cytomegalovirus sp.
<220> FEATURE:
<221> NAME/KEY: misc_feature
<222> LOCATION: (1)..(588)
<223> OTHER INFORMATION: CMV Promoter

<400> SEQUENCE: 17
tagttattaa tagtaatcaa ttacggggtc attagttcat agcccatata tggagttccg     60
cgttacataa cttacggtaa atggcccgcc tggctgaccg cccaacgacc cccgcccatt    120
gacgtcaata atgacgtatg ttcccatagt aacgccaata gggactttcc attgacgtca    180
atgggtggag tatttacggt aaactgccca cttggcagta catcaagtgt atcatatgcc    240
aagtacgccc cctattgacg tcaatgacgg taaatggccc gcctggcatt atgcccagta    300
catgacctta tgggactttc ctacttggca gtacatctac gtattagtca tcgctattac    360
catggtgatg cggttttggc agtacatcaa tgggcgtgga tagcggtttg actcacgggg    420
atttccaagt ctccacccca ttgacgtcaa tgggagtttg ttttggcacc aaaatcaacg    480
ggactttcca aaatgtcgta acaactccgc cccattgacg caaatgggcg gtaggcgtgt    540
acggtgggag gtctatataa gcagagctgg tttagtgaac cgtcagat                 588

<210> SEQ ID NO 18
<211> LENGTH: 458
<212> TYPE: DNA
<213> ORGANISM: Homo sapiens
<220> FEATURE:
<221> NAME/KEY: misc_feature
<222> LOCATION: (1)..(458)
<223> OTHER INFORMATION: promoter derived from human EF1alpha plus
      splice sites derived from human EF1alpha

<400> SEQUENCE: 18
ggctccggtg cccgtcagtg ggcagagcgc acatcgccca cagtccccga agttgggg       60 ggaggggtcg gcaattgaac cggtgcctag agaaggtggc gcggggtaaa ctgggaaagt    120
gatgtcgtgt actggctccg cctttttccc gagggtgggg gagaaccgta tataagtgca    180
gtagtcgccg tgaacgttct ttttcgcaac gggtttgccg ccagaacaca ggtaagtgcc    240
gtgtgtggtt cccgcgggcc tggcctcttt acgggttatg gcccttgcgt gccttgaatt    300
acttccacgc ccctggctgc agtacgtgat tcttgatccc gagctccctt ggaatttgcc    360 cttttttgagt ttggatcttg gttcattctc aagcctcaga cagtggttca aagttttttt    420
cttccatttc aggtgtcgag gcctgaattc gtcgactg                            458

<210> SEQ ID NO 19
<211> LENGTH: 4374
<212> TYPE: DNA
<213> ORGANISM: Homo sapiens
<220> FEATURE:
<221> NAME/KEY: misc_feature
<222> LOCATION: (1)..(4374)
<223> OTHER INFORMATION: coagulation factor FVIII SQ with deleted
      B-domain, codon optimized

<400> SEQUENCE: 19

-continued

```
atgcagatcg agctctctac ctgcttcttc ctgtgcctgc tgcggttctg cttcagcgcc    60
accagacggt actatctggg cgccgtggaa ctgagctggg actacatgca gagcgacctg   120
ggcgagctgc ccgtggatgc cagattccct ccaagagtgc caagagctt ccccttcaac    180
acctccgtgg tgtataagaa aaccctgttc gtggagttca ccgaccacct gttcaatatc   240
gccaagccca daccccctg datgggcctg ctgggaccta caattcaggc cgaggtgtac    300
gacaccgtcg tgatcaccct gaagaacatg ccagccacc ccgtgtctct gcatgccgtg    360
ggagtgtcct actggaaggc ctctgagggc gccgagtacg acgatcagac cagcagcgc    420
gagaaagagg acgacaaggt gttccctggc ggcagccaca cctacgtgtg gcaggtgctg   480
aaagaaaacg ccccatggc ctccgaccct ctgtgcctga catacagcta cctgagccac    540
gtggacctcg tgaaggacct gaacagcggc ctgatcggag ccctgctcgt gtgtagagag   600
ggcagcctgg ccaaagagaa acccagacc ctgcacaagt tcatcctgct gttcgccgtg    660
ttcgacgagg gcaagagctg gcacagcgag acaaagaaca gcctgatgca ggaccgggac   720
gccgcctctg ctagagcctg gcccaaaatg cacaccgtga acggctacgt gaacagaagc   780
ctgcccggac tgatcggctg ccaccggaag tctgtgtact ggcacgtgat cggcatgggc   840
accaccctg aggtgcacag catctttctg gaaggacaca cctttctcgt gcggaaccac    900
cggcaggcca gctggaaat cagccctatc accttcctga ccgcccagac actgctgatg   960
gacctgggcc agtttctgct gttctgccac atcagctccc accagcacga cggcatggaa  1020
gcctacgtga aggtggacag ctgccccgag gaacccagc tgcggatgaa gaacaacgag   1080
gaagccgagg actacgacga cgacctgacc gacagcgaga tggacgtggt gcgcttcgac  1140
gacgataaca gccccagctt catccagatc agaagcgtgg ccaagaagca ccccaagacc  1200
tgggtgcact atatcgccgc cgaggaagag gactgggatt acgcccctct ggtgctggcc  1260
cccgacgaca gaagctacaa gagccagtac ctgaacaatg ccccccagcg atcggccgg   1320
aagtacaaga agtgcgggtt catggcctac accgacgaga cattcaagac cagagaggcc  1380
atccagcacg agagcggcat cctgggccct ctgctgtatg gcgaagtggg cgacaccctg  1440
ctgatcatct tcaagaacca ggccagcaga ccctacaaca tctaccctca cggcatcacc  1500
gacgtgcggc ccctgtattc tcggagactg cccaagggcg tgaaacacct gaaggacttc  1560
cccatcctgc ccggcgagat cttcaagtac aagtggaccg tgaccgtgga agatggcccc  1620
accaagagcg accccagatg cctgacacgg tactacagca gcttcgtgaa catggaacgg  1680
gacctggcct ccggcctgat tggcccactg ctgatctgct acaaagaaag cgtgaccag   1740
cggggcaacc agatcatgag cgacaagcgg aacgtgatcc tgttagcgt gttcgatgag  1800
aaccggtcct ggtatctgac cgagaatatc cagcggttcc tgcccaaccc tgccggcgtg  1860
cagctggaag atcctgagtt ccaggcctcc aacatcatgc actccatcaa tggctatgtg  1920
ttcgacagcc tgcagctgag cgtgtgcctg cacgaggtgg cctactggta catcctgagc  1980
atcggggccc agaccgactt cctgtccgtg ttcttctccg gctacacctt caagcacaag  2040
atggtgtacg aggataccct gacctgttc ccctttagcg gcgaaaccgt gttcatgagc   2100
atggaaaacc ccggcctgtg gatcctgggc tgccacaaca gcgacttccg gaacagaggc  2160
atgaccgccc tgctgaaggt gtccagctgc gacaagaaca ccggcgacta ctacgaggac  2220
agctatgagg acatcagcgc ctacctgctg agcaagaaca tgccatcga gcccagaagc  2280
ttcagccaga acccccccgt gctgaagcgg caccagagag agatcacccg gaccacccct  2340
cagtccgacc aggaagagat cgattacgac gacaccatca gcgtggaaat gaagaaagaa  2400
```

```
gatttcgaca tctacgacga ggacgagaac cagagccccc ggtcctttca gaaaagacc    2460 cggcactact tcattgccgc tgtggaacgg ctgtgggact acggcatgag cagcagccct   2520
cacgtgctga aaacagggc ccagagcggc agcgtgcccc agttcaaaaa ggtggtgttc    2580
caggagttta ccgacggcag cttcacccag cctctgtacc ggggagagct gaacgagcac   2640
ctgggactgc tgggcccta tcagagccc gaagtggaag ataacatcat ggtcaccttc     2700
cggaatcagg cctcccggcc ctacagcttc tacagctccc tgatcagcta cgaagaggac   2760
cagagacagg gcgctgagcc ccggaagaac ttcgtgaagc ccaacgagac taagacctac   2820
ttttggaagg tgcagcacca catggcccct acaaaggacg agttcgactg caaggcctgg   2880
gcctacttct ccgatgtgga cctggaaaag gacgtgcact ctgggctgat cggccccctg   2940
ctcgtgtgcc acaccaacac cctgaatccc gcccacggca gacaagtgac agtgcaggaa   3000
tttgccctgt tcttcaccat cttcgacgaa acaaagagct ggtacttcac cgaaaacatg   3060
gaaagaaact gccgggctcc ctgcaacatc cagatggaag atcccacctt caagagaaac   3120
taccggttcc acgccatcaa cggctacatc atggacacac tgcccggcct cgtgatggct   3180
caggatcagc ggatccggtg gtatctgctg tccatgggct ccaacgagaa catccacagc   3240
atccacttca gcggccacgt gttcaccgtg cggaaaaaag aagagtacaa aatggccctg   3300
tataacctgt accccggcgt gttcgagaca gtggaaatgc tgcctagcaa ggccggcatc   3360
tggcgggtgg aatgtctgat cggcgagcat ctgcacgctg ggatgagcac actgtttctg   3420
gtgtactcca acaagtgcca gacacctctg ggcatggcct ctggccacat ccgggacttt   3480
cagatcacag ccagcggcca gtatggccag tgggccccaa aactggccag actgcactac   3540
agcggcagca tcaacgcctg gtccaccaaa gagcccttca gctggatcaa ggtgacctg    3600 ctggctccca tgatcatcca cggaatcaag acccagggcg ccagacagaa gttcagcagc   3660
ctgtatatca gccagttcat catcatgtac tccctggacg gcaagaagtg gcagacctac   3720
cggggcaata gcaccggcac cctgatggtg ttcttcggca acgtggactc cagcggcatt   3780
aagcacaaca tcttcaaccc ccccatcatt gcccggtaca tccggctgca ccccacccac   3840
tacagcatcc ggtccaccct gagaatggaa ctgatgggct gcgacctgaa ctcctgcagc   3900 atgccctgg ggatggaaag caaggccatc tccgacgccc agatcaccgc ctccagctac   3960
ttcaccaaca tgttcgccac ctggtccccc agcaaggccc ggctgcatct gcagggcaga   4020
agcaatgctt ggaggcccca agtgaacaac cccaaagaat ggctgcaggt ggacttccag   4080
aaaaccatga agtgaccgg cgtgaccacc cagggcgtga gtctctgct gacctctatg     4140 tacgtgaaag agttcctgat ctccagcagc caggacggcc accagtggac cctgttttc    4200 cagaacggca aagtgaaagt gtttcagggg aaccaggact ccttcacccc cgtcgtgaat   4260
agcctggacc ctccactgct gaccagatac cttcgaatcc accctcagtc ttgggtgcac   4320
cagattgctc tgcggatgga agtgctggga tgcgaggccc aggacctgta ctga         4374
```

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(42)
<223> OTHER INFORMATION: synthetic linker for replacement of B-domain in FVIII, codon optimized

<400> SEQUENCE: 20

```
agcttcagcc agaaccccc cgtgctgaag cggcaccaga ga                42
```

<210> SEQ ID NO 21
<211> LENGTH: 271
<212> TYPE: DNA
<213> ORGANISM: Homo sapiens
<220> FEATURE:
<221> NAME/KEY: misc_feature
<222> LOCATION: (1)..(271)
<223> OTHER INFORMATION: enhancer region in a UCOE

<400> SEQUENCE: 21

```
ctatccgccg ccaatggcgg gaaggctcta cgccccacct tacgccaaat gcgtactcct      60
cccacccttg cggccagaga cagtacccga cgttacttcc gtaaatgcgc tcaatgaatt     120
gcggaaggct agagtcctgc tagttactac ctcttggaat agggtcccgc cccctgcctt     180
ggcgcaaggc aggtgagaaa cggtcgcgca gtttgaaatt aacgccgacg ggagggggctt   240
aatccgcagc ctggagatcc agccccctca a                                    271
```

<210> SEQ ID NO 22
<211> LENGTH: 1201
<212> TYPE: DNA
<213> ORGANISM: Homo sapiens
<220> FEATURE:
<221> NAME/KEY: misc_feature
<222> LOCATION: (1)..(1201)
<223> OTHER INFORMATION: UCOE with CBX3 promoter and transcript, HNRNPA2
      promoter and transcript in reverse orientation and enhancer region

<400> SEQUENCE: 22

```
gactcagtcg cttcagcccg atttcccgca gccgagcgag atgagagaca tctccgcgga      60
cgaacacgaa ccggactcgt cctggcgctg tagtgagaac tgccgctgat cgagaaacaa    120
ctctgcgagg agcacctccg cacgggaccc ggcgctgctg ctactgccgc tagagccgct    180
gccgccgctt ttctagaacc ttcccccca ctaacgcgtc ttccgctacg tcaggccgtc     240
gcgtaaacgc cctatccgcc gccaatggcg ggaaggctct acgccccacc ttacgccaaa    300
tgcgtactcc tcccacccttt gcggccagag acagtacccg acgttacttc cgtaaatgcg   360
ctcaatgaat tgcggaaggc tagagtcctg ctagttacta cctcttggaa tagggtcccg    420
cccctgcct tggcgcaagg caggtgagaa acggtcgcgc agtttgaaat taacgccgac     480
gggaggggct taatccgcag cctggagatc cagccccctc aacccgggag gtggtccctg    540
cagttacgcc aatgataacc cccgccagaa aaatcttagt agccttccct ttttgtttc     600
cgtgccccaa ctcggcggat tgactcggcc ccttccggaa acaccgaat caacttctag     660
tcaaattatt gttcacgccg caatgaccca ccctggccc gcgtctgtgg aactgacccc    720
tggtgaacag gagagttcgc tgctgaaagt ggtcccaaag gggtactagt ttttaagctc    780
ccaactcccc ctcccccagc gtctggagga ttccacaccc tcgcaccgca ggggcgagga   840
agtgggcgga gtccggtttt ggcgccagcc gctgaggctg ccaagcagaa aagccaccgc    900
tgaggagact ccggtcactg tcctcgcccc gcctcccct tccctcccct tggggaccac    960
cgggcgccac gccgcgaacg ctaagtgccg cggtcgtcgg cgcctccgcc ctccccttg    1020
ggccccaatt cccagcgggc gcggcgcgcg gcccctcccc ccgccgggcg cgcgcccgct   1080
gccccgccct tcgtggccgc ccggcgtggg cggtgccacc cctcccccg gcggcccgc    1140
```

```
gcgcagctcc cggctccctc ccccttcgga tgtggcttga gctgtaggcg cggagggccg    1200
t                                                                    1201
```

<210> SEQ ID NO 23
<211> LENGTH: 461
<212> TYPE: PRT
<213> ORGANISM: Homo sapiens
<220> FEATURE:
<221> NAME/KEY: MISC_FEATURE
<222> LOCATION: (1)..(461)
<223> OTHER INFORMATION: amino acid sequence factor FIX

<400> SEQUENCE: 23

```
Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255

Val Asn Glu Lys Trp Ile Val Thr Ala Ala His Cys Val Glu Thr Gly
            260                 265                 270

Val Lys Ile Thr Val Val Ala Gly Glu His Asn Ile Glu Glu Thr Glu
        275                 280                 285

His Thr Glu Gln Lys Arg Asn Val Ile Arg Ile Ile Pro His His Asn
    290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335
```

```
Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Arg
        370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr
        450                 455                 460

<210> SEQ ID NO 24
<211> LENGTH: 460
<212> TYPE: PRT
<213> ORGANISM: Homo sapiens
<220> FEATURE:
<221> NAME/KEY: MISC_FEATURE
<222> LOCATION: (1)..(460)
<223> OTHER INFORMATION: amino acid sequence factor FIX padua

<400> SEQUENCE: 24

Met Gln Arg Val Asn Met Ile Met Ala Glu Ser Pro Gly Leu Ile Thr
1               5                   10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
```

```
                225                 230                 235                 240
        Gln Val Val Leu Asn Gly Lys Val Asp Ala Phe Cys Gly Gly Ser Ile
                        245                 250                 255

Val Asn Glu Lys Trp Ile Val Thr Ala Ala His Cys Val Glu Thr Gly
                        260                 265                 270

Val Lys Ile Thr Val Val Ala Gly Glu His Asn Ile Glu Thr Glu
                        275                 280                 285

His Thr Glu Gln Lys Arg Asn Val Ile Arg Ile Pro His His Asn
            290                 295                 300

Tyr Asn Ala Ala Ile Asn Lys Tyr Asn His Asp Ile Ala Leu Leu Glu
        305                 310                 315                 320

Leu Asp Glu Pro Leu Val Leu Asn Ser Tyr Val Thr Pro Ile Cys Ile
                        325                 330                 335

Ala Asp Lys Glu Tyr Thr Asn Ile Phe Leu Lys Phe Gly Ser Gly Tyr
                        340                 345                 350

Val Ser Gly Trp Gly Arg Val Phe His Lys Gly Arg Ser Ala Leu Val
                        355                 360                 365

Leu Gln Tyr Leu Arg Val Pro Leu Val Asp Arg Ala Thr Cys Leu Leu
            370                 375                 380

Ser Thr Lys Phe Thr Ile Tyr Asn Asn Met Phe Cys Ala Gly Phe His
        385                 390                 395                 400

Glu Gly Gly Arg Asp Ser Cys Gln Gly Asp Ser Gly Gly Pro His Val
                        405                 410                 415

Thr Glu Val Glu Gly Thr Ser Phe Leu Thr Gly Ile Ile Ser Trp Gly
                        420                 425                 430

Glu Glu Cys Ala Met Lys Gly Lys Tyr Gly Ile Tyr Thr Lys Val Ser
                        435                 440                 445

Arg Tyr Val Asn Trp Ile Lys Glu Lys Thr Lys Leu
            450                 455                 460

<210> SEQ ID NO 25
<211> LENGTH: 1064
<212> TYPE: PRT
<213> ORGANISM: Homo sapiens
<220> FEATURE:
<221> NAME/KEY: MISC_FEATURE
<222> LOCATION: (1)..(1064)
<223> OTHER INFORMATION: amino acid sequence FIX_albumin fusion

<400> SEQUENCE: 25

Met Gln Arg Val Asn Met Ile Met Ala Glu Ser Pro Gly Leu Ile Thr
        1               5                   10                  15

Ile Cys Leu Leu Gly Tyr Leu Leu Ser Ala Glu Cys Thr Val Phe Leu
                        20                  25                  30

Asp His Glu Asn Ala Asn Lys Ile Leu Asn Arg Pro Lys Arg Tyr Asn
                        35                  40                  45

Ser Gly Lys Leu Glu Glu Phe Val Gln Gly Asn Leu Glu Arg Glu Cys
            50                  55                  60

Met Glu Glu Lys Cys Ser Phe Glu Glu Ala Arg Glu Val Phe Glu Asn
        65                  70                  75                  80

Thr Glu Arg Thr Thr Glu Phe Trp Lys Gln Tyr Val Asp Gly Asp Gln
                        85                  90                  95

Cys Glu Ser Asn Pro Cys Leu Asn Gly Gly Ser Cys Lys Asp Asp Ile
                        100                 105                 110

Asn Ser Tyr Glu Cys Trp Cys Pro Phe Gly Phe Glu Gly Lys Asn Cys
                        115                 120                 125
```

```
Glu Leu Asp Val Thr Cys Asn Ile Lys Asn Gly Arg Cys Glu Gln Phe
    130                 135                 140
Cys Lys Asn Ser Ala Asp Asn Lys Val Val Cys Ser Cys Thr Glu Gly
145                 150                 155                 160
Tyr Arg Leu Ala Glu Asn Gln Lys Ser Cys Glu Pro Ala Val Pro Phe
                165                 170                 175
Pro Cys Gly Arg Val Ser Val Ser Gln Thr Ser Lys Leu Thr Arg Ala
            180                 185                 190
Glu Thr Val Phe Pro Asp Val Asp Tyr Val Asn Ser Thr Glu Ala Glu
        195                 200                 205
Thr Ile Leu Asp Asn Ile Thr Gln Ser Thr Gln Ser Phe Asn Asp Phe
    210                 215                 220
Thr Arg Val Val Gly Gly Glu Asp Ala Lys Pro Gly Gln Phe Pro Trp
225                 230                 235                 240
Gln Val Val Leu Asn Gly Lys Val Asp Ala Phe Cys Gly Gly Ser Ile
                245                 250                 255
Val Asn Glu Lys Trp Ile Val Thr Ala Ala His Cys Val Glu Thr Gly
            260                 265                 270
Val Lys Ile Thr Val Val Ala Gly Glu His Asn Ile Glu Glu Thr Glu
        275                 280                 285
His Thr Glu Gln Lys Arg Asn Val Ile Arg Ile Ile Pro His His Asn
    290                 295                 300
Tyr Asn Ala Ala Ile Asn Lys Tyr Asn His Asp Ile Ala Leu Leu Glu
305                 310                 315                 320
Leu Asp Glu Pro Leu Val Leu Asn Ser Tyr Val Thr Pro Ile Cys Ile
                325                 330                 335
Ala Asp Lys Glu Tyr Thr Asn Ile Phe Leu Lys Phe Gly Ser Gly Tyr
            340                 345                 350
Val Ser Gly Trp Gly Arg Val Phe His Lys Gly Arg Ser Ala Leu Val
        355                 360                 365
Leu Gln Tyr Leu Arg Val Pro Leu Val Asp Arg Ala Thr Cys Leu Arg
    370                 375                 380
Ser Thr Lys Phe Thr Ile Tyr Asn Asn Met Phe Cys Ala Gly Phe His
385                 390                 395                 400
Glu Gly Gly Arg Asp Ser Cys Gln Gly Asp Ser Gly Gly Pro His Val
                405                 410                 415
Thr Glu Val Glu Gly Thr Ser Phe Leu Thr Gly Ile Ile Ser Trp Gly
            420                 425                 430
Glu Glu Cys Ala Met Lys Gly Lys Tyr Gly Ile Tyr Thr Lys Val Ser
        435                 440                 445
Arg Tyr Val Asn Trp Ile Lys Glu Lys Thr Lys Leu Thr Pro Val Ser
450                 455                 460
Gln Thr Ser Lys Leu Thr Arg Ala Glu Thr Val Phe Pro Asp Val Asp
465                 470                 475                 480
Ala His Lys Ser Glu Val Ala His Arg Phe Lys Asp Leu Gly Glu Glu
                485                 490                 495
Asn Phe Lys Ala Leu Val Leu Ile Ala Phe Ala Gln Tyr Leu Gln Gln
            500                 505                 510
Cys Pro Phe Glu Asp His Val Lys Leu Val Asn Glu Val Thr Glu Phe
        515                 520                 525
Ala Lys Thr Cys Val Ala Asp Glu Ser Ala Glu Asn Cys Asp Lys Ser
530                 535                 540
```

```
Leu His Thr Leu Phe Gly Asp Lys Leu Cys Thr Val Ala Thr Leu Arg
545                 550                 555                 560

Glu Thr Tyr Gly Glu Met Ala Asp Cys Cys Ala Lys Gln Glu Pro Glu
                565                 570                 575

Arg Asn Glu Cys Phe Leu Gln His Lys Asp Asp Asn Pro Asn Leu Pro
            580                 585                 590

Arg Leu Val Arg Pro Glu Val Asp Val Met Cys Thr Ala Phe His Asp
        595                 600                 605

Asn Glu Glu Thr Phe Leu Lys Lys Tyr Leu Tyr Glu Ile Ala Arg Arg
    610                 615                 620

His Pro Tyr Phe Tyr Ala Pro Glu Leu Leu Phe Phe Ala Lys Arg Tyr
625                 630                 635                 640

Lys Ala Ala Phe Thr Glu Cys Cys Gln Ala Ala Asp Lys Ala Ala Cys
                645                 650                 655

Leu Leu Pro Lys Leu Asp Glu Leu Arg Asp Glu Gly Lys Ala Ser Ser
            660                 665                 670

Ala Lys Gln Arg Leu Lys Cys Ala Ser Leu Gln Lys Phe Gly Glu Arg
        675                 680                 685

Ala Phe Lys Ala Trp Ala Val Ala Arg Leu Ser Gln Arg Phe Pro Lys
    690                 695                 700

Ala Glu Phe Ala Glu Val Ser Lys Leu Val Thr Asp Leu Thr Lys Val
705                 710                 715                 720

His Thr Glu Cys Cys His Gly Asp Leu Leu Glu Cys Ala Asp Asp Arg
                725                 730                 735

Ala Asp Leu Ala Lys Tyr Ile Cys Glu Asn Gln Asp Ser Ile Ser Ser
            740                 745                 750

Lys Leu Lys Glu Cys Cys Glu Lys Pro Leu Leu Glu Lys Ser His Cys
        755                 760                 765

Ile Ala Glu Val Glu Asn Asp Glu Met Pro Ala Asp Leu Pro Ser Leu
    770                 775                 780

Ala Ala Asp Phe Val Glu Ser Lys Asp Val Cys Lys Asn Tyr Ala Glu
785                 790                 795                 800

Ala Lys Asp Val Phe Leu Gly Met Phe Leu Tyr Glu Tyr Ala Arg Arg
                805                 810                 815

His Pro Asp Tyr Ser Val Val Leu Leu Leu Arg Leu Ala Lys Thr Tyr
            820                 825                 830

Glu Thr Thr Leu Glu Lys Cys Cys Ala Ala Ala Asp Pro His Glu Cys
        835                 840                 845

Tyr Ala Lys Val Phe Asp Glu Phe Lys Pro Leu Val Glu Glu Pro Gln
    850                 855                 860

Asn Leu Ile Lys Gln Asn Cys Glu Leu Phe Glu Gln Leu Gly Glu Tyr
865                 870                 875                 880

Lys Phe Gln Asn Ala Leu Leu Val Arg Tyr Thr Lys Lys Val Pro Gln
                885                 890                 895

Val Ser Thr Pro Thr Leu Val Glu Val Ser Arg Asn Leu Gly Lys Val
            900                 905                 910

Gly Ser Lys Cys Cys Lys His Pro Glu Ala Lys Arg Met Pro Cys Ala
        915                 920                 925

Glu Asp Tyr Leu Ser Val Val Leu Asn Gln Leu Cys Val Leu His Glu
    930                 935                 940

Lys Thr Pro Val Ser Asp Arg Val Thr Lys Cys Cys Thr Glu Ser Leu
945                 950                 955                 960

Val Asn Arg Arg Pro Cys Phe Ser Ala Leu Glu Val Asp Glu Thr Tyr
```

-continued

```
              965                 970                 975

Val Pro Lys Glu Phe Asn Ala Glu Thr Phe Thr Phe His Ala Asp Ile
            980                 985                 990

Cys Thr Leu Ser Glu Lys Glu Arg Gln Ile Lys Lys Gln Thr Ala Leu
        995                1000                1005

Val Glu Leu Val Lys His Lys Pro Lys Ala Thr Lys Glu Gln Leu
   1010                1015                1020

Lys Ala Val Met Asp Asp Phe Ala Ala Phe Val Glu Lys Cys Cys
   1025                1030                1035

Lys Ala Asp Asp Lys Glu Thr Cys Phe Ala Glu Glu Gly Lys Lys
   1040                1045                1050

Leu Val Ala Ala Ser Gln Ala Ala Leu Gly Leu
   1055                1060

<210> SEQ ID NO 26
<211> LENGTH: 1064
<212> TYPE: PRT
<213> ORGANISM: Homo sapiens
<220> FEATURE:
<221> NAME/KEY: MISC_FEATURE
<222> LOCATION: (1)..(1064)
<223> OTHER INFORMATION: amino acid sequence FIX_padua albumin fusion

<400> SEQUENCE: 26

Met Gln Arg Val Asn Met Ile Met Ala Glu Ser Pro Gly Leu Ile Thr
1               5                  10                  15

Ile Cys Leu Leu Gly Tyr Leu Leu Ser Ala Glu Cys Thr Val Phe Leu
            20                  25                  30

Asp His Glu Asn Ala Asn Lys Ile Leu Asn Arg Pro Lys Arg Tyr Asn
        35                  40                  45

Ser Gly Lys Leu Glu Glu Phe Val Gln Gly Asn Leu Glu Arg Glu Cys
    50                  55                  60

Met Glu Glu Lys Cys Ser Phe Glu Glu Ala Arg Glu Val Phe Glu Asn
65                  70                  75                  80

Thr Glu Arg Thr Thr Glu Phe Trp Lys Gln Tyr Val Asp Gly Asp Gln
                85                  90                  95

Cys Glu Ser Asn Pro Cys Leu Asn Gly Gly Ser Cys Lys Asp Asp Ile
            100                 105                 110

Asn Ser Tyr Glu Cys Trp Cys Pro Phe Gly Phe Glu Gly Lys Asn Cys
        115                 120                 125

Glu Leu Asp Val Thr Cys Asn Ile Lys Asn Gly Arg Cys Glu Gln Phe
    130                 135                 140

Cys Lys Asn Ser Ala Asp Asn Lys Val Val Cys Ser Cys Thr Glu Gly
145                 150                 155                 160

Tyr Arg Leu Ala Glu Asn Gln Lys Ser Cys Glu Pro Ala Val Pro Phe
                165                 170                 175

Pro Cys Gly Arg Val Ser Val Ser Gln Thr Ser Lys Leu Thr Arg Ala
            180                 185                 190

Glu Thr Val Phe Pro Asp Val Asp Tyr Val Asn Ser Thr Glu Ala Glu
        195                 200                 205

Thr Ile Leu Asp Asn Ile Thr Gln Ser Thr Gln Ser Phe Asn Asp Phe
    210                 215                 220

Thr Arg Val Val Gly Gly Glu Asp Ala Lys Pro Gly Gln Phe Pro Trp
225                 230                 235                 240

Gln Val Val Leu Asn Gly Lys Val Asp Ala Phe Cys Gly Gly Ser Ile
                245                 250                 255
```

-continued

Val Asn Glu Lys Trp Ile Val Thr Ala Ala His Cys Val Glu Thr Gly
                260                 265                 270

Val Lys Ile Thr Val Val Ala Gly Glu His Asn Ile Glu Glu Thr Glu
            275                 280                 285

His Thr Glu Gln Lys Arg Asn Val Ile Arg Ile Pro His His Asn
290                 295                 300

Tyr Asn Ala Ala Ile Asn Lys Tyr Asn His Asp Ile Ala Leu Leu Glu
305                 310                 315                 320

Leu Asp Glu Pro Leu Val Leu Asn Ser Tyr Val Thr Pro Ile Cys Ile
                325                 330                 335

Ala Asp Lys Glu Tyr Thr Asn Ile Phe Leu Lys Phe Gly Ser Gly Tyr
            340                 345                 350

Val Ser Gly Trp Gly Arg Val Phe His Lys Gly Arg Ser Ala Leu Val
            355                 360                 365

Leu Gln Tyr Leu Arg Val Pro Leu Val Asp Arg Ala Thr Cys Leu Leu
    370                 375                 380

Ser Thr Lys Phe Thr Ile Tyr Asn Asn Met Phe Cys Ala Gly Phe His
385                 390                 395                 400

Glu Gly Gly Arg Asp Ser Cys Gln Gly Asp Ser Gly Gly Pro His Val
                405                 410                 415

Thr Glu Val Glu Gly Thr Ser Phe Leu Thr Gly Ile Ile Ser Trp Gly
            420                 425                 430

Glu Glu Cys Ala Met Lys Gly Lys Tyr Gly Ile Tyr Thr Lys Val Ser
            435                 440                 445

Arg Tyr Val Asn Trp Ile Lys Glu Lys Thr Lys Leu Thr Pro Val Ser
    450                 455                 460

Gln Thr Ser Lys Leu Thr Arg Ala Glu Thr Val Phe Pro Asp Val Asp
465                 470                 475                 480

Ala His Lys Ser Glu Val Ala His Arg Phe Lys Asp Leu Gly Glu Glu
                485                 490                 495

Asn Phe Lys Ala Leu Val Leu Ile Ala Phe Ala Gln Tyr Leu Gln Gln
            500                 505                 510

Cys Pro Phe Glu Asp His Val Lys Leu Val Asn Glu Val Thr Glu Phe
            515                 520                 525

Ala Lys Thr Cys Val Ala Asp Glu Ser Ala Glu Asn Cys Asp Lys Ser
    530                 535                 540

Leu His Thr Leu Phe Gly Asp Lys Leu Cys Thr Val Ala Thr Leu Arg
545                 550                 555                 560

Glu Thr Tyr Gly Glu Met Ala Asp Cys Cys Ala Lys Gln Glu Pro Glu
                565                 570                 575

Arg Asn Glu Cys Phe Leu Gln His Lys Asp Asp Asn Pro Asn Leu Pro
            580                 585                 590

Arg Leu Val Arg Pro Glu Val Asp Val Met Cys Thr Ala Phe His Asp
            595                 600                 605

Asn Glu Glu Thr Phe Leu Lys Lys Tyr Leu Tyr Glu Ile Ala Arg Arg
    610                 615                 620

His Pro Tyr Phe Tyr Ala Pro Glu Leu Leu Phe Phe Ala Lys Arg Tyr
625                 630                 635                 640

Lys Ala Ala Phe Thr Glu Cys Cys Gln Ala Ala Asp Lys Ala Ala Cys
                645                 650                 655

Leu Leu Pro Lys Leu Asp Glu Leu Arg Asp Glu Gly Lys Ala Ser Ser
            660                 665                 670

```
Ala Lys Gln Arg Leu Lys Cys Ala Ser Leu Gln Lys Phe Gly Glu Arg
            675                 680                 685

Ala Phe Lys Ala Trp Ala Val Ala Arg Leu Ser Gln Arg Phe Pro Lys
    690                 695                 700

Ala Glu Phe Ala Glu Val Ser Lys Leu Val Thr Asp Leu Thr Lys Val
705                 710                 715                 720

His Thr Glu Cys Cys His Gly Asp Leu Leu Glu Cys Ala Asp Asp Arg
                725                 730                 735

Ala Asp Leu Ala Lys Tyr Ile Cys Glu Asn Gln Asp Ser Ile Ser Ser
                740                 745                 750

Lys Leu Lys Glu Cys Cys Glu Lys Pro Leu Leu Glu Lys Ser His Cys
                755                 760                 765

Ile Ala Glu Val Glu Asn Asp Glu Met Pro Ala Asp Leu Pro Ser Leu
    770                 775                 780

Ala Ala Asp Phe Val Glu Ser Lys Asp Val Cys Lys Asn Tyr Ala Glu
785                 790                 795                 800

Ala Lys Asp Val Phe Leu Gly Met Phe Leu Tyr Glu Tyr Ala Arg Arg
                805                 810                 815

His Pro Asp Tyr Ser Val Val Leu Leu Leu Arg Leu Ala Lys Thr Tyr
                820                 825                 830

Glu Thr Thr Leu Glu Lys Cys Cys Ala Ala Ala Asp Pro His Glu Cys
                835                 840                 845

Tyr Ala Lys Val Phe Asp Glu Phe Lys Pro Leu Val Glu Glu Pro Gln
    850                 855                 860

Asn Leu Ile Lys Gln Asn Cys Glu Leu Phe Glu Gln Leu Gly Glu Tyr
865                 870                 875                 880

Lys Phe Gln Asn Ala Leu Leu Val Arg Tyr Thr Lys Lys Val Pro Gln
                885                 890                 895

Val Ser Thr Pro Thr Leu Val Glu Val Ser Arg Asn Leu Gly Lys Val
                900                 905                 910

Gly Ser Lys Cys Cys Lys His Pro Glu Ala Lys Arg Met Pro Cys Ala
                915                 920                 925

Glu Asp Tyr Leu Ser Val Val Leu Asn Gln Leu Cys Val Leu His Glu
                930                 935                 940

Lys Thr Pro Val Ser Asp Arg Val Thr Lys Cys Cys Thr Glu Ser Leu
945                 950                 955                 960

Val Asn Arg Arg Pro Cys Phe Ser Ala Leu Glu Val Asp Glu Thr Tyr
                965                 970                 975

Val Pro Lys Glu Phe Asn Ala Glu Thr Phe Thr Phe His Ala Asp Ile
                980                 985                 990

Cys Thr Leu Ser Glu Lys Glu Arg Gln Ile Lys Lys Gln Thr Ala Leu
                995                 1000                1005

Val Glu Leu Val Lys His Lys Pro Lys Ala Thr Lys Glu Gln Leu
    1010                1015                1020

Lys Ala Val Met Asp Asp Phe Ala Ala Phe Val Glu Lys Cys Cys
    1025                1030                1035

Lys Ala Asp Asp Lys Glu Thr Cys Phe Ala Glu Glu Gly Lys Lys
    1040                1045                1050

Leu Val Ala Ala Ser Gln Ala Ala Leu Gly Leu
    1055                1060

<210> SEQ ID NO 27
<211> LENGTH: 585
<212> TYPE: PRT
```

```
<213> ORGANISM: Homo sapiens
<220> FEATURE:
<221> NAME/KEY: MISC_FEATURE
<222> LOCATION: (1)..(585)
<223> OTHER INFORMATION: amino acid sequence mature albumin

<400> SEQUENCE: 27

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380
```

```
Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
            405                 410                 415

Gln Val Ser Thr Pro Thr Leu Val Glu Val Ser Arg Asn Leu Gly Lys
        420                 425                 430

Val Gly Ser Lys Cys Cys Lys His Pro Glu Ala Lys Arg Met Pro Cys
    435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 28
<211> LENGTH: 2802
<212> TYPE: DNA
<213> ORGANISM: Homo sapiens
<220> FEATURE:
<221> NAME/KEY: misc_feature
<222> LOCATION: (1)..(2802)
<223> OTHER INFORMATION: factor FIX, wt sequence

<400> SEQUENCE: 28
accactttca caatctgcta gcaaaggtta tgcagcgcgt gaacatgatc atggcagaat    60
caccaggcct catcaccatc tgccttttag gatatctact cagtgctgaa tgtacagttt   120
ttcttgatca tgaaaacgcc aacaaaattc tgaatcggcc aaagaggtat aattcaggta   180
aattggaaga gtttgttcaa gggaaccttg agagagaatg tatggaagaa agtgtagtt    240 ttgaagaagc acgagaagtt tttgaaaaca ctgaaagaac aactgaattt tggaagcagt   300
atgttgatgg agatcagtgt gagtccaatc catgtttaaa tggcggcagt tgcaaggatg   360
acattaattc ctatgaatgt tggtgtccct ttggatttga aggaaagaac tgtgaattag   420
atgtaacatg taacattaag aatggcagat gcgagcagtt ttgtaaaaat agtgctgata   480
acaaggtggt ttgctcctgt actgagggat atcgacttgc agaaaaccag aagtcctgtg   540
aaccagcagt gccatttcca tgtggaagag tttctgtttc acaaacttct aagctcaccc   600
gtgctgagac tgttttttcct gatgtggact atgtaaattc tactgaagct gaaaccattt   660
tggataacat cactcaaagc acccaatcat ttaatgactt cactcgggtt gttggtggag   720
aagatgccaa accaggtcaa ttcccttggc aggttgtttt gaatggtaaa gttgatgcat   780
tctgtggagg ctctatcgtt aatgaaaaat ggattgtaac tgctgcccac tgtgttgaaa   840
```

```
ctggtgttaa aattacagtt gtcgcaggtg aacataatat tgaggagaca gaacatacag    900
agcaaaagcg aaatgtgatt cgaattattc ctcaccacaa ctacaatgca gctattaata    960
agtacaacca tgacattgcc cttctggaac tggacgaacc cttagtgcta aacagctacg   1020
ttacacctat ttgcattgct gacaaggaat acacgaacat cttcctcaaa tttggatctg   1080
gctatgtaag tggctgggga agagtcttcc acaaagggag atcagcttta gttcttcagt   1140 acctagagt tccacttgtt gaccgagcca catgtcttcg atctacaaag ttcaccatct    1200
ataacaacat gttctgtgct ggcttccatg aaggaggtag agattcatgt caaggagata   1260 gtggggacc ccatgttact gaagtggaag ggaccagttt cttaactgga attattagct    1320
ggggtgaaga gtgtgcaatg aaaggcaaat atggaatata taccaaggta tcccggtatg   1380
tcaactggat taaggaaaaa acaaagctca cttaatgaaa gatggatttc caaggttaat   1440
tcattggaat tgaaaattaa cagggcctct cactaactaa tcactttccc atcttttgtt   1500
agatttgaat atatacattc tatgatcatt gcttttctc tttacagggg agaatttcat    1560
attttacctg agcaaattga ttagaaaatg gaaccactag aggaatataa tgtgttagga   1620
aattacagtc atttctaagg gcccagccct tgacaaaatt gtgaagttaa attctccact   1680
ctgtccatca gatactatgg ttctccacta tggcaactaa ctcactcaat tttccctcct   1740
tagcagcatt ccatcttccc gatcttcttt gcttctccaa ccaaaacatc aatgtttatt   1800
agttctgtat acagtacagg atctttggtc tactctatca caaggccagt accacactca   1860
tgaagaaaga acacaggagt agctgagagg ctaaaactca tcaaaaacac tactcctttt   1920
cctctaccct attcctcaat cttttacctt ttccaaatcc caatcccaa atcagttttt    1980 ctctttctta ctccctctct cccttttacc ctccatggtc gttaaaggag agatggggag   2040
catcattctg ttatacttct gtacacagtt atacatgtct atcaaaccca gacttgcttc   2100
cgtagtggag acttgctttt cagaacatag ggatgaagta aggtgcctga aaagtttggg   2160
ggaaaagttt ctttcagaga gttaagttat tttatatata taatatatat ataaaatata   2220
taatatacaa tataaaatata tagtgtgtgt gtatgcgtgt gtgtagacac acacgcatac   2280
acacatataa tggaagcaat aagccattct aagagcttgt atggttatgg aggtctgact   2340
aggcatgatt tcacgaaggc aagattggca tatcattgta actaaaaaag ctgacattga   2400
cccagacata ttgtactctt tctaaaaata ataataataa tgctaacaga aagaagagaa   2460
ccgttcgttt gcaatctaca gctagtagag actttgagga agaattcaac agtgtgtctt   2520
cagcagtgtt cagagccaag caagaagttg aagttgccta gaccagagga cataagtatc   2580
atgtctcctt taactagcat accccgaagt ggagaagggt gcagcaggct caaaggcata   2640
agtcattcca atcagccaac taagttgtcc ttttctggtt tcgtgttcac catggaacat   2700
tttgattata gttaatcctt ctatcttgaa tcttctagag agttgctgac caactgacgt   2760
atgtttccct ttgtgaatta ataaactggt gttctggttc at                      2802
```

TREATMENT OF MONOGENETIC DISORDERS

CROSS-REFERENCES TO RELATED APPLICATIONS

This application is a National Stage filing of International Application PCT/EP2018/054274, filed Feb. 21, 2018, entitled CONCEPT FOR THE TREATMENT OF MONOGENETIC DISORDERS, claiming priority to European Application Nos. EP 17 170 681.5, filed May 11, 2017, EP 17 177 443.3, filed Jun. 22, 2017, and to PCT/EP2017/074630, filed Sep. 28, 2017. The subject application claims priority to PCT/EP 2017/074630, to EP 17 170 681.5, to EP 17 177 443.3 and to PCT/EP2017/074630, and incorporates all by reference herein, in their entirety.

SEQUENCE LISTING

The instant application contains a Sequence Listing which has been submitted electronically in ASCII format and is hereby incorporated by reference in its entirety. Said ASCII copy, created on Jan. 16, 2020, is named 78-14750_SL.txt and is 87,494 bytes in size.

BACKGROUND OF THE INVENTION

The present invention relates to the medical field of monogenetic disorders, in particular monogenetic disorders associated with mutations in genes coding for proteins expressed for example in the liver.

In particular, the present invention relates to a nucleic acid expression cassette, preferably for the expression of a liver-specific and/or liver-expressed protein in a patient suffering from a monogenetic disorder caused by a mutation in the gene coding for the liver-specific and/or liver-expressed protein, and the use of such nucleic expression cassette.

Furthermore, the present invention relates to a vector and the inventive use of the vector according to the present invention.

A further subject of the present invention is a nanoparticle-based delivery system for a coding sequence as well as the preparation method and respective uses of the delivery system according to the present invention.

Additionally, the present invention relates to a composition, preferably for the use in the treatment of a monogenetic disorder resulting from a mutation in a gene coding for a liver-specific and/or liver-expressed protein. Likewise, subject-matter of the present invention is the use of the compositions according to the present invention.

The liver is a vital organ of the human body and has a wide range of functions, including the detoxification of various metabolites, protein synthesis and the production of biochemicals necessary for digestion. Furthermore, the liver plays a central role in metabolism, regulation of glycogen storage, decomposition of red blood cells and hormone production.

As outlined before, one main function of the liver is the production of proteins and their subsequent secretion into the blood. Proteins produced and secreted by the liver include major plasma proteins, carrier proteins, hormones, prohormones and apolipoproteins. In particular, the liver produces and secretes proteins and factors, which regulate hemostasis, i.e. blood clotting.

Furthermore, the liver produces and secretes proteins involved in lipometabolism, amino acid metabolism, bilirubin metabolism, urea cycle metabolism, carbohydrate metabolism, proteoglycan metabolism and sphingolipid metabolism. Additionally, the liver produces the antiprotease alpha-1-antitrypsin as well as proteins involved in transportation processes.

Hemostasis occurs when blood is present outside of the body or blood vessels. During hemostasis three steps occur in a rapid sequence. The first step includes a vascular spasm or a vasoconstriction, respectively. By vasoconstriction, the amount of blood flow can be reduced and the blood loss can be limited. Furthermore, collagen is exposed at the site of injury, thereby promoting platelets to adhere to the injury site. The second step of hemostasis includes the formation of platelet plugs.

Thereby, platelets adhere to the damaged endothelium to form a plug. This process is also called primary hemostasis. Once the plug has been formed, clotting factors begin creating the clot. Thereby, the clotting factors begin to form fibrin factor (FIa). Fibrin is a fibrous, non-globular protein, which is formed by the action of the protease thrombin factor (FII). This third step of hemostasis including the coagulation is also called secondary hemostasis. Thereby, the platelet plug is reinforced, wherein fibrin threads function as glue for the sticky platelets.

A multitude of factors and proteins is involved in the secondary hemostasis, for example fibrinogen (FI), prothrombin (FII), tissue factor/tissue thromboplastin (FIII), calcium (FIV), proaccelerin (FV), proconvertin (FVII), antihemophilic factor A (FVIII), antihemophilic factor B (FIX), Stuart-Prower factor (FX), plasma thromboplastin antecedent (FXI), Hageman factor (FXII) and fibrin-stabilizing factor (FXIII), wherein the list of factors is not exhaustive with respect to factors and proteins regulating hemostasis.

A diminished or absent production of blood clotting factors can lead to a phenotype or disease called hemophilia. Hemophilia is a term for a group of blood clotting disorders whose clinical symptoms are caused by a diminished or absent activity of blood clotting factors. Hemophilia is a mostly inherited in particular monogenetic disorder that impairs the body's ability to make blood clots, a process needed to stop bleeding. People suffering from hemophilia usually bleed longer after an injury and bruise easily. Furthermore, the disorder leads to an increased risk of bleeding inside joints or the brain.

The two most common subforms are hemophilia A with an incidence of 1:10.000 due to loss-of-function mutations in the gene coding for coagulation factor FVIII and hemophilia B with an incidence of 1:50.000 due to mutations in the factor FIX gene. Hemophilia A and B are caused by inherited and also de novo mutations in the X-chromosomally localized FVIII and FIX genes, which lead to loss of protein activity and thereby interfere with the coagulation cascade causing severe bleeding episodes. Because of the X-chromosomal recessive inheritance, almost exclusively boys and men are affected, while females as heterozygous germ-line mutation carriers show a reduction of the factor activity measurable in the laboratory, but are clinically healthy, i.e. without symptoms. Based on the residual activity of FVIII or FIX in the plasma, severe (less than 1% activity), moderate (1 to 5% activity), mild (6 to 24% activity) and subhemophilia (25 to 50% activity) can be distinguished. Notably, more than 50% of patients are affected by severe hemophilia. Patients with severe and also moderate hemophilia suffer about 30 to 40 severe bleeding episodes per year. Bleeding occurs spontaneously or after slight trauma. Mild and subhemophilia are clinically apparent only after surgery, trauma or treatment with acetylsalicylic acid or related drugs.

The WHO currently estimates that the number of patients worldwide is >400.000, of which approximately 10.000 hemophils are living in Germany. The current therapy for clinically severe moderate hemophilia involves a regular prophylactic use of concentrated FVIII or FIX products by intravenous injections. This prophylaxis allows an almost normal life expectancy and quality of life for hemophilia patients. According to the scientific publication of Oldenburg: "*Optimal treatment strategies for hemophilia: achievements and limitations of current prophylactic regiments*", published in Blood, 2015, 125(13):2038-44, in context with prophylactic treatment of hemophilia, concentrated FVIII or FIX products are either isolated as plasmatic factors from healthy blood donors or recovered as recombinant factors from specific cell cultures. A regular prophylaxis prevents long-lasting clinical consequences of the bleeding episodes including disabilities due to intracranial hemorrhage and chronic joint diseases and musculoskeletal crippling problems. Disadvantageously, the prophylactic treatment generates very high costs per year for each patient to be treated. Furthermore, the recurring treatments are rather stressful for the patients. Moreover, according to Peyvandi et al.: "*A randomized trial of factor VIII and neutralizing antibodies in hemophilia A*", published in N. Engl. J. Med., 2016, 374(21):2054-64, more than 50% of patients with severe hemophilia do not produce any endogenous FVIII or FIX. In this patients, administration of the exogenous proteins results in the development of neutralizing antibodies, so-called inhibitors, in up to 45% of the cases. These inhibitors neutralize the substituted factors and thereby render the factor replacement therapy ineffective. In patients with inhibitors, immune tolerance induction can be achieved by treatment with high doses of factors over a period of one to two years. However, this approach is only successful in 50 to 70% of patients. Additionally, the immune tolerance induction leads to a significant increase of costs per patient per year.

Since hemophilia is—in the majority of cases—a monogenetic disorder, multiple efforts to treat the disease with different gene therapy strategies have been pursued. The basic goal of all gene therapy approaches is the permanent introduction of an intact copy of the defective gene as complementary DNA (cDNA) into the nucleus of the target cell.

Recombinant gene delivery systems for the intact gene are so-called vectors, which are mostly derived from viral systems. These wild-type viruses are evolutionarily optimized in terms of their properties to efficiently transfer their genetic information to the target cell and into the nucleus of the cell, respectively.

The viral gene transfer system most frequently used for hemophilia originates from the adeno-associated virus (AAV), which exists in various different serotypes and can infect primary liver cells particularly well. The use of an AAV-based gene transfer system has been described by High and Anguela: "*Adeno-associated viral vectors for the treatment of hemophilia*", published in Hum. Mol. Genet., 2016, 25(R1):R36-41. In addition, lentiviral vectors derived from the human immunodeficiency virus (HIV-1) have been used and can very efficiently integrate into the DNA of dividing and also non-dividing cells. In all these viral approaches, the integration of the vector DNA into the genome of the target cell appears to be the greatest risk. Here, the function or expression of a gene located in the vicinity of the insertion site can be altered or modified by the integration event and thus can lead to a malignant transformation of the cell.

Another viral approach on the basis of a gene therapy for hemophilia B with an AAV-FIX vector was described by Nathwani et al. in the scientific publications "*Adenovirus-associated virus vector-mediated gene transfer in hemophilia B*", N. Engl. J. Med., 2011, 365(25):2357-65, and "Long-term safety and efficacy of factor IX gene therapy in hemophilia B", N. Engl. J. Med., 2014, 371(21):1994-2004. An important side effect or a severe adverse event, respectively, of the therapy was an increase of the liver enzymes. The liver toxicity required an additional cortisone therapy. Furthermore, patients once treated with a specific AAV serotype will develop lifelong immunity to the specific AAV envelope protein and can never be treated with the same vector or serotype again.

Similarly, a concept for a gene therapy for hemophilia A on the basis of an AAV-FVII vector has been developed. According to the scientific publication of Nault et al. "*Recurrent AAV2- related insertional mutagenesis in human hepatocellular carcinomas*", Nat. Genet, 2015, 47(10):1187-93, a therapy on the basis of wildtype AAV might be linked with the risk of developing hepatocellular carcinoma in humans.

Moreover, non-genetic approaches for the treatment of hemophilia consist in the use of antibodies. In this context, for the treatment of hemophilia A, a bispecific humanized recombinant antibody has been described by Muto et al.: "*Anti factor IXa/x bispecific antibody ACE910 prevents joint bleeds in a long-term primate model of acquired hemophilia A*", published in Blood, 2014, 124(20):3165-71 as well as Kitazawa et al.: "A bispecific antibody to factors IXa and X restores factor VIII hemostatic activity in hemophilia A model", published in Nat. Med. 2012, 18(10):1570-4. The respective antibody can replace the cross-linking of FIX or the active form FIXa, respectively, and FX as an essential function of FVIII in the coagulation cascade. Even though antibodies are not associated with the risk of mutagenesis, however, also a non-genetic therapy on the basis of antibodies can be linked with undesired side effects, in particular with respect to undesired immunological reactions.

Overall, there is a strong need for improved therapeutic concepts and/or approaches with respect to the treatment of monogenetic diseases associated with mutations in genes coding for proteins predominantly expressed in the liver, in particular proteins of the coagulation cascade and/or proteins involved in hemostasis. Especially, there is a strong need for improved therapeutic concepts for the treatment of hemophilia.

Against the background of the severe disadvantages of known therapeutic concepts for the treatment of monogenetic disorders, in particular hemophilia, as delineated before, the problem of the present invention is based on the supply of a new therapeutic concept for the treatment of monogenetic disorders associated with mutations in genes coding for liver-specific and/or liver-expressed proteins and/or proteins predominantly expressed in the liver, in particular proteins involved in hemostasis and/or proteins or factors of the coagulation cascade.

BRIEF SUMMARY OF THE INVENTION

In particular, the object of the present invention has to be seen in a therapeutic concept for the treatment of monogenetic disorders associated with the liver, especially hemophilia, which is well tolerated and leads to at least reduced side effects.

Especially, the therapeutic concept to be developed should eliminate potential risks and/or safety considerations of conventional therapeutic approaches, especially genetic approaches and/or gene therapies.

Furthermore, the therapeutic concept should be suitable for a long-term use, in particular in patients suffering from severe hemophilia and/or patients being resistant to replacement therapy, especially caused by inhibitors.

Additionally, a therapeutic concept allowing a user-friendly and convenient administration is desired. Finally, also an improvement of cost-efficiency with respect to the therapy of the aforementioned monogenetic disorders, in particular hemophilia, is desired.

The applicant has surprisingly found, that the aforementioned problem can be solved—according to the first aspect of the present invention—on the basis of a nucleic acid expression cassette as described below.

Additionally, the present invention relates to—according to the second aspect of the present invention—the inventive use of the expression cassette according to the respective independent claim; further, in particular advantageous embodiments of this aspect are similarly provided.

Furthermore, subject-matter of the present invention is—according to the third aspect of the present invention—a vector according to the respective independent claim; further, in particular advantageous embodiments of this aspect are provided.

The present invention also relates to—according to the fourth aspect of the present invention—the inventive use of the vector according to the respective independent claim; further, in particular advantageous embodiments of this aspect are described.

In addition, subject-matter of the present invention is—according to the fifth aspect of the present invention—a nanoparticle-based delivery system for a coding sequence according to the respective independent claim; further, in particular advantageous embodiments of this aspect are also provided.

Furthermore, the present invention relates to—according to a sixth aspect of the present invention—a method for the preparation of a delivery system according to the present invention.

The present invention also relates to—according to the seventh aspect of the present invention—the inventive use of the nanoparticle-based delivery system for a coding sequence according to the respective independent claim; further, in particular advantageous embodiments of this aspect are described below.

Furthermore, the present invention relates to—according to the eighth aspect of the present invention—an inventive composition.

Finally, the present invention relates to—according to the ninth aspect of the present invention—the inventive use of the composition.

Apart from this, a person skilled in the art can—depending on the application or depending on the individual case—deviate from the specified weights, specified quantities and specified ranges that are stated below without departing from the scope of the present invention.

Moreover, all specified values or specified parameters or the like that are mentioned below can absolutely be ascertained or determined using normed or standardized or explicitly specified determination methods or else using determination or measurement methods familiar per se to a person skilled in the art in this field.

With this said, the present invention will now be elucidated in detail below.

BRIEF DESCRIPTION OF THE DRAWINGS

FIG. 1A shows a schematic representation of a preferred embodiment of the nucleic acid expression cassette according to the present invention including a promoter, a coding sequence, an S/MAR-sequence, and a terminator;

FIG. 1B shows a schematic representation of a preferred embodiment of the nucleic acid expression cassette according to the present invention including a promoter derived from the human gene coding for Elongation Factor-1alpha, a coding sequence including a human codon usage-optimized nucleic acid sequence coding for a variant of coagulation factor FVIII, an S/MAR-sequence, and a terminator;

FIG. 1C shows a schematic representation of a preferred embodiment of the nucleic acid expression cassette according to the present invention including a promoter derived from the human gene coding for Elongation Factor-1alpha, a codon-optimized cDNA coding for the mutant variant of factor FIX, an S/MAR-sequence, and a terminator;

FIG. 1D shows a schematic representation of a preferred embodiment of the nucleic acid expression cassette according to the present invention including a CMV promoter, a coding sequence including a human codon usage-optimized nucleic acid sequence coding for a variant of coagulation factor FVIII, specifically FVIII SQ, an S/MAR-sequence, and a terminator;

FIG. 20A provides a graphic representation of the results of in vivo studies in fibrosarcoma cell line HT1080, wherein the expression of eGFP after transfection of fibrosarcoma cells with a delivery system according to the present invention using different variants of polyethylenimine was analyzed demonstrated that all variants of polyethylenimine as well as all amounts of DNA were sufficient to achieve a transfer of the nucleic acid molecules into the cells;

FIG. 22 shows the graphic representation of the results of the measurement of the factor level of fibrosarcoma cells (cell line HT1080) transfected with a coding sequence, which codes for a fusion protein of eGFP and factor FVIII SQ or factor FIX padua, respectively.

DETAILED DESCRIPTION OF THE INVENTION

Figure 2B:
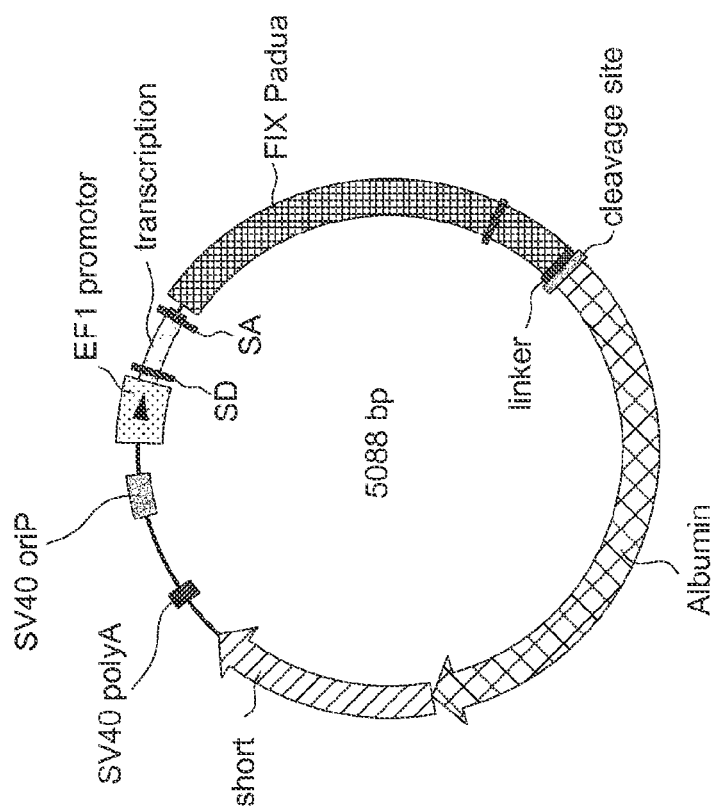
FIG. 2B shows a schematic representation of a preferred vector which contains a nucleic acid expression cassette as shown in FIG. 1C.

The present invention therefore provides—according to a first aspect of the present invention—a nucleic acid expression cassette, in particular for the expression of a liver-specific and/or liver-expressed protein and/or preferably physiologically active domains and/or fragments thereof in a patient suffering from a monogenetic disorder caused by a mutation in the gene coding for the liver-specific and/or liver-expressed protein, wherein the expression cassette comprises:
  (a) a promoter, preferably a promoter directing gene expression in mammalian, especially human cells;
  (b) a coding sequence containing a nucleic acid sequence coding for a human liver-specific and/or liver-expressed protein and/or preferably physiologically active domains and/or fragments thereof, wherein mutations in the nucleic acid sequence coding for the liver-specific and/or liver-expressed protein are associated with a monogenetic disorder;
  (c) a nucleic acid sequence derived from the scaffold/matrix attachment region of a eukaryotic, preferably human gene; and
  (d) a transcriptional termination signal.

The applicant has surprisingly found out that a nucleic acid expression cassette comprising a promoter, preferably derived from a human gene or from a virus, a coding sequence containing a nucleic acid sequence coding for a liver-specific and/or liver-expressed protein, a nucleic acid sequence on the basis of scaffold/matrix attachment region and a transcriptional termination signal is suitable for the use in gene therapy of monogenetic diseases, wherein the monogenetic disease or disorder is caused by a mutation in the gene coding for the liver-specific and/or liver-expressed protein. In other words, the nucleic acid expression cassette according to the present invention is suitable for the introduction of an intact copy of the mutated or defective gene coding for a liver-specific and/or liver-expressed protein, for example factors involved in hemostasis or proteins of the lipometabolism, into the nucleus of the target cells. On the basis of the expression of the nucleic acid sequence coding for the liver specific protein, the loss-of-function-mutation in the gene coding for the liver-specific and/or liver-expressed protein can be balanced or compensated.

The nucleic acid expression cassette, in particular a gene therapy on the basis of the nucleic acid expression cassette, according to the present invention is linked to several advantages, which are delineated hereinafter:

A gene therapy on the basis of a nucleic acid expression cassette according to the present invention is suitable for a broad range of patients suffering from different monogenetic disorders since the expression cassette is suitable for the expression of any liver-specific and/or liver-expressed protein linked with a monogenetic disorder in a patient. In this context, the expression cassette is suitable to balance defects in gene expression, i.e. a total loss of gene expression as a result of the monogenetic disorder, as well as deficiencies in gene expression, i.e. a partial loss of gene expression or a reduced activity of the respective liver-specific and/or liver-expressed protein.

In particular, the expression cassette is suitable for the expression of factors and proteins involved into hemostasis. On this basis, a highly efficient therapeutic concept in particular for the treatment of monogenetic disorders linked with a reduced or impaired hemostasis or blood clotting, in particular hemophilia, especially hemophilia A or B, is established. The expression cassette of the present invention is suitable for the treatment of patients with mild as well as severe or moderate hemophilia. In particular, the therapeutic concept is highly efficient in the treatment of patients, which have become resistant to conventional therapeutic concepts for the treatment of hemophilia. Likewise, the expression cassette is suitable for the expression of proteins involved in lipometabolism or proteins linked with monogenetic lipometabolic disorders.

A gene therapy on the basis of the nucleic acid expression cassette according to the present invention should be associated with an excellent patient compliance due to the non-viral approach. The expression cassette is suitable for a gene therapy, wherein the integration of the expression cassette into the genome of the target cells on the basis of viral vectors is not intended. Instead, the use of the scaffold/matrix attachment region in the nucleic acid expression cassette provides an episomal replication and persistence of the expression cassette in the target cells. On this basis, the risk of insertions of the transferred nucleic acid molecules into the genome leading to malignant transformations of the cells is minimized. Therefore, on the basis of the present invention a concept for the treatment of monogenetic disorders is provided, which eliminates potential risks and safety considerations of conventional therapeutic approaches in particular on the basis of viral systems, especially genetic approaches, for the treatment of monogenetic disorders.

In this context, a gene therapy on the basis of the nucleic acid expression cassette according to the present invention overcomes the risk of carcinogenicity. Furthermore, a gene therapy on the basis of the expression cassette is not linked with the disadvantage immunogenicity. In particular, the therapeutic concept provided on the basis of the present invention is also suitable for patients resistant to conventional replacement therapies, for example the prophylactic application of concentrated coagulation factor products, especially for patients where immune tolerance induction has failed. Furthermore, a gene therapy on the basis of the nucleic acid expression cassette according to the present invention does not trigger immunological reactions as gene therapies on the basis of viral systems do, for example on the basis of adeno-associated virus (AAV).

The excellent compliance of the therapeutic concept in patients will be linked with significantly reduced side effects. As a result, no supporting therapies for the treatment of side-effects, as observed in several therapeutic concepts for the treatment of hemophilia, should be necessary. In particular, there should be no need for therapies to achieve a immunosuppression due to the occurrence of neutralizing antibodies or inhibitors. Furthermore, there is no need of additional therapies with steroids, in particular cortisone, as observed in connection with gene therapies of monogenetic disorders in particular hemophilia, on the basis of viral systems, for example on the basis of adeno-associated virus. Moreover, a gene therapy on the basis of the expression cassette according to the present invention allows for a repeated application and a long-term application in patients suffering from a monogenetic disorder, in particular hemophilia.

With respect to the application, a convenient administration of a drug on the basis of the expression cassette of the present invention is possible, in particular an intravenous application. Furthermore, since the expression cassette according to the present invention directs a highly efficient expression of the coding sequence, i. e. a highly efficient expression of the liver-specific and/or liver-expressed protein, the dosing intervals can be reduced, i. e. the time lag between the treatment units can be prolonged, compared to conventional therapeutic concepts.

Furthermore, the gene therapy or therapeutic concept on the basis of the expression cassette according to the present invention has economic advantages compared to conventional therapeutic concepts for the treatment of monogenetic disorders, in particular hemophilia. A specific advantage is the fact that the nucleic acid expression cassette as such as well as therapeutics on the basis of the expression cassette according to the present invention are—especially in contrast to the manufacturing of antibodies—suitable for an unlimited industrial manufacturing under good manufacturing practice (GMP) conditions. Furthermore, the production costs can be kept relatively low.

Advantages and/or preferred embodiments of the present invention will be described in the following. Furthermore, the following terms or definitions are provided to aid in the understanding of the present invention.

The term "monogenetic disorder", "monogenetic disease" or "single-gene disorder" refers to diseases or disorders, which result from modifications, in particular mutations, in a single gene occurring in all cells of the preferably human body. The mutations are in general linked with a partial or complete loss of the physiological function of the protein ("loss-of-function-mutation"). In particular, monogenetic disorders can result from sex-linked, recessive or dominant heredity. Furthermore, monogenetic disorders can result from sporadic mutations in a single gene.

Against this background, the present invention relates to therapeutic concepts for the treatment of monogenetic disorders caused by mutations in genes coding for liver-specific and/or liver-expressed proteins. According to the present invention, the term "liver-specific and/or liver-expressed protein" relates to proteins expressed and/or produced and secreted by the liver. Particularly, liver-specific and/or liver-expressed proteins include major plasma-proteins, factors involved in hemostasis and fibrinolysis, carrier proteins, hormones, prohormones and apolipoproteins. The major plasma proteins, which are produced and secreted by the liver include in particular human serum albumin, alpha-fetoprotein, soluble plasma fibronectin and C-reactive protein. Furthermore, various globulins are produced and secreted by the liver. Examples for carrier proteins specifically produced in the liver are albumin, ceruloplasmin, transportin, heptoglobin, hemopexin, insulin-like growth factor-binding protein, low density lipoprotein (LDL) receptor, p-type ATPase, cystic fibrosis transmembrane conductance regulator, major urinary proteins, retinol binding protein, sex hormone-binding globulin, thyroxine-binding globulin, transthyretin, transferrin and vitamin-D-binding protein. Furthermore, liver-specific and/or liver-expressed proteins include proteins involved in lipometabolism, amino acid metabolism, bilirubin metabolism, urea metabolism and/or cycle, carbohydrate metabolism, proteoglycan metabolism and sphingolipid metabolism.

Factors involved in hemostasis and fibrinolysis are of particular importance for the present invention, since mutations in genes coding for such factors or proteins, in particular factors of the coagulation cascade, lead to a group of monogenetic disorders subsumed as hemophilia. Liver-specific and/or liver-expressed proteins involved in hemostasis and fibrinolysis are in particular all factors of the coagulation cascade, especially fibrinogen (FI), prothrombin (FII), tissue factor or tissue thromboplastin (FIII), proaccelurin or labile factor (FV), stable factor or proconvertin (FVII), antihemophilic factor A (FVIII), antihemophilic factor B, synonymously also known as Christmas factor (FIX), Stuart-Prower factor (FX), plasma thromboplastin antecedent (FXI), Hageman factor (FXII), fibrin-stabilizing factor (FXIII), von Willebrand factor (VWF), Fletcher factor, synonymous also prekallicrein, high-molecular weight kininogen or Fitzgerald factor, fibronectin, antithrombin III, heparin-co-factor II, protein-C, protein-S, protein-Z, plasminogen, alpha2-antiplasmin, tissue plasminogen activator, urokinase and plasminogen activator inhibitor-1 (PAI1). Mutations in genes coding for the aforementioned coagulation factors and related substances can lead to genetic disorders, in particular to different types or subforms of hemophilia.

Further liver-specific and/or liver-expressed proteins of particular interest with respect to the present invention are proteins of the amino acid metabolism, in particular fumarylacetoacetate hydrolase, p-hydroxyphenylpyruvate hydroxylase and/or phenylalanine-4-hydroxylase, antiproteases, in particular alpha-1 antitrypsin, proteins of the bilirubin metabolism, in particular uridine diphospho-glucuronosyl-transferase, proteins of the urea cycle, in particular arginase, argininosuccinate synthase and/or ornithine transcarbamylase, proteins of the carbohydrate metabolism, in particular alpha-glucan phosphorylase, amylo-1,6-glucosidase and/or glucose-6-phosphatase, proteins of the proteoglycan metabolism, in particular idursulfase, proteins of the sphingolipid metabolism, in particular glucocerebrosidase, and/or proteins involved in transport processes, in particular p-type ATPase, cystic fibrosis transmembrane regulator and/or low-density lipoprotein (LDL) receptor.

The term "nucleic acid expression cassette" or "expression cassette" used according to the present invention refers to nucleic acid molecules that include at least one element for transcriptional control, in particular at least one promoter. Furthermore, control elements on the basis of enhancers, regulatory elements, polyadenylation sequences or introns that direct the expression of a nucleic acid sequence coding for at least one protein or domains or fragrance of a protein in cells can be optionally contained in an expression cassette. Furthermore, a nucleic acid expression cassette according to the present invention comprises at least one coding sequence containing a nucleic acid sequence coding for at least one liver-specific and/or liver-expressed protein or domains of fragments of a protein. Nucleic acid expression cassettes according to the present invention can comprise further elements ensuring the replication and stable expression of the coding sequence in the target cells, for example elements effecting an attachment of the nucleic acid expression cassette to the genomic DNA and/or to the genome or further transcriptional regulators, for example termination signals.

The term "promoter" as used according to the present invention relates to a DNA (desoxyribonucleic acid) or nucleic acid sequence, in particular a regulatory sequence, which is required for the expression of a coding sequence linked to the promoter, in particular a corresponding coding sequence located 3' or downstream to the promoter. In order to achieve a stable and reliable expression of the nucleic acid sequence coding for a liver-specific and/or liver-expressed protein, the nucleic acid expression cassette according the present invention comprises preferably a promoter derived from a eukaryotic, in particular human gene or a promoter derived from a virus. On this basis, the compliance of the nucleic acid expression cassette, on the one hand, in the patient and the efficiency of expression of the coding sequence, on the other hand, can be improved. A promoter according to the present invention can comprise a core promoter, including a transcription start site, a binding site for RNA polymerases and binding sites for general transcription factors.

The promoter in the sense of the present invention can comprise further regulatory elements, in particular parts of 3' untranslated regions (3' UTR), introns of genes or part of introns or parts of 5' untranslated regions (5' UTR). Furthermore, according to the present invention, the promoter can be tissue- and/or cell-specific or suitable for the direction of expression in various cell types. Moreover, the expression of the coding sequence under the control of the promoter can be inducible or constitutive. Preferably, the promoter used according to the present invention is constitutively active, leading to a constant and stable expression of the coding sequence in the target cells.

The term "coding sequence", "coding region" or "nucleic acid coding sequence" refers to a nucleic acid sequence coding for a protein or domains or fragments of a protein. Furthermore, the coding sequence can refer to a nucleic acid sequence coding for fusion proteins, in particular fusion proteins on the basis of a liver-specific and/or liver-expressed protein and an albumin. In other words, the coding sequence according to the present invention contains a nucleic acid sequence coding for a liver-specific and/or liver-expressed protein and/or domains and/or fragments thereof and can contain further nucleic acid sequences, which results in a coding sequence coding for a fusion protein. In particular, according to a preferred embodiment of the present invention, the coding sequence is based on the cDNA sequence coding for a protein and/or domains or fragments of a protein.

According to the present invention, the expression cassette and/or the sequence elements to be protected can also comprise the 5' untranslated region and/or the 3' untranslated region. Furthermore, the nucleic acid sequence of the coding sequence can correspond to the native nucleic acid sequence of the gene coding for the respective protein to be expressed. Likewise, the coding sequence can be optimized for human codon usage or comprise an optimized nucleic acid sequence.

The term "scaffold/matrix attachment region", also indicated as "S/MAR element" or "scaffold-attachment region" or "matrix-associated region", refers to DNA sequences of eukaryotic chromosomes where the nuclear matrix attaches. Scaffold/matrix attachment regions of the eukaryotic DNA consist of about 70% T-rich regions and naturally mediate the structural organization of the chromatin within in the nucleus. In particular, the S/MAR elements constitute anchor points of the DNA for the chromatin scaffold and serve to organize the chromatin into structural domains. According to the present invention, it was surprisingly found that the use of the nucleotide sequence of a scaffold/matrix attachment region in the expression cassette according to the present invention mediates the attachment of the expression cassette to the nuclear matrix or the chromatin. On this basis, the non-integration of the nucleic acid expression cassette or a vector containing the nucleic expression cassette can be assured, thereby still allowing a stable expression of the coding sequence and a replication of the introduced nucleic acid molecule in particular during the S-phase of mitosis. The use of a scaffold/matrix attachment region increases the long-term episomal persistence of the nucleic expression cassette or a vector on the basis of the nucleic expression cassette transferred into the target cells. Overall, the use of a nucleic acid sequence derived from a scaffold/matrix attachment region of a human gene is linked with a central advantage of the present invention, namely the prevention of an integration of the transferred transgenic nucleic acid molecules into the genomic DNA of the target cells. On this basis, the risk of further mutations, which can lead to the occurrence of malignant cells, can be significantly reduced.

The term "transcriptional termination signal" or "polyadenylation signal" as used according to the present invention refers to the section of a nucleic acid sequence that marks the end of a gene and/or a coding sequence during transcription. This sequence mediates the transcriptional termination by providing signals in the newly synthesized mRNA that trigger processes, which release the mRNA from the transcriptional complex. With respect to the present invention, the use of any transcriptional terminator suitable for the use in humans can be intended. The selection of a transcriptional termination signal and/or a polyadenylation signal does not represent a problem for the skilled practitioner.

Preferred embodiments of the nucleic expression cassette according to the present invention are delineated in the following:

In order to optimally direct the expression of the coding sequence, the arrangement of the different elements of nucleic acid sequences within the expression cassette is of significance. In context with explanations concerning the assembly and/or arrangement of the nucleic acid sequence elements within the expression cassette, the term "5' to . . . " is used synonymously to "upstream to . . . ". Likewise, the term "3' to . . . " is used synonymously to "downstream to . . . ". In other words, the terms upstream ("5' to . . . ") and downstream ("3' to . . . ") relate to the 5' to 3' direction in which RNA transcription takes place. In relation to double-stranded DNA, upstream is toward the 5' end of the coding strand for the respective coding sequence and downstream is toward the 3' end of the coding strand.

According to a preferred embodiment of the present invention, the promoter is located 5' to the coding sequence and/or the nucleic acid sequence derived from the scaffold/matrix attachment region of a human gene and/or the transcriptional termination signal.

In other words, the promoter and the nucleic acid sequence as well as the scaffold/matrix attachment region and the transcriptional termination signal are operably linked or arranged relative to each other such that the elements are functionally connected and able to interact with each other. In particular, the elements, especially the promoter and the coding sequence, are arranged that the promoter can direct the expression of the coding sequence.

Furthermore, according to the present invention it can be intended that the coding sequence is located 3' (i.e. downstream) to the promoter. Likewise, it can be intended that the coding sequence is located 5' to the nucleic acid sequence derived from the scaffold/matrix attachment region of a human gene and/or the transcriptional termination signal.

Likewise, according to a preferred embodiment of the present invention, the nucleic acid sequence derived from the scaffold/matrix attachment region of a eukaryotic, in particular human gene is located 3' to the promoter and/or the coding sequence. Furthermore, the nucleic acid sequence derived from the human scaffold/matrix attachment region of a human gene is located 5' to the transcriptional termination signal. On this basis, a stable expression of the coding sequence and a high episomal persistence are provided.

With respect to the transcriptional termination signal, it is preferred when the transcriptional termination signal is located 3' to the promoter and/or the coding sequence and/or the nucleic acid sequence derived from the scaffold/matrix attachment region of a human gene. As delineated before, the transcriptional termination signal is located such that the termination of the transcription of the coding sequence is enabled.

In particular, it is preferred when the nucleic acid expression cassette according to the present invention directs expression of a therapeutic amount of the liver-specific and/or liver-expressed protein and/or preferably physiologically active domains and/or fragments thereof in mammalian cells, in particular human cells, preferably liver cells and/or fibroblasts, especially hepatocytes and/or fibroblasts. In this context, it is further preferred when the expression is directed for a period of at least 14 days, especially at least 25 days, in particular at least 40 days, preferred at least 50 days, preferably at least 100 days, more preferred at least 150 days, further preferred at least 200 days. In other words, on the basis of the expression cassette according to the present invention it is intended to provide a long-term expression of the liver-specific and/or liver-expressed protein in the target cells, in particular liver cells. On this basis, it is possible to achieve an excellent efficacy of a therapeutic concept on the basis of the expression cassette according to the present invention. The high efficacy allows that patients suffering from a monogenetic disorder require a reduced number of treatment units, compared to conventional therapeutic concepts for the treatment of monogenetic disorders, for example concepts for the treatment of hemophilia. In other words, on the basis of the therapeutic concept of the present invention, the treatment free episodes are prolonged compared to conventional therapeutic concepts, which is comfortable for the patients.

According to the present invention, the specificity of the promoter or the specificity of the expression directed by the promoter is variable and can be purposefully tailored or adjusting. In particular, any promoter directing a preferably constitutive expression of the coding sequence in several mammalian cells, cell types or tissues can be used in the expression cassette according to the present invention.

According to a first embodiment of the present invention, the use of a cell- or tissue-specific promoter is preferred. Likewise, the use of a promoter, which is active or directs gene expression in various cell types can be preferred. Furthermore, it is possible that expression of the coding sequence directed by the promoter is inducible and/or constitutive, especially constitutive, in mammalian cells, in particular human cells, preferably liver cells and/or fibroblasts, especially hepatocytes and/or fibroblasts. On this basis, the expression of the coding sequence can be purposefully targeted or adjusted. In particular, the promoter can be tailored and/or selected depending on the target cells, the severeness of the monogenetic disorder and the coding sequence to be expressed. In particular, in connection with the expression of coding sequences having nucleic acid sequence coding for a protein involved in hemostasis, the use of a constitutively active promoter is preferred.

According to a preferred embodiment of the present invention, the promoter is derived from the gene coding for human Elongation Factor-1 alpha (EF1a). In particular, according to a further preferred embodiment of the present invention, the promoter is derived from the promoter of the gene coding for human Elongation Factor-1 alpha (EF1a) and the first intron and/or a fragment of the first intron of the gene coding for human Elongation Factor-1 alpha (EF1a). A promoter derived from human Elongation Factor-1 alpha (EF1a) directs a reliable and constant expression of the coding sequences in mammalian cells, in particular human cells, preferably liver cells and/or fibroblasts, especially hepatocytes and/or fibroblasts. In this context, reference is also made to the working examples performed by the applicant. The working examples performed by applicant show that a promoter derived from the gene coding for human Elongation Factor-1 leads to a stable long-term expression of the coding sequence in several cell types, for example liver cells or fibroblasts.

According to another preferred embodiment of the present invention, the promoter is derived from Cytomegalovirus (CMV), in particular human CMV. In other words, according to this embodiment of the present invention, the promoter is the CMV promoter. The CMV promoter directs a stable and reliable gene expression in several mammalian cell types, for examples liver cells, in particular hepatocytes, or fibroblasts. With respect to the expression level of the coding sequence, reference is made to the working examples performed by applicant, which verify the stable expression of the coding sequence under control of the CMV promoter.

Furthermore, according to the present invention it can be intended that the promoter comprises a codon-optimized nucleic acid sequence and/or a nucleic acid sequence optimized for human gene expression and/or human codon usage. In particular, this applies for embodiments with a promoter containing further regulatory elements, for example on the basis of introns or parts of introns of a gene, especially of the gene the promoter is derived from.

According to a preferred embodiment of the present invention, the promoter has a nucleotide sequence according to SEQ ID NO. 1 or SEQ ID NO. 17 or SEQ ID NO. 18, preferably SEQ ID NO. 1 or SEQ ID NO. 18. Likewise, according to a preferred embodiment of the present invention, the promoter has a nucleic acid sequence having at least 85%, in particular at least 90%, preferably at least 95% identity to SEQ ID NO. 1 or SEQ ID NO. 17 or SEQ ID NO. 18, preferably SEQ ID NO. 1 or SEQ ID NO. 18.

A preferred promoter sequence contained in the expression cassette according to the present invention is derived from the gene, in particular the promoter, of human Elongation Factor-1 alpha (EF1a). The constitutively active promoter fragment of human origin further contains a sequence optimized first intron, which has been considerably shortened. Furthermore, a cryptic splice site contained in the native nucleotide sequence has been deleted. The promoter according to SEQ ID NO. 1 or SEQ ID NO. 18 leads to a stable and highly efficient expression of the coding sequence in mammalian cells, in particular in liver cells. With respect to the expression directed by this promoter fragment, reference is also made to the working examples performed by the applicant.

A preferred design of the coding sequence contained in the nucleic acid expression cassette according to the present invention is delineated in the following:

With respect to an improvement of the expression of the coding sequence, according to a preferred embodiment it is intended that the nucleic acid sequence of the coding sequence is codon-optimized for human gene expression and/or human codon usage. The introduction of synonymous mutations, i.e. mutations that lead to the same translational product, leads to an efficiency enhancement of the protein expression. On the basis of a replacement of rare codons with preferred codons, the expression of the coding sequence and the production of the target protein in the target cells can be further improved.

With respect to the selection of the coding sequence, according to a preferred embodiment of the present invention, the coding sequence has a nucleic acid sequence coding for a liver-specific and/or liver-expressed protein selected from proteins produced and/or expressed in the liver. As delineated before, the production and secretion of proteins belong to the main functions of the liver. The proteins produced and secreted by the liver in particular include proteins involved in hemostasis, i.e. proteins regulating blood clotting. Mutations in genes coding for liver-specific and/or liver-expressed proteins can lead to a reduced or completely lacking production of the protein. Furthermore, mutations can result in the production of defective proteins, i.e. proteins that lost their physiological functionality (so called loss-of-function-mutation).

According to a preferred embodiment of the present invention, the coding sequence has a nucleic acid sequence coding for a human liver-specific and/or liver-expressed protein selected from the group of:
  (i) major plasma proteins, in particular human serum albumin, alpha-fetoprotein, soluble plasma fibronectin, C-reactive protein and/or preferably physiologically active domains and/or fragments thereof;
  (ii) stimulators and/or factors for coagulation, preferably coagulation factor FVII, FVIII, FIX, FX, FXI, FXII, FXIII and/or preferably physiologically active domains and/or fragments thereof, preferably FVIII, FIX and/or preferably physiologically active domains and/or fragments thereof;
  (iii) inhibitors of coagulation, preferably alpha2-macroglobulin, alpha1-antitrypsin, antithrombin III, protein S, protein C and/or preferably physiologically active domains and/or fragments thereof;

(iv) stimulators of fibrinolysis, preferably plasminogen and/or preferably physiologically active domains and/or fragments thereof; and/or (v) inhibitors of fibrinolysis, preferably alpha2-antiplasmin and/or preferably physiologically active domains and/or fragments thereof; and/or (vi) proteins of the amino acid metabolism, in particular fumarylacetoacetate hydrolase, p-hydroxyphenylpyruvate hydroxylase and/or phenylalanine-4-hydroxylase; and/or (vii) antiproteases, in particular alpha-1 antitrypsin; and/or (viii) proteins of the bilirubin metabolism, in particular uridine diphospho-glucuronosyltransferase; and/or (ix) proteins of the urea cycle, in particular arginase, argininosuccinate synthase and/or ornithine transcarbamylase; and/or (x) proteins of the carbohydrate metabolism, in particular alpha-glucan phosphorylase, amylo-1,6-glucosidase and/or glucose-6-phosphatase; and/or (xi) proteins of the proteoglycan metabolism, in particular idursulfase; and/or (xii) proteins of the sphingolipid metabolism, in particular glucocerebrosidase; and/or (xiii) proteins involved in transport processes, in particular p-type ATPase, cystic fibrosis transmembrane regulator and/or low-density lipoprotein (LDL) receptor; and/or (xiv) proteins involved in lipometabolism and/or proteins linked with monogenetic lipometabolic disorders.

In particular, mutations in genes coding for coagulation factors are associated with genetic disorders, which are commonly summed up as hemophilia, in particular hemophilia A (factor FVIII deficiency), hemophilia B (factor FIX deficiency), von Willebrand disease (von Willebrand factor deficiency) and the rare factor deficiencies including deficiencies in factor FI, FII, FV, FVII, FX, FXI, FXII and/or FXIII. The expression cassette according to the present invention can be used to transfer an intact copy of the genes coding for coagulation factors into the target cells, in particular liver cells. On this basis, the physiological deficiency with respect to respective coagulation factor can be balanced and/or improved through the stable expression of the coding sequence in the target cells, in particular liver cells.

It is especially preferred when the coding sequence has a nucleic acid sequence coding for a coagulation factor, in particular coagulation factor FVII, FVIII, FIX, FX, FXI, FXII, FXIII and/or preferably physiologically active domains and/or fragments thereof, preferably coagulation factor FVIII, FIX and/or preferably physiologically active domains and/or fragments thereof.

More particularly preferred is an embodiment of the present invention, wherein the coding sequence has a nucleic acid sequence coding for coagulation factor FVIII and/or preferably physiologically active domains and/or fragments thereof. In hemostasis, factor FVIII functions as cofactor for factor FIXa, which is necessary for the formation of factor FX. Mutations, in particular loss-of-function-mutations, in the gene coding for factor FVIII are linked with hemophilia A.

According to a particularly preferred embodiment of the present invention, the coding sequence has a nucleic acid sequence coding for coagulation factor FVIII with a deleted B-domain. The native FVIII protein has a total length of 2.351 amino acids with the so-called B-domain constituting of 911 amino acids. The B-domain is a highly glycosylated region of the protein but is not required for the physiological procoagulation activity of FVIII. On the basis of the deletion of the B-domain and the replacement of the B-domain by a short 14 amino acid linker, a fully functional fragment of FVIII can be provided which shows—due to the reduction of the length—an improved expression in the target cells.

Therefore, according to a further preferred embodiment in this context, the coding sequence has a nucleic acid sequence coding for coagulation factor FVIII with a deleted B-domain, wherein the nucleic acid sequence coding for the B-domain of coagulation factor FVIII is replaced by a nucleic acid sequence according to SEQ ID NO. 9 and/or SEQ ID NO. 20 and/or a nucleic acid sequence having at least 85%, in particular at least 90%, preferably at least 95% identity with SEQ ID NO. 9 and/or SEQ ID NO. 20. Likewise, the coding sequence has a nucleic acid sequence coding for coagulation factor FVIII with a deleted B-domain, in particular wherein the B-domain of coagulation factor FVIII is replaced by an amino acid according to SEQ ID NO. 10 and/or an amino acid sequence having at least 85%, in particular at least 90%, preferably at least 95% identity with SEQ ID NO. 10.

With respect to an expression cassette comprising a coding sequence for the expression of a protein, which carries out the physiological functions of coagulation factor FVIII, according to a preferred embodiment of the present invention the coding sequence contains a nucleic acid sequence according to SEQ ID NO. 2 and/or SEQ ID NO. 19 and/or a nucleic acid sequence having at least 85%, in particular at least 90%, preferably at least 95% identity with SEQ ID NO. 2 and/or SEQ ID NO. 19. Likewise, the coding sequence has a nucleic acid sequence corresponding to the nucleic acid sequence of the native cDNA coding for human coagulation factor FVIII and/or the coding sequence codes for a protein having an amino acid sequence according to SEQ ID NO. 3 and/or an amino acid sequence having at least 85%, in particular at least 90%, preferably at least 95% identity with SEQ ID NO. 3.

According to a likewise preferred embodiment of the present invention, the coding sequence has a nucleic acid sequence coding for coagulation factor FIX and/or preferably physiologically active domains and/or fragments thereof. The physiological function of factor FIX is, together with $Ca^{2+}$, membrane phospholipids and a factor FVIII cofactor, the formation of factor FX. Mutations, especially loss-of-function-mutations, in the gene coding for coagulation factor FIX result in hemophilia B. An expression cassette comprising a nucleic acid sequence coding for coagulation factor FIX is therefore suitable for the use in a gene therapy for the treatment of hemophilia B in order to balance the loss of function caused by the mutation.

With respect to an expression cassette comprising a coding sequence for the expression of a protein, which carries out the physiological functions of coagulation factor FIX, according to a preferred embodiment the coding sequence has a nucleic acid sequence containing a nucleic acid sequence according to SEQ ID NO. 4 or SEQ ID NO. 5 or SEQ ID NO. 28 and/or a nucleic acid sequence having at least 85%, in particular at least 90%, preferably at least 95% identity with SEQ ID NO. 4 or SEQ ID NO. 5 or SEQ ID NO. 28. Likewise, the coding sequence can have a nucleic acid sequence corresponding to the nucleic acid sequence of the native cDNA coding for human coagulation factor FIX. Furthermore, according to another embodiment of the present invention, the coding sequence codes for a protein having an amino acid sequence according to SEQ ID NO. 23 or SEQ ID NO. 24 and/or an amino acid sequence having at least 85%, in particular at least 90%, preferably at least 95% identity with SEQ ID NO. 23 or SEQ ID NO. 24.

According to a further preferred embodiment of the present invention, the coding sequence has a nucleic acid sequence coding for a fusion protein on the basis of a coagulation factor and/or preferably physiologically active domains and/or fragments thereof, in particular coagulation factor FVIII and/or FIX, preferably coagulation factor FIX, and an albumin and/or domains and/or fragments thereof. On the basis of a fusion of coagulation factors to albumin, the pharmacokinetic properties of the coagulation factors can be significantly improved. In particular, coagulation factors on the basis of fusions with albumin comprise an extended half-life time. On this basis, the treatment intervals of the patients suffering from monogenetic disorders, in particular hemophilia, can be prolonged, i.e. a less frequent dosing is enabled.

In this context, according to a preferred embodiment of the present invention, the nucleic acid sequence coding for an albumin and/or domains and/or fragments thereof has a nucleic acid sequence according to SEQ ID NO. 8 and/or a nucleic acid sequence having at least 85%, in particular at least 90%, preferably at least 95% identity with SEQ ID NO. 8. Likewise, the nucleic acid sequence coding for an albumin and/or domains and/or fragments thereof codes for a protein having an amino acid sequence according to SEQ ID NO. 27 and/or an amino acid sequence having at least 85%, in particular 90%, preferably at least 95% identity with SEQ ID NO. 27.

With respect to an embodiment on the basis of a coding sequence coding for a fusion protein on the basis of coagulation factor FIX and albumin, the coding sequence has a nucleic acid sequence according to SEQ ID NO. 6 or SEQ ID NO. 7 and/or a nucleic acid sequence having at least 85%, in particular at least 90%, preferably at least 95% identity with SEQ ID NO. 6 or SEQ ID NO. 7. Likewise, the coding sequence coding for a fusion protein on the basis of coagulation factor FIX and albumin can code for a protein having an amino acid sequence according to SEQ ID NO. 25 or SEQ ID NO. 26 and/or an amino acid sequence having at least 85%, in particular at least 90%, preferably at least 95% identity with SEQ ID NO. 25 or SEQ ID NO. 26.

According to a very preferred embodiment of the present invention, the coding sequence comprises a nucleic acid sequence according to SEQ ID NO. 2, SEQ ID NO. 4, SEQ ID NO. 5, SEQ ID NO. 6, SEQ ID NO. 7, SEQ ID NO. 19 and/or SEQ ID NO. 28 and/or a nucleic acid sequence having at least 85%, in particular at least 90%, preferably at least 95% identity with SEQ ID NO. 2, SEQ ID NO. 4, SEQ ID NO. 5, SEQ ID NO. 6, SEQ ID NO. 7, SEQ ID NO. 19 and/or SEQ ID NO. 28. Likewise, the coding sequence can code for a protein having an amino acid sequence according to SEQ ID NO. 3, SEQ ID NO. 23, SEQ ID NO. 24, SEQ ID NO. 25 or SEQ ID NO. 26 and/or an amino acid sequence having at least 85%, in particular at least 90%, preferably at least 95% identity with SEQ ID NO. 3, SEQ ID NO. 23, SEQ ID NO. 24, SEQ ID NO. 25 or SEQ ID NO. 26.

Nevertheless, the list of coding sequences is not exhaustive, since the nucleic acid sequences coding for any liver-specific and/or liver-expressed protein associated with a monogenetic disorder can be integrated into the nucleic acid expression cassette according to the present invention.

As delineated before, in order to overcome the main problem or risk of conventional gene therapy, namely an insertion of the transferred nucleic acid molecules into the genome or the genomic DNA of the target cells, applicant has surprisingly found out that the episomal persistence of the nucleic acid expression cassette according to the present invention in the target cells can be improved or ensured, respectively, on the basis of a scaffold/matrix attachment region in the expression cassette. In this context, particularly goods results can be achieved when the nucleic acid sequence of the scaffold/matrix attachment region is derived from the gene coding for human Interferon-beta (IFN-beta), in particular derived from the 5' region of the gene coding for human Interferon-beta.

With respect to the episomal persistence of the nucleic acid expression cassette, reference is made to the working examples performed by the applicant, which are an indicator for the episomal persistence on the basis of a scaffold/matrix attachment region derived from human Interferon-beta in liver cells, in particular malignant liver cells.

In this context, it is especially preferred when the nucleic acid sequence of a human scaffold/matrix attachment region has a nucleic acid sequence according to SEQ ID NO. 11 or SEQ ID NO. 12, in particular SEQ ID NO. 11. Likewise, the use of a nucleic acid sequence having at least 85%, in particular at least 90%, preferably at least 95% identity with SEQ ID NO. 11 or SEQ ID NO. 12, in particular SEQ ID NO. 11, is used. The working examples performed by the applicant show that both variants of the scaffold/matrix attachment region are suitable in order to ensure an episomal persistence of the transgenic nucleic acid molecules. Particularly good results could be achieved with the shortened variant of the scaffold/matrix attachment region according to SEQ ID NO. 11.

Furthermore, in order to interrupt and/or end transcription, it is preferred when the transcriptional termination signal is a polyadenylation signal, especially the SV40 transcriptional termination signal or derived from the SV40 transcriptional termination signal. Even though it is preferred and/or intended that the expression cassette does not contain viral components or elements, in particular nucleic acid sequences coding for viral proteins, an exception can be made with respect to the termination signal, since the SV40 terminator is substantially free from negative side effects when used in gene therapy.

In order to further stabilize the expression level of the coding sequence, according to a preferred embodiment of the present invention, the expression cassette can comprise a Ubiquitous Chromatin-Opening Element (UCOE). On the basis of a UCOE, the expression of the coding sequence in the target cells can be further improved through the effects of the UCOE on the structure and/or state of chromatin. In particular, the use of a UCOE prevents transcriptional silencing of the coding sequence and therefore leads to a consistent, stable and high-level gene expression irrespective of the attachment position or location of the transferred nucleic acid molecule in the chromosome and/or chromatin and/or vector. In particular, on the basis of UCOE sequences, a transcriptionally active open chromatin environment can be created, enabling the stable and high-level transcription of the coding sequence.

With respect to an embodiment of the present invention with an UCO E, it is preferred when the expression cassette further comprises a nucleic acid sequence derived from the promoter of the gene coding for human Chromobox Protein Homolog 3 (CBX3) as well as a respective transcript and/or a nucleic acid sequence derived from the promoter of the gene coding for human Heterogeneous Nuclear Ribonucleo-protein A2 (HNRNPA2) as well as a respective transcript. According to a preferred embodiment, the nucleic acid sequence derived from the promoter of the gene coding for human Heterogeneous Nuclear Ribonucleoprotein A2 (HNRNPA2) as well as the respective transcript are arranged and/or oriented in reverse orientation. Furthermore, the UCOE may comprise an enhancer region. Preferably, the expression cassette further comprises nucleic acid sequences building a Ubiquitous Chromatin-Opening Element (UCOE).

In particular, with respect to a UCOE, the expression cassette further comprises nucleic acid sequences having a nucleic acid sequence according to SEQ ID NO. 13 and/or SEQ ID NO. 14 and/or SEQ ID NO. 15 and/or SEQ ID NO. 16 and/or SEQ ID NO. 21 and/or a nucleic acid sequence having at least 85%, in particular at least 90%, preferably at least 95% identity with SEQ ID NO. 13 and/or SEQ ID NO. 14 and/or SEQ ID NO. 15 and/or SEQ ID NO. 16 and/or SEQ ID NO. 21, especially wherein the sequences function as Ubiquitous Chromatin-Opening Element (UCOE).

In this context, the use of a UCOE on the basis of a nucleic acid sequence derived from the promoter of human CBX3 (SEQ ID NO. 13) and a respective transcript (SEQ ID NO. 14), a nucleic acid sequence derived from the promoter of human HNRNPA2 (SEQ ID NO. 15) and a respective transcript (SEQ ID NO. 16) and an enhancer region (SEQ ID NO. 21) is preferred. Likewise, nucleic acid sequences having at least 85%, in particular at least 90%, preferably at least 95% identity with the SEQ ID NO. 13 and/or SEQ ID NO. 14 and/or SEQ ID NO. 15 and/or SEQ ID NO. 16 and/or SEQ ID NO. 21 are preferred as Ubiquitous Chromatin-Opening Element (UCOE).

Furthermore, the expression cassette may comprise as UCOE a nucleic acid sequence having a nucleic acid sequence according to SEQ ID NO. 22 and/or a nucleic acid sequence having at least 85%, in particular at least 90%, preferably at least 95% identity with SEQ ID NO. 22. The nucleotide sequence according to SEQ ID NO. 22 is based on a promoter derived from the gene coding for human Chromobox Protein Homolog 3 (CBX3) as well as a respective transcript, a nucleic acid sequence derived from the promoter of the gene coding for human Heterogeneous Nuclear Ribonucleoprotein A2 (HNRNPA2) as well as the respective transcript and an enhancer region.

The position and/or location of the Ubiquitous Chromatin-Opening Element in the nucleic acid expression cassette according to the present invention is variable. In particular, with respect to an enhancement of the expression of the coding sequence it is preferred when the Ubiquitous Chromatin-Opening Element (UCOE), in particular the further nucleic acid sequences as described in context with the formation of a Ubiquitous Chromatin-Opening Element are located 3' to the promoter or 5' to the promoter, preferably 5' to the promoter. Furthermore it is preferred when the further nucleic acid sequences are located 3' to the coding sequence or 5' to the coding sequence, preferably 5' to the coding sequence. Likewise, the further nucleic acid sequences can be located 3' to the nucleic acid sequence derived from the scaffold/matrix attachment region of a eukaryotic gene or 5' to the nucleic acid sequence derived from the scaffold/matrix attachment region of a eukaryotic gene, preferably 5' to the nucleic acid sequence derived from the scaffold/matrix attachment region of a eukaryotic gene. The best results with respect to an enhancement of the expression are achieved when the further nucleic acid sequences, in particular for the formation of a UCOE, are located 5' and/or upstream to the promoter derived from a eukaryotic gene.

With respect to the use of expression cassettes according to the present invention, in particular the use in the treatment of a monogenetic disorder resulting from a mutation in a gene coding for a liver-specific and/or liver-expressed protein can be intended. On the basis of the expression cassette according to the present invention, an intact copy of the mutated gene can be transferred into the target cells. The episomal persistence of the transferred nucleic acid molecules can be ensured by the use of a S/MAR element, avoiding an integration of the transferred nucleic acid molecule into the genome or the genomic DNA of the target cells on the basis of an attachment of the transferred nucleic acid molecules to the nuclear matrix. Therefore, with expression cassettes as described, the risk of mutagenesis by the gene therapy is significantly reduced. Furthermore, the elements of the expression cassette according to the present invention enable a stable and highly efficient expression of the coding sequence.

In particular, the expression cassette according to the present invention is suitable for the treatment of monogenetic disorders, particularly but not exclusively associated with an impaired and/or reduced hemostasis and/or blood clotting, especially wherein the disorder is a hemophilia, in particular hemophilia A and/or hemophilia B. Furthermore, the expression cassette according to the present invention is suitable for the treatment of monogenetic lipometabolic disorders.

Furthermore, subject-matter of the present invention—according to a second aspect of the present invention—is the use of an expression cassette as described before, in the treatment of a monogenetic disorder resulting from a mutation in a gene coding for a liver-specific and/or liver-expressed protein and/or for the preparation of a medicament for the treatment of a monogenetic disorder resulting from a mutation in a gene coding for a liver-specific and/or liver-expressed protein.

With respect to the term "medicament", synonymously the terms "drug", "pharmaceutical drug" and/or "agent" can be used. In context with the present invention, the aforementioned terms particularly relate to a drug used to diagnose, cure, treat or prevent diseases.

In particular, the monogenetic disorder is associated with an impaired and/or reduced hemostasis and/or blood clotting, especially wherein the disorder is a hemophilia, in particular hemophilia A and/or hemophilia B.

For further details concerning this aspect of the invention, reference can be made to the above explanations in relation to the first inventive aspect, referring to the nucleic acid expression cassette according to the present invention, said explanations also applying accordingly with regard to this aspect of the invention.

Furthermore, subject-matter of the present invention is—according to a third aspect of the present invention—a vector, which comprises an expression cassette as described before.

The vector according to the present invention is a suitable vehicle for gene therapy, which can be used for the transfer of the expression cassette as described before into the target cells.

Advantages embodiments of the vector according to the present invention are delineated in the following.

In particular, it can be intended that the vector according to the present invention is a minicircle and/or a vector that is at least 90% free from nucleic acids of viral and/or prokaryotic origin and/or that the vector is a circular vector. Free from nucleic acid sequence of prokaryotic and/or viral origin means in this context that the vector does not contain nucleic acid sequences of prokaryotic or viral origin coding for viral or prokaryotic proteins, in particular viral envelope proteins, that might trigger an immunological reaction in the target cells. In particular, the vector according to the present invention does not—unlike lentiviral vector systems—integrate into the genome and/or genomic DNA of the target cells. According to a preferred embodiment of the present invention, the vector is a non-viral vector.

On the basis of a circular vector without nucleic acids of viral and/or prokaryotic origin, the immune compatibility of the nucleic acid molecules transferred into the target cells can be improved. In particular, nucleic acid sequences of viral origin, for example proteins of the viral envelope, can induce immunological reactions in the patient body, resulting in a recognition and/or an attack of the modified cells by the immune system.

Furthermore, a long-term persistence of antibodies against proteins expressed on the basis of viral nucleic acid sequences can lead to immunity against the respective therapeutic concepts on the basis of the specific viral system. On the basis of the provision of a substantially non-viral vector (with the exception of the SV40 termination signal) according to the present invention, the respective problems known from the prior art and particularly from current genetic approaches for the treatment of monogenetic disorders, in particular hemophilia A and B, are overcome.

In particular, the vector according to the present invention is suitable for the use in the treatment of a monogenetic disorder resulting from a mutation in a gene coding for a liver-specific and/or liver-expressed protein.

According to a preferred embodiment, the monogenetic disorder is associated with an impaired and/or reduced hemostasis and/or blood clotting, especially wherein the disorder is a hemophilia, in particular hemophilia A and/or hemophilia B.

For further details concerning this aspect of the present invention, reference can be made to the above explanations in relation to the above described aspects of the present invention, in particular the first aspect relating to the expression cassette according to the present invention, said explanations also applying accordingly with regard to this aspect to the invention.

Another aspect of the present invention is—according to a fourth aspect of the present invention—the use of a vector as described before in the treatment of a monogenetic disorder resulting from a mutation in a gene coding for a liver-specific and/or liver-expressed protein and/or for the preparation of a medicament for the treatment of a monogenetic disorder resulting from a mutation in a gene coding for a liver-specific and/or liver-expressed protein.

In particular, according to a preferred embodiment of this aspect of the present invention, the monogenetic disorder is associated with an impaired and/or reduced hemostasis and/or blood clotting, especially wherein the disorder is a hemophilia, in particular hemophilia A and/or hemophilia B.

For further details concerning this aspect of the invention, reference can be made to the above explanations in relation to the further aspects, said explanations also applying accordingly with regard to this aspect of the invention.

Furthermore, subject-matter of the present invention is—according to a fifth aspect of the present invention—a nanoparticle-based delivery system for a coding sequence, in particular for the expression of a liver-specific and/or liver-expressed protein and/or preferably physiologically active domains and/or fragments thereof in a patient suffering from a monogenetic disorder caused by a mutation in the gene coding for the liver-specific and/or liver-expressed protein, wherein the delivery system comprises:

(a) gold nanoparticles, preferably ligand-free gold nanoparticles;
(b) polyethylenimine and/or derivatives and/or salts thereof; and
(c) nucleic acid molecules comprising (i) a promoter, preferably a promoter directing gene expression in mammalian, especially human cells; (ii) a coding sequence containing a nucleic acid sequence coding for a liver-specific and/or liver-expressed protein and/or preferably physiologically active domains and/or fragments thereof, wherein mutations in the nucleic acid sequence coding for the liver-specific and/or liver-expressed protein are associated with a monogenetic disorder; (iii) a nucleic acid sequence derived from the scaffold/matrix attachment region of a eukaryotic, preferably human gene; and (iv) a transcriptional termination signal.

On the basis of the present invention, a preferably non-viral gold nanoparticle-based gene transfer and/or delivery system has been established.

According to the present invention, the term "nanoparticle" refers to particles having an average particle diameter between 1 and 100 nm. Nanoparticles according to the present invention are based on inorganic material, preferably ligand-free gold. Nanoparticles of this kind are particularly suitable for medical purposes, especially for the transfer and/or delivery of nucleic acid molecules, since they are substantially chemically inert. Surprisingly, on the basis of the present invention, gold nanoparticles have turned out as particularly well-suited carriers for nucleic acid molecules comprising nucleic acid sequences coding for liver-specific and/or liver-expressed proteins due to their non-toxicity and excellent biocompatibility, on the one hand, and their transfection efficiency, in particular with respect to liver cells, on the other hand. Gold nanoparticles are well tolerated in various mammals. After intravenous injection, they are preferably taken up by the liver and then excreted again via the bile.

The term "polyethylenimine", synonymous also "PEI", "poly[imino(1,2-ethanediyl)]" a "polyaziridine", as used according to the present invention, especially refers to a polycationic polymer with repeating units of an amine group and two carbon aliphatic $CH_2CH_2$ as a spacer between the repeating units of the amine groups. The chemical name of this polymer according to IUPAC is poly(iminoethylene). Linear polyethylenimines contain all secondary amines, wherein branched polyethylenimines contain primary, secondary and tertiary amino groups. Polyethylenimine was one of the first discovered transfection agents. When used as transfection agent—without being bound to this theory—, polyethylenimine condenses DNA into positively charged particles, which bind to anionic cell surface residues. The complex on the basis of DNA and polyethylenimine is then brought into the cell via endocytosis. Subsequently, the polyethylenimine causes an influx of water molecules into the endosomes, resulting in a bursting of the endosomes and a release of the DNA into the cytoplasm. According to the present invention, it was surprisingly found that polyethylenimines are not only suitable for the mediation of transfection as such, but also as a ligand for gold nanoparticles in order to build a gold nanoparticle/PEI/DNA complex. With respect to further information concerning polyethylenimine, reference is made to the encyclopedia RÖMPP Chemielexikon, 1999, $10^{th}$ edition, Georg Thieme Verlag Stuttgart, N.Y., page 3448, key word "polyethylenimine".

Examples for variants of polyethylenimine for the delivery system according to the present invention are commercially available from Sigma-Aldrich Chemie GmbH, Munich, DE (branched PEI, 25 kDa), Polysciences Inc., Warrington, US (linear PEI, 10 kDa; linear PEI, 25 kDa) and/or Polyplus Inc., Illkirch, FR (jetPEI™, linear PEI).

The nanoparticle-based delivery system for a coding sequence is linked with several advantages, as delineated in the following:

The delivery system of the present invention is suitable for the preparation of a user-friendly drug for simple intravenous administration in the patients. In this context, the delivery system is designed to eliminate potential risks or safety considerations of conventional gene transfer and/or delivery systems, in particular virus-based transfer and/or delivery systems, for example on the basis of AAV-systems. In particular—and unlike for example lentiviral vectors—the delivery system according to the present invention is not linked with an integration of the coding sequence into the genome of the patient.

Furthermore, the nucleic acid expression cassette and/or the vector according to the present invention, which are preferably used in the delivery system of the present invention, are optimized for human application and human codon usage and express a coding sequence which codes for at least one protein usually produced and/or secreted in and/or by the liver, preferably a protein involved in hemostasis, in particular a factor for coagulation.

In particular, a modular design of the nanoparticle-based delivery system for a coding sequence can be intended. According to an advantageous embodiment of this aspect, the nanoparticle-based delivery system comprises a core on the basis of gold nanoparticles, in particular linear polyethylenimine as the transfection ligand and/or reagent, and the nucleic acid molecules comprising a nucleic acid sequence coding for a liver-specific and/or liver-expressed protein and/or domains and/or fragments thereof. The delivery system of the present invention shows by nature a high specificity for the liver, in particular liver cells, for example hepatocytes.

The nanoparticle-based delivery system according to the present invention is linked with the advantage of non-immunogenicity. In contrast to gene transfer systems known from the prior art, in particular gene and/or nucleic acid transfer systems on the basis of adeno-associated virus (AAV), the nanoparticle-based delivery system according to the present invention does not trigger or induce immunological reactions in the patient's body. Furthermore, gold nanoparticles are well tolerated by intravenous injection without problems and in vivo preferably taken up by the liver and then excreted again via the bile.

Furthermore, compared to biological products, for example antibodies and viruses, the nanoparticle-based delivery system according to the present invention can be produced relatively inexpensive on an industrial scale with consistent quality and is thus economically advantageous.

The underlying mechanism of the nanoparticle-based delivery system according to the present invention—without being bound to this theory—is described in the following:

The binding of the nucleic acid molecules carrying the coding sequence to be expressed, in particular in the form of an expression cassette and/or a circular vector as described before, to the gold nanoparticle surfaces is mediated by derivatives and/or salts of polyethylenimine. Besides the function to bind the negatively charged nucleic acid molecules to the also negatively charged gold nanoparticles, the polyethylenimine mediates the transfer of the nucleic acid molecules into the cells. The uptake of the loaded gold nanoparticles into the cells presumably occurs by clathrin- and caveolin-mediated endocytosis. In this context, the polyethylenimine prevents the nucleic acid molecules to be destroyed and degraded in endosomes and/or lysosomes by acidification. Instead, polyethylenimine is thought to cause the water molecules to flow into the endosomes causing the endosomes to burst (so called "proton-sponge effect"). As a result, the nucleic acid molecules are released into the cytoplasm prior to acidification of the endosomes.

The nuclear import of the nucleic acid molecules then occurs passively during cell division after dissolution of the nuclear membrane or actively in non-dividing cells via a sequence-specific import pathway. In the nucleus, the nucleic acid molecules bind to the nuclear matrix where it is then replicated. In particular, the binding of the nucleic acid molecules to the nuclear matrix is mediated by a nucleic acid sequence of a scaffold/matrix attachment region.

According to a preferred embodiment of the nanoparticle-based delivery system of to the present invention, the transport and/or the targeting of the nanoparticle-based delivery system can be further improved by the use of targeting units directing a delivery to the liver, in particular to liver cells and/or hepatocytes. In this context, the use of PreS1 peptide derived from hepatitis B virus or a domain or fragment thereof is advantageous. On the basis of a PreS1 peptide, preferably bound to the nanoparticle-based delivery system, a highly efficient targeting of the delivery system to liver cells, in particular hepatocytes, is achieved. Furthermore, the risk of non-specificity can be further reduced, since the sodium/bile acid cotransporter is specific for liver cells, in particular hepatocytes. The PreS1 peptide is further linked with an excellent compatibility when applied in humans. Overall, the coupling of the PreS1 peptide to the gold nanoparticles further improves an efficient and specific absorption of the nanoparticle-based delivery system into the liver cells.

According to another preferred embodiment of the present invention, an improved transport and/or targeting of the nanoparticle-based delivery system to the liver, in particular liver cells and/or hepatocytes, can be mediated by the use of agonists for galactose-specific membrane lectins, e.g. the asialo-glycoprotein receptor. Suitable agonists in this context are galactose and/or derivatives and/or residues thereof. In particular, a galactose-conjugated polyethylenimine can be used as a targeting agent.

Overall, according to the present invention, a nanoparticle-based delivery system has been established, which is suitable for the use in therapeutic concepts to correct disorders linked with a lack of physiologically functional proteins predominantly expressed in the liver. In particular, the nanoparticle-based delivery system can be used to correct an impaired and/or reduced hemostasis and/or blood clotting, especially hemophilia, preferably hemophilia A and/or B.

Preferred embodiments of the nanoparticle-based delivery system according to the present invention are delineated in the following:

It was surprisingly found by the applicant, that the use of gold-nanoparticles having a defined average particle diameter is linked with improved efficiency of the transfer a coding sequence and/or transfection efficiency. It is preferred when the gold nanoparticles have an average particle diameter $d_p$ [nm] in the range from 2 to 100 nm, in particular from 3 to 75 nm, especially from 4 to 60 nm, preferred from 4 to 30 nm, for example determined by means of analytical disc centrifugation and/or transmission electron microscopy and/or UV/VIS spectra.

In particular, the absorption efficiency of the gold nanoparticles by the cells can be significantly increased on the basis of the use of gold nanoparticles having the aforementioned size. Furthermore, a purposefully selection of a defined size or average particle diameter is relevant with respect to avoid the potential toxicity of gold nanoparticles. In particular, gold nanoparticles with a size below the aforementioned ranges behave different in cells leading to a certain toxicity. Gold nanoparticles having a size above the aforementioned ranges, however, are not able to penetrate the cell membrane and are therefore not suitable for a transfer of nucleic acid molecules. The use of gold nanoparticles having the aforementioned sizes leads to an efficiency enhancement with respect to the transfection efficiency, on the one hand, and a reduced, preferably non-existent toxicity—in other words an improved biocompatibility—with respect to the cells.

Further information with respect to the determination of the particle diameter of the gold nanoparticles on the basis of analytical disc centrifugation and/or transmission electron microscopy are evident from the scientific publication of Fissan et al.: "*Comparison of different characterization methods for nanoparticle dispersions before and after aerosolization*", published in Anal. Methods, 2014, 6: 7324-7334, the disclosure of which is hereby incorporated by reference. With respect to the determination of the particle diameter of the gold nanoparticles by UV/VIS spectra, further information are evident from the scientific publication of Haiss et al.: "*Determination of Size and Concentration of Gold Nanoparticles from UV-Vis Spectra*", published in Anal. Chem., 2007, 79(11), 4215-4221, wherein the disclosure of the publication, in particular with respect to the details of the determination methods, is hereby incorporated by reference.

With respect to the conjugation of the gold nanoparticles used for the nanoparticle-based delivery system of the present invention, it can be advantageous when the polyethylenimine and/or derivatives and/or salts thereof are bound to the gold nanoparticles, in particular covalently bound. According to a preferred embodiment of the present invention, the gold nanoparticles are coated with polyethylenimine and/or derivatives and/or salts thereof.

Suitable nanoparticles coated with polyethylenimine are commercially available, for example from Nanopartz™ Inc., Loveland, US, or from nanoComposix Inc., San Diego, US.

As delineated before, the polyethylenimine has several functions in the nanoparticle-based delivery system. On the one hand, the polymer binds the nucleic acid molecules to the gold nanoparticles surfaces and secures a stable binding of the nucleic acid molecules to be transferred. On the basis of the proton sponge effect, the polyethylenimine provides the basis for an efficient release of the nucleic acid molecules into the cytoplasm.

As it can be seen from the working examples performed by the applicant, various variants or derivatives of polyethylenimine are suitable for a use in the nanoparticle-based delivery system of the present invention. In particular, it is preferred when the polyethylenimine and/or derivatives and/or salts thereof are selected from the group of linear, branched and/or monosaccharide-conjugated polyethylenimines and/or derivatives and/or salts thereof, preferably linear polyethylenimines and/or monosaccharide-conjugated polyethylenimines and/or derivatives and/or salts thereof. The use of the aforementioned derivatives of polyethylenimine with gold nanoparticles is linked with high transfection efficiency and a stable binding of the nucleic acid molecules to be transferred. Furthermore, the aforementioned polyethylenimines and/or derivatives and/or salts thereof are linked with a size and concentration dependent insignificant toxicity with respect to the cells to be transferred.

According to a specific embodiment of the present invention, the monosaccharide-conjugated polyethylenimine is a galactose-conjugated polyethylenimine and/or derivatives and/or salts thereof. The use of a monosaccharide-conjugated polyethylenimine, in particular a galactose-conjugated polyethylenimine, is linked with an additional function of the polyethylenimine. For, on this basis a targeting of the nanoparticle-based delivery system is possible. In particular liver cells, especially hepatocytes, comprise in their membrane galactose specific cell surface receptors, for example galactose-specific membrane lectin. By the use of polyethylenimines conjugated with galactose, the delivery system can specifically bind to the respective receptors in the cell surface of liver cells, followed by an uptake of the conjugated gold nanoparticles, i. e. the delivery system according to the present invention, by the cells. On this basis, the specificity of the nanoparticle-based delivery system of the present invention can be further improved. Galactose-conjugated polyethylenimine is commercially available from Polyplus Inc., Illkirch, FR.

Furthermore, the transfection efficiency and compatibility of the delivery system according to the present invention can be further improved on the basis of the use of polyethylenimines and/or derivatives and/or salts thereof having a defined number average molecular weight ($M_n$). In particular it is preferred, when the polyethylenimine and/or derivatives and/or salts thereof have a number average molecular weight $M_n$, in the range from 10 Da to 200 kDa, in particular from 100 Da to 150 kDa, especially from 1 kDa to 100 kDa, particularly from 2 kDa to 50 kDa, preferably from 5 kDa to 40 kDa, more preferably from 8 kDa to 30 kDa, in particular determined according by means of gel permeation chromatography and/or according to DIN 55672-3:2016-03. In this context, reference is made to the working examples performed by the applicant which show that on a basis of the purposeful selection of polyethylenimine and/or derivatives and/or salts thereof having a certain molecular weight leads to an improved transfection efficiency as well as a reduced toxicity.

Furthermore, the transfer of nucleic acid molecules can be improved on the basis of a defined weight related ratio of polyethylenimine to nucleic acid molecules. In particular goods results are achieved, when the weight related ratio of polyethylenimine to nucleic acid molecules is in the range from 1:100 to 60:1, in particular from 1:50 to 40:1, especially from 1:30 to 20:1, preferably from 1:10 to 10:1, more preferred from 1:2 to 5:1. Likewise it is preferred, according to an advantageous embodiment of the present invention, when the weight related ratio of gold nanoparticles to nucleic acid molecules is in the range from 1:200 to 200:1, in particular from 1:100 to 100:1, especially from 1:50 to 95:1, preferably from 1:10 to 85:1, more preferred from 1:1 to 50:1, even further preferred from 2:1 to 30:1.

With respect to the weight related ratios of the components of the delivery system according to the present invention, reference is also made to the working examples performed by applicant, which show that paying attention to the weight related ratios leads to an improvement of the transfection efficiency and the resulting transfer of nucleic acid molecules into the target cells.

Furthermore, with respect to an efficient transfer of the nucleic acid molecules into the target cells, it is preferred when the nucleic acid molecules are bound to the gold nanoparticles by polyethylenimine and/or derivatives and/or salts thereof. As delineated before and without being bound to this theory, the polyethylenimine binds the negatively charged nucleic acid molecules to the also negative charged gold nanoparticles. Once the conjugated gold nanoparticles with the nucleic acid molecules bound thereto have been taken up by the cells in endosomes, polyethylenimine causes water molecules to flow into the endosomes causing the endosomes to burst. As a result, the nucleic acid molecules are released into the cytoplasm with subsequent nuclear import.

With respect to the nucleic acid molecules to be transferred it is preferred, when the nucleic acid molecules comprise and/or are selected from an expression cassette as described before, i. e. according to the first aspect of the present invention and/or a vector as described before, i.e. according to the third aspect of the present invention. The previous explanations with respect to the expression cassette and/or the vector according to the present invention self-evidently also apply with respect to the nanoparticle-based delivery system according to this aspect of the present invention.

With respect to a purposefully targeting, in particular with respect to an increase of the cell- and/or tissue specificity of the nanoparticle-based delivery system according to the present invention, it is preferred when the delivery system comprises an agonist for a cell surface receptor of liver cells, in particular hepatocytes. On this basis, a specific targeting of the delivery system to the liver after a preferably intravenous application of the delivery system to the patient can be achieved. In this context, it is especially preferred when the cell surface receptor is specific for liver cells, in particular hepatocytes. On this basis, a transfection of undesired cells can be avoided, which in turn leads to a reduced risk of side effects.

According to a preferred embodiment of the present invention, the cell surface receptor is a galactose-specific membrane lectin and/or a sodium/bile acid cotransporter, preferably a sodium/bile acid cotransporter. Liver cells, in particular hepatocytes, specifically feature an expression of galactose-specific membrane lectins and/or sodium/bile acid cotransporters. Galactose-specific membrane lectins specifically bind galactose and/or derivatives thereof. By the use of such agonists for galactose-specific membrane lectins, the delivery system according to the present invention can be purposefully targeted to liver cells, in particular hepatocytes. Furthermore, the sodium/bile acid cotransporter—also known as $Na^+$-taurocholate cotransporting peptide or liver bile acid transporter—is a protein that in humans is encoded by the SLC10A1 gene. Sodium/bile acid cotransporters are integral membranes glycoproteins, which are involved in the reabsorption of bile acids in the intestines. Sodium/bile acid cotransporters are specifically expressed in the basolateral membranes of hepatocytes. The use of agonists for sodium/bile acid cotransporter in the delivery system of the present invention results in a highly efficient targeting of the transfer of the nucleic acid molecules to the selected target cells.

According to a preferred embodiment of the present invention, the agonist for a cell surface receptor in liver cells is a preferably synthetic peptide derived from the PreS1 region of hepatitis B virus. The PreS1 Peptide is a peptide derived from hepatitis B virus, which binds to the receptor of the sodium/bile acid cotransporter. The peptide is available under the trade name MyrcludexB® from the MYR GmbH, Burgwedel, DE. On this basis, the specificity of the delivery system can be further improved. Additionally, the targeting and the transport of the delivery system to the liver can be further accelerated. For further information with respect to the PreS1 peptide, reference is also made to EP 1 281 761 B1, wherein the disclosure is incorporated herein by reference.

According to another embodiment of the present invention, the agonist binds to galactose-specific membrane lectins, in particular asialo-glyocprotein receptors (ASGR-R), especially wherein the agonist is galactose and/or a galactose residue and/or N-acetylgalactosamine and/or a N-acetylgalactosamine residue, preferably galactose and/or a galactose residue.

With respect to this embodiment, the agonists for galactose-specific membrane lectins in the delivery system of the present invention can be provided on the basis of a galactose-conjugated polyethylenimine, as described before in connection with the selection of the polyethylenimine.

The nanoparticle-based delivery system according to the present invention provides a promising therapeutic concept for the treatment of monogenetic disorders in order to introduce an intact copy of the mutated and/or deficient gene into the target cells for directing the expression of the protein the mutated gene codes for. In this context, the delivery system according to the present invention is intended for the use in the treatment of a monogenetic disorder resulting from a mutation in a gene coding for a liver-specific and/or liver-expressed protein.

In this context, the disorder is preferably associated with an impaired and/or reduced hemostasis and/or blood clotting, especially wherein the disorder is a hemophilia, in particular hemophilia A and/or hemophilia B.

A further subject of the present invention is—according to as ix t h aspect of the present invention—a method for preparing a delivery system as described before, wherein the method comprises the following method steps:

(a) preparation of gold nanoparticles comprising preferably covalently bound polyethylenimine and/or derivatives and/or salts thereof, in particular by coating of the gold nanoparticles with polyethylenimine and/or derivatives and/or salts thereof; subsequent (b) admixing the gold nanoparticles comprising preferably covalently bound polyethylenimine and/or derivatives and/or salts with nucleic acid molecules, in particular nucleic acid molecules comprising (i) a promoter, preferably a promoter directing gene expression in mammalian, especially human cells; (ii) a coding sequence containing a nucleic acid sequence coding for a liver-specific and/or liver-expressed protein and/or preferably physiologically active domains and/or fragments thereof, wherein mutations in the nucleic acid sequence coding for the liver-specific and/or liver-expressed protein are associated with a monogenetic disorder; (iii) a nucleic acid sequence derived from the scaffold/matrix attachment region of a eukaryotic gene; and (iv) a transcriptional termination signal.

For further details concerning this aspect of the invention, reference can be made to the above explanations in relation to the aspects outlined before, said explanations also applying accordingly with regard to this aspect of the present invention.

Also subject-matter of the present invention is—according to a seventh aspect of the present invention—the use of a delivery system according as described before in the treatment of a monogenetic disorder resulting from a mutation in a gene coding for a liver-specific and/or liver-expressed protein and/or for the preparation of a medicament for the treatment of a monogenetic disorder resulting from a mutation in a gene coding for a liver-specific and/or liver-expressed protein.

In particular, the monogenetic disorder is associated with an impaired and/or reduced hemostasis and/or blood clotting, especially wherein the disorder is a hemophilia, in particular hemophilia A and/or hemophilia B.

For further details concerning this aspect of the invention, reference can be made to the above explanations in relation to the aspects outlined before, said explanations also applying accordingly with regard to this aspect of the present invention.

Furthermore, the present invention relates—according to an eighth aspect of the present invention—to a composition, in particular pharmaceutical composition, preferably for the use in the treatment of a monogenetic disorder resulting from a mutation in a gene coding for a liver-specific and/or liver-expressed protein, comprising a delivery system according as described before and a pharmaceutically acceptable carrier.

The term "composition" as used according to the present invention particularly means a composition including a preferably pharmaceutical medicament, drug or agent. Likewise, the terms "formulation" or "dosage form" can be synonymously used.

According to a preferred embodiment of the composition according to the present invention, it is preferred when the composition is prepared for a systemic application, in particular an intravenous and/or oral, preferably systemic application.

For further details concerning this aspect of the invention, reference can be made to the above explanations in relation to the aspects outlined before, said explanations also applying accordingly with regard to this aspect of the present invention.

Likewise, the present invention relates—according to a ninth aspect of the present invention—to the use of a composition as described before in the treatment of a monogenetic disorder resulting from a mutation in a gene coding for a liver-specific and/or liver-expressed protein and/or for the preparation of a medicament for the treatment of a monogenetic disorder resulting from a mutation in a gene coding for a liver-specific and/or liver-expressed protein.

In this context it is preferred, when the monogenetic disorder is associated with an impaired and/or reduced hemostasis and/or blood clotting, especially wherein the disorder is a hemophilia, in particular hemophilia A and/or hemophilia B.

For further details concerning this aspect of the invention, reference can be made to the above explanations in relation to the aspects outlined before, said explanations also applying accordingly with regard to this aspect of the present invention.

Figure 13:
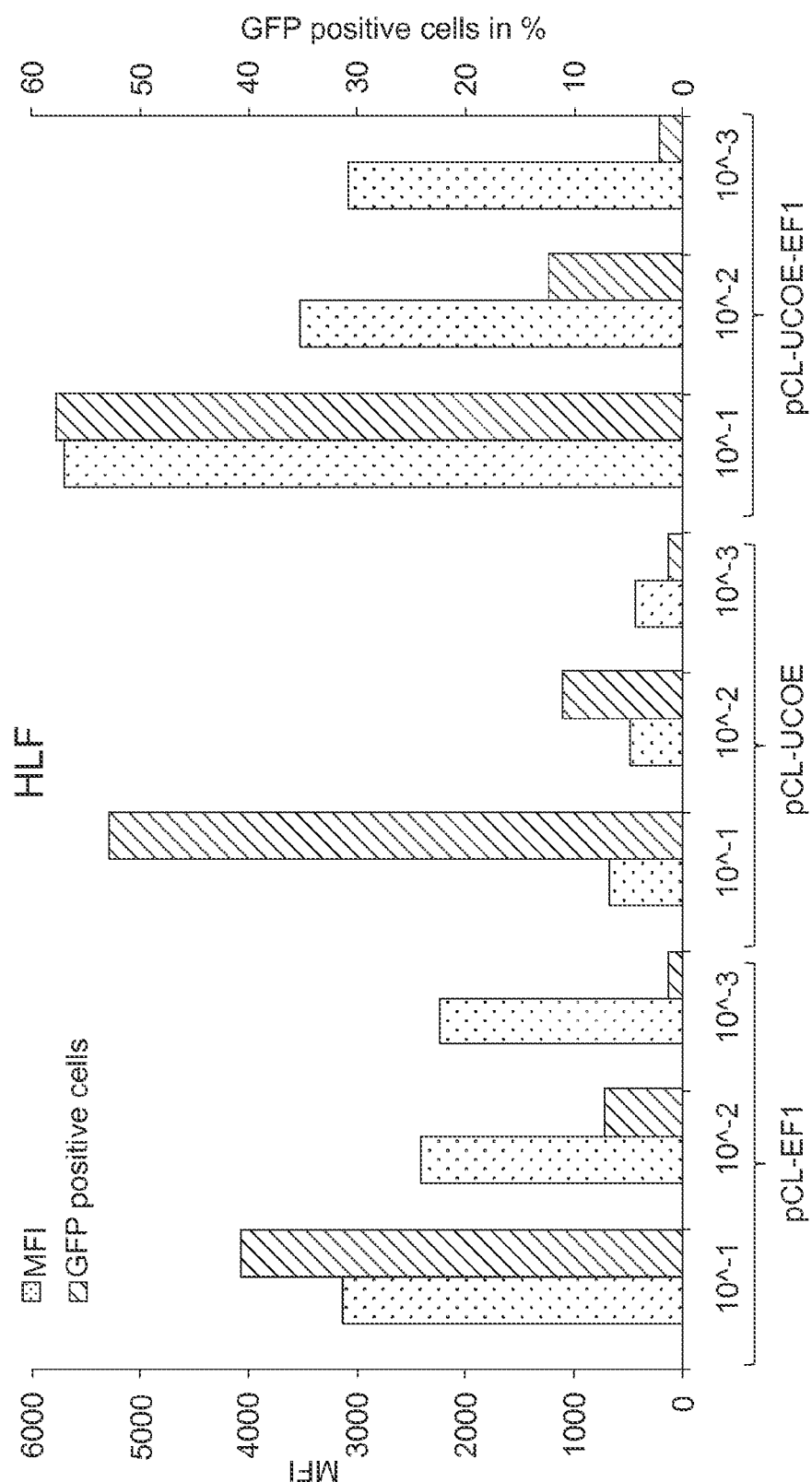
FIG. 13 shows the graphic representation of the results of in vivo studies in liver cancer cell line HLF with a lentiviral-based system, wherein the influence of the UCOE on the expression of eGFP was analyzed.
Figure 14:
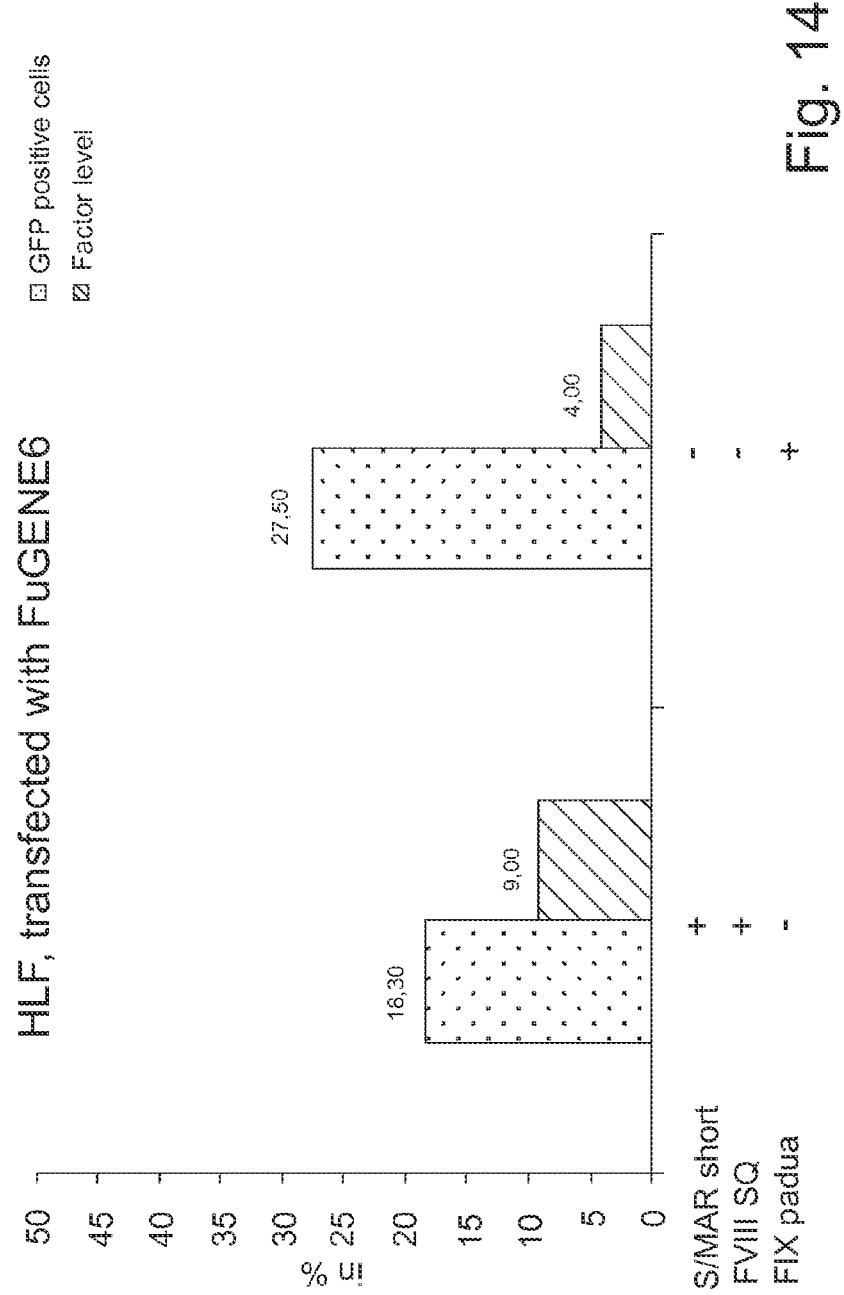
FIG. 14 shows the graphic representation of the results of the measurement of the factor level of HLF cells transfected with a coding sequence, which codes for a fusion protein of eGFP and factor FVIII SQ or factor FIX padua, respectively.
Figure 15:
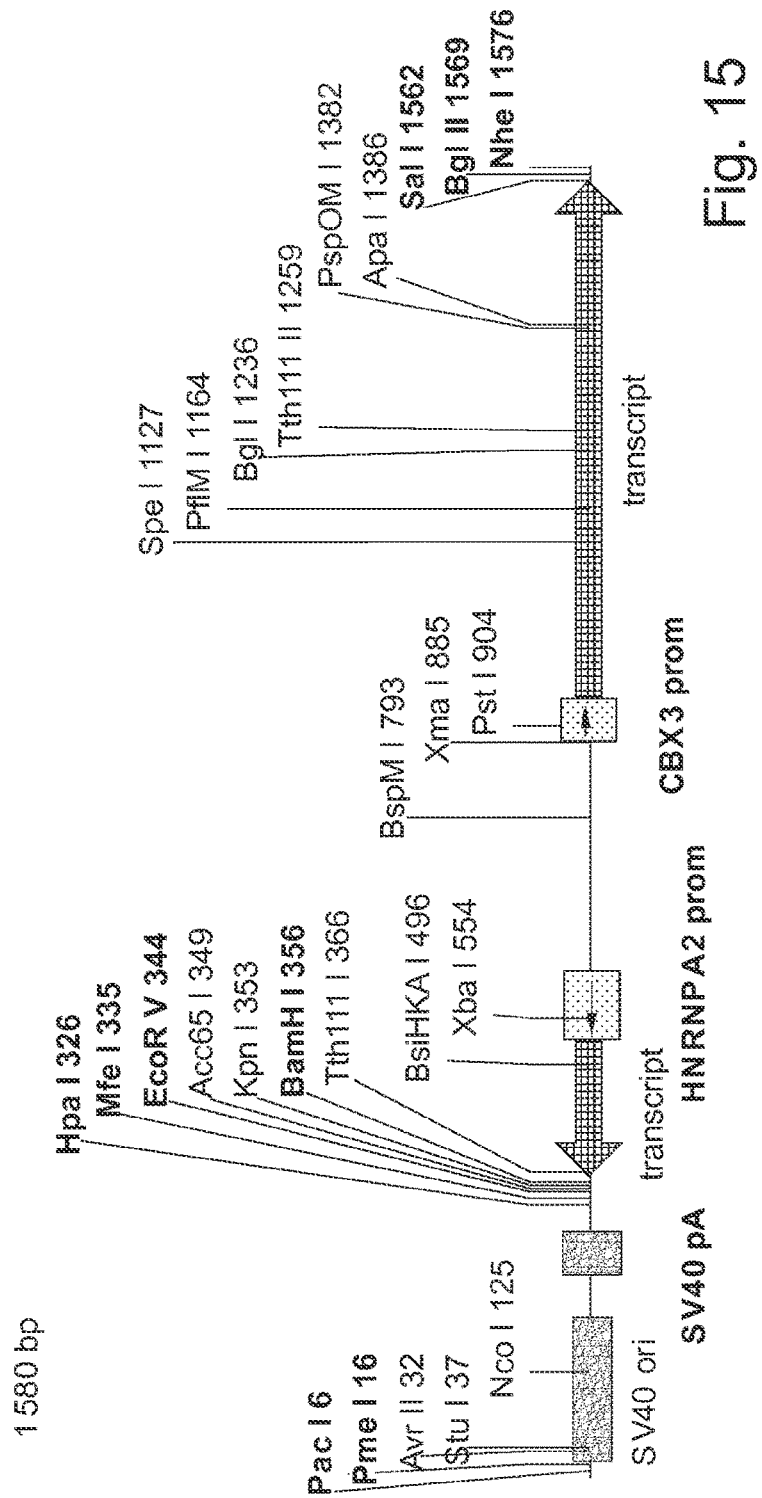
FIG. 15 shows a schematic representation of a preferred design of a UCOE used in expression cassettes according to the present invention.
Figure 16:
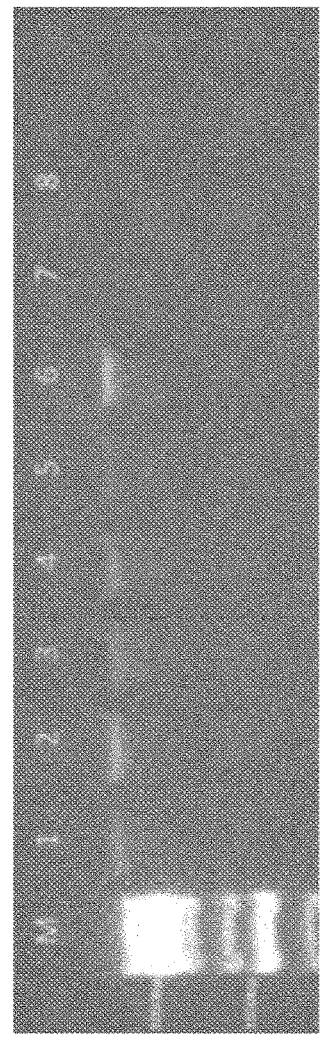
FIG. 16 shows the graphic representation of the results with respect to the episomal persistence of the vectors pEPI1-SM-L (FIG. 5A) and pEPI1-SM-S (FIG. 5B) in HLE cells.
Figure 21:
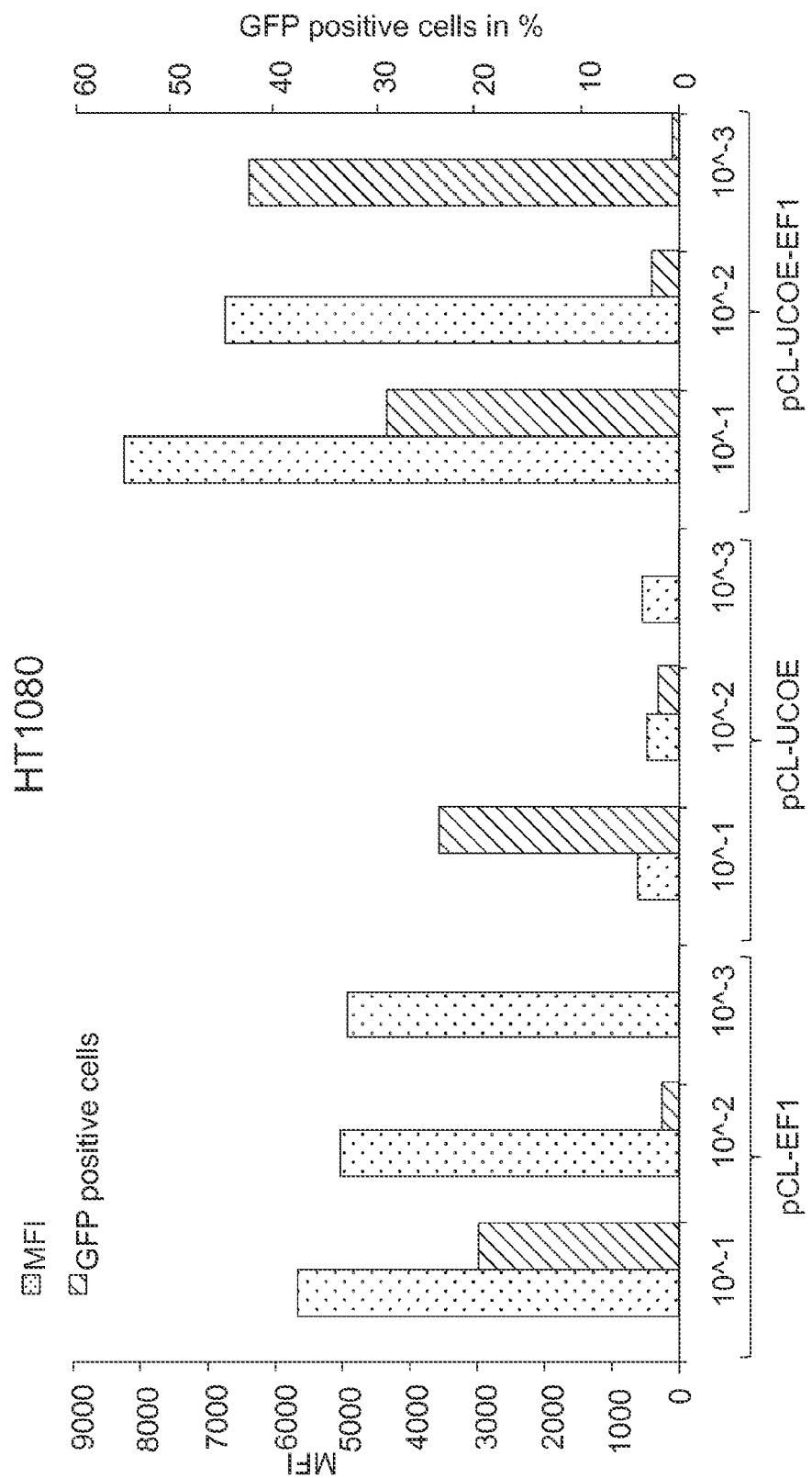
FIG. 21 shows the graphic representation of the results of in vivo studies in fibrosarcoma cell line HT1080 with a lentiviral-based system, wherein the influence of the UCOE on the expression of eGFP was analyzed.

Further advantages, properties and features of the present invention are apparent from the following description of preferred examples of the present invention shown in the drawings:

FIG. 1 shows a schematic representation of preferred embodiments of the nucleic acid expression cassette according to the first aspect of the present invention;

FIG. 2 shows schematic representations of preferred embodiments of vectors according to the present invention;

FIG. 3 shows a schematic representation of preferred embodiments of nanoparticle-based delivery systems for a coding sequence according to the present invention;

FIG. 4 shows schematic representations of the transfection mechanism for the transfer of nucleic acid molecules into liver cells, in particular hepatocytes, on the basis of schematic illustrations of a section of a hepatocyte during transfection with the delivery system according to the present invention;

FIG. 5 shows schematic representations of plasmids and/or vectors, respectively, used for transfection experiments and in vivo studies in order to analyze the functionality of the elements used for the preparation of nucleic acid expression cassettes and/or vectors according to the present invention;

FIG. 6 shows a graphic representation of the results of in vivo studies in liver cancer cell line HLE concerning the effect of the presence of S/MAR elements on the long-term expression levels in transfected cells;

FIG. 7 shows a graphic representation of the results of in vivo studies in liver cancer cell line HLF concerning the effect of the presence of S/MAR elements on the long-term expression levels of eGFP in transfected cells;

FIG. 8 shows the graphic representation of the results of in vivo studies in liver cancer cell line HLF concerning the effect of the presence of S/MAR elements on the long-term expression levels of eGFP in transfected cells;

FIG. 9 shows the graphic representation of the results of in vivo studies in liver cancer cell line HLF concerning the influence of the weight related ratio of polyethylenimine as transfection reagent to nucleic acid molecules on the expression of eGFP in the target cells;

FIG. 10 shows a graphic representation of the results of in vivo studies in liver cancer cell line HLF, wherein the influence of different variants of polyethylenimine at a defined weight related ratio of polyethylenimine to nucleic acid molecules on the expression of eGFP in the target cells has been analyzed;

FIG. 11 shows a graphic representation of the results of in vivo studies in liver cancer cell line HLF, wherein the expression efficiency of an optimized intermediate EF-1alpha (EF1a) promoter on the eGFP expression in the target cells has been analyzed;

FIG. 12 shows the graphic representation of the results of in vivo studies in liver cancer cell line HLF, wherein the expression of eGFP after transfection of liver cancer cells with a delivery system according to the present invention using different variants of polyethylenimine was analyzed;

FIG. 13 shows the graphic representation of the results of in vivo studies in liver cancer cell line HLF with a lentiviral-based system, wherein the influence of the UCOE on the expression of eGFP was analyzed;

FIG. 14 shows the graphic representation of the results of the measurement of the factor level of HLF cells transfected with a coding sequence, which codes for a fusion protein of eGFP and factor FVIII SQ or factor FIX padua, respectively;

FIG. 15 shows a schematic representation of a preferred design of a UCOE used in expression cassettes according to the present invention;

FIG. 16 shows the graphic representation of the results with respect to the episomal persistence of the vectors pEPI1-SM-L (FIG. 5A) and pEPI1-SM-S (FIG. 5B) in HLE cells;

FIG. 17 shows a graphic representation of the results of in vivo studies in fibrosarcoma cell line HT1080 concerning the effect of the presence of S/MAR elements on the long-term expression levels in transfected cells;

FIG. 18 shows a graphic representation of the results of in vivo studies in fibrosarcoma cell line HT1080, wherein the influence of different variants of polyethylenimine at a defined weight related ratio of polyethylenimine to nucleic acid molecules on the expression of eGFP in the target cells has been analyzed;

FIG. 19 shows a graphic representation of the results of in vivo studies in fibrosarcoma cell line HT1080, wherein the expression efficiency of an optimized intermediate EF-1alpha (EF1a) promoter on the eGFP expression in the target cells has been analyzed;

FIG. 20 shows the graphic representation of the results of in vivo studies in fibrosarcoma cell line HT1080, wherein the expression of eGFP after transfection of fibrosarcoma cells with a delivery system according to the present invention using different variants of polyethylenimine was analyzed;

FIG. 21 shows the graphic representation of the results of in vivo studies in fibrosarcoma cell line HT1080 with a lentiviral-based system, wherein the influence of the UCOE on the expression of eGFP was analyzed; and FIG. 22 shows the graphic representation of the results of the measurement of the factor level of fibrosarcoma cells (cell line HT1080) transfected with a coding sequence, which codes for a fusion protein of eGFP and factor FVIII SQ or factor FIX padua, respectively.

FIG. 1 shows the schematic representation of nucleic acid expression cassettes according to the present invention. In particular, FIG. 1A shows a preferred embodiment of a general assembly of the elements of the nucleic acid expression cassette according to the present invention. According to this embodiment of the present invention, the nucleic acid expression cassette comprises a promoter directing gene expression in mammalian, in particular human cells. With respect to a particularly preferred embodiment, the expression cassette can optionally comprise preferably upstream of the promoter a Ubiquitous Chromatin Opening Element (UCOE) (not shown in FIG. 1A). Downstream of the promoter, the nucleic acid expression cassette comprises a coding sequence, wherein the coding sequence codes for a liver-specific and/or liver-expressed protein and/or domains and/or fragments thereof. Furthermore, downstream to the coding sequence a scaffold/matrix attachment region element (S/MAR element) is located. As delineated before, on the basis of the S/MAR element, the episomal persistence of the nucleic acid expression cassette in the transfected target cells can be ensured or provided. Finally, in order to provide a sufficient termination of the transcription of the coding sequence, the nucleic acid expression cassette contains a terminator element.

FIG. 1B shows a particularly preferred embodiment of an expression cassette according to the present invention. The expression cassette according to this embodiment comprises a promoter derived from the human gene coding for Elongation Factor-1alpha. Preferably, this constitutively active promoter fragment of human origin also contains an optimized first intron, which has been considerably shortened; leading to a stable and highly efficient expression of operably linked coding sequences. Preferably, the promoter has a nucleic acid according to SEQ ID NO. 1 or SEQ ID NO. 18. Furthermore, according to this preferred embodiment, the nucleic acid expression cassette according to the present invention contains as coding sequence a human codon usage-optimized nucleic acid sequence coding for a variant of coagulation factor FVIII, in this context indicated as FVIII SQ. FVIII SQ codes for coagulation factor FVIII with a deleted B-domain, wherein the B-domain is replaced by a short linker comprising 14 amino acids. The protein FVIII SQ codes for is physiologically functional, since the B-domain is not required the procoagulation activity of factor FVIII. Preferably, the coding sequence has a nucleic acid sequence according to SEQ ID NO. 2 or SEQ ID NO. 19. Furthermore, downstream of the coding sequence a S/MAR element derived from the human gene coding for Interferon-beta (IFN-beta) is located on the nucleic acid cassette. According to a particularly preferred embodiment of the present invention, the S/MAR element has a nucleic acid sequence according to SEQ ID NO. 11 or SEQ ID NO. 12 or a nucleic acid sequence having at least 85% identity with the aforementioned sequences.

FIG. 1C shows a likewise preferred embodiment of the nucleic acid expression cassette according to the present invention. In contrast to the nucleic expression cassette according to FIG. 1B, the expression cassette of FIG. 1C comprises as the coding sequence a codon-optimized cDNA of factor FIX. Particularly, the nucleic acid expression cassette according to this preferred embodiment suitable for the treatment of hemophilia B can comprise a codon-optimized cDNA coding for the mutant variant of factor FIX, the so-called FIX-Padua, wherein arginine on position of 338 of the amino acid sequence has been replaced by leucine. Preferably, in this context the coding sequence has a nucleic acid sequence according to SEQ ID NO. 4 or SEQ ID NO. 5 or at least 85% identity with the aforementioned sequences. Likewise, the coding sequence can code for a fusion protein on the basis of factor FIX and albumin, in particular on the basis of a sequence according to SEQ ID NO. 6 or SEQ ID NO. 7.

FIG. 1D shows another likewise preferred embodiment of a nucleic acid expression cassette according to the present invention. The expression cassette according to FIG. 1D comprises the CMV promoter, which is suitable to direct a stable and constitutive gene expression in mammalian, in particular human cells. Preferably, the CMV promoter has a nucleic acid sequence according to SEQ ID NO. 17 or at least 85% identity with the respective sequence. Furthermore, according to this preferred embodiment, the nucleic acid expression cassette according to the present invention contains as coding sequence a human codon usage-optimized nucleic acid sequence coding for a variant of coagulation factor FVIII, in this context indicated as FVIII SQ. FVIII SQ codes for coagulation factor FVIII with a deleted B-domain, wherein the B-domain is replaced by a short linker comprising 14 amino acids. The protein FVIII SQ codes for is physiologically functional, since the B-domain is not required the procoagulation activity of factor FVIII. Preferably, the coding sequence has a nucleic acid sequence according to SEQ ID NO. 2 or SEQ ID NO. 19. Furthermore, downstream of the coding sequence a S/MAR element derived from the human gene coding for Interferon-beta (IFN-beta) is located on the nucleic acid cassette. According to a particularly preferred embodiment of the present invention, the S/MAR element has a nucleic acid sequence according to SEQ ID NO. 11 or SEQ ID NO. 12 or a nucleic acid sequence having at least 85% identity with the aforementioned sequences.

The expression cassettes as described before are suitable for the preparation of vectors and/or for the preparation of therapeutic agents for the treatment of monogenetic disorders resulting from a mutation in a gene coding for a liver-specific and/or liver-expressed protein, in particular coagulation factors FVIII and FIX. According to a preferred embodiment of the present invention, the afore-described nucleic acid expression cassettes are suitable for the use in the preparation of therapeutics for the treatment of hemophilia, especially hemophilia A and B.

FIG. 2 shows the schematic representation of vectors according to a preferred embodiment of the present invention. Preferably, the vectors according to the present invention are in the form of minicircles and/or minicircular vectors that have been freed from most of the prokaryotic vector parts. They are particularly suitable carriers of coding sequences for the genetic modification of eukaryotic, especially mammalian cells. On this basis, the vectors are less likely to be perceived as foreign with subsequent degradation.

Figure 2A:
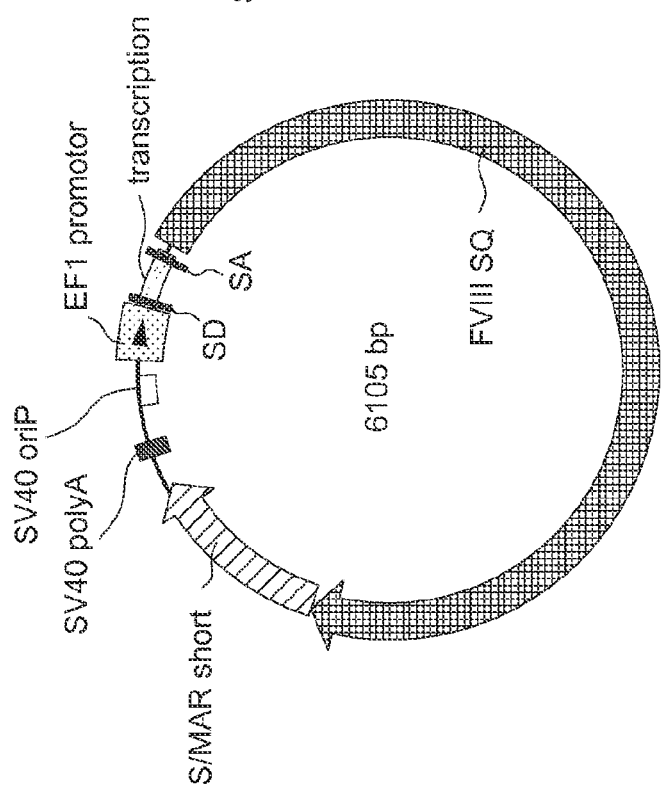
FIG. 2A shows a schematic representation of a preferred vector, which contains a nucleic acid expression cassette as shown in FIG. 1B.

FIG. 2A shows a preferred vector, which contains a nucleic acid expression cassette according to FIG. 1B. The vector according to FIG. 2A can be used for the preparation of a delivery system according to the present invention. A delivery system on the basis of the vector according to FIG. 2A can be particularly used for the preparation of a therapeutic and/or medicament for the treatment of hemophilia A. The vector according to FIG. 2B contains a nucleic acid expression cassette as shown in FIG. 1C. The vector depicted in FIG. 2B can be used for the preparation of a gold nanoparticle-based delivery system according to the present invention, which is suitable for the treatment of hemophilia B.

FIG. 3 shows preferred embodiments of gold nanoparticle-based delivery systems according to the present invention for the transfer of nucleic acid molecules into eukaryotic cells, in particular human liver cells or fibrous tissue cells.

Figure 3A:
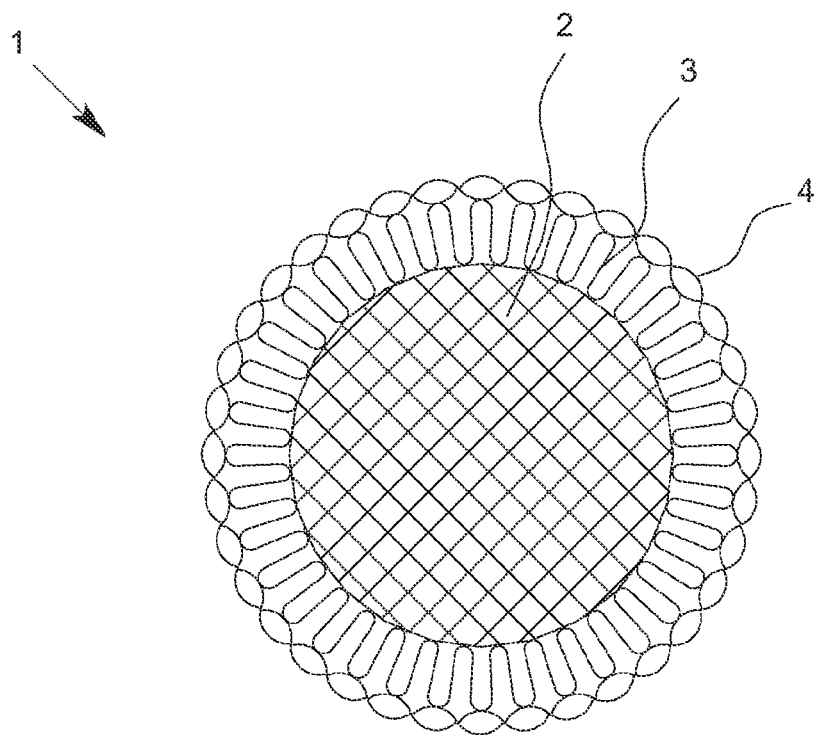
FIG. 3A shows a schematic representation of an embodiment of a delivery system (1) that includes a gold nanoparticle (2) bonded to polyethyleneimine (3) which is further bonded to nucleic acid molecules (4), and lacking a specific targeting unit.
Figure 3B:
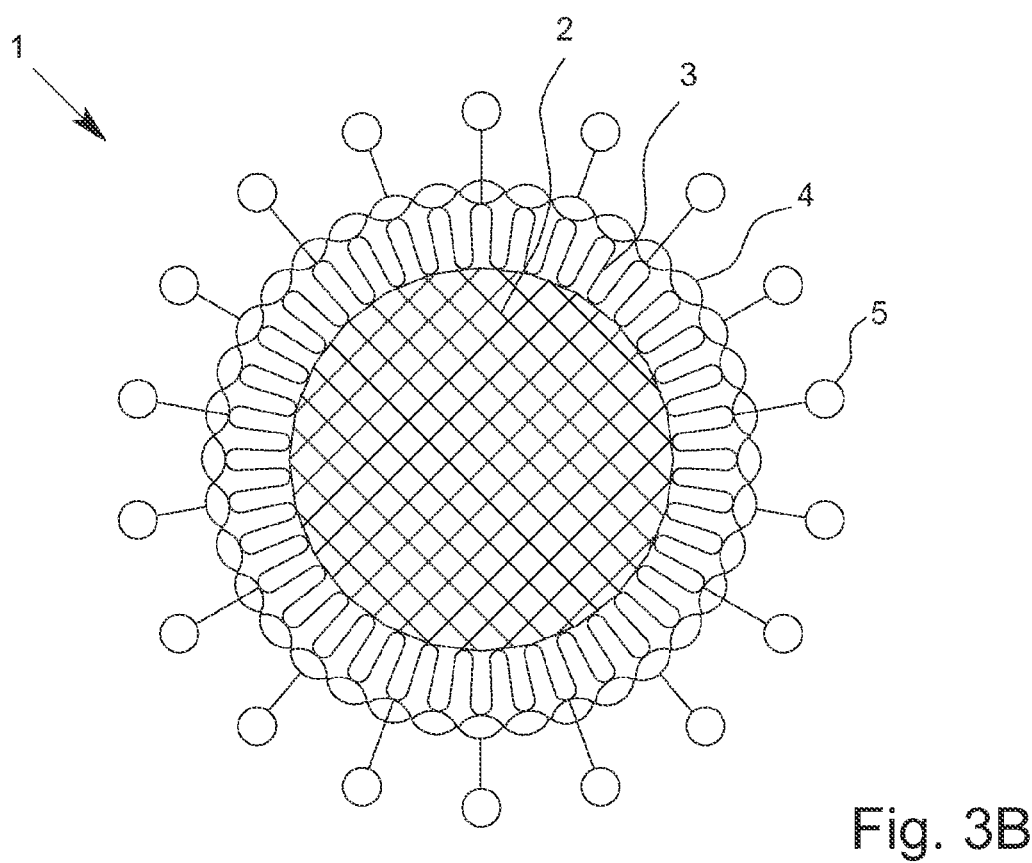
FIG. 3B shows a schematic representation of a delivery system (1) illustrated in FIG. 3A with added targeting units (5)
Figure 3C:
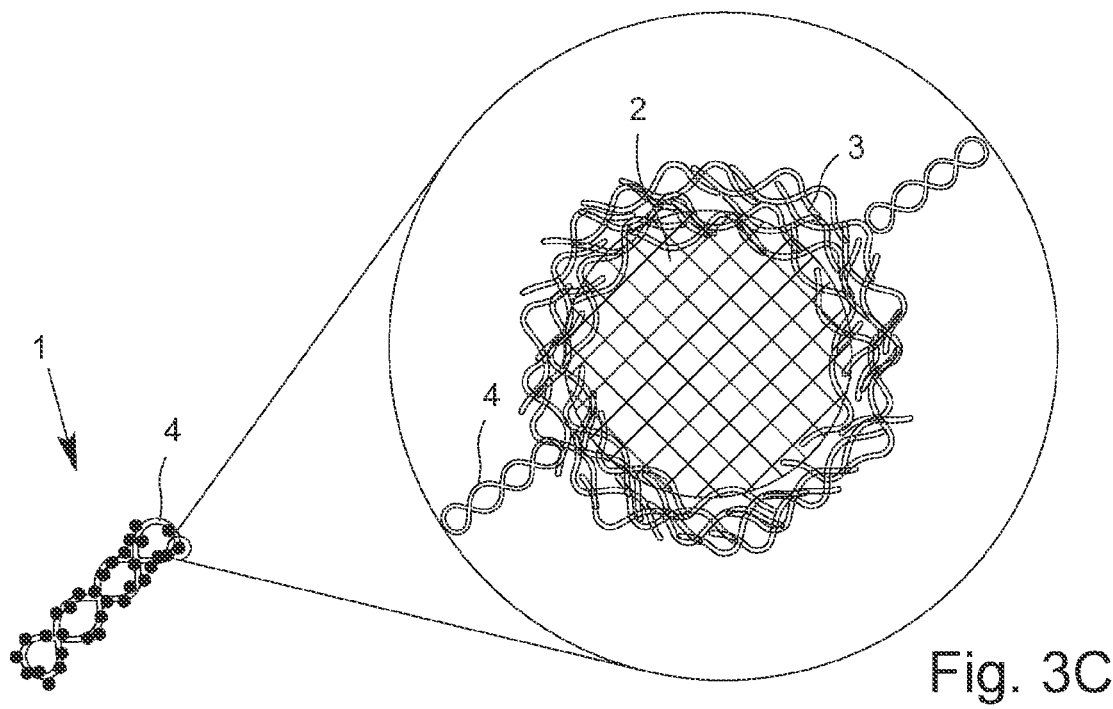
FIG. 3C shows a schematic representation of an embodiment of a delivery system (1) including the gold nanoparticle (2), the polyethylenimine (3) and the nucleic acid molecules (4) but lacking a specific targeting unit (5)
Figure 3D:
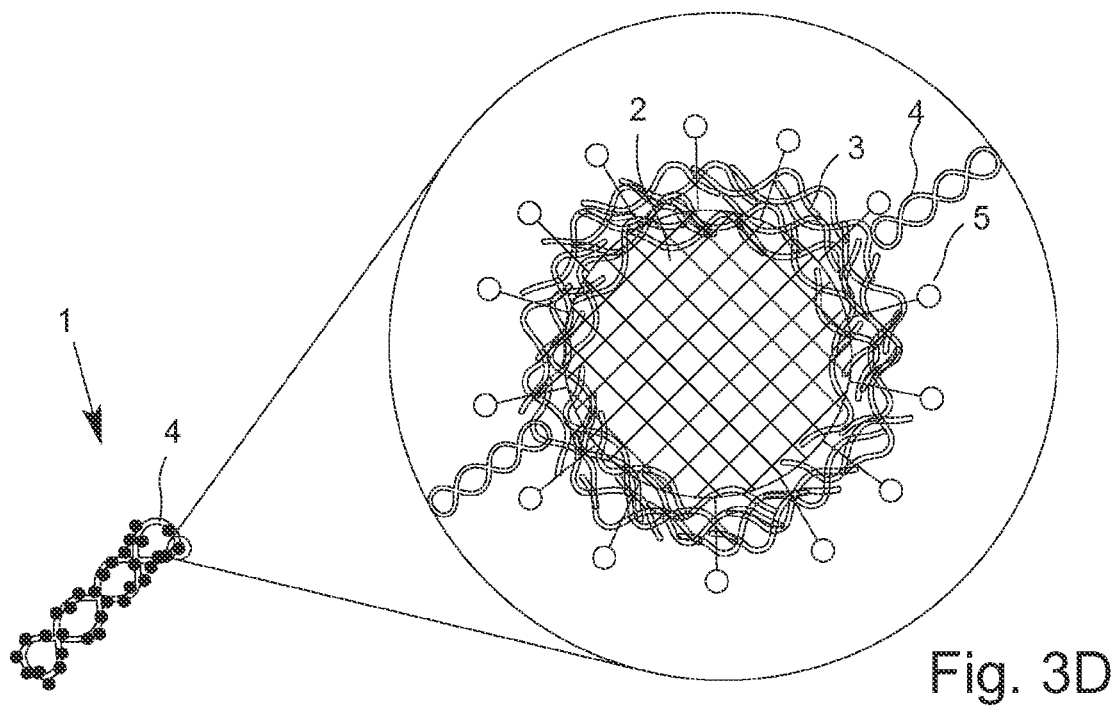
FIG. 3D shows a schematic representation of an embodiment of a delivery system (1) including the gold nanoparticle (2), the polyethylenimine (3) and the nucleic acid molecules (4) and additionally including a targeting unit (5)

FIG. 3A and FIG. 3C show embodiments according to which the delivery system does not contain a specific targeting unit. The representations of FIG. 3A and FIG. 3C differ with respect to the size proportions of the gold nanoparticles 2, on the one hand, in comparison to the further components, in particular the nucleic acid molecules 4 and the polyethylenimine 3, on the other hand. Without being bound to this theory, proportions according to FIG. 3C are more likely. FIG. 3B and FIG. 3D show embodiments according to which the delivery system contains a targeting unit 5. FIG. 3B and FIG. 3D also depict similar embodiments, but showing different size proportions of the components of the delivery system. Without being bound to this theory, size proportions as depicted according to FIG. 3D are more likely.

With respect to FIGS. 3A to 3D, the nanoparticle-based delivery system 1 comprises a gold nanoparticle 2. The gold nanoparticle 2 comprises covalently bound polyethylenimine 3 and/or derivatives and/or salts thereof. In particular, the gold nanoparticle 2 is coated with polyethylenimine 3. Furthermore, on the basis of the bound polyethylenimine 3, nucleic acid molecules 4 are bound to the polyethylenimine/nanoparticle complex. On this basis, the polyethylenimine 4 fulfills several functions in the nanoparticle-based delivery system according to the present invention. On the one hand, the polyethylenimine 3 mediates the binding of the nucleic acid molecules 4 to the surface of the gold nanoparticles 2. On the other hand, polyethylenimine serves as the transfection reagent improving the transfer of the nucleic acid molecules into the cells, in particular—without being bound to this theory—on the basis of the proton sponge effect. Furthermore, the delivery system according to a preferred embodiment of the present invention as depicted in FIG. 3B and FIG. 3D can comprise at least one targeting unit 5 in order to direct a targeted and specific transfer of the nucleic acid molecules into specific and purposefully selected cell types and/or tissues. The targeting unit is preferably an agonist for a cell surface receptor of the target cells. On the basis of the targeting unit, the nanoparticle-based delivery system can specifically bind to the surface of the target cells, with subsequent uptake of the delivery system by the cells by endocytosis.

FIG. 4 shows on the basis of an illustration of a section of a hepatocyte a schematic representation of the underlying concept of the transfer of nucleic acid molecules into liver cells, mediated by the nanoparticle-based delivery system according to the present invention. FIG. 4A shows the transfection mechanism without the use of a targeting, wherein FIG. 4B shows the transfection mechanism under the use of a targeting unit FIG. 4C and FIG. 4D show a further representation of the embodiment of FIG. 4A without targeting unit (FIG. 4C) and of FIG. 4B with the use of a targeting unit (FIG. 4D).

Figure 4A:
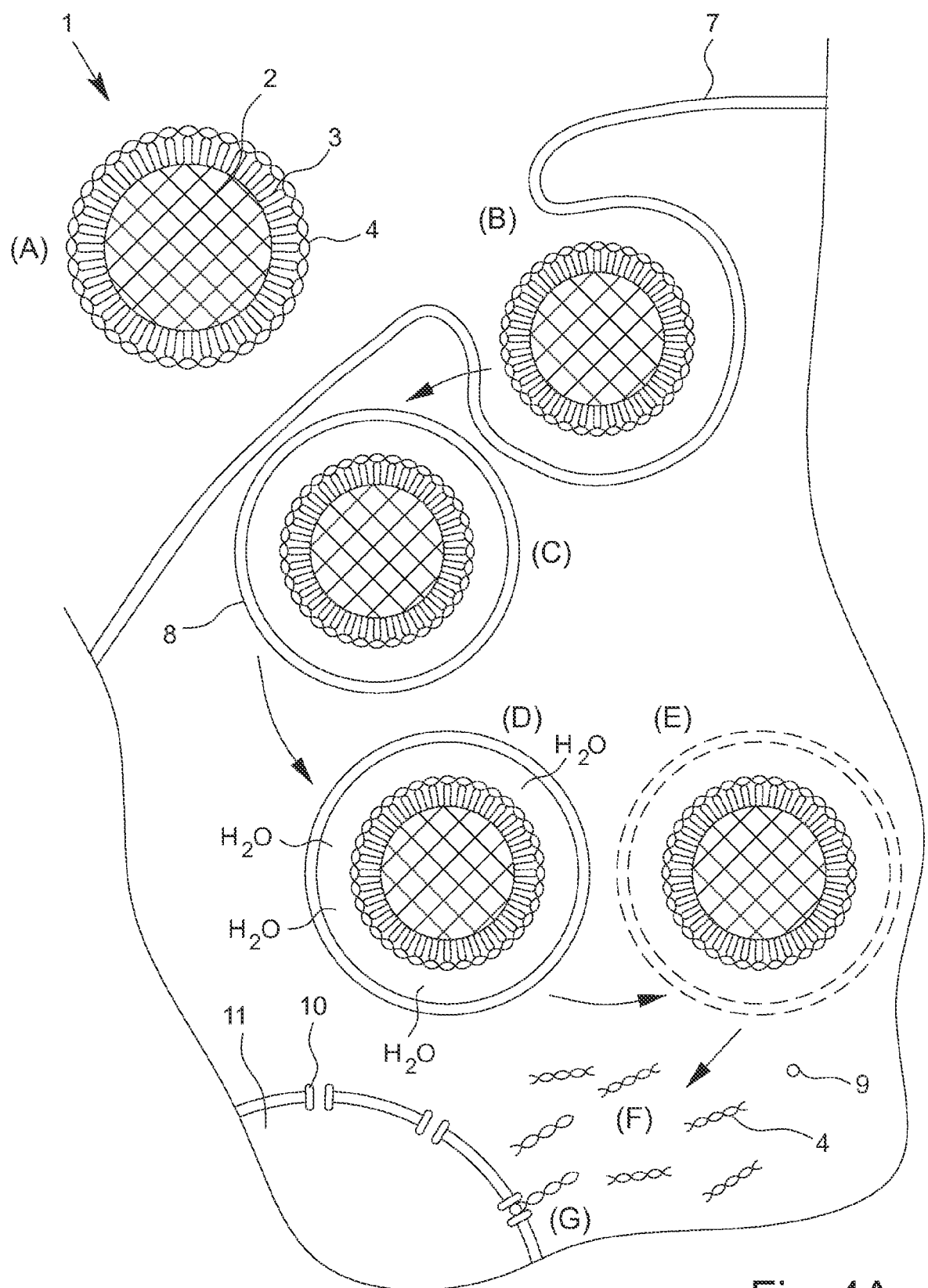
FIG. 4A illustrates the transfection mechanism utilizing the delivery system (1) of FIG. 3A without the use of a targeting unit, where (A) through (G) illustrate stages of the mechanism involving the formation of the endosome (8) formed about the delivery system (1) illustrated in stage (A) wherein the mechanism involves the steps of endocytosis, stage (B), formation of an endosome (8) stage (C), the uptake of water into the endosome (8), stage (D), the bursting of endosome (8), stage (E) with the release of nucleic acid molecules (4) and importin (9) into the cytoplasm, and finally in stage (F), the uptake of the nucleic acid molecules (4) into the nucleus (11) through nuclear pores (10)
Figure 4B:
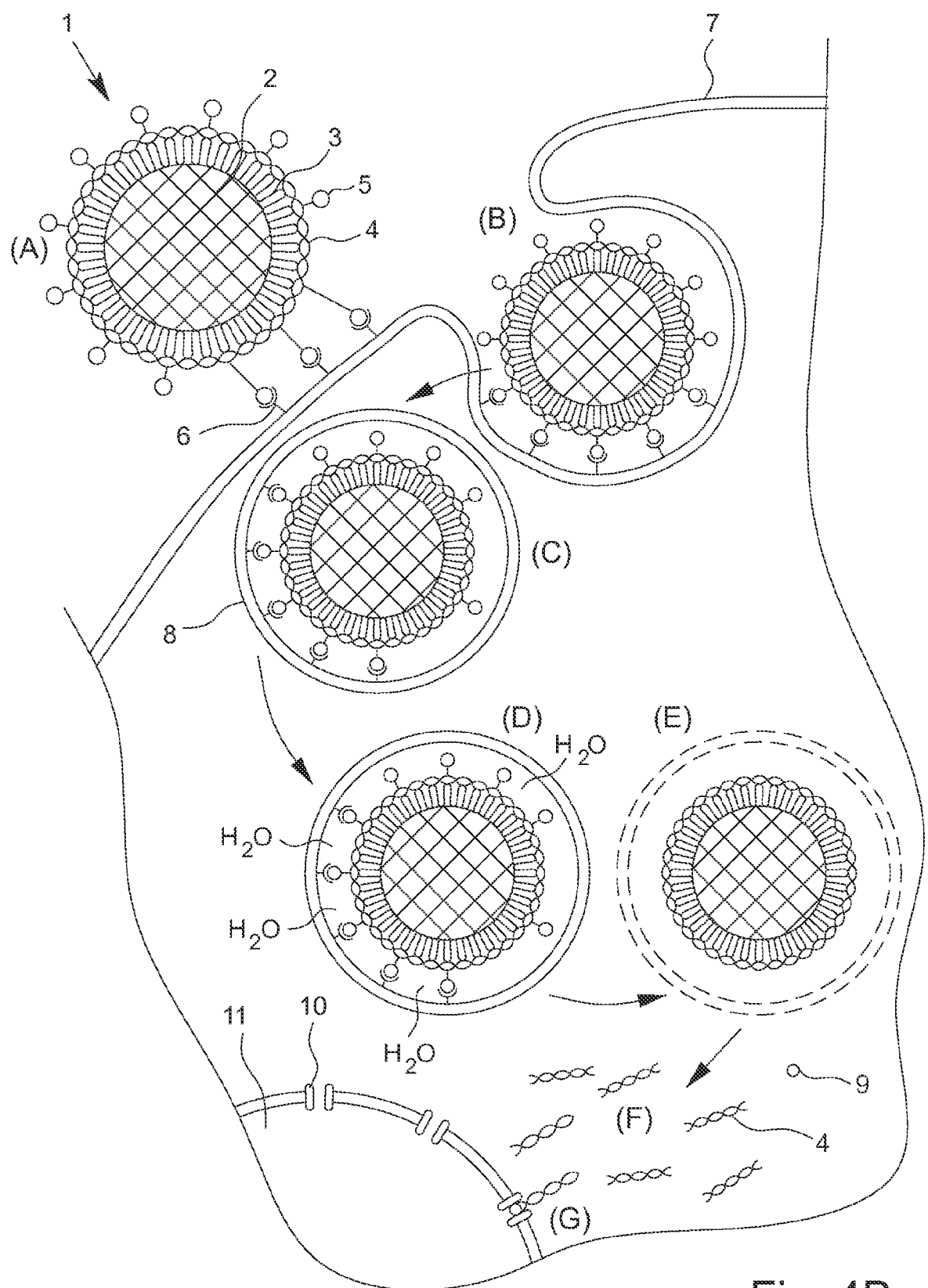
FIG. 4B illustrates the transfection mechanism provided in FIG. 4A utilizing the delivery system (1) provided in FIG. 3B including the targeting system (5)
Figure 4C:
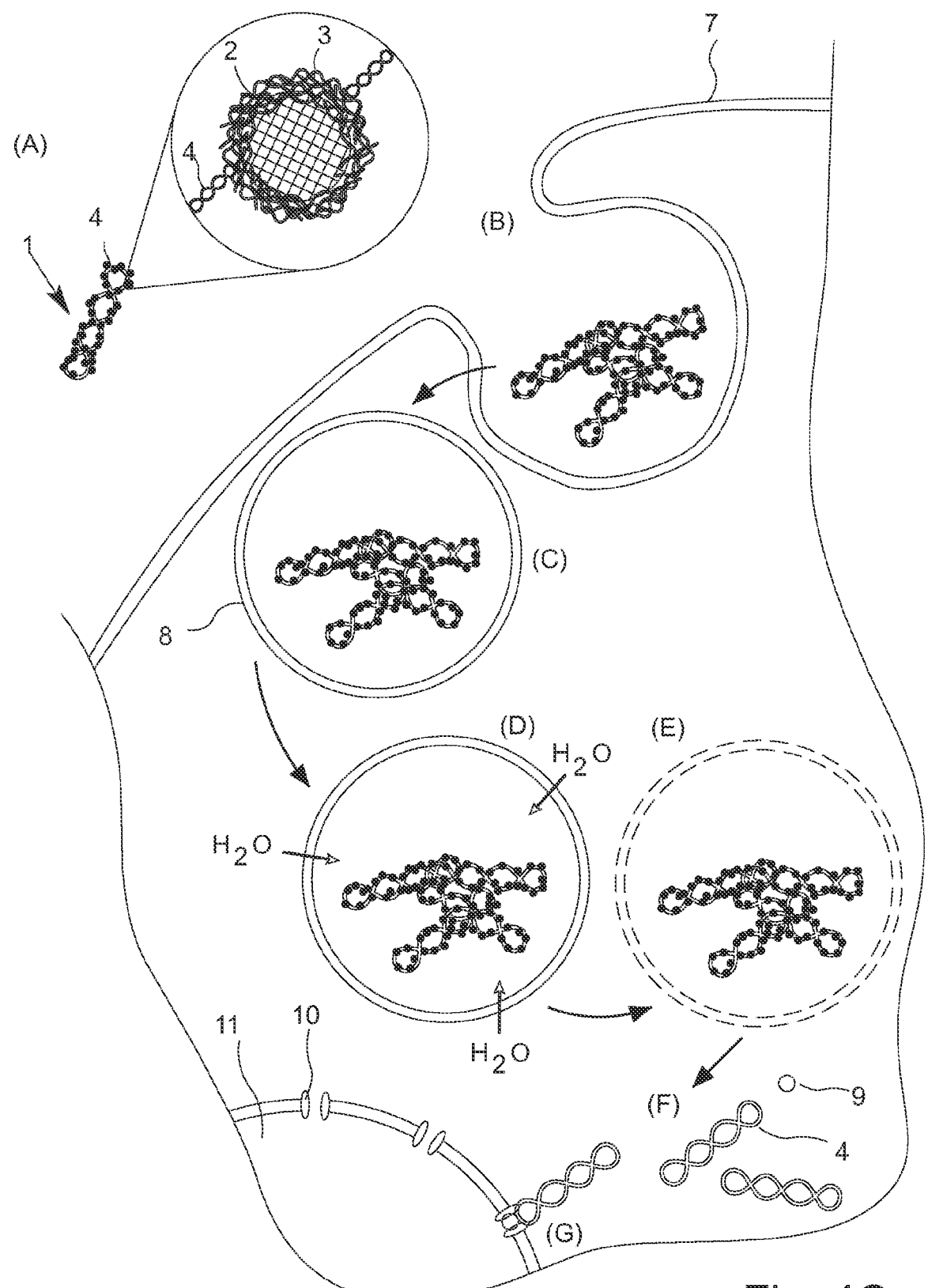
FIG. 4C illustrates the transfection mechanism provided in FIG. 4A utilizing the delivery system (1) provided in FIG. 3C without the targeting system (5)
Figure 4D:
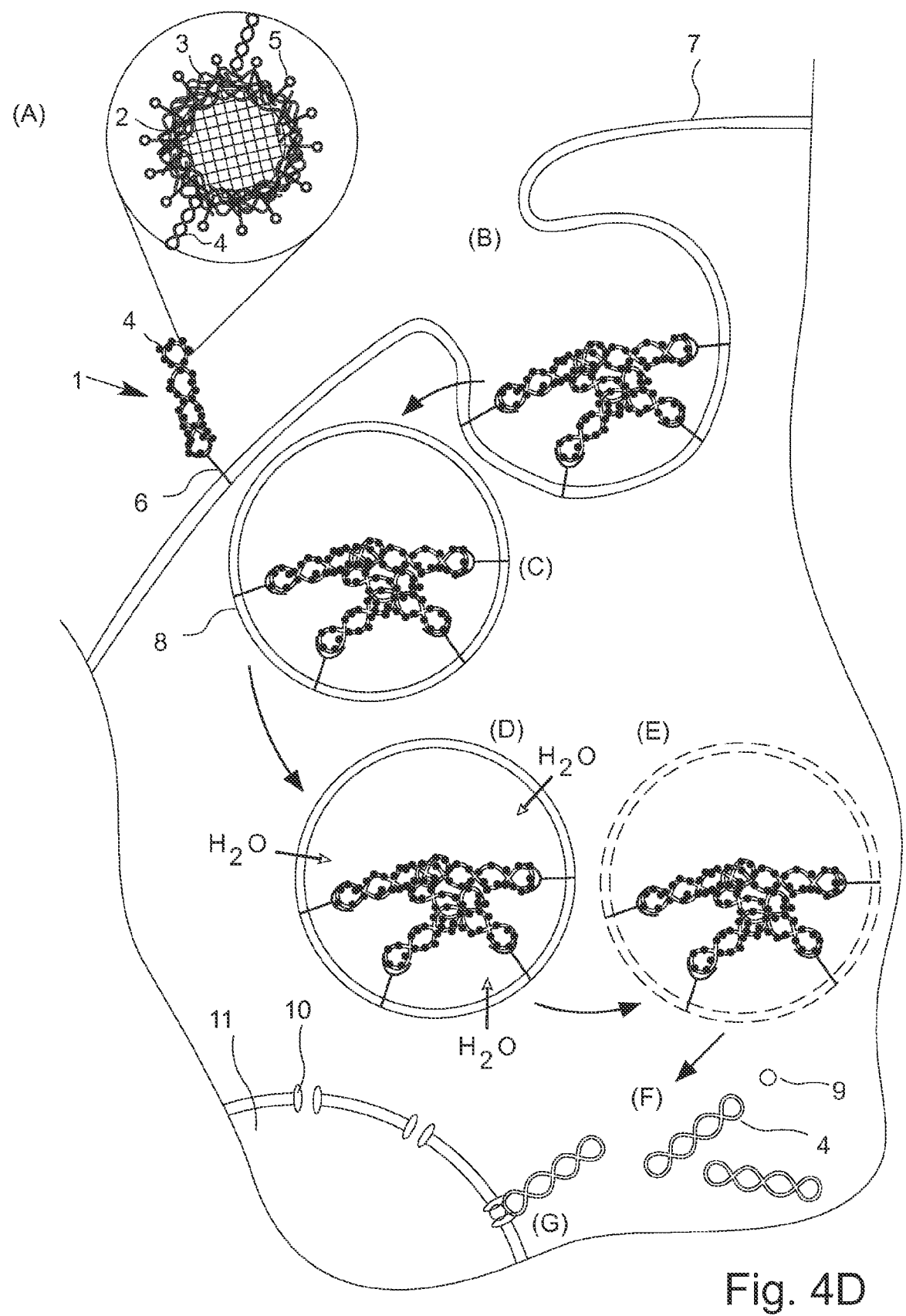
FIG. 4D illustrates the transfection mechanism provided in FIG. 4A utilizing the delivery system (1) provided in FIG. 3D including the targeting system (5)

In particular, FIG. 4B and FIG. 4D show the liver cell-specific targeting of the nanoparticle-based delivery system, containing gold nanoparticles 2, polyethylenimine 3, nucleic acid molecules 4 and a targeting unit 5 that specifically binds to cell surface receptors 6 on a hepatocyte 7 or other target cells.

Starting point is a nanoparticle-based delivery system 1 according to the present invention, in particular as depicted in FIG. 3B and FIG. 3D. In order to achieve a transfection of the target cells on the basis of a hepatocyte 7, the conjugated gold nanoparticles 1 bind with the targeting unit 5 to the cell surface receptors 6 of the target cells on the basis of hepatocytes 7 (A).

The uptake of the conjugated gold nanoparticles into the cells occurs by endocytosis (B), resulting in the formation of an endosome 8 (C), which contains the conjugated gold nanoparticle or nanoparticle-based delivery system 1 carrying the nucleic acid molecules 4 to be transferred. From the endosomes 8, the nucleic acid molecules 4 cannot directly enter the cytoplasm. On the basis of the polyethylenimine 3 bound to the gold nanoparticles 2, water molecules flow into the endosomes (D), causing the endosomes to burst (E). As a result, the nucleic acid molecules 4 to be transferred for transgenic expression of a coding sequence in the target cells are released into the cytoplasm (F).

The nuclear import (G) of the nucleic acid molecules 4 into the nucleus 11 then occurs passively during cell division after dissolution of the nuclear membrane or actively in non-dividing cells through nuclear pores 10 on the basis of transport molecules, in particular importins 9. In the nucleus 11, the nucleic acid molecules 4 according to the present invention comprising the S/MAR element bind to the core matrix and are replicated and expressed, resulting in the production of the liver-specific and/or liver-expressed protein.

Likewise, a transfection of liver cells on the basis of the nanoparticle-based delivery system without the use of a targeting unit is possible, as depicted in FIG. 4A and FIG. 4C. Gold nanoparticles are mainly taken up by the liver after intravenous injection when used as carriers for nucleic acid sequences. Therefore, the delivery system according to the present invention comprises by nature a high specificity for the liver. According to the present invention, the binding of the conjugated nanoparticles to the surface of the liver cells is—without being bound to this theory—mediated by the transfection reagent on the basis of polyethylenimine. Since the delivery system according to the present invention as such already provides a high liver-specificity, an embodiment of the present invention without the use of any targeting agent is likewise preferred.

FIG. 5 contains schematic illustrations of expression vectors and/or plasmids constructed for in vivo experiments and/or transfection experiments in order to analyze the functionality of the elements of the nucleic acid expression cassette and the vector according to the present invention.

The vectors as illustrated in FIG. 5A to FIG. 5G have been generated using standard cloning techniques.

Figure 5A:
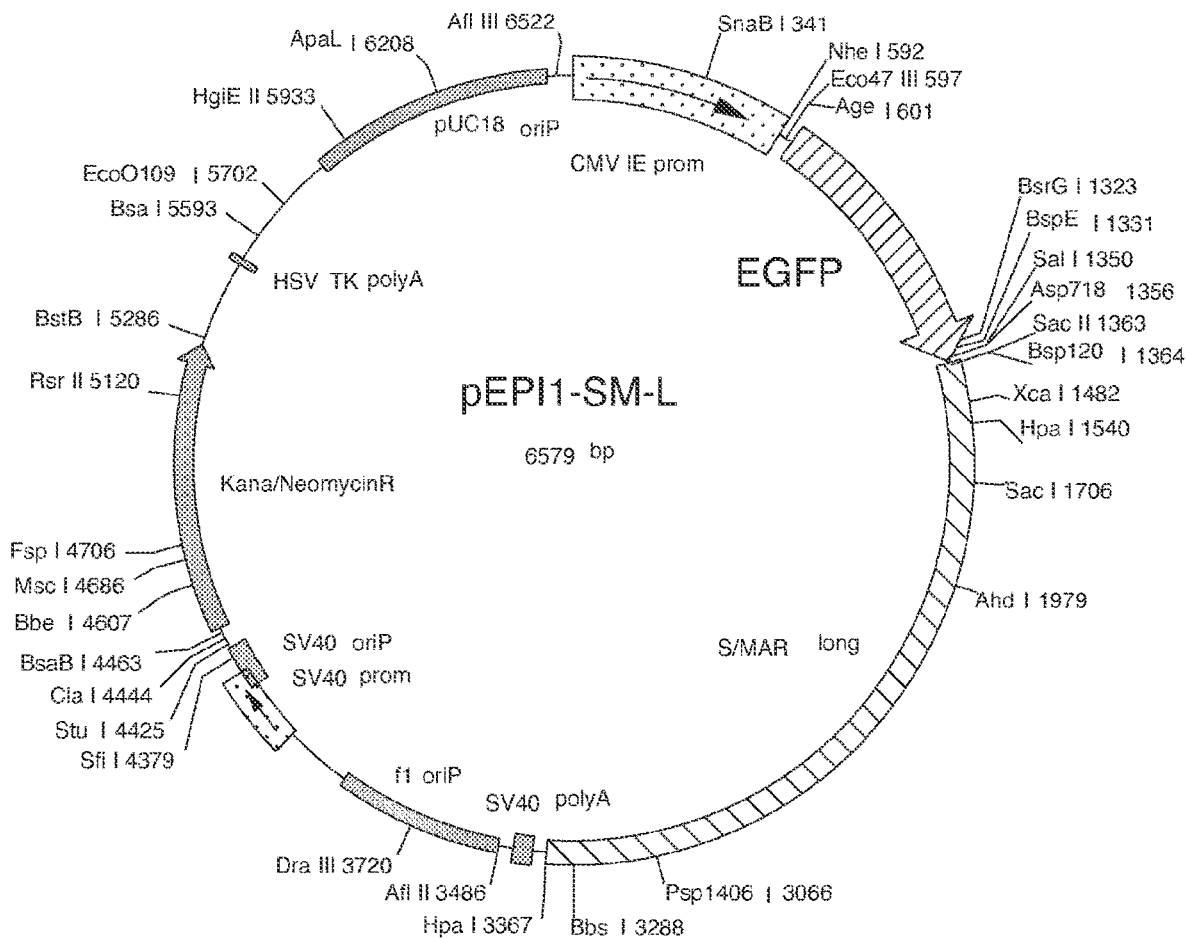
FIG. 5A illustrates a schematic representation of the vector pEPI1-SM-L additionally containing the 1.995 base pair long scaffold/matrix attachment region (S/MAR) from the 5' region of the human gene coding for Interferon-beta, in particular with a nucleic acid sequence according to SEQ ID NO. 12.
Figure 5B:
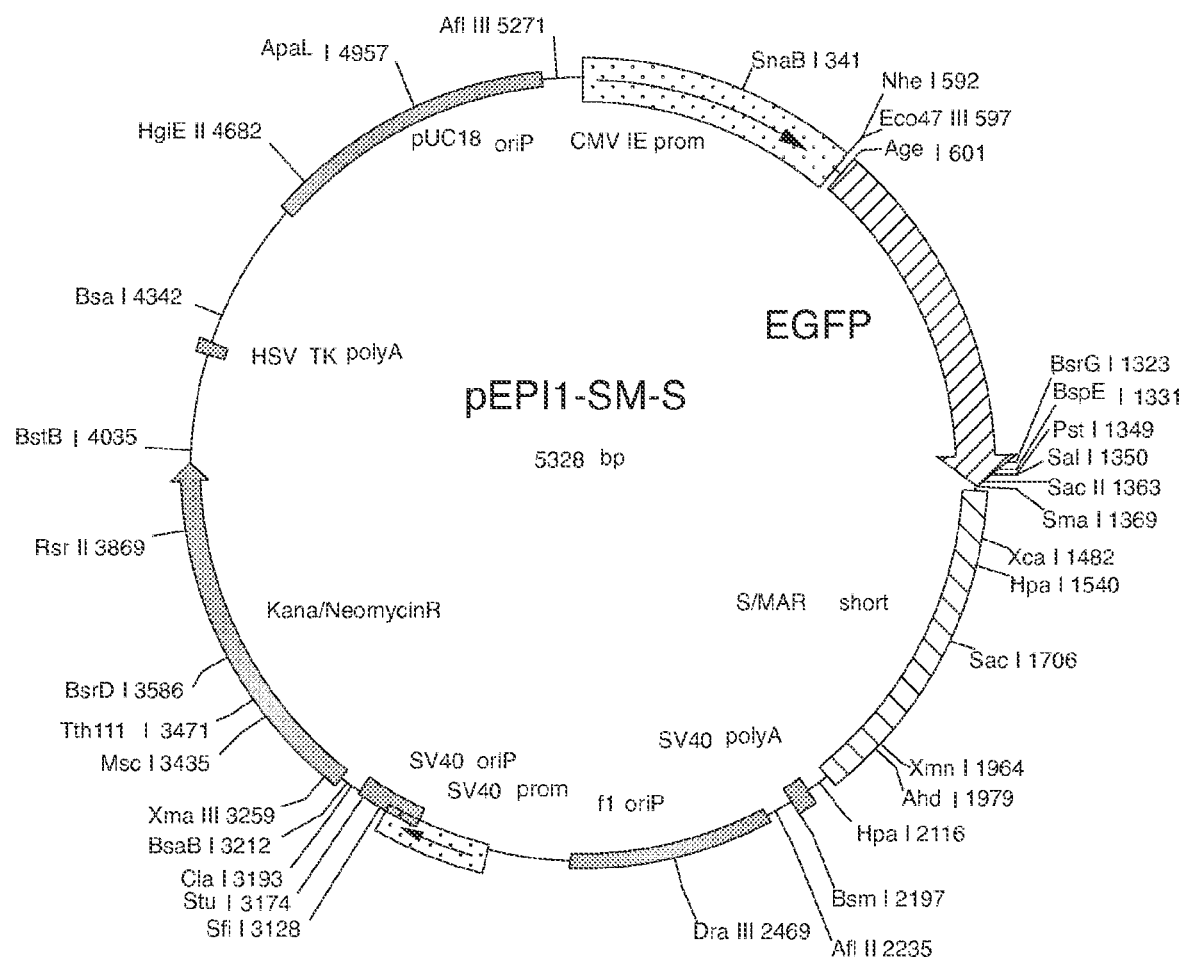
FIG. 5B illustrates a schematic representation of the vector pEPI1-SM-S in contrast to the vector in FIG. 5A having a shortened version of the S/MAR element derived from the human gene coding for interferon beta, in particular with a nucleic acid according to SEQ ID No. 11.
Figure 5C:
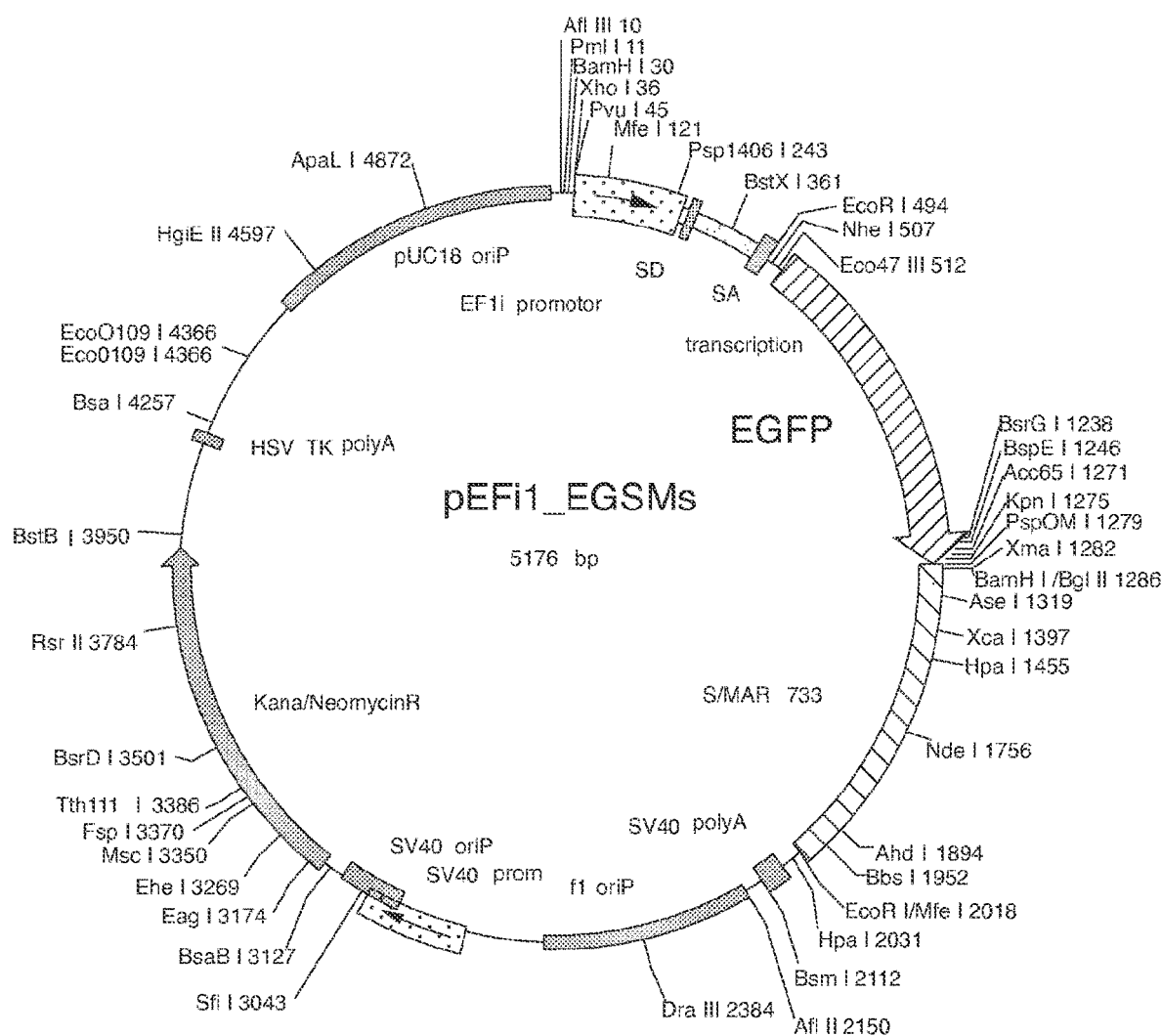
FIG. 5C illustrates a schematic representation of the vector pEFi1-EGSMs including a shortened variant of the S/MAR element with a nucleic acid according to SEQ ID NO. 11 with the CMV promoter exchanged for a human promoter derived from the human gene coding for Elongation Factor-1 alpha (EF1a), wherein the promoter has a nucleotide sequence according to SEQ ID NO. 1 or SEQ ID NO. 18.
Figure 5D:
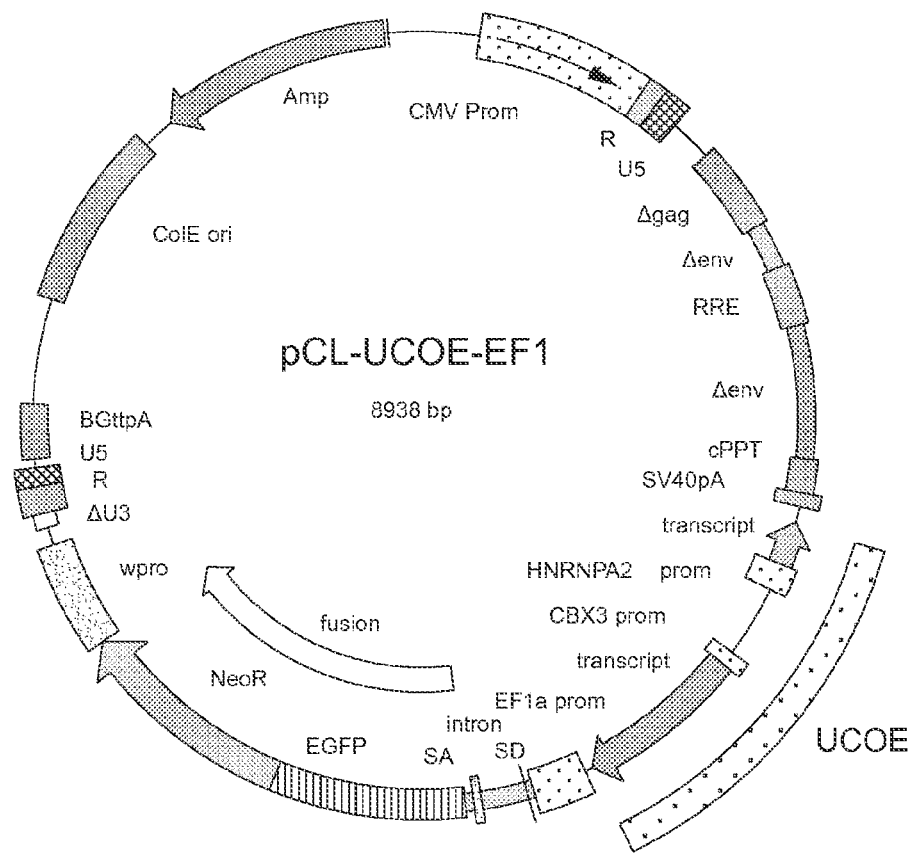
FIG. 5D illustrates a schematic representation of the vector pCL-UCOE-EF1 constructed as a lentiviral vector, containing a nucleic acid sequence coding for a fusion protein on the basis of eGFP and a protein providing neomycin resistance protein under the control of a UCOE on the basis of the promoter CBX3 (SEQ ID NO. 13 or SEQ ID NO. 21) with a corresponding transcript (SEQ ID NO. 14 or SEQ ID NO. 22) and the promoter HNRNPA2 (SEQ ID NO. 15 or SEQ ID NO. 23) with a corresponding transcript (SEQ ID NO. 16 or SEQ ID NO. 24), an enhancer region (SEQ ID NO. 25) and the promoter derived from the human gene coding for Elongation Factor-1 alpha (SEQ ID NO. 1 or SEQ ID NO. 18)
Figure 5E:
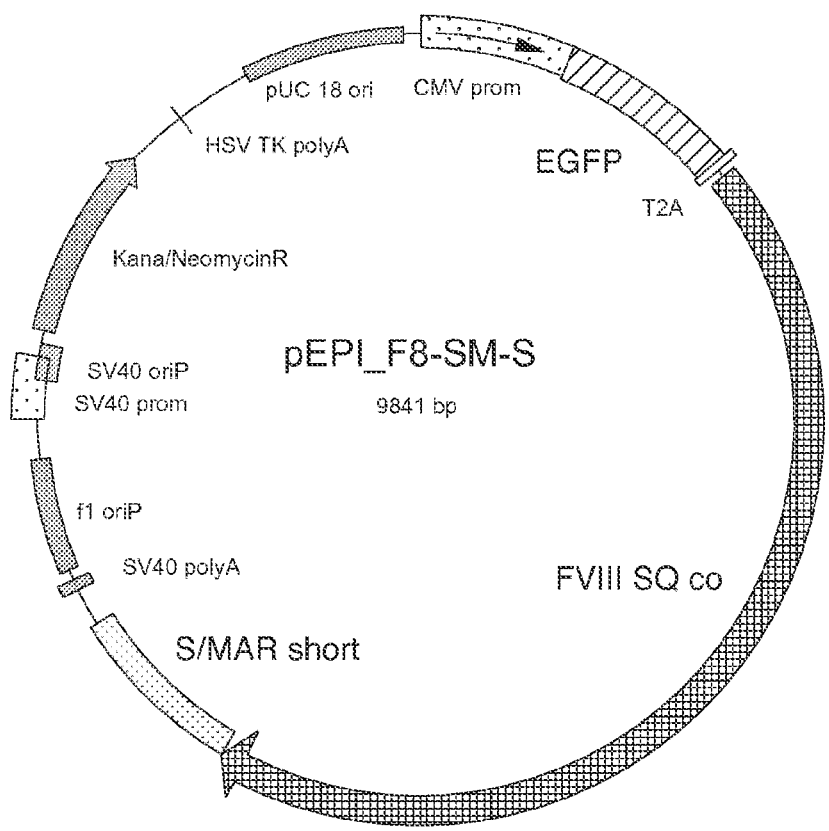
FIG. 5E illustrates a schematic representation of the vector pEPI_F8-SM-S including a coding sequence for a fusion protein of eGFP and factor FVIII with deleted B-domain (nucleic acid sequence for factor FVIII with deleted B-domain according to SEQ ID NO. 2 or SEQ ID NO. 19) further including downstream of the coding sequence, a shortened variant of the S/MAR element according to SEQ ID NO. 11 and upstream of the coding sequence, a promoter derived from Cytomegalovirus (CMV promoter, SEQ ID NO. 17)
Figure 5F:
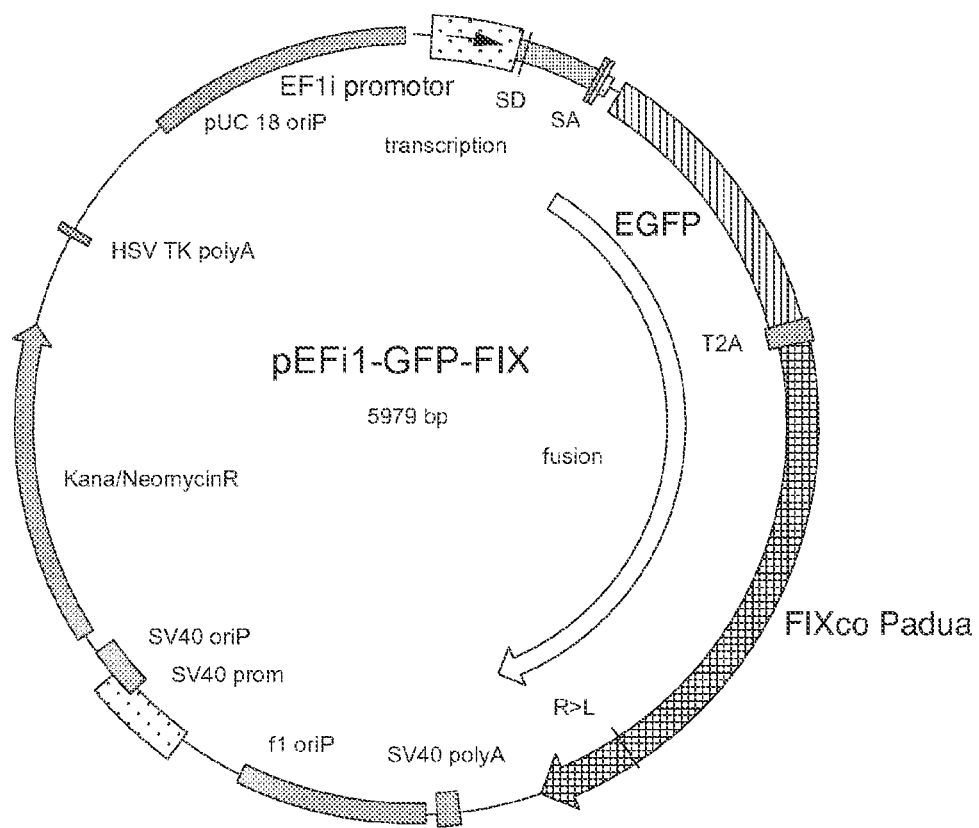
FIG. 5F illustrates a schematic representation of the vector pEFi1-GFP-FIX including a coding sequence for a fusion protein of eGFP and the padua variant of factor FIX (nucleic acid sequence for factor FIX padua according to SEQ ID NO. 5), further including upstream of the coding sequence, a promoter derived from the human gene coding for Elongation Factor-1 alpha (SEQ ID NO. 1 or SEQ ID NO. 18)
Figure 5G:
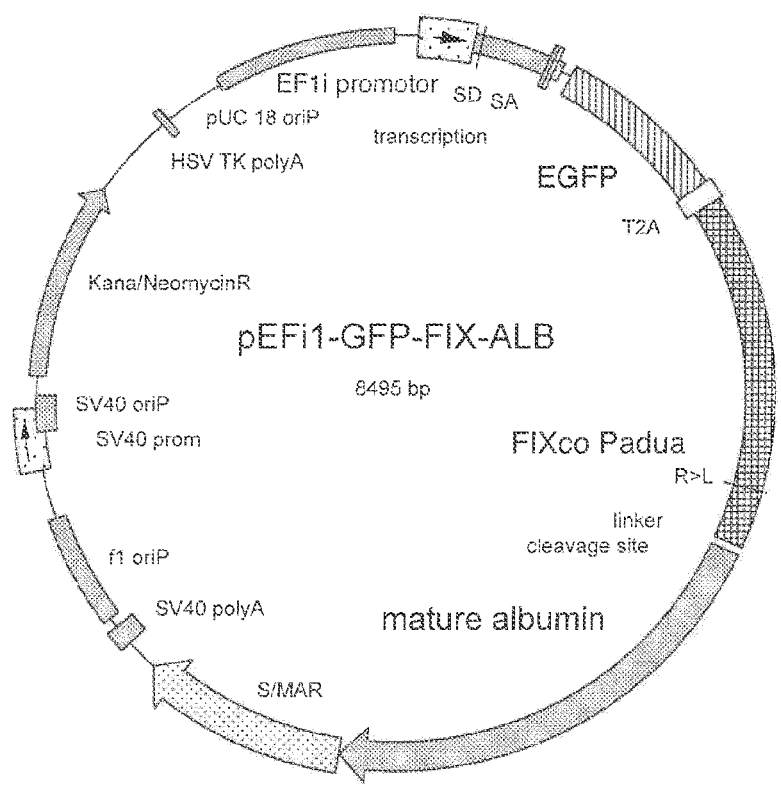
FIG. 5G illustrates a schematic representation of the vector pEFi1-GFP-FIX-ALB including a coding sequence for a fusion protein of eGFP, the padua variant of factor FIX (nucleic acid sequence for factor FIX padua according to SEQ ID NO. 5) and albumin (nucleic acid sequence for albumin according to SEQ ID NO. 8), further including upstream of the coding sequence, a promoter derived from the human gene coding for Elongation Factor-1 alpha (SEQ ID NO. 1 or SEQ ID NO. 18) and downstream of the coding sequence, a S/MAR element derived from the human gene coding for Interferon-beta, in particular with a nucleic acid according to SEQ ID NO. 11.

As a starting point, the plasmid pEGFP-C1, which is commercially available from Clontec, Mountain View, Calif., US, has been used for the vectors according to FIG. 5A to FIG. 5C as well as FIG. 5E to FIG. 5G. The plasmid contains a promoter derived from cytomegalovirus (CMV) and the coding sequence for the enhanced Green Fluorescent Protein (eGFP). Furthermore, the vector contains a neomycin/kanamycin resistance cassette in the plasmid backbone.

The vector according to FIG. 5A additionally contains the 1.995 base pair long scaffold/matrix attachment region (S/MAR) from the 5' region of the human gene coding for Interferon-beta, in particular with a nucleic acid sequence according to SEQ ID NO. 12. A detailed description of the manufacturing of this vector is also contained in the working examples described hereinafter.

The vector according to FIG. 5B contains in contrast to the vector according to FIG. 5A a shortened version of the S/MAR element derived from the human gene coding for Interferon-beta, in particular with a nucleic acid according to SEQ ID NO. 11.

The vector pEFi1-EGSMs according to FIG. 5C comprises the shortened variant of the S/MAR element, in particular with a nucleic acid according to SEQ ID NO. 11. Furthermore, the CMV promoter has been exchanged for a human promoter derived from the human gene coding for Elongation Factor-1 alpha (EF1a). In particular, the promoter has a nucleotide sequence according to SEQ ID NO. 1 or SEQ ID NO. 18.

FIG. 5D shows a schematic representation of the vector pCL-UCOE-EF1. pCL-UCOE-EF1 is constructed as a lentiviral vector, which contains a nucleic acid sequence coding for a fusion protein on the basis of eGFP and a protein providing neomycin resistance protein under the control of a UCOE on the basis of the promoter CBX3 (SEQ ID NO. 13 or SEQ ID NO. 21) with a corresponding transcript (SEQ ID NO. 14 or SEQ ID NO. 22) and the promoter HNRNPA2 (SEQ ID NO. 15 or SEQ ID NO. 23) with a corresponding transcript (SEQ ID NO. 16 or SEQ ID NO. 24), an enhancer region (SEQ ID NO. 25) and the promoter derived from the human gene coding for Elongation Factor-1 alpha (SEQ ID NO. 1 or SEQ ID NO. 18). Additionally (not depicted), the vectors pCL-UCOE and pCL-EF1 have been constructed. Both vectors are identical to pCT-UCOE-EF1, with the difference that pCL-UCOE comprises the coding sequence only under control of UCOE and pCL-EF1 comprises the coding sequence only under control of the promoter EF1-alpha.

FIG. 5E shows a schematic representation of the vector pEPI_F8-SM-S. The vector contains a coding sequence for a fusion protein of eGFP and factor FVIII with deleted B-domain (nucleic acid sequence for factor FVIII with deleted B-domain according to SEQ ID NO. 2 or SEQ ID NO. 19). Downstream of the coding sequence, the vector comprises the shortened variant of the S/MAR element according to SEQ ID NO. 11. Upstream of the coding sequence, the vector comprises a promoter derived from Cytomegalovirus (CMV promoter, SEQ ID NO. 17).

FIG. 5F shows a schematic representation of the vector pEFi1-GFP-FIX. The respective vector contains a coding sequence for a fusion protein of eGFP and the padua variant of factor FIX (nucleic acid sequence for factor FIX padua according to SEQ ID NO. 5).

Upstream of the coding sequence, the vector comprises a promoter derived from the human gene coding for Elongation Factor-1 alpha (SEQ ID NO. 1 or SEQ ID NO. 18).

FIG. 5G shows a schematic representation of the vector pEFi1-GFP-FIX-ALB. The respective vector contains a coding sequence for a fusion protein of eGFP, the padua variant of factor FIX (nucleic acid sequence for factor FIX padua according to SEQ ID NO. 5) and albumin (nucleic acid sequence for albumin according to SEQ ID NO. 8). Upstream of the coding sequence, the vector comprises a promoter derived from the human gene coding for Elongation Factor-1 alpha (SEQ ID NO. 1 or SEQ ID NO. 18). Downstream of the coding sequence, the vector comprises a S/MAR element derived from the human gene coding for Interferon-beta, in particular with a nucleic acid according to SEQ ID NO. 11.

FIG. 6 shows a graphic representation of the results of in vivo studies performed in liver cancer cell line HLE, wherein the effect of the presence of S/MAR-elements on the long-term expression level of the reporter gene coding for eGFP has been analyzed. In this context, the expression of eGFP on the basis of the vector pEPI-SM-L (cf. FIG. 5A) has been compared with the expression of eGFP on the basis of the vector pEPI1-SM-S (cf. FIG. 5B). In this context, 10 µg of DNA per 6-well with 300.000 cells was introduced by mixing with 30 µl of FuGENE6 as transfection reagent. The cells were splitted twice a week and the eGFP expression levels have been assessed once per week by flow cytometry. Since liver cancer cell lines are fast dividing cells, in order to ensure the stability of the vector DNA in the cells, geneticin (G418) has been used for selection.

Figure 6A:
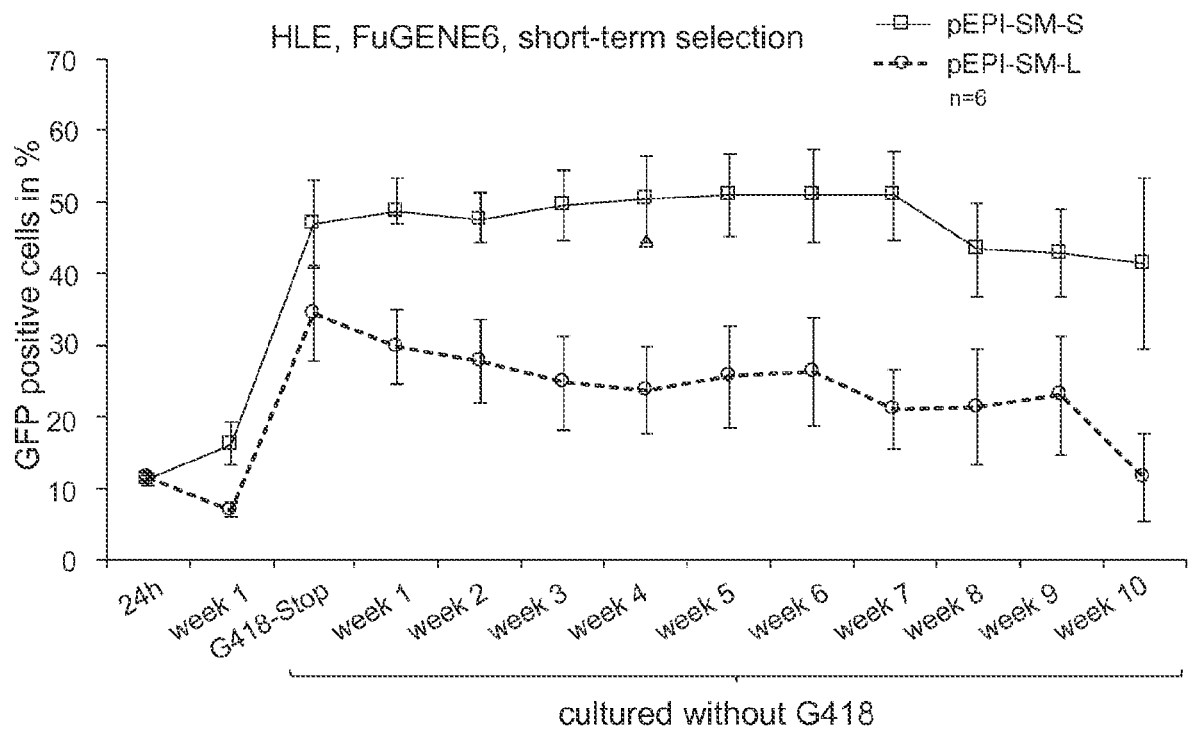
FIG. 6A illustrated the results of the GFP expression in a test series, where a short-term selection with G418 for about 10 days was applied.

FIG. 6A shows the results of the GFP expression in a test series, where a short-term selection with G418 for about 10 days was applied.

Figure 6B:
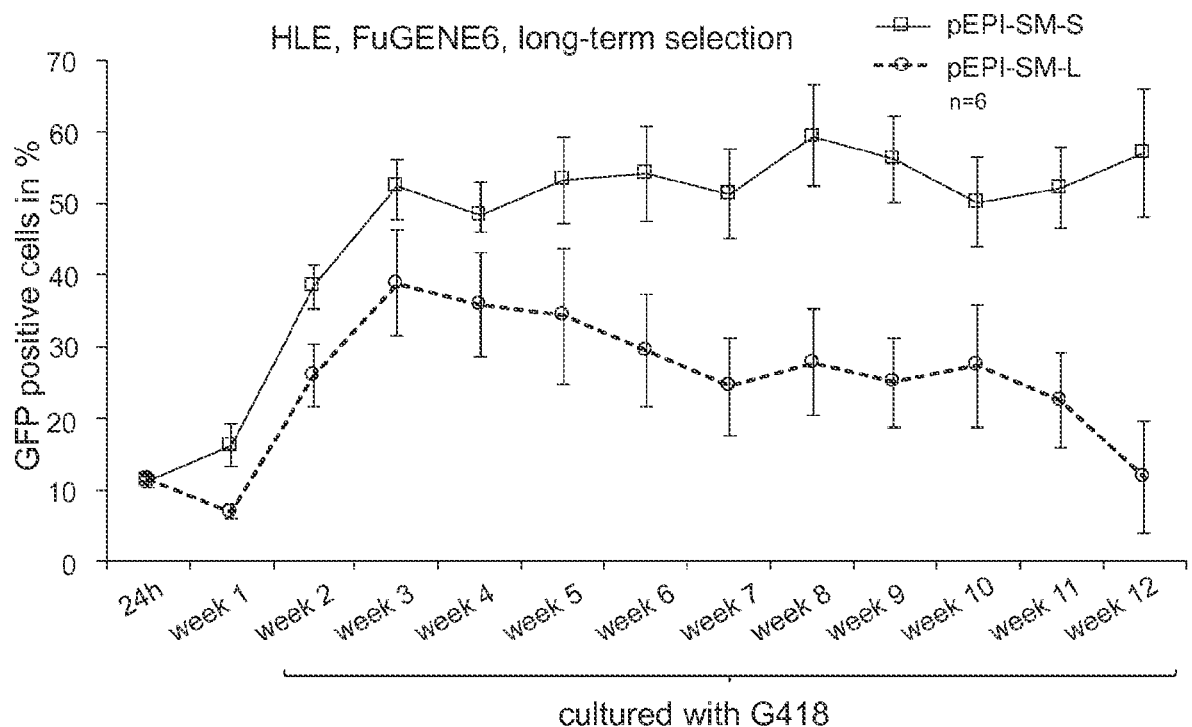
FIG. 6B provides the result of the test series where a long-term selection over the whole observation time of 12 weeks with G418 has been applied demonstrating that both variants of the S/MAR-element, i.e. the long as well as the shortened variant, lead to a long-term expression of eGFP in the transfected cells and that the long-term expression of GFP can be even improved on the basis of the shortened variant of the S/MAR-element.

FIG. 6B contains the result of the test series where a long-term selection over the whole observation time of 12 weeks with G418 has been applied. In this context, it can be seen that both variants of the S/MAR-element, i.e. the long as well as the shortened variant, lead to a long-term expression of eGFP in the transfected cells. Furthermore, the long-term expression of GFP can be even improved on the basis of the shortened variant of the S/MAR-element. Both variants of the S/MAR-element ensure an episomal persistence of the transferred nucleic acid molecules in the target cells, as can be deduced from the expression of eGFP over the whole observation time of 12 weeks. Furthermore, the shortened variant leads to a higher percentage of GFP positive cells, indicating an improved episomal persistence of the transferred nucleic acid molecules in the cells.

FIG. 7 shows the graphic representation of the results of in vivo studies in liver cancer cell line HLF, wherein the effect of the presence of S/MAR-elements on a long-term expression of eGFP has been analyzed. For this purpose, HLF cells have been transfected with the vector pEPI1-SM-L on the one hand, and pEPI1-SM-S, on the other hand. In this context, 10 µg of DNA per 6-well with 300.000 cells was introduced by mixing with 30 µl FuGENE6 as the transfection reagent. Cells were splitted twice a week and the eGFP expression levels were assessed once per week by flow cytometry. Since HLF cells are fast dividing cells, a selection on the basis of geneticin (G418) has been applied in order to prevent a loss of the transferred DNA.

Figure 7A:
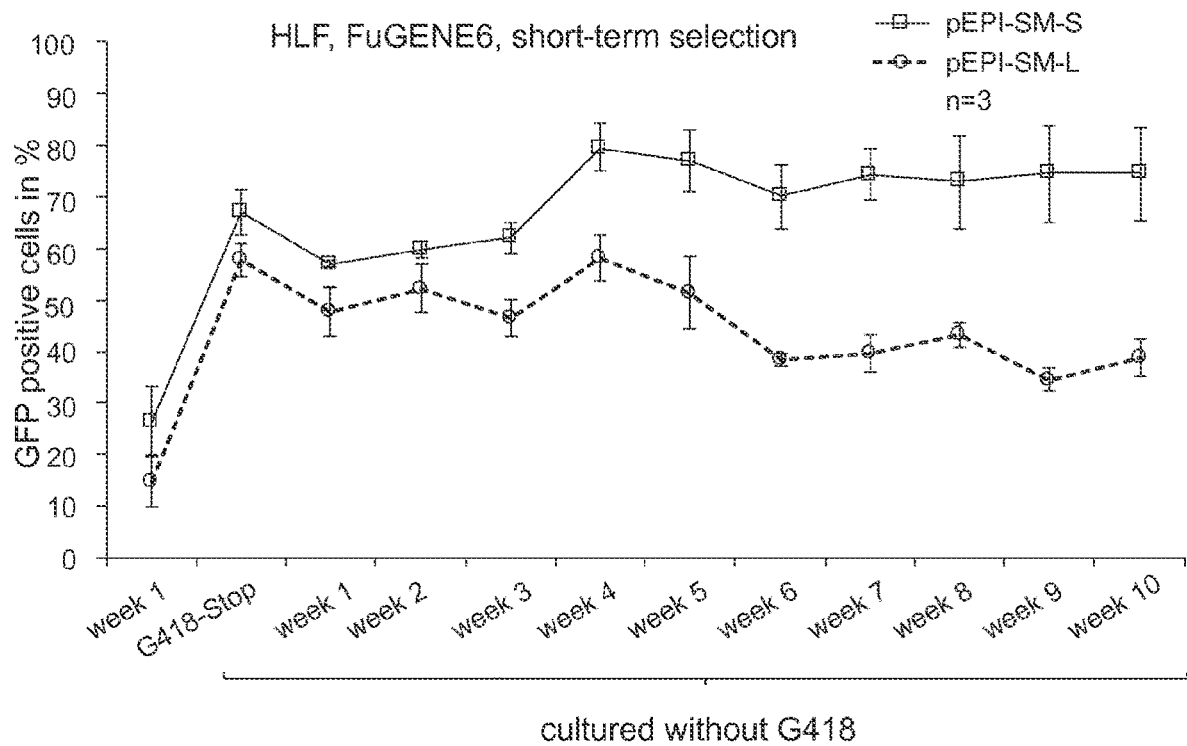
FIG. 7A provides the results of a test series under short-term selection with G418, wherein the selection was performed during the first 10 days of cultivation and after 10 days, the cultivation with G418 was stopped for the rest of the observation time of further 10 weeks.

FIG. 7A contains the results of a test series under short-term selection with G418, wherein the selection has been performed during the first 10 days of cultivation. After 10 days, the cultivation with G418 was stopped for the rest of the observation time of further 10 weeks. As can be seen from FIG. 7A, both variants of the S/MAR-element lead to a long-term expression of eGFP in the transfected cells after short-term selection. A higher percentage of eGFP positive cells can surprisingly be achieved with the shortened variant of the S/MAR-element.

Figure 7B:
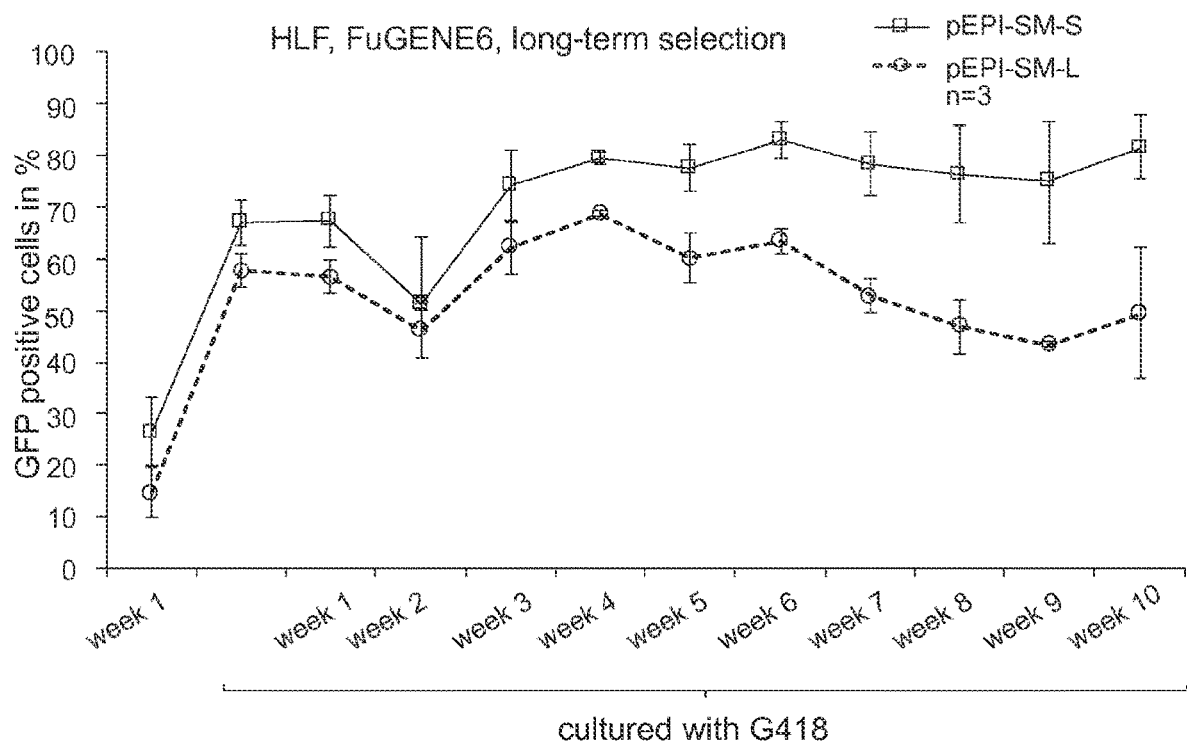
FIG. 7B provides the results of the test series where a long-term selection with G418 was performed during the whole observation time of 10 weeks.

FIG. 7B contains the results of the test series where a long-term selection with G418 has been performed during the whole observation time of 10 weeks. As can be seen from FIG. 7B, both variants of the S/MAR-element lead to a long-term expression of eGFP in the transfected cells under long-term selection with G418. Surprisingly, the long-term expression can be improved on the basis of the shortened variant of the S/MAR-element, independent from the selection conditions.

Figure 8A:
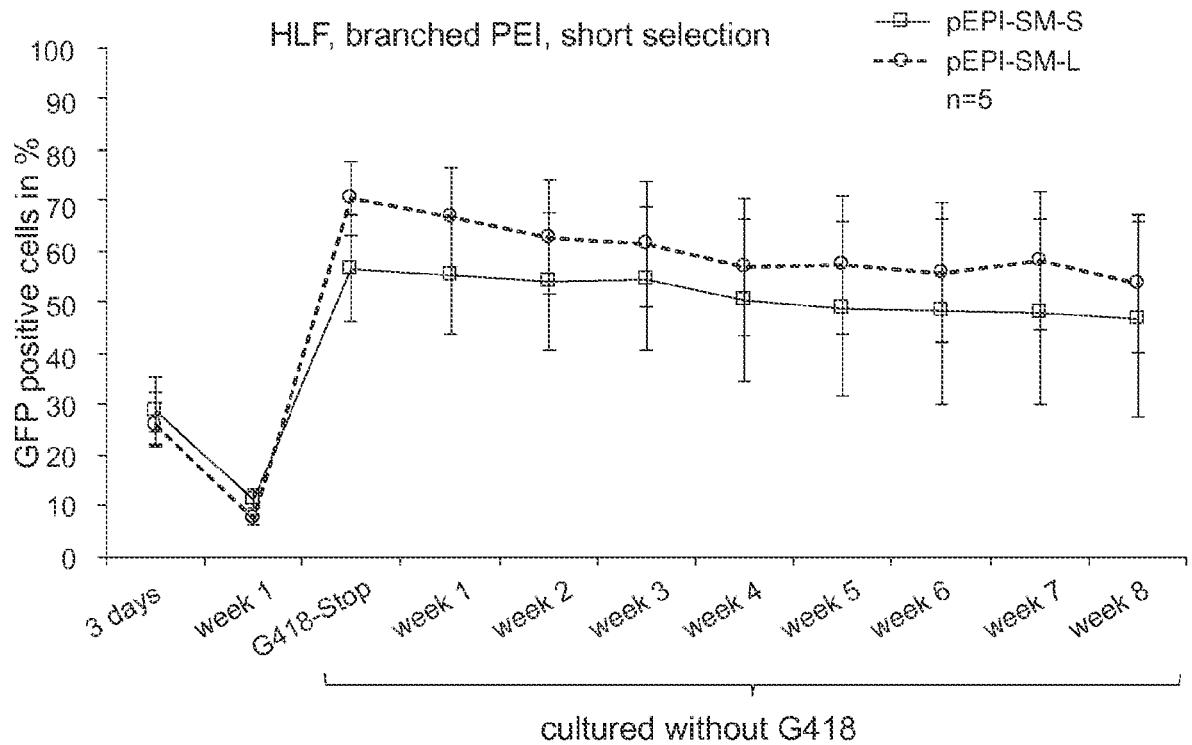
FIG. 8A provides the graphic representation of in vivo studies in liver cancer cell line HLF, wherein the effect of the presence of S/MAR-elements on the short-term expression levels of eGFP has been analyzed under a short-term selection with geneticin (G418) for two weeks.
Figure 8B:
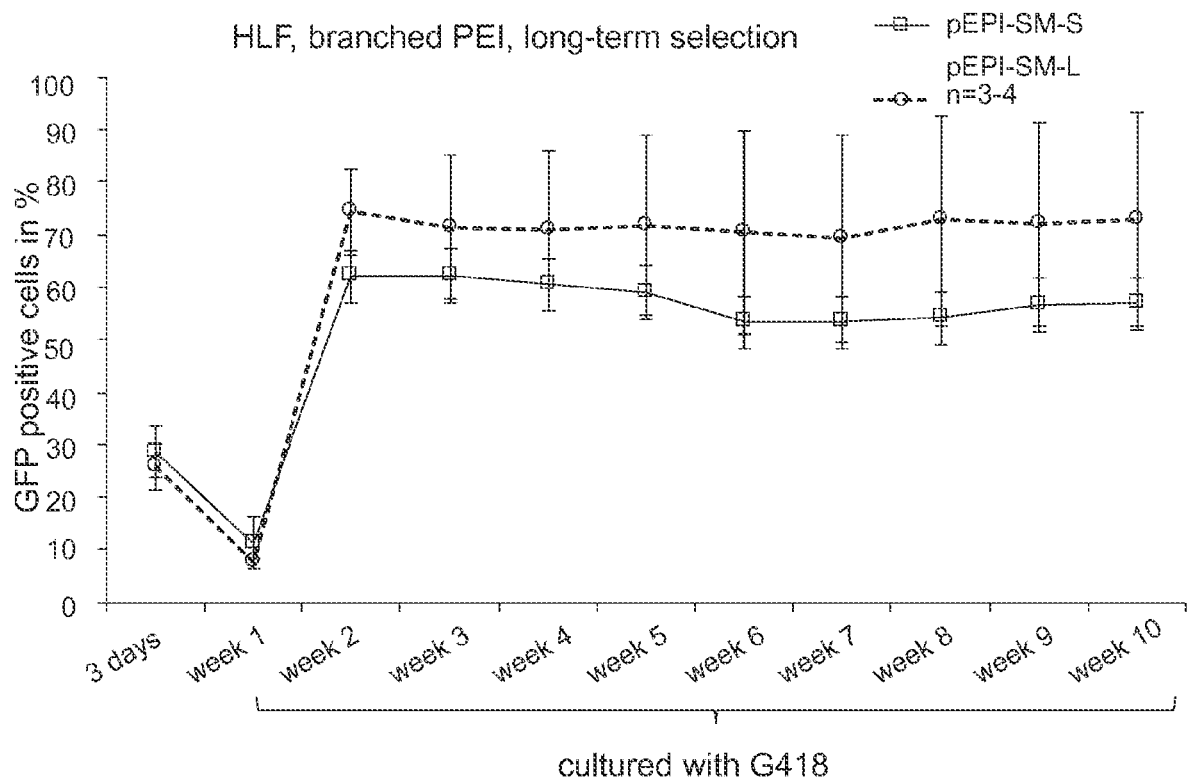
FIG. 8B provides the graphic representation of in vivo studies in liver cancer cell line HLF, wherein the effect of the presence of S/MAR-elements on the long-term expression levels of eGFP has been analyzed with the test performed under continuous G418 selection over seven weeks.

FIG. 8 shows the graphic representation of in vivo studies in liver cancer cell line HLF, wherein the effect of the presence of S/MAR-elements on the long-term expression levels of eGFP has been analyzed. Thereby, polyethylenimine has been used as transfection reagent. In this context, the cells have been transfected either with the vector pEPI1-SM-L or pEPI1-SM-S, respectively. For this purpose, 6 µg of DNA per 6-well with 300.000 cells was introduced by mixing with 18 µg branched polyethylenimine with a molecular weight of 25 kDa. The cells were splitted twice a week and the eGFP expression levels were assessed once per week by flow cytometry. A first test series has been performed under a short-term selection with geneticin (G418) for two weeks (FIG. 8A). In this context, after the first week of growing, the cells were selected for two weeks with 0.9 mg/ml G418. Afterwards, the cells were grown for additional eight weeks. The expression level of eGFP has been measured once a week. The second test series was performed under continuous G418 selection over seven weeks (FIG. 8B). As can be seen from FIG. 8A, cells transfected with branched polyethylenimine with the plasmids pEPI1-SM-S and pEPI1-SM-L show a stable long-term expression level of eGFP. The expression level under the shortened variant of the S/MAR-element is slightly superior. The same applies for the second test series, performed under long-term selection with G418 with the results depicted in FIG. 8B. Also under long-term selection, 60 to 80% of the cells could be detected as eGFP positive. The long-term expression under the shortened variant of the S/MAR-element is slightly superior compared to the full or long version of the S/MAR-element, independent from selection conditions.

FIG. 9 shows the graphic representation of the results of in vivo studies in liver cancer cell line HLF, wherein the impact of different weight related ratios of polyethylenimine to nucleic acid molecules on the expression level of the transgene has been analyzed. For this purpose, cells of the liver cancer cell line HLF were transfected with the vector pEPI1-SM-S (cf. FIG. 5B), wherein different amounts of polyethylenimine and nucleic acid molecules have been used. In this context, the indicated amounts of DNA (µg) per well of a 6-well plate with 200.000 cells were introduced by mixing the DNA amounts with 9 µg of branched or linear polyethylenimine, both with a molecular weight of 25 kDa. Cells were analyzed for eGFP expression three days after transfection by flow cytometry. Furthermore, the cell viability, i.e. the percentage of non-apoptotic cells, has been determined.

Figure 9A:
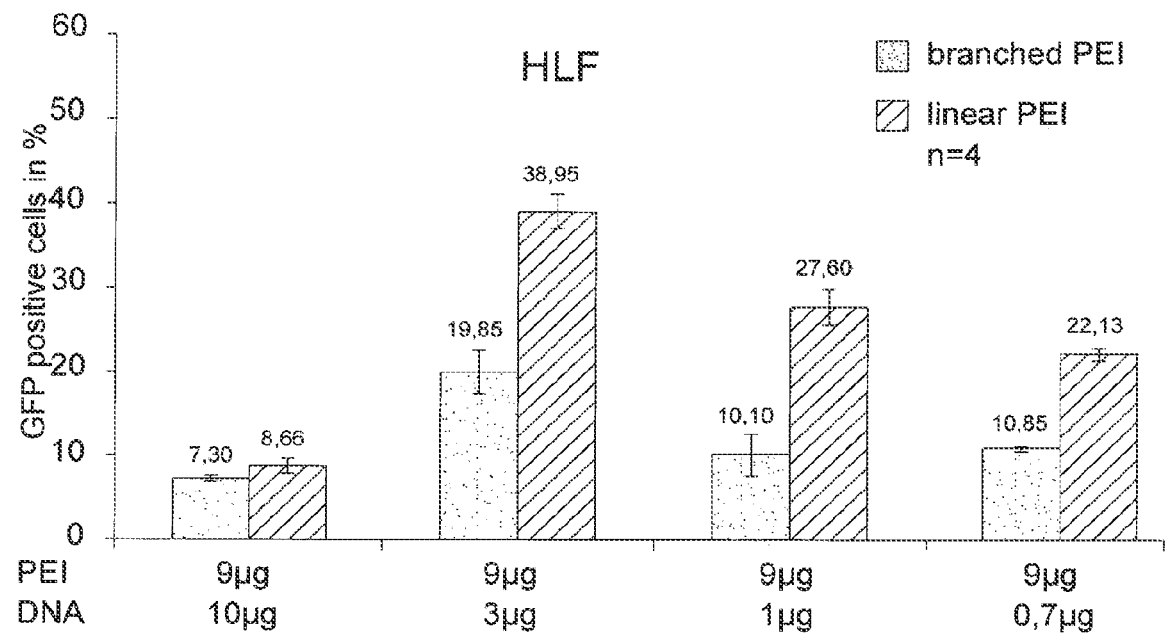
FIG. 9A provides the results of the analysis of the eGFP expression of test series with 10 μg DNA, 3 μg DNA, 9 μg DNA and 0.7 μg DNA, wherein in each case 9 μg of the respective polyethylenimine was used.

FIG. 9A shows the results of the analysis of the eGFP expression of test series with 10 µg DNA, 3 µg DNA, 9 µg DNA and 0.7 µg DNA, wherein in each case 9 µg of the respective polyethylenimine have been used. In this context, it can be seen from FIG. 9A that all tested weight related ratios of polyethylenimine to nucleic acid molecules are suitable to achieve an expression of the coding sequence, which is eGFP in the present case, in the transfected cells. Furthermore, the best results were achieved with a weight related ratio of polyethylenimine to nucleic acid molecules of 3:1. Furthermore, linear polyethylenimine with a molecular weight of 25 kDa is superior in comparison to branched polyethylenimine with a molecular weight of 25 kDa.

Figure 9B:
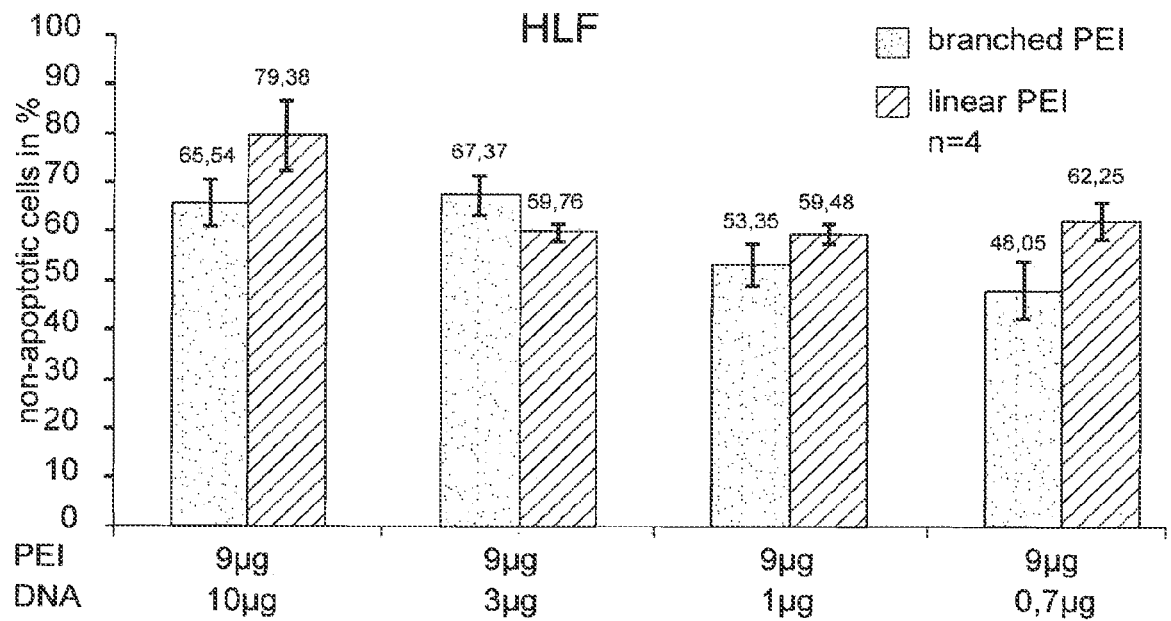
FIG. 9B provides the results of the determination of the cell viability on the basis of the percentage of non-apoptotic cells utilizing a test series with 10 μg DNA, 3 μg DNA, 9 μg DNA and 0.7 μg DNA, wherein in each case 9 μg of the respective polyethylenimine.

FIG. 9B contains the results of the determination of the cell viability on the basis of the percentage of non-apoptotic cells. As can be seen from FIG. 9B, the cell viability in all test series with all tested weight related ratios and both variants of polyethylenimine was satisfying. The best results are achieved with a weight-related ratio of polyethylenimine to nucleic acid molecules of 9:10 or 3:1.

Figure 10A:
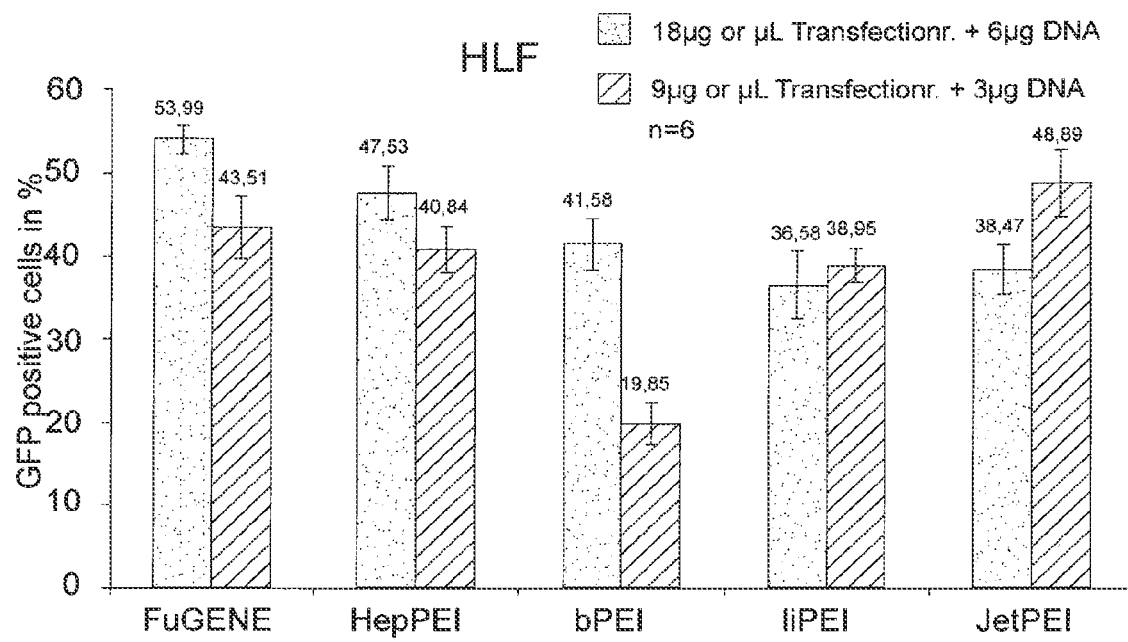
FIG. 10A provides a graphic representation concerning the percentage of GFP positive cells involved with in vivo studies performed in liver cancer cell line HLF, wherein the influence of different variants of polyethylenimine at a defined weight or volume related ratio of polyethylenimine to nucleic acid molecules of 3:1 for transfection have been used.
Figure 10B:
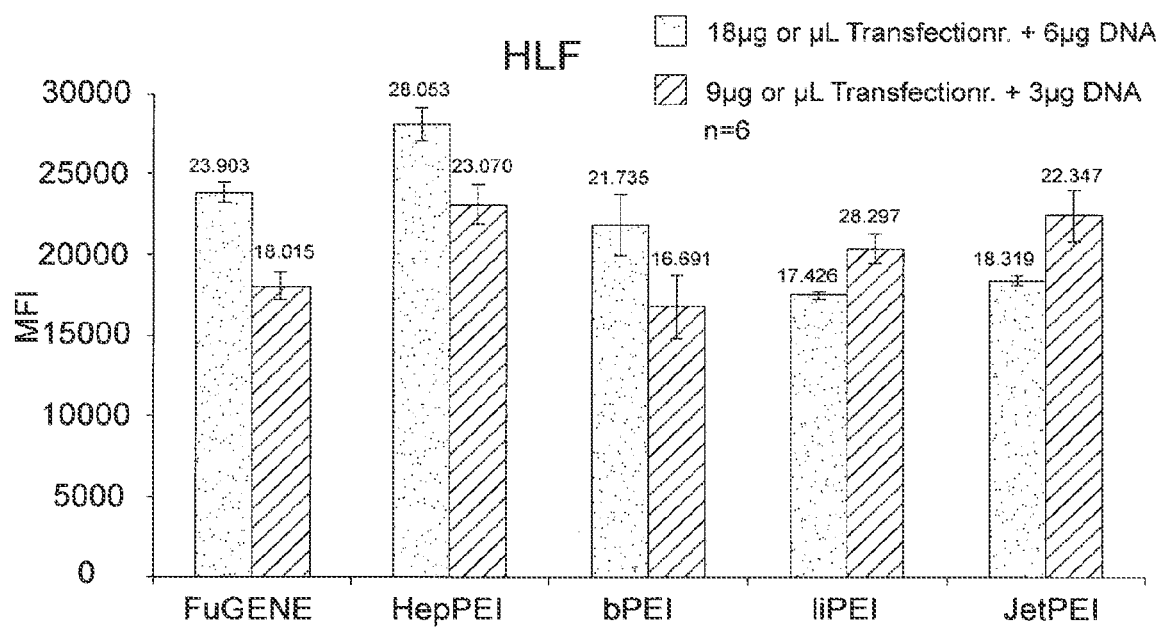
FIG. 10B provides further confirmation of the results included in FIG. 10A with the results of the determination of the mean fluorescence intensity (MFI) of eGFP in the cells.
Figure 10C:
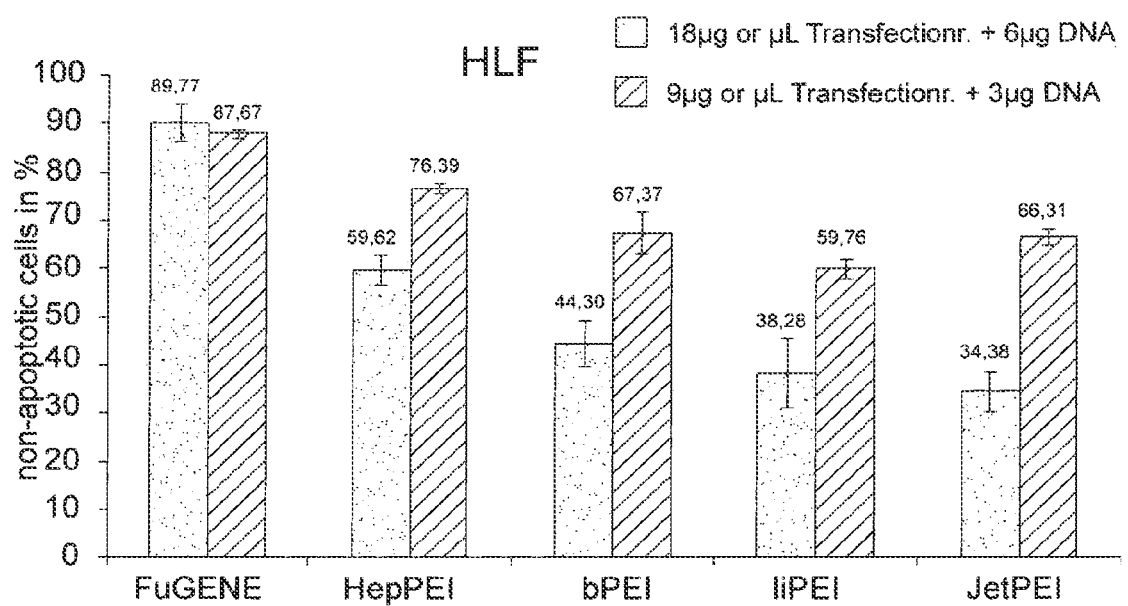
FIG. 10C provides confirmation that the transfection with all variants of polyethylenimine is linked with a sufficient cell viability and that the use of 9 μg or 9 μl of the transfection reagent and 3 μg of DNA leads to a further improvement of the cell viability.

FIG. 10 shows the graphic representation of the results of in vivo studies performed in liver cancer cell line HLF, wherein the influence of different variants of polyethylenimine at a defined weight or volume related ratio of polyethylenimine to nucleic acid molecules of 3:1 for transfection have been used. In this context, the expression of eGFP transgene expression has been analyzed or determined. For this purpose, cells of the liver cancer cell line HLF have been transfected with the vector pEPI1-SM-S (cf. FIG. 5B), wherein different variants of polyethylenimine have been used at two different concentrations in order to introduce the vector DNA into the HLF target cells. As transfection reagents, the following variants of polyethylenimine have been used: glucose-conjugated polyethylenimine (Hep PEI), commercially available from Polyplus Inc., Illkirch, FR under the trade name jetPEI®-hepatocyte, branched polyethylenimine with a molecular weight of 25 kDa (bPEI), linear polyethylenimine with a molecular weight of 24 kDa (liPEI) and JetPEI a commercially available polyethylenimine from Polyplus Inc., Illkirch, FR. Furthermore, as the positive control, the transfection has been also performed with FuGENE6 as a well-known and established transfection reagent. All test series have been performed with a fixed weight related ratio of polyethylenimine to DNA of 3:1. For each transfection reagent, a first approach using 18 µl or 18 µg transfection reagent in combination with 6 µg DNA and a second approach with 9 µl or 9 µg of the transfection reagent in combination with 3 µg DNA have been performed. For the purpose of transfection, the mixtures of polyethylenimine and nucleic acid molecules were incubated with 200.000 cells in a well of 6-well plate. The expression of eGFP has been analyzed three days after transfection by flow cytometry. FIG. 10A contains the results concerning the percentage of GFP positive cells in the different approaches. In this context, it can be seen that all variants of polyethylenimine in all concentrations lead to a sufficient transfection of the liver cancer cells with the vector. The results are further confirmed by the results of the determination of the mean fluorescence intensity (MFI) of eGFP in the cells, which are depicted in FIG. 10B. Furthermore, the cell viability on the basis of the determination of the percentage of non-apoptotic cells has been analyzed three days after transfection. As can be seen from FIG. 10C, the transfection with all variants of polyethylenimine is linked with a sufficient cell viability. Furthermore, the use of 9 µg or 9 µl of the transfection reagent and 3 µg of DNA leads to a further improvement of the cell viability.

Figure 11A:
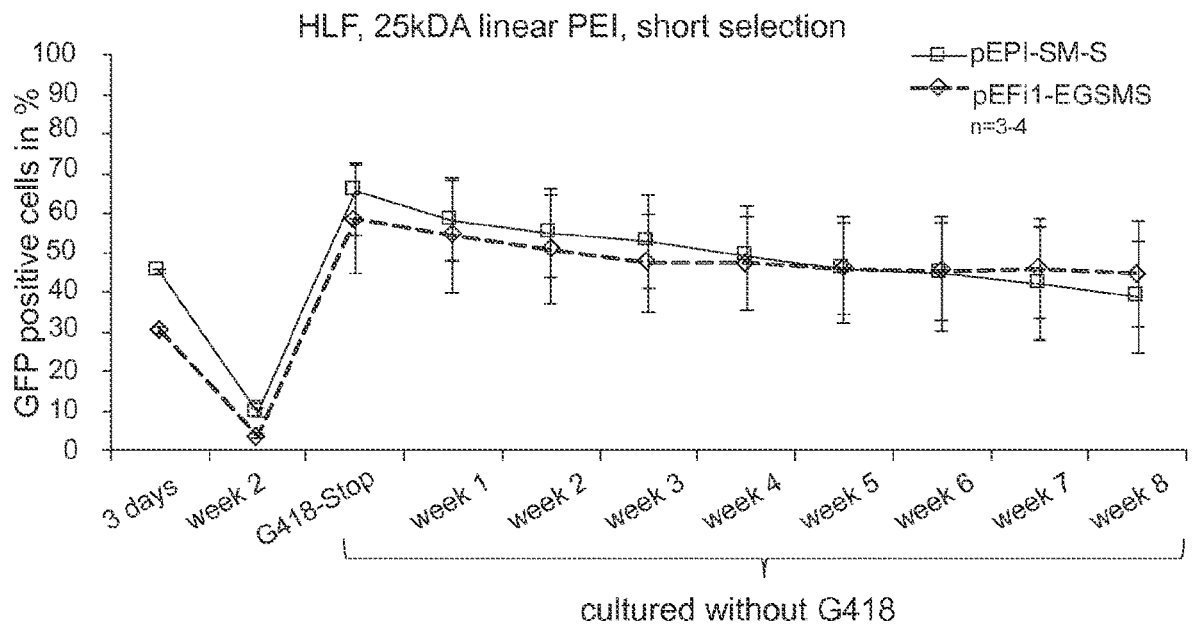
FIG. 11A shows the graphic representation of the results of in vivo studies performed in liver cancer cell line HLF, wherein the influence of an optimized intermediate promoter derived from the gene coding for human Elongation Factor-1 alpha on the expression level of eGFP was analyzed and where the test series was performed under a short-term selection with G418 for two weeks with a subsequent cultivation for additional eight weeks without any selection.
Figure 11B:
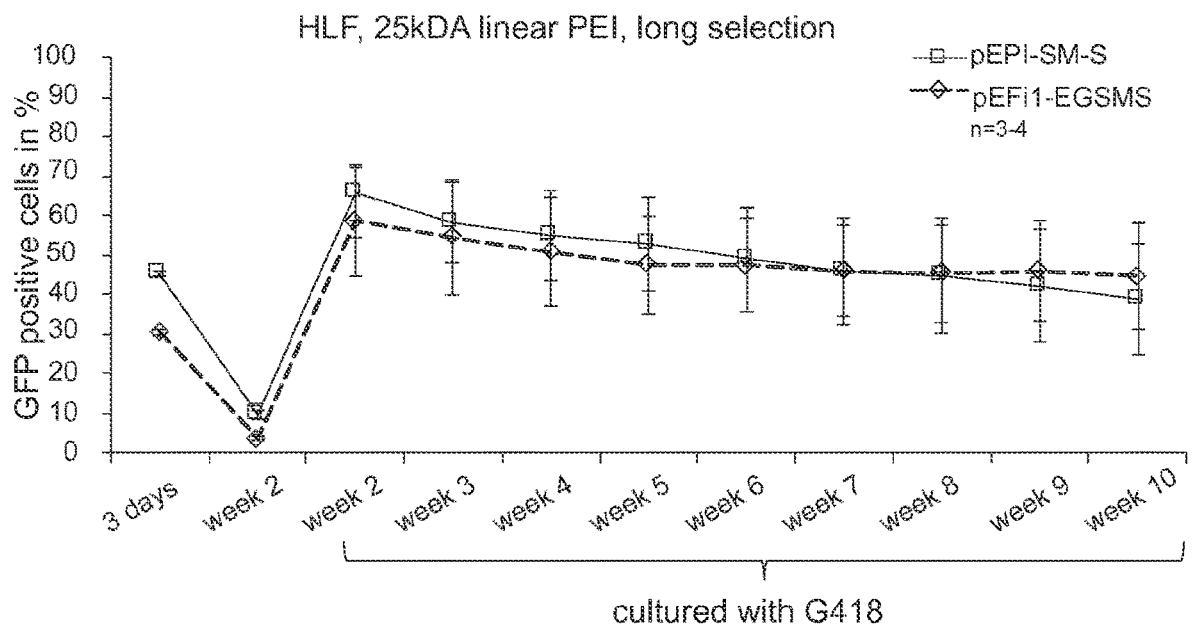
FIG. 11B shows the graphic representation of the results of in vivo studies performed in liver cancer cell line HLF, wherein the influence of an optimized intermediate promoter derived from the gene coding for human Elongation Factor-1 alpha on the expression level of eGFP was analyzed and where the test series was performed under long-term selection with G418 over an observation time of ten weeks.

FIG. 11 shows the graphic representation of the results of in vivo studies performed in liver cancer cell line HLF, wherein the influence of an optimized intermediate promoter derived from the gene coding for human Elongation Factor-1 alpha on the expression level of eGFP has been analyzed. For this purpose, cells of the liver cancer cell line HLF have been transfected with the vector pEPI1-SM-S (cf. FIG. 5B), on the hand, and pEFi1_EGSMs (cf. FIG. 5C), on the other hand. For this purpose, 3 μg of DNA per well of a 6-well plate with 200.000 cells was mixed with 9 μg of linear PEI having a molecular weight of 25 kDa and then transfected. The cells were splitted twice a week and the eGFP expression levels were assessed once per week by a flow cytometry. The test series has been performed under a short-term selection with G418 for two weeks with a subsequent cultivation for additional eight weeks without any selection (FIG. 11A). Furthermore, the approach was performed under long-term selection with G418 over an observation time of ten weeks (FIG. 11B). As can be seen from FIG. 11A and FIG. 11B, the promoter derived from the human gene coding for Elongation Factor-1 alpha leads to a stable expression of the transgene, in this case the cDNA coding for eGFP, in the cells. A promoter derived from the human gene coding for Elongation Factor-1 alpha (EF1a) is suitable to direct a stable and long-term expression of coding sequences in liver cells.

FIG. 12 shows the graphic representation of the results of in vivo studies in liver cancer cell line HLF, wherein the transfection efficacy of gold nanoparticles comprising variants of polyethylenimine covalently bound as vehicle for the transfer of the episomal expression vector pEPI1-SM-S (FIG. 5B) into the target cells has been analyzed. In this context, for each variant of polyethylenimine, several approaches with different amounts of DNA (50 ng, 1 μg, 3 μg, 6 μg, 9 μg and 20 μg) have been performed. In this context, linear polyethylenimine with a molecular weight of 10 kDa, linear polyethylenimine with a molecular weight of 25 kDa and branched polyethylenimine with a molecular weight of 25 kDa have been used. For the purpose of transfection, the indicated amounts of DNA (μg) were mixed with 30 μg gold nanoparticles with an average diameter of 5 nm for 5 minutes at room temperature. Then the mix was added to one well of a 6-well plate with 200.000 cells. The cells were harvested and analyzed for GFP expression three days after transfection by flow cytometry.

Figure 12A:
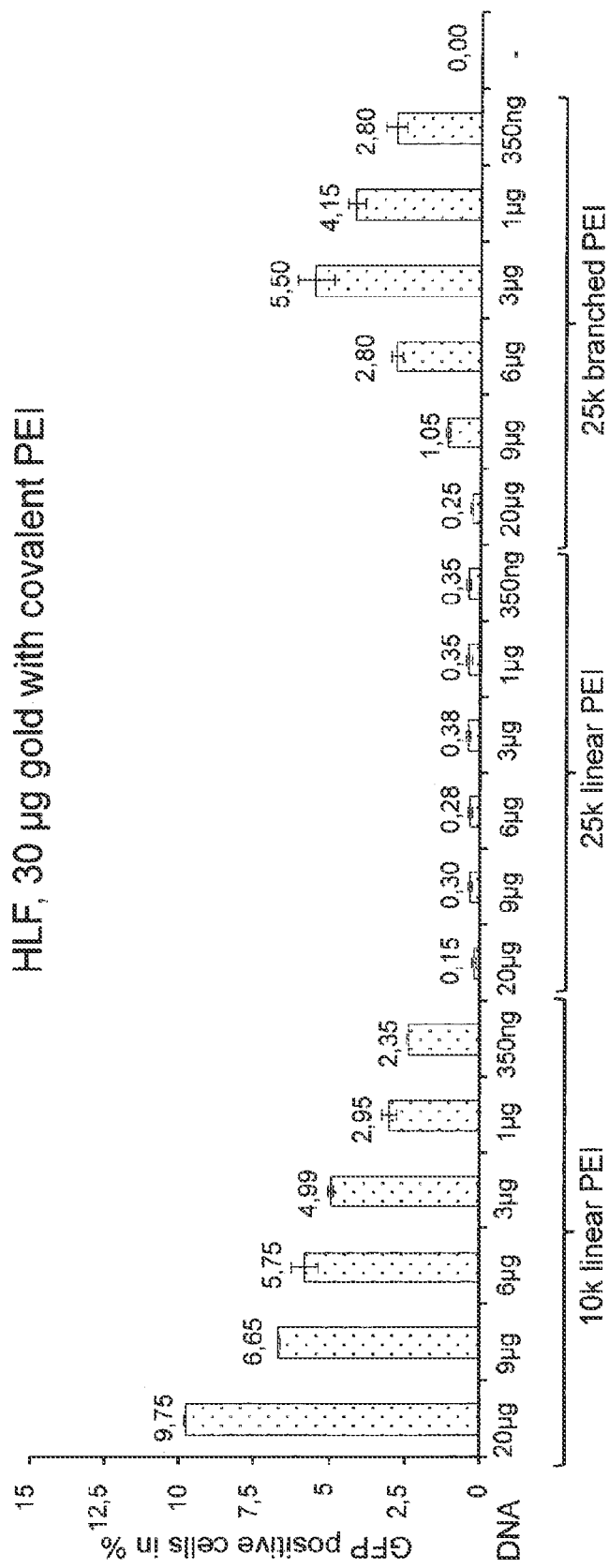
FIG. 12A provides a graphic representation of the results of in vivo studies in liver cancer cell line HLF, wherein the transfection efficacy of gold nanoparticles comprising variants of polyethylenimine covalently bound as vehicle for the transfer of the episomal expression vector pEPI1-SM-S (FIG. 5B) into the target cells has been analyzed demonstrating that all variants of polyethylenimine as well as all amounts of DNA are sufficient in order to achieve a transfer of the nucleic acid molecules into the cells.
Figure 12B:
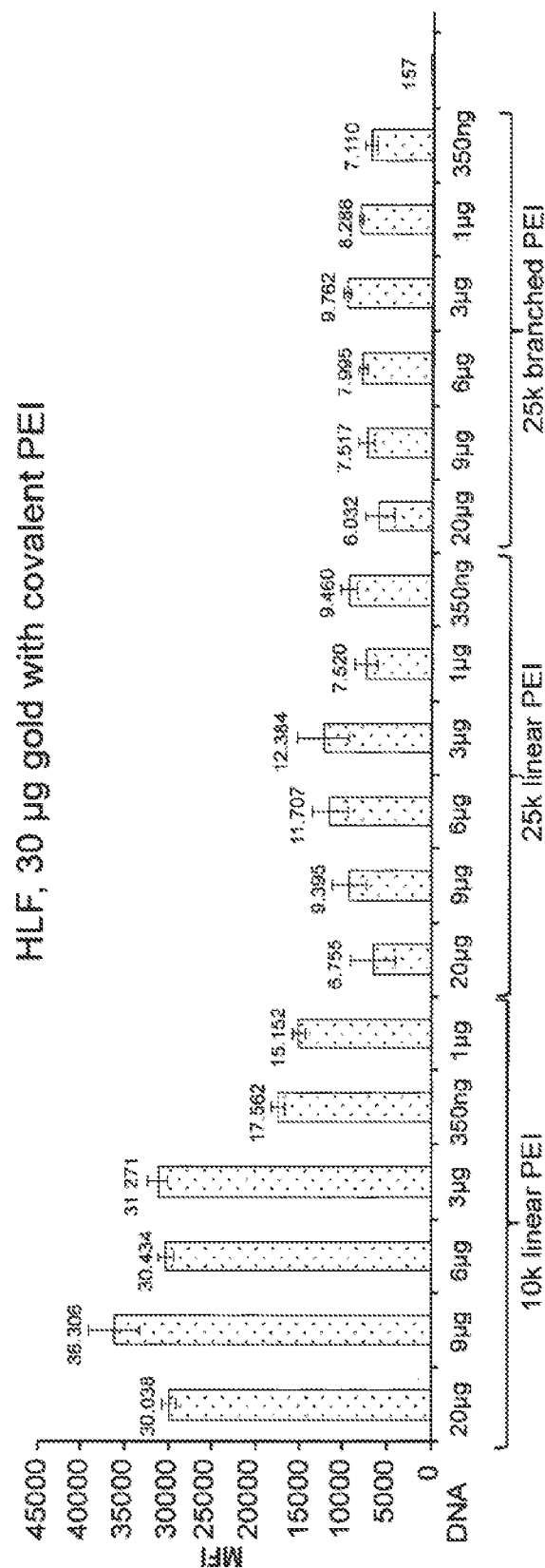
FIG. 12B provides a graphic representation of the results of in vivo studies in liver cancer cell line HLF, utilizing the mean fluorescence intensity (MFI) of the GFP in the cells demonstrating that all variants of polyethylenimine as well as all amounts of DNA are sufficient in order to achieve a transfer of the nucleic acid molecules into the cells.

FIG. 12A shows the percentage of GFP positive cells three days after transfection. It can be seen that all variants of polyethylenimine as well as all amounts of DNA are sufficient in order to achieve a transfer of the nucleic acid molecules into the cells. Furthermore, the mean fluorescence intensity (MFI) of the GFP in the cells has been determined (FIG. 12B). The determination of the mean fluorescence intensity also confirms that all variants of polyethylenimine as well as all amounts of DNA, which have been tested, lead to a transfection of the cells with the nucleic acid molecules on the basis of the vector pEPI1-SM-S into the target cells.

Figure 12C:
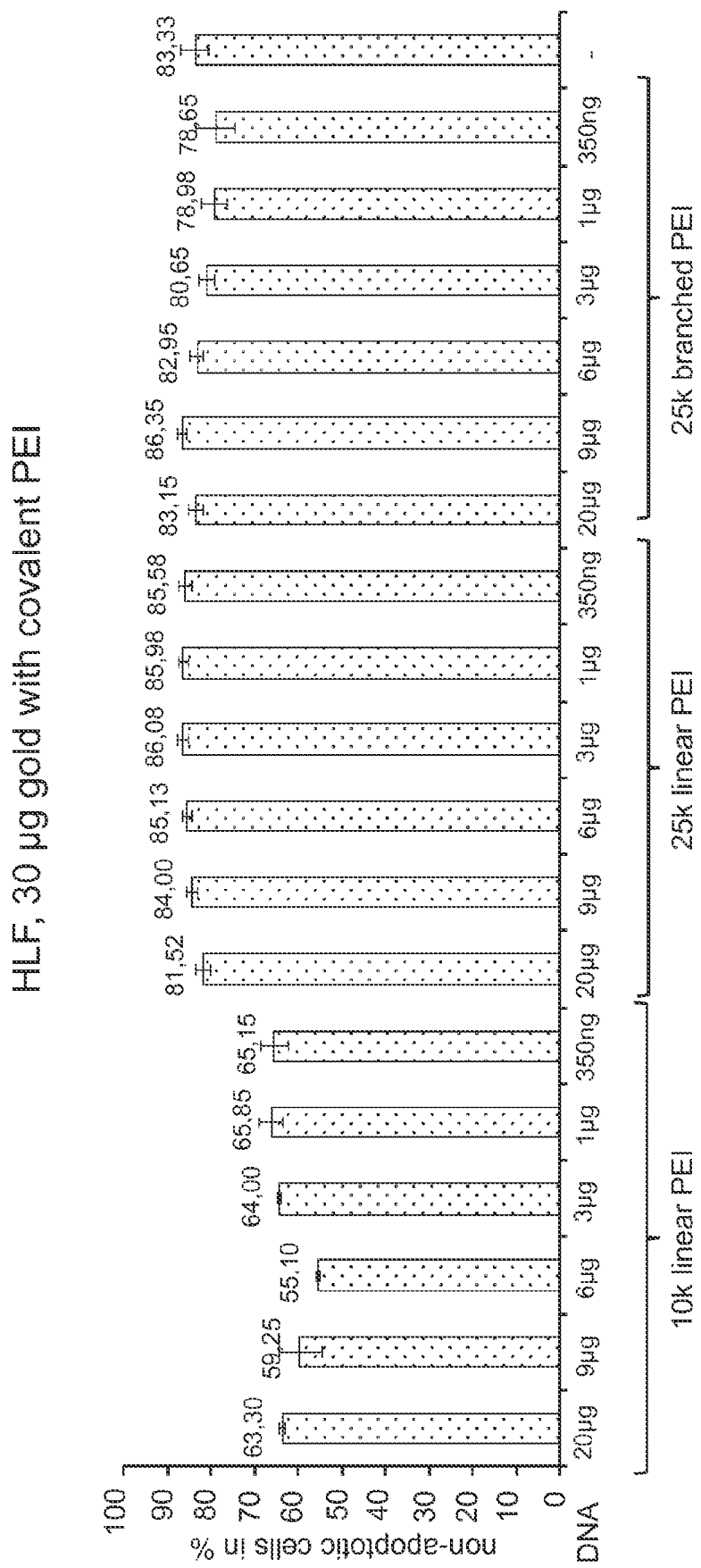
FIG. 12C shows the results of an analysis of the cell viability on the basis of the determination of the percentage of non-apoptotic cells three days after transfection demonstrating that all variants of polyethylenimine as well as all amounts of DNA used for transfection lead to a sufficient viability of the transfected cells.

FIG. 12C shows the results of an analysis of the cell viability on the basis of the determination of the percentage of non-apoptotic cells three days after transfection. As can be seen from FIG. 12C, all variants of polyethylenimine as well as all amounts of DNA used for transfection lead to a sufficient viability of the transfected cells. The best viability can be achieved by the use of linear PEI with a molecular weight of 25 kDa or branched PEI with a molecular weight of 25 kDa.

FIG. 13 shows the graphic representation of the results of in vivo studies in liver cancer cell line HLF with a lentiviral-based system, wherein the influence of the UCOE on the expression of eGFP in liver cancer cells has been analyzed. For this purpose, liver cancer cells of cell line HLF have been transfected with the vector pCL-UCOE-EF1 (cf. FIG. 5D). Furthermore, for comparative purposes, HLF cells have been transfected with a vector pCL-EF1, which is identical with pCL-UCOE-EF1, except with respect to the presence of a UCOE. In other words, the expression of the coding sequence in pCL-EF1 is only directed by the EF1 promoter. In addition, HLF cells have been transfected with a vector pCL-UCOE, which is identical with pCL-UCOE-EF1, except with respect to the presence of the EF1 promoter. In other words, the expression of the coding sequence in pCL1-EF1 is only directed by the UCOE, in particular the nucleic acid sequences forming the UCOE. The transfection of the cells has been performed with $10^{-3}$ to $10^{-1}$ diluted nucleic acid molecules on the basis of the vectors. The expression of eGFP has been analyzed three days after transfection on the basis of measuring the percentage of cells expression eGFP and the mean fluorescence intensity (MFI) of the GFP in the cells via FACS analysis. As can be seen from FIG. 13, the vector, which additionally comprises the UCOE leads to a significantly higher percentage of cells expressing eGFP compared to the vectors containing the coding sequence under control of UCOE and the EF1-promoter alone, respectively. The significant enhancement of the expression of the coding sequence directed by a combined use of the EF1-alpha promoter, on the one hand, and the UCOE, on the other hand, is a clear indication for the presence of a synergistic effect.

FIG. 14 shows the graphic representation of the results of in vivo studies in liver cancer cell line HLF, wherein the factor level in cells transfected with pEPI_F8-SM-S and pEFi1-GFP-FIX has been analyzed. For this purpose, cells of the liver cancer cell line HLF have been transfected with the vector pEPI_F8-SM-S (cf. FIG. 5E), on the hand, and pEFi1-GFP-FIX (cf. FIG. 5F), on the other hand. For this purpose, 6 μg of DNA per well of a 6-well plate with 200.000 cells was mixed with 18 μl FuGENE6 as transfection reagent and then transfected. On the second day after transfection, cell culture medium was removed and cells were incubated for another 24 hours with 1 ml medium per 6-well. Afterwards, the medium was removed and immediately frozen. Cell culture supernatant was analyzed by a functional factor level measurement with ACL Top 500 (Werfen GmbH, Kirchheim near Munich, DE). Additionally, on the same day, cells were harvested and GFP expression was measured via FACS. As can be seen from FIG. 14, HLF cells transfected with either vector pEPI_F8-SM-S or pEFi1-GFP-FIX show a production of fusion proteins comprising either factor FVIII or factor FIX. On this basis it can be concluded that the expression system according to the present invention—in particular on the basis of the promoter EF1-alpha, a coding sequence with a nucleic acid sequence coding for a liver-specific and/or liver-expressed protein, especially a factor involved in hemostasis, and a S/MAR element—mediates an episomal expression of the liver-specific and/or liver-expressed proteins in target cells, which is sufficient to compensate loss-of-function mutations of monogenetic disorders, in particular hemophilia A and/or B.

FIG. 15 shows the schematic representation of a preferred design of a UCOE for the expression cassettes and/or vectors according to the present invention. The UCOE comprises a SV40 terminator and a polyadenylation signal. Furthermore, the UCOE comprises the HNRNPA2 promoter, preferably according to SEQ ID NO. 15 or SEQ ID NO. 23, with the respective transcript, preferably according to SEQ ID NO. 16 or SEQ ID NO. 24, as well as the CBX3 promoter, preferably according to SEQ ID NO. 13 or SEQ ID NO. 21, with the respective transcript, preferably according to SEQ ID NO. 14 or SEQ ID NO. 22. In addition, the UCOE comprises an enhancer region, preferably according to SEQ ID NO. 25. According to a preferred embodiment of the nucleic acid expression cassettes and/or vectors according to the present invention, the UCOE is located upstream to the promoter.

FIG. 16 shows the graphic representation of the results of an episomal DNA extraction conducted with liver cancer cell line HLE, confirming the episomal persistence of the transfected vectors. For this purpose, the vectors pEPI1-SM-L (FIG. 5A) and pEPI1-SM-S (FIG. 5B) have been used for transfection. In order to confirm episomal persistence of the vectors, 300.000 HLE cells were seeded in 6-well plates. After 24 hours, cells were transfected with 10 µg of vector DNA (either pEPI1-SM-L or pEPI1-SM-S) and 30 µl FuGENE6 as transfection reagent. Cells were splitted twice a week and cultivated for a total of 10 weeks, with an initial 2-week selection by adding G418 to the medium. After the cultivation period, cells were harvested and episomal DNA extraction was performed. As a control, episomal DNA extraction was also conducted with cells that were not transfected with DNA or cells that were transduced with a lentivirus that stably integrated into the genome of the cells. Afterwards, the extracted DNA was run on a 1 wt.-% agarose gel. As can be seen from FIG. 16, cells that were transfected with pEPI1-SM-L (lane 1 and 2) or pEPI1-SM-S (lanes 3 to 6) with a vector containing a S/MAR element show visible DNA bands. In contrast to this, no episomal DNA was harvested from HLE cells that were not transfected with a vector (lane 7) or with a lentivirus (lane 8). The results indicate the episomal persistence and/or the stable episomal replication in transfected cells mediated through nucleic expression cassettes and/or vectors containing a S/MAR element.

Furthermore, the above described studies have been performed in fibrosarcoma (synonymously fibroblastic sarcoma) cells. Fibrosarcoma is a malignant mesenchymal tumor derived from fibrous connective tissue and characterized by the presence of immature proliferating fibroblasts. Analyses and studies in fibrosarcoma cells are revealing with respect to an expression in cell types other than liver cells, in particular fibroblasts. In this context, fibrosarcoma cells of cell line HT1080 have been used:

FIG. 17 shows a graphic representation of the results of in vivo studies performed in fibrosarcoma cell line HT1080, wherein the effect of the presence of S/MAR-elements on the long-term expression level of the reporter gene coding for eGFP has been analyzed. In this context, the expression of eGFP on the basis of the vector pEPI-SM-L (cf. FIG. 5A) has been compared with the expression of eGFP on the basis of the vector pEPI1-SM-S (cf. FIG. 5B). In this context, 10 µg of DNA per 6-well with 300.000 cells was introduced by mixing with 30 µl of FuGENE6 as transfection reagent. The cells were splitted twice a week and the eGFP expression levels have been assessed once per week by flow cytometry. Since fibrosarcoma cells are fast dividing cells, in order to ensure the stability of the vector DNA in the cells, geneticin (G418) has been used for selection.

Figure 17A:
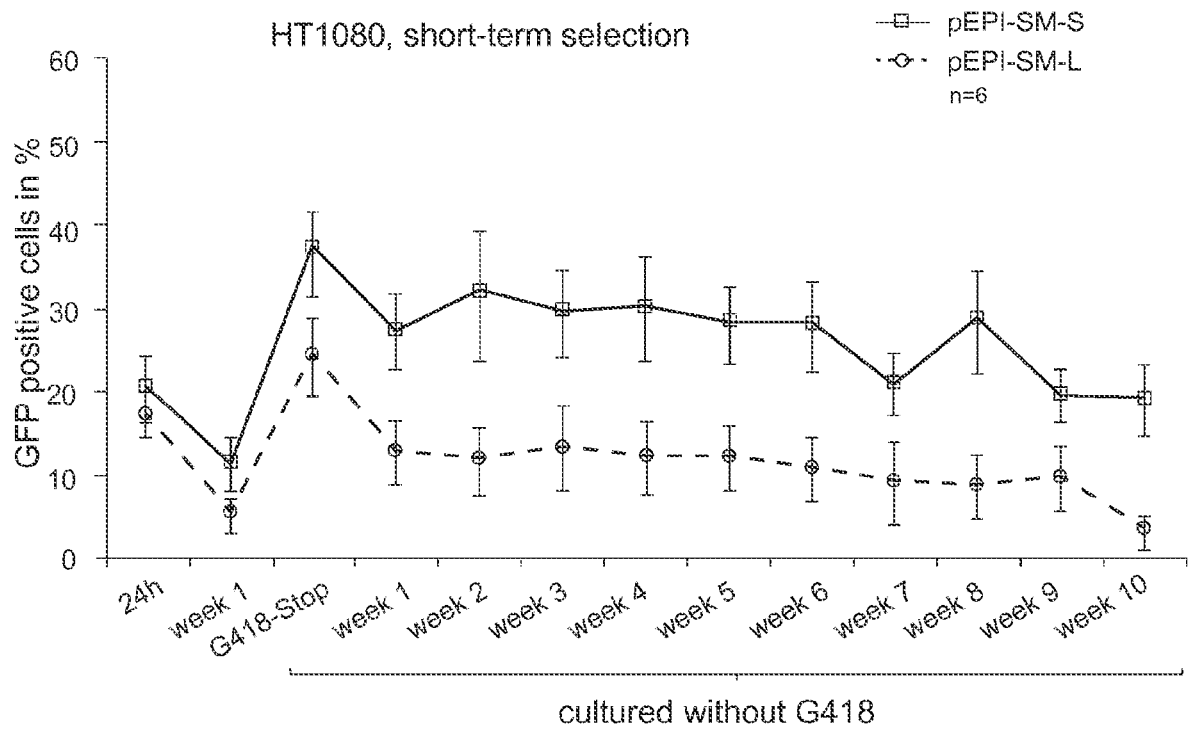
FIG. 17A shows a graphic representation of the results of in vivo studies in fibrosarcoma cell line HT1080 concerning the effect of the presence of S/MAR elements on the short-term expression levels in transfected cells cultured without G418.
Figure 17B:
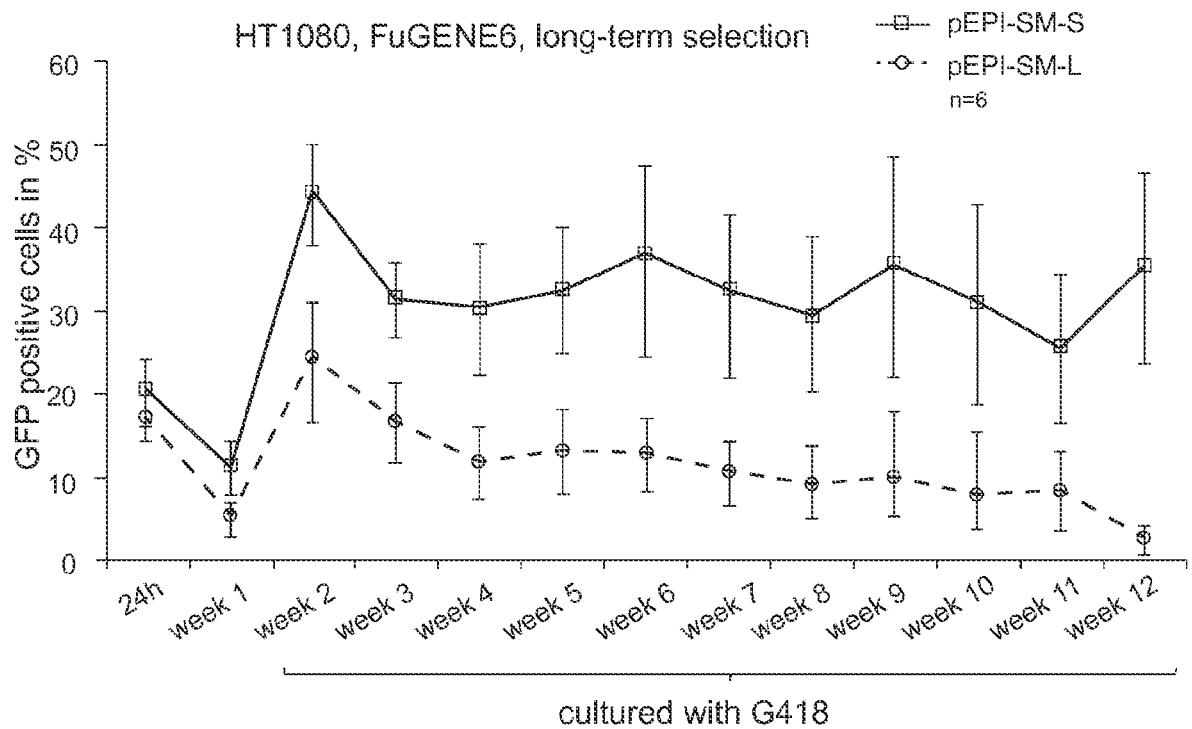
FIG. 17B shows a graphic representation of the results of in vivo studies in fibrosarcoma cell line HT1080 concerning the effect of the presence of S/MAR elements on the long-term expression levels in transfected cells cultured with G418.

FIG. 17A shows the results of the GFP expression in a test series, where a short-term selection with G418 for about 10 days was applied. FIG. 17B contains the result of the test series where a long-term selection over the whole observation time of 12 weeks with G418 has been applied. In this context, it can be seen that both variants of the S/MAR-element, i.e. the long as well as the shortened variant, lead to a long-term expression of eGFP in the transfected cells. Furthermore, the long-term expression of GFP can be even improved on the basis of the shortened variant of the S/MAR-element Both variants of the S/MAR-element ensure an episomal persistence of the transferred nucleic acid molecules in the target cells, as can be deduced from the expression of eGFP over the whole observation time of 12 weeks. Furthermore, the shortened variant leads to a higher percentage of GFP positive cells, indicating an improved episomal persistence of the transferred nucleic acid molecules in the cells. Overall, the S/MAR element is also suitable to improve the gene expression in non-liver cells, in particular cells derived from fibrous and/or connective tissues.

FIG. 18 shows the graphic representation of the results of in vivo studies performed in fibrosarcoma cell line HT1080, wherein the influence of different variants of polyethylenimine at a defined weight or volume related ratio of polyethylenimine to nucleic acid molecules of 3:1 for transfection have been used. In this context, the expression of eGFP transgene expression has been analyzed or determined. For this purpose, cells of the fibrosarcoma cell line HT1080 have been transfected with the vector pEPI1-SM-S (cf. FIG. 5B), wherein different variants of polyethylenimine have been used at two different concentrations in order to introduce the vector DNA into the fibrosarcoma target cells. As transfection reagents, the following variants of polyethylenimine have been used: glucose-conjugated polyethylenimine (Hep PEI), commercially available from Polyplus Inc., Illkirch, FR under the trade name jetPEI®-hepatocyte, branched polyethylenimine with a molecular weight of 25 kDa (bPEI), linear polyethylenimine with a molecular weight of 24 kDa (liPEI) and JetPEI a commercially available polyethylenimine from Polyplus Inc., Illkirch, FR. Furthermore, as the positive control, the transfection has been also performed with FuGENE6 as a well-known and established transfection reagent. All test series have been performed with a fixed weight related ratio of polyethylenimine to DNA of 3:1. For each transfection reagent, a first approach using 18 µl or 18 µg transfection reagent in combination with 6 µg DNA and a second approach with 9 µl or 9 µg of the transfection reagent in combination with 3 µg DNA have been performed. For the purpose of transfection, the mixtures of polyethylenimine and nucleic acid molecules were incubated with 200.000 cells in a well of 6-well plate. The expression of eGFP has been analyzed three days after transfection by flow cytometry.

Figure 18A:
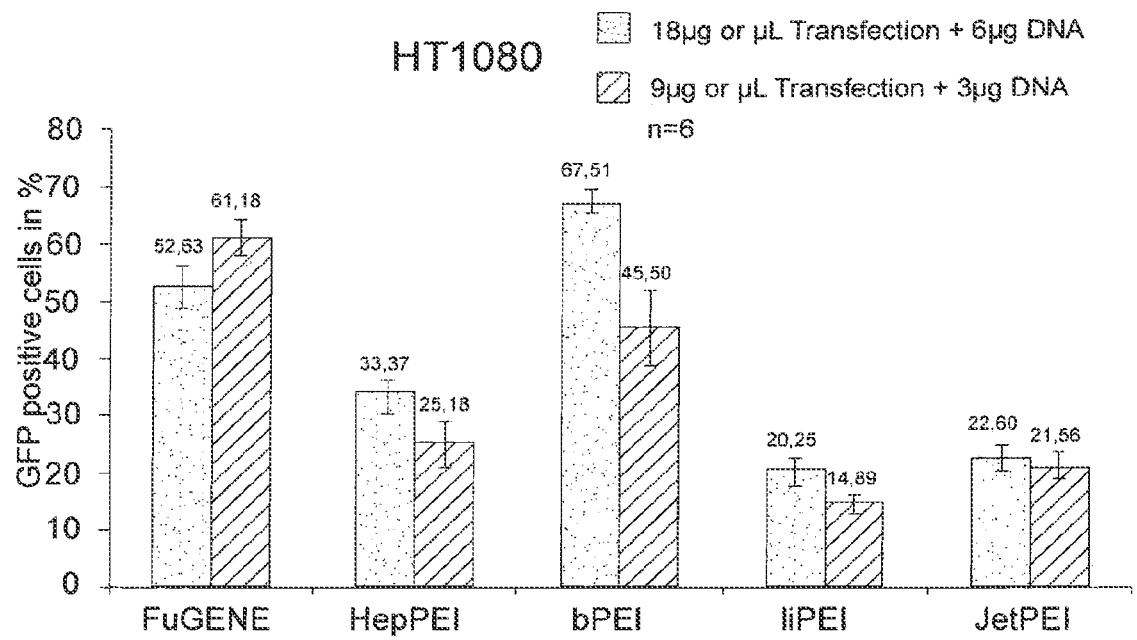
FIG. 18A illustrates the positive effect of all variants of polyethylenimine in all concentrations on the percentage of GFP positive cells obtained in the different determinations carried out.
Figure 18B:
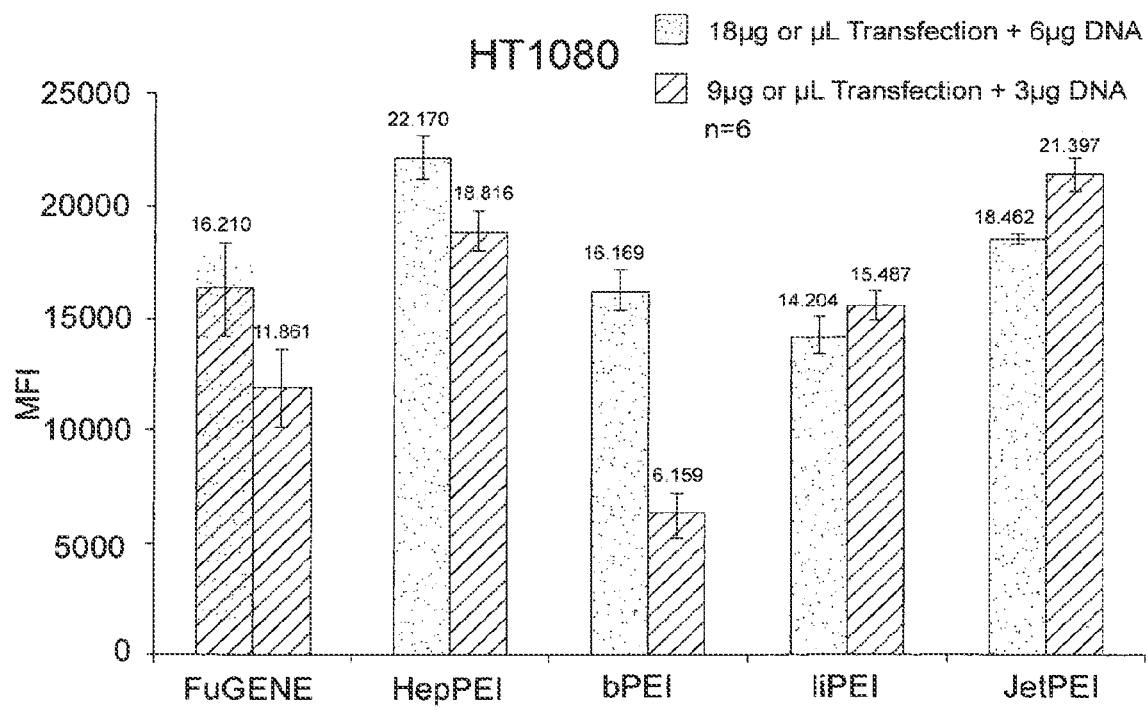
FIG. 18B provides confirmation of the positive effect of all variants of polyethylenimine in all concentrations on the percentage of GFP positive cells determined through the mean fluorescence intensity (MFI) of eGFP in the cells.
Figure 18C:
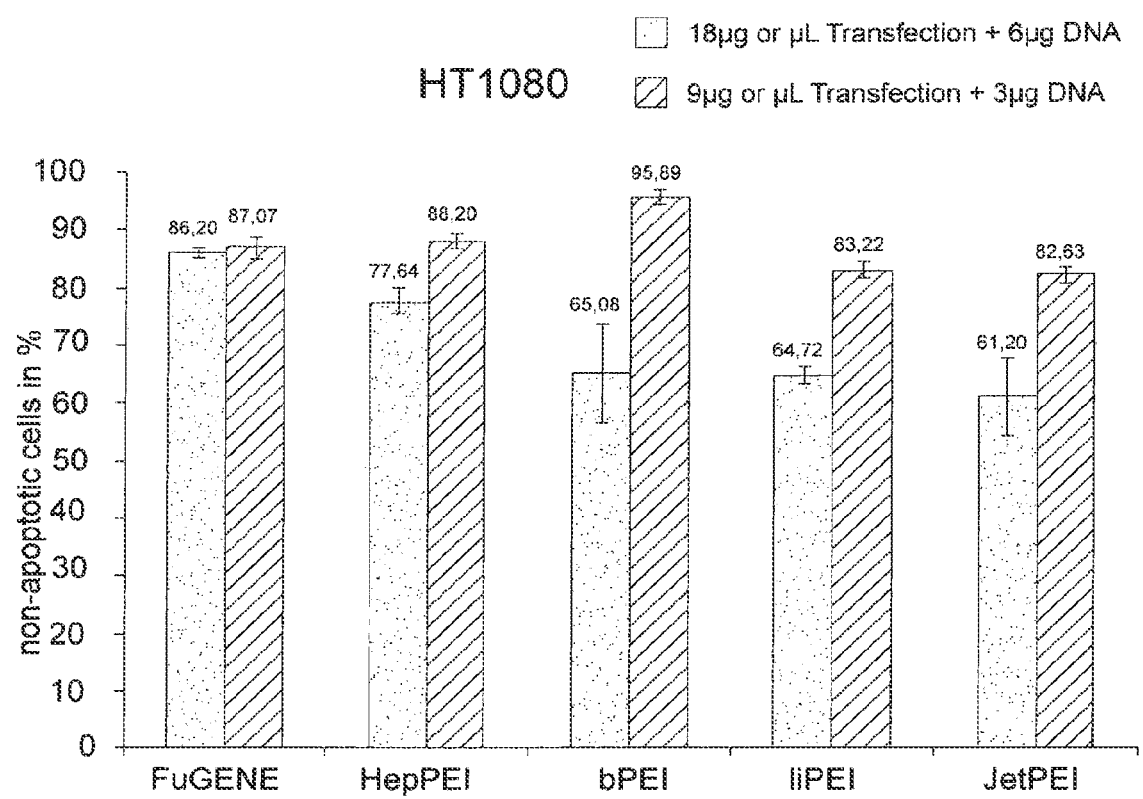
FIG. 18C provides confirmation of cell viability based on the determination of the percentage of non-apoptotic cells analyzed three days after transfection with all variants of polyethylenimine.

FIG. 18A contains the results concerning the percentage of GFP positive cells in the different approaches. In this context, it can be seen that all variants of polyethylenimine in all concentrations lead to a sufficient transfection of the fibrosarcoma cells with the vector. The results are further confirmed by the results of the determination of the mean fluorescence intensity (MFI) of eGFP in the cells, which are depicted in FIG. 18B. Furthermore, the cell viability on the basis of the determination of the percentage of non-apoptotic cells has been analyzed three days after transfection. As can be seen from FIG. 18C, the transfection with all variants of polyethylenimine is linked with a sufficient cell viability. Furthermore, the use of 9 µg or 9 µl of the transfection reagent and 3 µg of DNA leads to a further improvement of the cell viability.

Figure 19A:
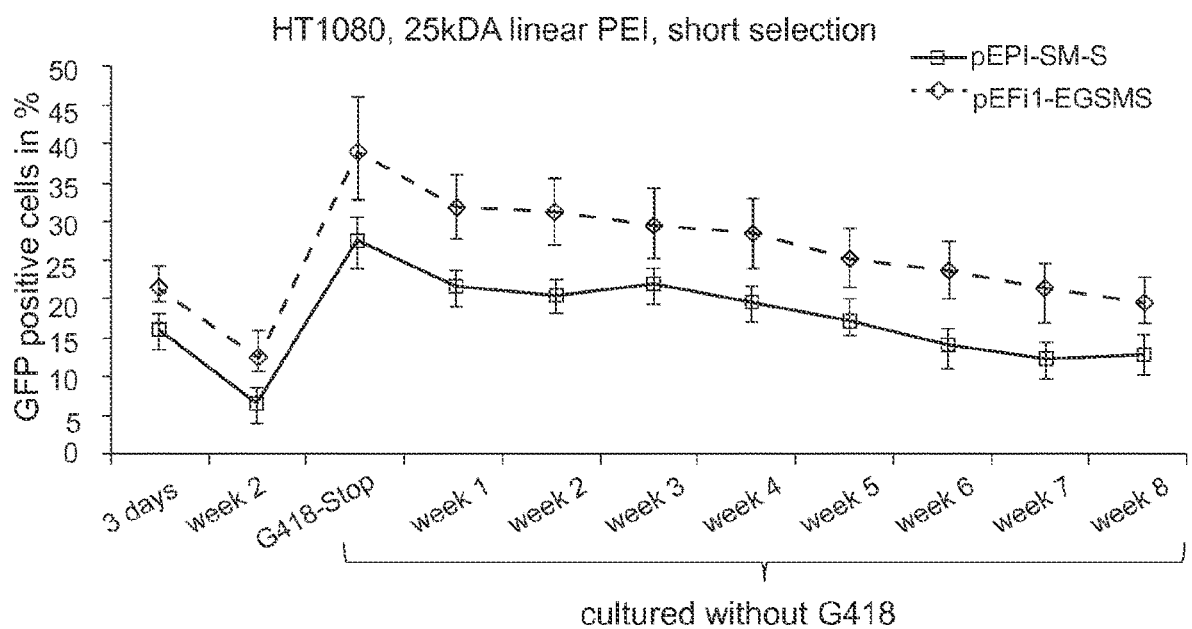
FIG. 19A provides a graphic representation of the results of in vivo studies in fibrosarcoma cell line HT1080, wherein the expression efficiency of an optimized intermediate EF-1alpha (EF1a) promoter on the eGFP expression in the target cells being analyzed, wherein the test series was performed under a short-term selection with G418 for two weeks with a subsequent cultivation for additional eight weeks without any selection.
Figure 19B:
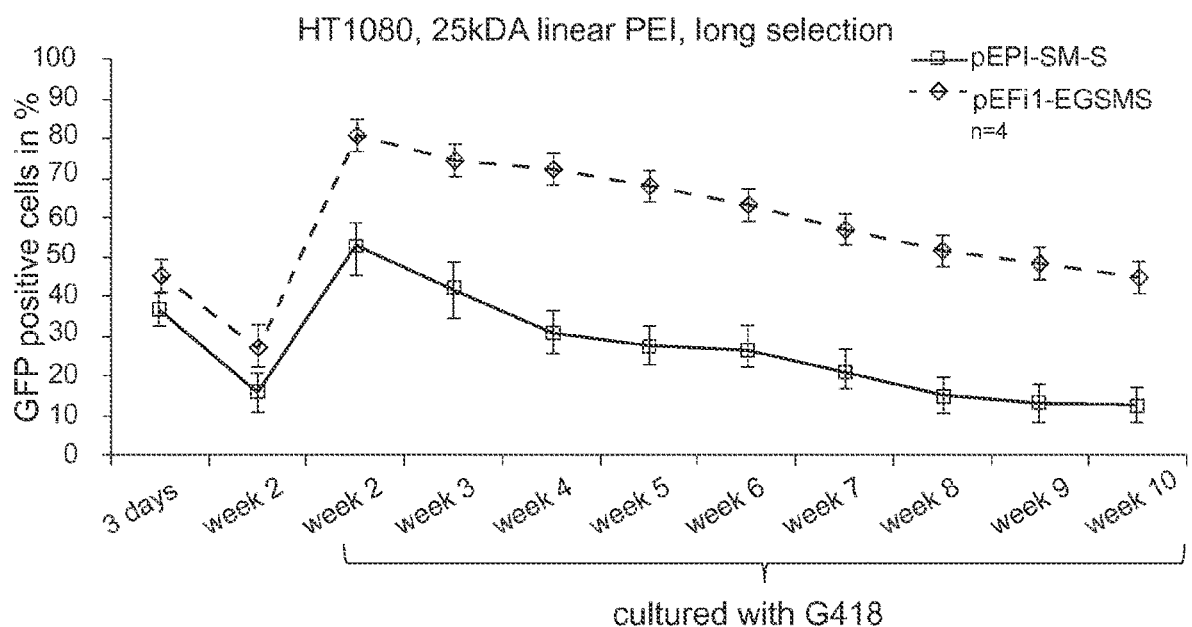
FIG. 19B provides a graphic representation of the results of in vivo studies in fibrosarcoma cell line HT1080, wherein the expression efficiency of an optimized intermediate EF-1alpha (EF1a) promoter on the eGFP expression in the target cells being analyzed, wherein the test series was performed under a long-term selection with G418 over an observation time of ten weeks.

FIG. 19 shows the graphic representation of the results of in vivo studies performed in fibrosarcoma cell line HT1080, wherein the influence of an optimized intermediate promoter derived from the gene coding for human Elongation Factor-1 alpha on the expression level of eGFP has been analyzed. For this purpose, cells of the fibrosarcoma cell line HT1080 have been transfected with the vector pEPI1-SM-S (cf. FIG. 5B), on the hand, and pEFi1_EGSMs (cf. FIG. 5C), on the other hand. For this purpose, 3 µg of DNA per well of a 6-well plate with 200.000 cells was mixed with 9 µg of linear PEI having a molecular weight of 25 kDa and then transfected. The cells were splitted twice a week and the eGFP expression levels were assessed once per week by a flow cytometry. The test series has been performed under a short-term selection with G418 for two weeks with a subsequent cultivation for additional eight weeks without any selection (FIG. 19A). Furthermore, the approach was performed under long-term selection with G418 over an observation time of ten weeks (FIG. 19B). As can be seen from FIG. 19A and FIG. 19B, the promoter derived from the human gene coding for Elongation Factor-1 alpha leads to a stable expression of the transgene, in this case the cDNA coding for eGFP, in the fibrosarcoma cells. Overall, a promoter derived from the human gene coding for Elongation Factor-1 alpha (EF1a) is suitable to direct a stable and long-term expression of coding sequences not only in liver cells, but also in non-liver cells (cf. FIG. 10), in particular cells derived from fibrous tissue.

FIG. 20 shows the graphic representation of the results of in vivo studies in fibrosarcoma cell line HT1080, wherein the transfection efficacy of gold nanoparticles comprising variants of polyethylenimine covalently bound as vehicle for the transfer of the episomal expression vector pEPI1-SM-S (FIG. 5B) into the target cells has been analyzed. In this context, for each variant of polyethylenimine, several approaches with different amounts of DNA (50 ng, 1 µg, 3 µg, 6 µg, 9 µg and 20 µg) have been performed. In this context, linear polyethylenimine with a molecular weight of 10 kDa, linear polyethylenimine with a molecular weight of 25 kDa and branched polyethylenimine with a molecular weight of 25 kDa have been used. For the purpose of transfection, the indicated amounts of DNA (µg) were mixed with 30 µg gold nanoparticles with an average diameter of 5 nm for 5 minutes at room temperature. Then the mix was added to one well of a 6-well plate with 200.000 cells. The cells were harvested and analyzed for GFP expression three days after transfection by flow cytometry.

Figure 20B:
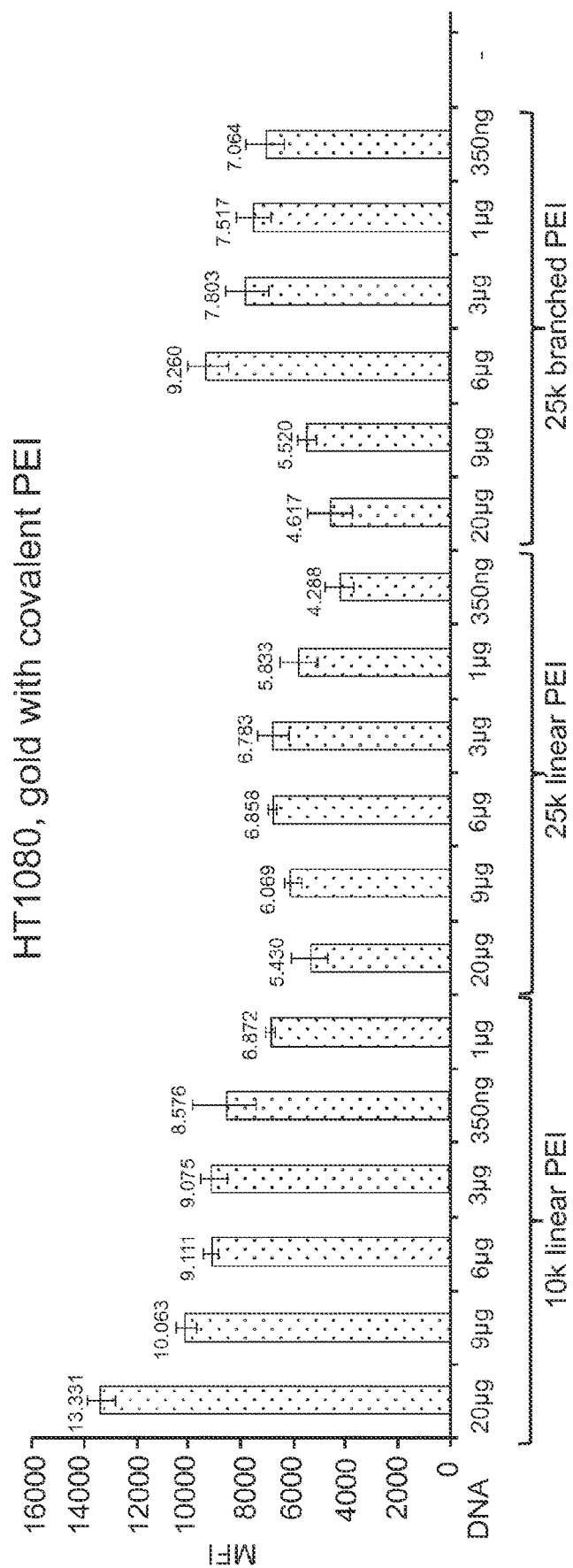
FIG. 20B provides a graphic representation of the results of in vivo studies in fibrosarcoma cell line HT1080, determined by the mean fluorescence intensity confirming that the expression of eGFP after transfection of fibrosarcoma cells with a delivery system according to the present invention using different variants of polyethylenimine was analyzed demonstrated that all variants of polyethylenimine as well as all amounts of DNA were sufficient to achieve a transfer of the nucleic acid molecules into the cells.

FIG. 20A shows the percentage of GFP positive cells three days after transfection. It can be seen that all variants of polyethylenimine as well as all amounts of DNA are sufficient in order to achieve a transfer of the nucleic acid molecules into the cells. Furthermore, the mean fluorescence intensity (MFI) of the GFP in the cells has been determined (FIG. 20B). The determination of the mean fluorescence intensity also confirms that all variants of polyethylenimine as well as all amounts of DNA, which have been tested, lead to a transfection of the cells with the nucleic acid molecules on the basis of the vector pEPI1-SM-S.

Figure 20C:
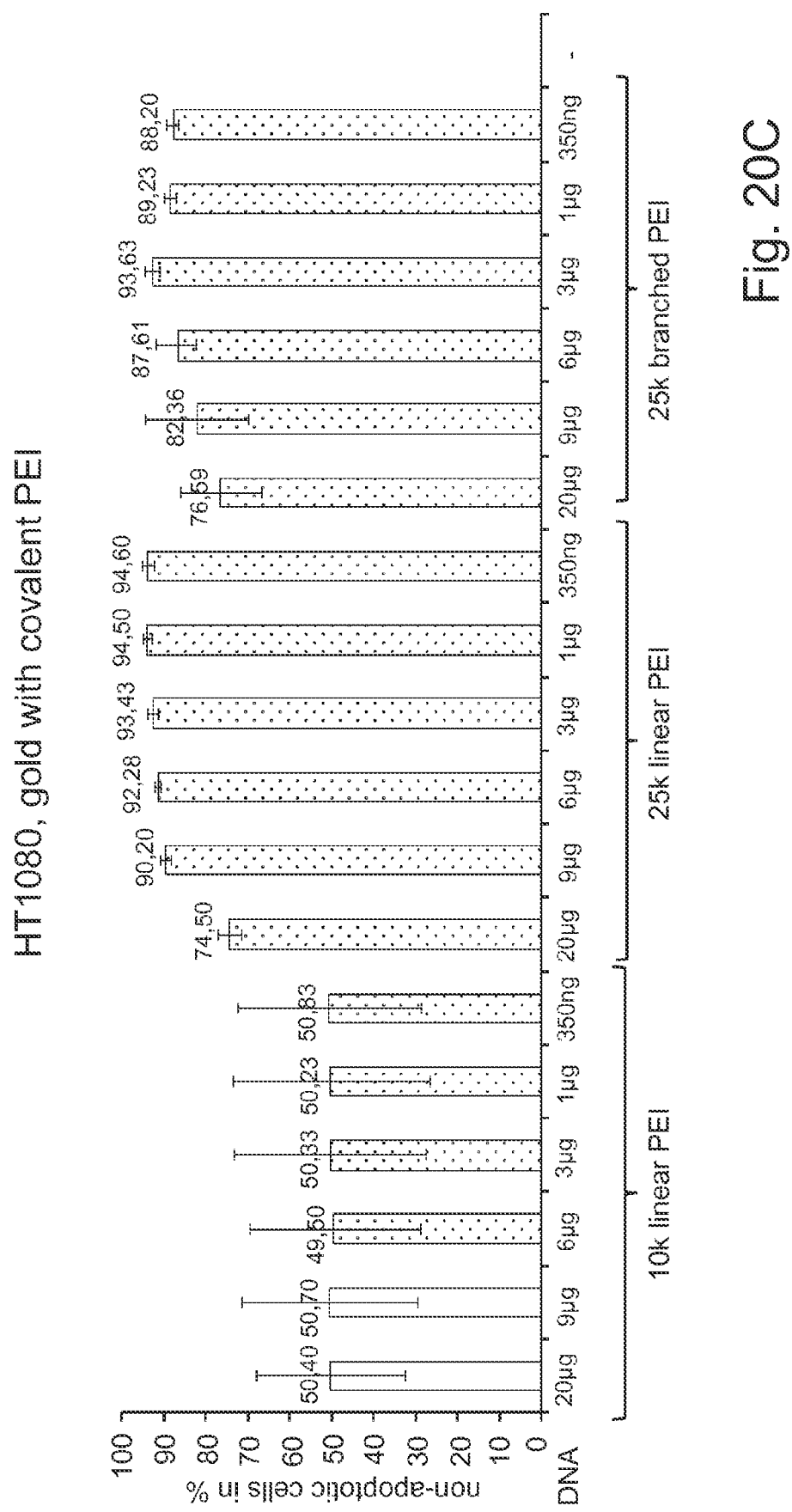
FIG. 20C provides a graphic representation of the results of an analysis of the cell viability on the basis of the determination of the percentage of non-apoptotic cells three days after transfection demonstrating that all variants of polyethylenimine as well as all amounts of DNA used for transfection lead to a sufficient viability of the transfected cells and that the best viability can be achieved by the use of linear PEI with a molecular weight of 25 kDa or branched PEI with a molecular weight of 25 kDa.

FIG. 20C shows the results of an analysis of the cell viability on the basis of the determination of the percentage of non-apoptotic cells three days after transfection. As can be seen from FIG. 20C, all variants of polyethylenimine as well as all amounts of DNA used for transfection lead to a sufficient viability of the transfected cells. The best viability can be achieved by the use of linear PEI with a molecular weight of 25 kDa or branched PEI with a molecular weight of 25 kDa.

FIG. 21 shows the graphic representation of the results of in vivo studies in fibrosarcoma cell line HT1080 with a lentiviral-based system, wherein the influence of the UCOE on the expression of eGFP in fibrosarcoma cells has been analyzed. For this purpose, fibrosarcoma cells of cell line HT1080 have been transfected with the vector pCL-UCOE-EF1 (cf. FIG. 5D). Furthermore, for comparative purposes, HT1080 cells have been transfected with a vector pCL-EF1, which is identical with pCL-UCOE-EF1, except with respect to the presence of a UCOE. In other words, the expression of the coding sequence in pCL-EF1 is only directed by the EF1 promoter. In addition, HT1080 cells have been transfected with a vector pCL-UCOE, which is identical with pCL-UCOE-EF1, except with respect to the presence of the EF1 promoter. In other words, the expression of the coding sequence in pCL1-EF1 is only directed by the UCOE, in particular the nucleic acid sequences forming the UCOE. The transfection of the cells has been performed with $10^{-3}$ to $10^{-1}$ diluted nucleic acid molecules on the basis of the vectors. The expression of eGFP has been analyzed three days after transfection on the basis of measuring the percentage of cells expression eGFP and the mean fluorescence intensity (MFI) of the GFP in the cells via FACS analysis. As can be seen from FIG. 21, the vector, which additionally comprises the UCOE leads to a significantly higher percentage of cells expressing eGFP compared to the vectors containing the coding sequence under control of UCOE and the EF1-promoter alone, respectively. The significant enhancement of the expression of the coding sequence directed by a combined use of the EF1-alpha promoter, on the one hand, and the UCOE, on the other hand, is a clear indication for the presence of a synergistic effect.

FIG. 22 shows the graphic representation of the results of in vivo studies in fibrosarcoma cell line HT1080, wherein the factor level in cells transfected with pEPI_F8-SM-S and pEFi1-GFP-FIX has been analyzed. For this purpose, cells of the fibrosarcoma cell line HT1080 have been transfected with the vector pEPI_F8-SM-S (cf. FIG. 5E), on the hand, and pEFi1-GFP-FIX (cf. FIG. 5F), on the other hand. For this purpose, 6 µg of DNA per well of a 6-well plate with 200.000 cells was mixed with 18 µl FuGENE6 as transfection reagent and then transfected. On the second day after transfection, cell culture medium was removed and cells were incubated for another 24 hours with 1 ml medium per 6-well. Afterwards, the medium was removed and immediately frozen. Cell culture supernatant was analyzed by a functional factor level measurement with ACL Top 500 (Werfen GmbH, Kirchheim near Munich, DE). Additionally, on the same day, cells were harvested and GFP expression was measured via FACS. As can be seen from FIG. 22, HT1080 cells transfected with either vector pEPI_F8-SM-S or pEFi1-GFP-FIX show a production of fusion proteins comprising either factor FVIII or factor FIX. On this basis it can be concluded that the expression system according to the present invention—in particular on the basis of the promoter EF1-alpha, a coding sequence with a nucleic acid sequence coding for a liver-specific and/or liver-expressed protein, especially a factor involved in hemostasis, and a S/MAR element—mediates an episomal expression of the liver-specific and/or liver-expressed proteins not only in liver cells, but also in non-liver cells, in particular cells derived from fibrous and/or connective tissue, for example fibroblasts, which is sufficient to compensate loss-of-function mutations of monogenetic disorders, in particular hemophilia A and/or B.

The following working examples better illustrate the subject-matter of the present invention, and they should not be considered limiting the application.

WORKING EXAMPLES

In order to illustrate the present invention, in particular the underlying principles and advantages, various in vivo studies with malignant liver cells and malignant fibroblasts have been performed. Furthermore, delivery systems according to the present invention for the use in the treatment of hemophilia A and B have been exemplarily prepared.

1. In Vivo Studies in Malignant Liver Cells (a) Vectors Designed for In Vivo Studies The vectors were generated using standard cloning techniques. In particular, preparation of purified plasmid DNA in high quantities was performed with the NucleoBond® Xtra Maxi Kit (Macherey-Nagel, Duren, Germany) according to manufacturer's instructions after transformation of chemically competent One Shot® TOP10 E. coli (Thermo Fisher Scientific, Waltham, Mass., USA).

For in vivo studies with cell cultures on the basis of various cell types, the following vectors containing a nucleotide sequence coding for an enhanced variant the Green Fluorescent Protein (GFP) as reporter gene or protein, respectively, have been prepared:

The vectors, hereinafter also referred to as plasmids, were generated on the basis of the commercially available plasmid pEGFP-C1 (available from Clontech, Mountain View, Calif., USA). The plasmid pEGFP-C1 contains a promoter derived from Cytomegalovirus (CMV), a cDNA coding for the enhanced green fluorescent protein (GFP) and a multiple cloning site located between the coding sequence for EGFP and the terminator on the basis of SV40 poly A. Furthermore, the vector contains a neomycin/kanamycin resistance cassette in the plasmid backbone. The vector pEGFP-C1 was used as starting point for the generation of the vectors pEPI-1-SM-L (FIG. 5A)), pEPI1-SM-S (FIG. 5B)) and pEFi1_EGSMs (FIG. 5C)).

For plasmid pEPI1-SM-L, the 1.995 bp long nucleotide sequence of a scaffold/matrix attachment region (S/MAR) from the 5' region of the gene coding for human Interferon-beta (IFN-beta) gene was amplified (cf. SEQ ID NO. 12). Restriction sites have been added. At the 5' region, restriction sites for StuI, AvrII, XbaI and EcoRI have been added. At the 3' region, restriction sites for MfeI and BglII have been added. The DNA was synthesized by GeneArt (Thermo Fischer Scientific Inc., Regensburg, Germany) and then cloned into the pEGFP-C1 vector using BglII and MfeI. For the generation of pEPI-1_SM-S, a shortened variant of the nucleotide sequence of the S/MAR element from human Interferon-beta (IFNbeta) (cf. SEQ ID NO. 11) with appropriate restriction sites was designed and synthesized by GeneArt (Thermo Fischer Scientific Inc., Regensburg, Germany), cut with the restriction enzymes BglII and EcoRI (NEB, Ipswich, Mass., USA) and cloned into pEGFP-C1 using restriction sites MfeI and BamHI. Sanger sequencing has verified the nucleotide sequences of both variants of scaffold/matrix attachment regions. For the preparation of pEFi1_EGSMs, the vector pEPI-SM-S was used as the starting point. The viral CMV promoter has been exchanged for a promoter derived from the gene coding for human Elongation Factor-1 alpha, having a nucleic acid sequence according to SEQ ID NO. 1 or SEQ ID NO. 18. The vector pCL-UCOE (FIG. 5D) is constructed as a lentiviral vector, which contains a nucleic acid sequence coding for a fusion protein on the basis of eGFP and a protein providing neomycin resistance protein under the control of a UCOE on the basis of the promoter CBX3 (SEQ ID NO. 13 or SEQ ID NO. 21) with a corresponding transcript (SEQ ID NO. 14 or SEQ ID NO. 22) and the promoter HNRNPA2 (SEQ ID NO. 15 or SEQ ID NO. 23) with a corresponding transcript (SEQ ID NO. 16 or SEQ ID NO. 24) and the promoter derived from the human gene coding for Elongation Factor-1 alpha (SEQ ID NO. 1 or SEQ ID NO. 18).

(b) General Experimental Procedures

Cell Cultures

For transfection analyses, the liver cancer cell lines HLF and HLE have been used. Both cell lines originate from human hepatocellular carcinoma. The HLF and HLE cells derived from the same patient have been obtained form the Riken Tissue bank in Japan. Furthermore, the cell line HT1080 has been used in order to analyze the transfection and expression in non-liver tissue, in particular fibroblasts. The cell line HT1080 is a human fibrosarcoma cell line (DMSZ, Braunschweig, Germany). The cells were grown in Dulbecco's Eagle's Medium (DMEM) with 4.6 mM glucose and 2 mM GlutaMAX™ supplement with 10 wt.-% fetal bovine serum, 100 U/ml penicillin and 100 µg/ml streptomycin. For antibiotic selection with the neomycin analogue geneticin (G418), the medium was supplemented with 1 mg/ml geneticin (commercially available from Gibco BRL, Thermo Fisher Scientific). All cells are adherent and form monolayers in culture; they have been split two to three times a week. For splitting, the cultures were washed with a solution on the basis of phosphate buffered saline (PBS, commercially available from Gibco BRL, Thermo Fisher Scientific) and incubated with Trypsin-EDTA until the monolayer dissociated. Cells were then transferred into new cell culture dishes based to their proliferation rate. Cells were grown at 37° C. in an atmosphere with 5 vol.-% $CO_2$.

General Transfection Protocol

The transfection as such has been performed according to standard protocols. In particular, for transfection 200.000 cells were seeded in 6-well tissue-culture plates. Cell counting of the different cell lines has been performed by using a Neubauer counting chamber. At the next day, cells were transfected with vector DNA using different transfection reagents. In this context, cells were cultured in 1 ml standard culture medium with the transfection reagent 6 hours after transfection, standard medium was added to the cell culture wells. 24 hours after transfection, the medium was exchanged. After two days, GFP-expression was determined via Fluorescence-activated cell sorting (FACS) analysis.

Preparation of Branched and Linear Polyethylenimine (PEI)

Branched PEI (Sigma Aldrich, 25 kDa) is a highly viscous solution. It was weighed, dissolved in PBS and adjusted to a 100 mg/ml stock solution. For use, stock solution was diluted to 1 mg/ml, filtered through a 0.22 µm membrane and stored at 4° C. The 10 kDa and 25 kDa linear PEIs (Polysciences Inc., Warrington, Pa., USA) were bought as powder and dissolved in water before using. To this end, the PEI was mixed with UltraPure distilled water at a concentration of 1 mg/ml and then heated to 80° C. until the solution was clear. The PEI solution was then cooled to room temperature and the pH value was adjusted to 7.0 using HCl. The PEI solution was then sterile filtered through a 0.22 µm membrane filter and stored at 4° C. The molecular weight of PEI has been determined by means of gel permeation chromatography or according to DIN 55672-3: 2016-03, respectively.

Transfection with Polyethylenimine

For transfection with PEI as transfection reagent, DNA and PEI were separately diluted in 100 µl 150 mM NaCl. The PEI solution was then added to the DNA solution. The PEI/DNA solution was mixed, incubated for 15 minutes at room temperature and then added to the cells.

Transfection with FuGENE6

FuGENE6 (Promega, Madison, Wis., USA) was pre-warmed to room temperature and the specific amount of transfection reagent was mixed with also pre-warmed 500 µL standard culture medium. Different amounts of DNA were then added to the FuGENE6/medium and mixed immediately according to the manufacturer's recommendations. The transfection reagent/DNA mixture was incubated for 15 minutes at room temperature and then added to the cells.

Transfection with AuNP with Covalently Bound PEI

HLF cells and HT1080 cells were transfected with AuNPs covalently bound to three different PEI-variants. All particles were of the same size (5 nm), determined by, analytical disc centrifugation and transmission electron microscopy, and were tested with 25 kDa branched PEI (nanoComposix Europe, Prague, CZ) and two different sizes (25 kDa and 10 kDa) of linear PEI (Nanopartz Inc, Loveland, Calif.). Due to the high concentration, the gold nanoparticles were diluted with ddH$_2$O to a concentration of 160 µg/ml before using. Afterwards, the nanoparticles were mixed with the DNA and incubated for 2 to 5 minutes before adding to the cells.

Fluorescence-Activated Cell Sorting (FACS)

FACS analyses were conducted to determine the number of GFP-expressing cells, as well as the mean fluorescent intensity (MFI) and the amount of non-apoptotic cells three days after transfection. In this context, cells were washed once with 2 ml phosphate buffered saline (PBS). Afterwards the cells were trypsinized with 0.5 ml Trypsin-EDTA (0.05 wt.-% Trypsin, 0.02 wt.-% EDTA) and the reaction was stopped by adding cell culture medium. The detached cells were transferred into a FACS tube and centrifuged for 5 min at 1.200 rpm. The supernatant was then removed and the cell pellet dissolved using PBS containing 2 wt.-% fetal calf serum (FCS) and 4',6-diamidino-2-phenylindole (DAPI). For every FACS analysis a sample without DAPI-staining was furthermore analyzed. Data analysis was conducted using BD FACSDiva™ as software.

Factor Level Measurement

In order to determine the factor level, 24 hours after transfection, the cell culture medium was removed and the cells were cultured in 1 ml medium. After another 24 hours, the cell culture supernatant was collected and immediately frozen at −80° C. until factor level measurement was performed. During factor level measurement the amount of time, which is required for a plasma sample to clot, is recorded. Coagulation endpoints have been assessed by measuring changes in optical density with a turbidimetric method. All measurements were conducted using an ACL Top 500 (Werfen GmbH, Kirchheim near Munich, DE).

(c) Transfection Experiments and In Vivo Studies

With respect to the establishment of a nanoparticle-based delivery system for a coding sequence suitable for the use in gene-therapy of patients suffering from a monogenetic disorder caused by a mutation in a gene coding for a liver-specific and/or liver-expressed protein, in particular proteins involved in hemostasis, in vivo studies with malignant liver carcinoma cells and fibrosarcoma cells have been performed. The in vivo studies serve as basis for the development of an expression cassette and/or expression vector to be used for the preparation of the delivery system according to the present invention.

Influence of the S/MAR Element on Episomal Persistence

In order to establish an optimal S/MAR variant with respect to a long-term expression—i. e. episomal persistence—of the coding sequence in the target cells, in particular the liver or fibrous tissue, the long-term expression of GFP under different S/MAR variants in various cell types transfected with the afore described test vectors pEPI1-SM-L and pEPI1-SM-S was recorded.

Transfection of Cell Lines

In order to test the influence of different S/MAR variants on the episomal persistence of nucleic acid molecules, liver cancer cells of the human hepatoma cell lines HLE and HLF have been transfected with the afore described vectors pEPI1-SM-S (shortened S/MAR variant) and pEPI1-SM-L (full S/MAR variant). Furthermore, fibrosarcoma cell line HT1080 has been transfected with the afore described vectors. Transfection has been carried out by using FuGENE 6 as transfection reagent and 10 µg vector DNA. Additionally, liver cancer cells of type HLF have been transfected with pEPI1-SM-S and pEPI1-SM-L, using branched PEI with a molecular weight of 25 kDa as the transfection reagent.

Test Procedure

The expression of GFP in the transfected cells was measured as the indicator for episomal persistence 24 hours after transfection. Afterwards, GFP expression in the cells was measured weekly. Since the malignant cell lines used for the test series are—in contrast to healthy liver cells, in particular hepatocytes, and healthy fibrous tissue cells—fast dividing cells, the test series were performed under short-term selection conditions on the basis of geneticin (G418) present for 2 weeks and long-term selection conditions on the basis of geneticin (G418) present over the whole observation period. In order to measure the expression of GFP, cells were harvested and analyzed by flow cytometry. In this context, the percentage of cells expressing GFP was determined. Furthermore, the MFI has been determined.

Results

The results of the transfection experiments regarding the influence of different variants of the S/MAR elements on episomal persistence are graphically depicted in FIG. 6 to FIG. 8 as well as FIG. 17. In this context, FIG. 6 shows the results of HLE cells transfected with FuGENE 6 as transfection reagent, FIG. 7 shows the results of HLF cells transfected with FuGENE 6 as transfection reagent and FIG. 8 shows the results of cell line HLF transfected with branched PEI as the transfection reagent FIG. 17 shows the results of HT1080 cells transfected with FuGENE 6 as transfection reagent.

As can be seen from FIGS. 6 to 8 as well as FIG. 17, independently from cell type and transfection reagent, cells transfected with pEPI1-SM-S, comprising the shortened variant of the S/MAR element, show the most stable expression of GFP, determined on the basis of the percentage of cells expressing GFP. This applies for cells cultured under short-term selection with geneticin as well as for cells cultured with long-term selection with geneticin.

With concern in particular to HLE cells transfected with FuGENE 6 (FIG. 6), the cells expressed pEPI1-SM-S relatively stable, even under short-term selection conditions. The episomal stability of pEPI1-SM-L was inferior under short-term selection as well as under long-term selection, but still sufficient. Under short-term selection, 40 to 50% of the cells transfected with pEPI1-SM-S showed an expression of GFP, wherein 20 to 30% of the cells transfected with pEPI1-SM-L showed an expression of GFP over 10 weeks (FIG. 6A). Under long-term selection, 40 to 60% of the cells transfected with pEPI1-SM-S showed an expression of GFP over 12 weeks, wherein 10 to 40% of the cells transfected with pEPI1-SM-L showed an expression of GFP (FIG. 6B).

Similar results have been observed in HLF cells transfected with FuGENE 6 as transfection reagent (FIG. 7). Under short-term selection (FIG. 7A), 50 to 80% of the cells transfected with pEPI1-SM-S showed an expression of GFP, wherein 40 to 60% of the cells transfected with pEPI-SM-L showed an expression of GFP over 10 weeks. Under long-term selection (FIG. 7B), 50 to 85% of the cells transfected with pEPI1-SM-S showed an expression of GFP over 12 weeks, wherein 45 to 75% of the cells transfected with pEPI1-SM-L showed an expression of GFP.

Also in HLF cells transfected with branched PEI having a molecular weight of 25 kDa, the shortened variant of the S/MAR element led to a higher episomal persistence of the vector (FIG. 8). Under short-term selection (FIG. 8A), 60 to 70% of the cells transfected with pEPI1-SM-S showed an expression of GFP, wherein 50 to 60% of the cells transfected with pEPI-SM-L showed an expression of GFP over 8 weeks. Under long-term selection (FIG. 8B), 70 to 80% of the cells transfected with pEPI1-SM-S showed an expression of GFP over 10 weeks, wherein 50 to 60% of the cells transfected with pEPI1-SM-L showed an expression of GFP.

Finally, with respect to HT1080 cells transfected with FuGENE 6 (FIG. 17), the cells expressed pEPI1-SM-S relatively stable, even under short-term selection conditions. The episomal stability of pEPI1-SM-L was inferior under short-term selection as well as under long-term selection, but still sufficient. Under short-term selection, 20 to 40% of the cells transfected with pEPI1-SM-S showed an expression of GFP, wherein 5 to 25% of the cells transfected with pEPI1-SM-L showed an expression of GFP over 10 weeks (FIG. 17A). Under long-term selection, 25 to 45% of the cells transfected with pEPI1-SM-S showed an expression of GFP over 12 weeks, wherein 5 to 25% of the cells transfected with pEPI1-SM-L showed an expression of GFP (FIG. 17B).

Overall, it can be concluded that both variants of the S/MAR element lead to a sufficient episomal persistence of the transferred nucleic acid molecules in different types of malignant liver cells. Surprisingly, on the basis of the shortened variant of the S/MAR element, the episomal persistence can be further improved. Furthermore, it was shown that the same effect can be achieved in non-liver cells, in particular fibrosarcoma cells or cells derived from fibrous and/or connective tissue.

Establishment of an Optimal Ratio of DNA to Transfection Reagent

In order to establish an optimal weight-related ratio of DNA to transfection reagent, the GFP expression in liver cancer cell line HLF transfected with pEPI1-SM-S was measured. As transfection reagents, two different PEI variants, namely linear and branched PEI both with a molecular weight of 25 kDa, were used. The percentage of cells expressing eGFP was counted with flow cytometry.

Transfection of Cells

To establish an optimal ratio of DNA and PEI as a transfection reagent, four different amounts of DNA, namely 10 µg, 3 µg, 1 µg and 0.7 µg, were transfected with a stable amount of 9 µg PEI in HLF cells. Transfections were carried out using a linear PEI with a number average molecular weight of 25 kDa and branched PEI also with a number average molecular weight of 25 kDa.

Results

The results are graphically depicted in FIG. 9. As can be seen from FIG. 9A, for both PEI variants the best GFP expression levels were observed with a weight related ratio of PEI to DNA of 3:1 (9 µg PEI and 3 µg DNA). Furthermore, higher expression levels of GFP were obtained with linear PEI (39%) compared to the branched PEI variant (20%). The toxicities were comparable for all conditions and not influenced by the DNA amount (cf. FIG. 9B).

Overall, it can be concluded that a weight related ratio of PEI to DNA of about 3:1 leads to the highest percentage of cells expressing GFP. Even though both variants of PEI led to a sufficient transfection of the cells with a resulting GFP expression, by using linear PEI the expression of the coding sequence could be even further improved.

Influence of Different Transfection Reagents on Transfection Efficiency

Furthermore, the influence of different transfection reagents on the transfection efficiency and the resulting GFP expression was analyzed. In this context, different PEI variants, namely galactose-conjugated PEI (Hep-PEI), branched PEI (bPEI), linear (liPEI) PEI and jetPEI®, which is a linear PEI commercially available from Polyplus Inc. (Illkirch, FR), have been used as transfection reagents. Furthermore, FuGENE 6 as an established transfection reagent has been used as control. The transfection reagents and the DNA were used in a weight related ratio of 3:1 for the transfection of liver cancer cell line HLF as well as fibrosarcoma cell line HT1080. A first test series was conducted by using 18 µg or ill of the transfection reagent and 6 µg DNA. A second test series was conducted by using 9 µg or µl of the transfection reagent and 3 µg DNA. The percentage of cells expressing GFP was readout in flow cytometry.

Results

The results regarding the influence of different transfection reagents on transfection efficiency are graphically depicted in FIG. 10 and FIG. 18:

As can be seen from FIG. 10A, the percentage of GFP positive cells is similar for both DNA concentrations of 3 µg and 6 µg DNA per well, except for branched PEI, where the double amount of DNA led to almost the double percentage of GPF positive cells. Furthermore, there is no major difference in the results achieved by measuring the mean fluorescence intensity (MFI) in the cells (cf. FIG. 10B) compared to the percentage of GFP positive cells (cf. FIG. 10A). As can be seen from FIG. 10C, the higher amount of DNA and transfection reagent is linked with a higher toxicity.

Similar results have been achieved with the transfected HT1080 cells. As can be seen from FIG. 18A, the percentage of GFP positive cells is similar for both DNA concentrations of 3 µg and 6 µg DNA per well, except for branched PEI, where the double amount of DNA led to a significantly higher percentage of GPF positive cells. Furthermore, there is no major difference in the results achieved by measuring the mean fluorescence intensity (MFI) in the cells (cf. FIG. 18B) compared to the percentage of GFP positive cells (cf. FIG. 18A), except for branched PEI. As can be seen from FIG. 18C, the higher amount of DNA and transfection reagent is linked with a higher toxicity.

Overall, all tested variants of PEI lead to a sufficient transfection efficiency and are therefore suitable for the applications according to the present invention. The best results taking into account, GFP expression, on the one hand, and toxicity, on the other hand, were achieved with galactose-conjugated PEI. Furthermore, in HLF cells linear PEI leads at lower concentrations of transfection reagent and DNA to superior transfection results compared to branched PEI.

Expression Level of GFP Under Human Promoter EF1-Alpha

Since the viral CMV promoter is not ideal for the application in humans, the expression level of GFP under the control of a promoter derived from the promoter of the gene coding for human EF1-alpha has been analyzed. The constitutively active promoter fragment of human origin contained furthermore an optimized first intron, which was considerably shortened. Additionally, a cryptic splice site was deleted (sequence according to SEQ ID NO. 1 or SEQ ID NO. 18).

Transfection of Cells

Liver cancer cells from cell line HLF and fibrosarcoma cells from cell line HT1080 were transfected with the vector pEFi1_EGSMs (FIG. 5C). For this purpose, 3 µg of DNA per well of a 6-well with 200.000 cells were mixed with 9 µg of linear PEI having a number average molecular weight of 25 kDa and then transfected.

Test Procedure

The test series were performed under short-term selection conditions on the basis of geneticin (G418) present for 2 weeks and long-term selection conditions on the basis of geneticin (G418) present over the whole observation period of 10 weeks. In order to measure the expression of GFP, cells were harvested and analyzed by flow cytometry. The GFP expression of HLF cells transfected with pEFG1-SM-S was compared to the GFP expression in HLF cells transfected with pEPI1-SM-S as described before. Likewise, the GFP expression of HT1080 cells transfected with pEFG1-SM-S was compared to the GFP expression in HT1080 cells transfected with pEPI1-SM-S.

Results

The results concerning the activity of a promoter derived from the gene coding for human EF1-alpha in liver cancer cells of cell line HLF are graphically depicted in FIG. 11. The results concerning the activity of a promoter derived from the gene coding for human EF1-alpha in fibrosarcoma cells of cell line HT1080 are graphically depicted in FIG. 19.

As can be seen from FIG. 11A, under short-term selection 50 to 70% of the liver cancer cells show an expression of GFP. This applies for cells transfected with pEPI1-SM-S as well as cells transfected with pEFi1_EGSMs. Under long-term selection (FIG. 11B), about 70% of the cells transfected with pEPI1-SM-S expressed GFP over the observation time of 10 weeks wherein 40 to 60% of the cells transfected with pEPFi1_EGSMs expressed GFP.

As can be seen from FIG. 19A, under short-term selection 25 to 45% of the fibrosarcoma cells transfected with pEFi1_EGSMs show an expression of GFP. With respect to cells transfected with pEPI1-SM-S, 18 to 30% of the cells show an expression of GFP. Under long-term selection (FIG. 19B), about 30 to 50% of the cells transfected with pEFi1_EGSMs expressed GFP over the observation time of 10 weeks wherein 5 to 25% of the cells transfected with pEPI1-SM-S expressed GFP.

Overall, it can be summarized that the promoter derived from the gene coding for human EF1-alpha directs a sufficient expression level of the transgene in liver cancer cells as well as fibrosarcoma cells. On this basis, a sufficient expression level directed by a promoter derived from the gene coding for EF1-alpha in hepatocytes in clinical application can be assumed. Furthermore, a sufficient expression level in non-liver cells, for example fibroblasts, in clinical applications can be expected.

Transfection Efficiency of Gold Nanoparticles with Covalently Bound PEI

Furthermore, the transfection efficiency of gold nanoparticles with various covalently bound PEI variants in liver cancer cells of cell line HLF as well as fibrosarcoma cells of cell line HT1080 has been evaluated. In this context, linear PEI with a molecular weight 10 kDa, linear PEI with a molecular weight of 25 kDa and branched PEI with a molecular weight of 25 kDa at different DNA concentrations of 350 ng, 1 µg, 3 µg, 6 µg, 9 µg and 20 µg have been used.

Preparation of Gold Nanoparticles with Covalently Bound PEI

Gold nanoparticles with covalently bound PEI have been prepared according to the above-described manufacturing procedure.

Transfection of Cells and Test Procedure

For the purpose of transfection, the indicated amount of DNA (µg) was mixed with 30 µg gold nanoparticles comprising covalently bound PEI for five minutes at room temperature. Then, the mix was added to one well of a 6-well plate with 200.000 cells. Cells were harvested and analyzed for GFP expression three days after transfection by flow cytometry.

Results

The results with respect to the transfection efficiency of gold nanoparticles with covalently bound PEI in HLF cells are graphically depicted in FIG. 12. The results with respect to the transfection efficiency of gold nanoparticles with covalently bound PEI in HT1080 cells are graphically depicted in FIG. 20.

As can be seen from FIG. 12A, which shows the percentage of GFP positive cells, gold nanoparticles are a suitable carrier for the transfer of transgenes into malignant liver cells. Furthermore, also FIG. 12B shows that HLF cells can be sufficiently transfected with carrier system on the basis of gold nanoparticles with covalently bound PEI. FIG. 12B indicates the mean fluorescence intensity (MFI) of GFP in the cells. On the basis of the results shown in FIG. 12C, it can be assumed that gold nanoparticles with covalently bound PEI are associated with only a minor toxicity, in particular gold nanoparticles comprising linear PEI with a molecular weight of 25 kDa or branched PEI with a molecular weight of 25 kDa. A high percentage of 78 to 86% of the cells transfected with gold nanoparticles comprising linear PEI with a molecular weight of 25 kDa or branched PEI with a molecular weight of 25 kDa were non-apoptotic. The use of PEI with a molecular weight of 10 kDa was associated with a higher toxicity. The percentage of non-apoptotic cells varied between 55 and 65%, depending on the DNA concentration.

As can be seen from FIG. 20A, which shows the percentage of GFP positive cells, gold nanoparticles are a suitable carrier for the transfer of transgenes not only into malignant liver cells, but also into fibrosarcoma cells. Furthermore, also FIG. 20B shows that HT1080 cells can be sufficiently transfected with carrier system on the basis of gold nanoparticles with covalently bound PEI. FIG. 20B indicates the mean fluorescence intensity (MFI) of GFP in the cells. On the basis of the results shown in FIG. 20C, it can be assumed that gold nanoparticles with covalently bound PEI are associated with only a minor toxicity in fibrosarcoma cells, in particular gold nanoparticles comprising linear PEI with a molecular weight of 25 kDa or branched PEI with a molecular weight of 25 kDa. A high percentage of 74 to 95% of the cells transfected with gold nanoparticles comprising linear PEI with a molecular weight of 25 kDa or branched PEI with a molecular weight of 25 kDa were non-apoptotic. The use of PEI with a molecular weight of 10 kDa was associated with a higher toxicity. The percentage of non-apoptotic cells was around 50%. There were no major differences at different DNA concentrations.

It can be summarized that gold nanoparticles with covalently bound PEI variants are suitable for the transfection of liver cells as well as non-liver cells, for example fibroblasts. Furthermore, the use of linear PEI with a molecular weight of 25 kDa or branched PEI with a molecular weight of 25 kDa is associated with a reduced toxicity compared to linear PEI with a molecular weight of only 10 kDa. The reduced toxicity of 25 kDa linear PEI and 25 kDa branched in comparison to 10 kDa linear PEI applies to both tested cells types.

Influence of UCOE Sequences on the Expression Level

In order to analyze the influence of a UCOE on the basis of CBX3 promoter and the respective transcript as well as the HNRNPA2 promoter and the respective transcript on the expression of a coding sequence in liver cells as well as non-liver tissue, liver cancer cells of cell line HLF and fibrosarcoma cells of cell line HT1080 were transduced with the lentiviral vectors pCL-UCOE-EF1 (FIG. 5D), pCL-UCOE (not depicted) and pCL-EF1 (not depicted). Lentiviral transduction of the cells was performed at limiting dilutions since limiting the number of positive or transduced cells is important to ensure that only one integration of the vector occurred per target cell genome. For this purpose, viral particles were produced in 293T cells (commercially available via Thermo Fisher Scientific GmbH, Dreieich, DE), diluted with a medium from $10^{-3}$ to $10^{-1}$ and then added to the cells overnight. The percentage of cells expressing GFP and the mean fluorescent intensity value (MFI) were measured three days after transfection via FACS analysis.

Results

The results with respect to the HLF cells are depicted in FIG. 13. As can be seen from FIG. 13, the highest MFI value throughout all tested dilutions was achieved with the vector pCL-UCOE-EF1, which comprises the coding sequence under control of UCOE and the EF1-alpha promoter. The lowest MFI value was achieved with cells transfected with pCL-UCOE.

The results with respect to the HT1080 cells are depicted in FIG. 21. As can be seen from FIG. 21, the highest MFI value throughout all tested dilutions was also achieved with the vector pCL-UCOE-EF1. The lowest MFI value was achieved with cells transfected with pCL-UCOE.

The results show that the combined use of the EF1-alpha promoter and a UCOE on the basis of the CBX3 promoter and the HNRNPA2 promoter lead to a further enhancement of the expression of the coding sequence in the target cells. The enhancement of the expression applies to both tested cell types.

Factor Production in Liver Cancer Cell Line HLF

Furthermore, the factor synthesis or production in cells transfected with an episomal expressing vector comprising the coding sequence for fusion proteins of GFP and factor FVIII (with deleted B-domain) or FIX (padua variant), respectively, has been analyzed.

Transfection of Cells and Test Procedure

For this purpose, cells of liver cancer cell line HLF as well as fibrosarcoma cell line HT1080 have been transfected with the vector pEPI_F8-SM-S (FIG. 5E) or pEFi1-GFP-FIX (FIG. 5F), respectively. As transfection reagent, FuGENE6 was used. For the purpose of transfection, 6 μg of nucleic acid molecules per 6-well with 200.000 cells were introduced by mixing with 18 μl FuGENE6. On the second day after transfection, cell culture medium was removed and the cells were cultured in 1 ml medium. After another 24 hours, the cell culture supernatant was collected and stored at 80° C. until factor level measurement.

The factor measurement was conducted using an ACL Top 500 (Werfen GmbH, Kirchheim near Munich, DE). Further information concerning the factor measurement is evident from the respective text passage in section 1 (b) of the working examples. Furthermore, at the same point of time, cells were harvested and the percentage of cells expressing GFP was analyzed via FACS.

Results

The results of the measurement of factor production in HLF cells are depicted in FIG. 14. The results of the measurement of factor production in HT1080 cells are depicted in FIG. 22.

FIG. 14 shows that cells transfected with both vectors produce a quantifiable amount of factor FVIII and FIX, respectively. With fibrosarcoma cell line HT1080, an even higher factor level with respect to the amount of factor FVIII and FIX, respectively, was achieved (cf. FIG. 22).

For the purpose of evidence and detection, the factor level measurement has been performed on the basis of a nucleic acid sequence, which codes for a fusion protein on the basis of GFP and the respective factor. However, due to a shortened sequence, it can be expected that the production of factors will be enhanced on the basis of a coding sequence coding only for the respective liver-specific and/or liver-expressed protein and/or domains and/or fragments thereof without GFP.

Analysis of S/MAR Directed Episomal Persistence in Liver Cancer Cell Line HLE

The episomal persistence of vectors containing a S/MAR element in transfected cells has been analyzed. For this purpose, the vectors pEPI1-SM-L (FIG. 5A) and pEPI1-SM-S (FIG. 5B) have been used for transfection.

Transfection of Cells and Test Procedure

In order to confirm episomal persistence of the vectors, 300.000 HLE cells were seeded in 6-well plates. After 24 hours, cells were transfected with 10 µg of vector DNA (either pEPI1-SM-L or pEPI1-SM-S) and 30 µl FuGENE6 as transfection reagent Cells were splitted twice a week and cultivated for a total of 10 weeks, with an initial 2-week selection by adding G418 to the medium.

After the cultivation period, cells were harvested and episomal DNA extraction was performed. Episomal DNA extraction was performed using the QIAprep Spin Miniprep Kit (Qiagen, Hilden, DE). As a control, episomal DNA extraction was also conducted with cells that were not transfected with DNA or cells that were transduced with a lentivirus that stably integrated into the genome of the cells. Afterwards, the extracted DNA was run on a 1 wt.-% agarose gel.

Results

The results are depicted in FIG. 16. As can be seen from FIG. 16, cells that were transfected with pEPI1-SM-L (lane 1 and 2) or pEPI1-SM-S (lanes 3 to 6) with a vector containing a S/MAR element show visible DNA bands. In contrast to this, no episomal DNA was harvested from HLE cells that were not transfected with a vector (lane 7) or with a lentivirus (lane 8). The results verify the episomal persistence and/or the stable episomal replication in transfected cells mediated through nucleic expression cassettes and/or vectors containing a S/MAR element.

Overall, on the basis of the in vivo studies, the applicant found out that the episomal persistence of the coding sequences, in particular on the basis of vectors, in the target cells can be significantly improved when the vector additionally contains a scaffold/matrix attachment region. In this context, the shortened variant of the S/MAR element according to SEQ ID No. 11 is superior in comparison to the full length S/MAR element according to SEQ ID No. 12, even though both variants are suitable for the use in expression cassettes and/or vectors according to the present invention. The respective results apply for liver tissue, in particular liver cells, as well as non-liver tissue, in particular fibrous tissue and/or fibroblasts.

Furthermore, the ratio of DNA to transfection agent has a significant impact on transfection efficiency. On the basis of the transfection experiments applicant found out that a wide range of a weight-related ratio of DNA to transfection reagent is suitable for the transfection of liver cells and non-liver cells, in particular fibroblasts or cells originating from fibrous tissue. Especially good results are achieved with a weight-related ratio of transfection reagent on the basis polyethylenimine to nucleic acid molecules, in particular DNA, is 3:1.

Additionally, it was found out that all variants of polyethylenimine, namely galactose-conjugated PEI, branched PEI, linear PEI and jetPEI®, are suitable for the transfection of liver cells and non-liver cells.

With respect to a promoter in order to direct the expression of the coding sequence in liver cells and non-liver cells, in particular cells derived from fibrous tissue, which is particularly suitable for the use in humans, a promoter sequence derived from the gene coding for human Elongation Factor-1 alpha, in particular with a nucleic acid sequence according to SEQ ID NO. 1 or SEQ ID NO. 18, was found to be appropriate for expression in liver cells and non-liver cells. Furthermore, the transfection experiments performed by the applicant showed that gold nanoparticles comprising different variants of PEI, in particular linear PEI with a molecular weight of 10 kDa, linear PEI with a molecular weight of 25 kDa and branched PEI with a molecular weight of 25 kDa, are suitable for the transfection of liver cells and non-liver cells with nucleic acid molecules. Furthermore, gold nanoparticles with covalently bound PEI variants are associated with only a minor toxicity when it used for transfection.

Furthermore, it was surprisingly found that the expression of the coding sequence in the target cells, in particular liver cells and non-liver cells, for example cells originating from fibrous and/or connective tissue, can be further improved when the nucleic expression cassette and/or the vector comprises upstream of the promoter a UCOE.

Finally, on the basis of the in vivo studies, it was shown that target cells which have been transfected with a nucleic acid expression cassette comprising a coding sequence for liver-specific and/or liver-expressed proteins, in particular the factors of hemostasis FVIII and FIX, produce the proteins in measurable amounts. It can be expected that such nucleic acid expression cassettes or vectors comprising such nucleic acid expression cassettes are a suitable genetic approach for the treatment of patients suffering from monogenetic disorders on the basis of loss-of-function-mutations in genes coding for liver-specific and/or liver-expressed proteins. On this basis, an intact copy of the mutated gene coding for the liver-specific and/or liver-expressed protein can be introduced into the target cells, in particular liver cells or non-liver cells, for example cells from fibrous tissue, mediating the expression of a physiologically functional variant of the liver-specific and/or liver-expressed protein.

2. Preparation of a Delivery System According to the Present Invention

Furthermore, an exemplary delivery system according to the present invention suitable for the transfer of coding sequence for coagulation factors FVIII or FIX, respectively, into a patient suffering from hemophilia A or B, respectively, has been prepared.

Preparation of Non-Viral Minicircle Vectors

Nucleic acid molecules suitable for the nanoparticle-based delivery system of the present invention, in particular vectors and/or expression cassettes according to the present invention, can be generated by standard cloning and/or synthesizing techniques.

For the preparation of a nanoparticle-based delivery system of the present invention, a first non-viral minicircle vector according to FIG. 2A containing an expression cassette for the expression of coagulation factor FVIII has been prepared. The vector comprises an expression cassette containing a constitutively active promoter derived from the gene coding for human Elongation Factor-1 alpha (EF1-alpha). The promoter further contains an optimized first intron, which has been considerably shortened. In addition, a cryptic splice site has been deleted. Downstream of the promoter, the vector contains as coding sequence the cDNA sequence coding for factor FVIII with a deleted B-domain and a 14 amino acid linker, wherein the linker is to replace the B-domain of FVIII. Downstream of the coding sequence a shortened nucleic acid sequence of a scaffold/matrix attachment region (S/MAR) is located.

Additionally, a non-viral minicircle vector according to FIG. 2B containing an expression cassette for the expression of coagulation factor FIX has been prepared. The minicircle vector for the expression of coagulation factor FIX in fusion with albumin complies with respect to the assembly the afore described vector for the expression of factor FVIII, with the difference that the coding sequence is the cDNA sequence coding for a fusion protein of factor FIX and albumin.

The vectors as shown in FIG. 2A and FIG. 2B, preferably having coding sequences according to SEQ ID NO. 2 or SEQ ID NO. 19 (FIG. 2A) and SEQ ID NO. 5 (FIG. 2B), respectively, are suitable for the preparation of a nanoparticle-based delivery system for the coding sequences of coagulation factors FVIII, in particular with a deletion of the B-domain, and FIX. Likewise, vectors comprising the coding sequences for any protein predominantly expressed in the liver, in particular factors for coagulation and/or blood clotting, can be produced for the preparation of nanoparticle-based delivery system suitable for the expression of the respective coding sequence in the liver in order to treat monogenetic disorders resulting from a mutation in the corresponding gene.

Polyethylenimine-Coated Gold Nanoparticles

Gold nanoparticles suitable for a delivery system according to the present invention are commercially available for example from Nanopartz™ Inc., Loveland, US, or from nanoComposix Inc., San Diego, US. The nanoparticles comprise an average diameter of 5 nm, determined by means of UV/Vis spectra and transmission electron microscopy.

Preparation of the Delivery System

For the preparation of a delivery system suitable for the transfection of target cells, in particular liver cells, the gold nanoparticles are diluted with ddH$_2$O to a concentration between 50 and 250 µg/ml, in particular between 100 and 200 µg/ml. After dilution of the gold nanoparticles, nucleic acid molecules are added to the diluted gold nanoparticles. The weight-based amount of nucleic acid molecules is variable and depends on the amount of gold nanoparticles used for transfection. For an amount of 30 µg coated gold nanoparticles, particularly good transfection results have been achieved with an amount of nucleic acid molecules in the range from 350 ng and 20 µg. Gold nanoparticles and nucleic acid sequences are incubated at a temperature in the range from 10° C. to 35° C., preferably room temperature, for 1 to 15 minutes, in particular to ensure a binding of the nucleic acid molecules to the gold nanoparticles, especially the polyethylenimine. The delivery system can be used for transfection of cells.

Transfection with the Delivery System

For transfection, the delivery system as described before is mixed with the target cells, for example target cells on a well-plate with a defined number of cells per well. Furthermore, for transfection of target cells, in particular liver cells of a patient, the delivery system can be integrated into a pharmaceutically composition, preferably for intravenous application, for the use in the treatment of a patient suffering from a monogenetic disorder.

LIST OF REFERENCE SIGNS 1 delivery system
2 gold nanoparticle
3 polyethylenimine
4 nucleic acid molecules
5 targeting unit
6 cell surface receptor
7 hepatocyte (membrane)
8 endosome
9 importin
10 nuclear pore
11 nucleus

The invention claimed is:

1. A non-viral vector, comprising a nucleic acid expression cassette, wherein the expression cassette comprises:
    (a) a promoter directing gene expression in human cells;
    (b) a coding sequence containing a nucleic acid sequence coding for coagulation factor FVIII;
    (c) a nucleic acid sequence derived from the scaffold/matrix attachment region of a eukaryotic gene, wherein said nucleic acid sequence has a nucleic acid sequence according to SEQ ID NO. 11 or at least 95% identity to SEQ ID NO. 11; and
    (d) a transcriptional termination signal.

2. The non-viral vector according to claim 1, wherein the promoter is derived from the gene coding for human Elongation Factor-1 alpha (EF1a) and/or wherein the promoter is derived from the promoter of the gene coding for human Elongation Factor-1 alpha (EF1a) and the first intron and/or a fragment of the first intron of the gene coding for human Elongation Factor-1 alpha (EF1a) and/or wherein the promoter is derived from Cytomegalovirus (CMV), in particular human CMV and/or wherein the promoter is the CMV promoter.

3. The non-viral vector according to claim 1, wherein the promoter has a nucleotide sequence selected from the group consisting of SEQ ID NO. 1, SEQ ID NO. 17, and SEQ ID NO. 18.

4. The non-viral vector according to claim 1, wherein the coding sequence has a nucleic acid sequence selected from the group consisting of SEQ ID NO. 2 and SEQ ID NO. 19.

5. The non-viral vector according claim 1, wherein the non-viral vector further comprises at least one nucleic acid sequence selected from the group consisting of SEQ ID NO. 13, SEQ ID NO. 14, SEQ ID NO. 15, SEQ ID NO. 16, and SEQ ID NO. 21, wherein the at least one nucleic acid sequence functions as a Ubiquitous Chromatin-Opening Element (UCOE).

6. The non-viral vector according to claim 1, wherein the non-viral vector further comprises as Ubiquitous Chromatin-Opening Element (UCOE) a nucleic acid sequence according to SEQ ID NO. 22.

7. A method of treating a monogenetic disorder resulting from a mutation in a gene coding for coagulation factor FVIII, said method using the vector according to claim 1.

8. A nanoparticle-based delivery system for a coding sequence, wherein the delivery system comprises:
  (a) gold nanoparticles;
  (b) polyethylenimine and/or derivatives and/or salts thereof; and
  (c) the vector according to claim 1.

* * * * *